US008609405B2

(12) United States Patent
Ono et al.

(10) Patent No.: US 8,609,405 B2
(45) Date of Patent: Dec. 17, 2013

(54) GABA NEURON PROGENITOR CELL MARKER 65B13

(75) Inventors: Yuichi Ono, Hyogo (JP); Yasuko Nakagawa, Hyogo (JP); Eri Mizuhara, Hyogo (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 884 days.

(21) Appl. No.: 12/524,153

(22) PCT Filed: Feb. 7, 2008

(86) PCT No.: PCT/JP2008/052039
§ 371 (c)(1), (2), (4) Date: Feb. 25, 2010

(87) PCT Pub. No.: WO2008/096817
PCT Pub. Date: Aug. 14, 2008

(65) Prior Publication Data

US 2010/0303771 A1 Dec. 2, 2010

(30) Foreign Application Priority Data

Feb. 9, 2007 (JP) ................................ 2007-031075

(51) Int. Cl.

| | |
|---|---|
| ***C07K 16/18*** | (2006.01) |
| ***C12N 15/09*** | (2006.01) |
| ***C12Q 1/08*** | (2006.01) |
| ***C12Q 1/68*** | (2006.01) |
| ***G01N 33/53*** | (2006.01) |

(52) U.S. Cl.
USPC ........ 435/325; 435/7.21; 530/387.9; 530/839

(58) Field of Classification Search
None
See application file for complete search history.

(56) References Cited

U.S. PATENT DOCUMENTS

| | | | |
|---|---|---|---|
| 2006/0239978 A1 | 10/2006 | Nakagawa et al. |
| 2007/0122882 A1 | 5/2007 | Nakagawa et al. |
| 2008/0213757 A1 | 9/2008 | Ono et al. |
| 2010/0203570 A1 | 8/2010 | Nakagawa et al. |

FOREIGN PATENT DOCUMENTS

| | | |
|---|---|---|
| EP | 1854881 A1 | 11/2007 |
| WO | WO 2004/038018 A1 | 5/2004 |
| WO | WO 2006/022243 A1 | 3/2006 |
| WO | WO 2006/082826 A1 | 8/2006 |

OTHER PUBLICATIONS

Leto et al., Different Types of Cerebellar GABAergic Interneurons Originate from a Common Pool of Multipotent Progenitor Cells. The Journal of Neuroscience, Nov. 8, 2006 o 26(45):11682-11694.*
U.S. Appl. No. 13/057,838, which is a U.S. National Phase of PCT/JP2009/063915, filed Aug. 6, 2009, 284 pgs.

(Continued)

*Primary Examiner* — Jeffrey Stucker
*Assistant Examiner* — Aurora M Fontainhas
(74) *Attorney, Agent, or Firm* — Fish & Richardson P.C.

(57) ABSTRACT

The present inventors identified a selective marker 65B13 for GABA neuron progenitor cells of the spinal dorsal horn and cerebellum, and successfully isolated GABA neuron progenitor cells using antibodies that bind to a protein encoded by the gene. 65B13 was demonstrated to be useful as a marker to isolate GABA-producing neuron progenitor cells in the spinal dorsal horn and cerebellum. GABA neuron progenitor cells can be efficiently identified or isolated by using the identified marker as an indicator.

38 Claims, 11 Drawing Sheets

(56) References Cited

OTHER PUBLICATIONS

Mizuhara, E., et al., "Corl1, a Novel Neuronal Lineage-specific Transcriptional Corepressor for the Homeodomain Transcription Factor Lbx1," *J. Biol. Chem.*, vol. 280(5), pp. 3645-3655 (Feb. 4, 2005, Epub Nov. 4, 2004).

Nguyen-Legros, J., et al., "Dopaminergic and GABAergic Retinal Cell Populations in Mammals," *Microsc Res Tech.*, vol. 36(1), pp. 26-42 (Jan. 1, 1997).

Database EMBL [Online], Database Accession No. AK049284, 2 pgs. (Dec. 18, 2002).

Database Geneseq [Online], Database Accession No. ADN14448, 1 pg. (Jul. 29, 2004).

Database UniProt [Online], Database Accession No. Q6UWL6, 3 pgs. (Oct. 25, 2004).

Database Geneseq [Online], Database Accession No. AA026267, 1 pg. (May 29, 2003).

Database Geneseq [Online], Database Accession No. ADN14453, 1 pg. (Jul. 29, 2004).

Database UniProt [Online], Database Accession No. Q7TSU7, 2 pgs. (Oct. 1, 2003).

Database Geneseq [Online], Database Accession No. ADN14451, 1 pg. (Jul. 29, 2004).

Database Geneseq [Online], Database Accession No. ADN14450, 1 pg. (Jul. 29, 2004).

U.S. Appl. No. 13/141,063, which is a US National Phase of PCT/JP2009/071089, filed Dec. 18, 2009, 130 pages.

International Search Report for PCT/JP2008/052039, 4 pages, dated May 1, 2008.

European Search Report and Written Opinion for 08710918.7, 10 pages, dated Apr. 21, 2011.

Glasgow, S., et al., "Ptf1a determines GABAergic over glutamatergic neuronal cell fate in the spinal cord dorsal horn," *Development*, vol. 132(24), pp. 5461-5469 (Dec. 2005, Epub Nov. 16, 2005).

Hoshino, M. et al., "*Ptf1a*, a bHLH Transcriptional Gene, Defines GABAergic Neuronal Fates in Cerebellum," *Neuron*, vol. 47(2), pp. 201-213 (Jul. 21, 2005).

Kosaka, T., et al., "Catecholaminergic neurons containing GABA-like and/or glutamic acid decarboxylase-like immunoreactivities in various brain regions of the rat," *Exp Brain Res.*, vol. 66(1), pp. 191-210 (1987).

Minaki, Y., et al., "Migrating postmitotic neural precursor cells in the ventricular zone extend apical processes and form adherens junctions near the ventricle in the developing spinal cord," *Neuroscience Research*, vol. 52(3), pp. 250-262 (Jul. 2005, Epub Apr. 26, 2005).

Miyoshi, G., et al., "Identification of a Novel Basic Helix-Loop-Helix Gene, *Heslike*, and Its Role in GABAergic Neurogenesis," *The Journal of Neuroscience*, vol. 24(14), pp. 3672-3682.

Gines, et al., "Differences between human and mouse embryonic stem cells," *Dev Biol.*, vol. 269(2), pp. 360-380 (May 15, 2004).

Nakatani, et al., "Helt determines GABAergic over glutamatergic neuronal fate by repressing Ngn genes in the developing mesencephalon," *Development*, vol. 134(15), pp. 2783-2793 (Aug. 2007, Epub Jul. 4, 2007).

Sun, et al., "*Kirrel2*, a novel immunoglobulin superfamily gene expressed primarily in β cells of the pancreatic islets," *Genomics*, vol. 82(2), pp. 130-142 (Aug. 2003).

Vergaño-Vera, et al., "Generation of GABAergic and dopaminergic interneurons from endogenous embryonic olfactory bulb precursor cells," *Development*, vol. 133(21), pp. 4367-4379 (Nov. 2006).

Japanese Office Action for App. Ser. No. 2008-557154, issued on Dec. 19, 2012, 7 pages, with English translation.

* cited by examiner

A

B

| | | |
|---|---|---|
| EARLY STAGE | dI1—LH2A/B, Brn3a | |
| | dI2—Lim1/2, Brn3a | |
| | dI3—Isl1, Brn3a | |
| | dI4—Lbx1, Pax2, Lim1/2, Corl1 | —GABAergic |
| | dI5—Lbx1, Lmx1b, Brn3a, Corl1 | —Glutamatergic |
| | dI6—Lbx1, Pax2, Lim1/2 | |
| LATE STAGE | dILA—Lbx1, Pax2, Lim1/2, Corl1 | —GABAergic |
| | dILB—Lbx1, Lmx1b, Brn3a, Corl1 | —Glutamatergic |

SEQUENCE LISTING

```
<160> NUMBER OF SEQ ID NOS: 61

<210> SEQ ID NO 1
<211> LENGTH: 2876
<212> TYPE: DNA
<213> ORGANISM: Mus musculus

<400> SEQUENCE: 1

gatgagccag atttcgggga ctctgggcca gacataaaat cttccagccc ggagagaatt     60

gtgtgcagag aggggctcca gtccagcgtg gtgtgagagg cgtgctatca agaaagaagt    120

tggaggggaa ccagtgcaac cctaactcta cgagatcttg gggtacacac actcgggatg    180

ctggcctccg ccctcctcgt tttcctttgc tgtttcaaag gacatgcagg ctcatcgccc    240

catttcctac aacagccaga ggacatggtg gtgctgttgg gggaggaagc ccggctgccc    300

tgcgctctgg gcgcgtacag gggggctcgtg cagtggacta aggatgggct ggctctaggg    360

ggcgaaagag accttccagg gtggtcccgg tactggatat cggggaattc agccagtggc    420

cagcatgacc tccacattaa gcctgtggaa ttggaagatg aggcatcgta tgagtgccag    480

gcttcgcaag caggtctccg atcacgacca gcccaactgc acgtgatggt ccccccagaa    540

gctccccagg tactaggcgg cccctctgtg tctctggttg ctggagttcc tggaaatctg    600

acctgtcgga gtcgtgggga ttcccgacct gcccctgaac tactgtggtt ccgagatggg    660

atccggctgg atgcgagcag cttccaccag accacgctga aggacaaggc cactggaaca    720

gtggaaaaca ccttattcct gaccccttcc agtcatgatg atggcgccac cttgatctgc    780

agagcgcgaa gccaggccct gcccacaggg agggacacag ctgttacact gagccttcag    840

tatcccccaa tggtgactct gtctgctgag ccccagactg tgcaggaggg agagaaggtg    900

actttcctgt gtcaagccac tgcccagcct cctgtcactg gctacaggtg ggcgaagggg    960

ggatccccgg tgctcggggc acgtgggcca aggttggagg tcgttgcaga tgccactttc   1020

ctgactgagc cggtgtcctg cgaggtcagc aacgcggtcg gaagcgccaa ccgcagcacg   1080

gcgctggaag tgttgtatgg acccattctg caggcaaaac ctaagtccgt gtccgtggac   1140

gtggggaaag atgcctcctt cagctgtgtc tggcgcggga acccacttcc acggataacc   1200
```

-continued

```
tggacccgca tgggtggctc tcaggtgctg agctccgggc ccacgctgcg gcttccgtcc   1260

gtggcactgg aggatgcggg cgactatgta tgcagggctg agccgaggag aacgggtctg   1320

ggaggcggca aagcgcaggc gaggctgact gtgaacgcac cccctgtagt gacagccctg   1380

caacctgcac cagcctttct gaggggtcct gctcgcctcc agtgtgtggt gtttgcctcc   1440

cctgccccag actcggtggt ttggtcttgg gacgagggct tcttggaggc aggctcactg   1500

ggcaggttcc tagtggaagc cttcccagcc ccggaagtgg aggggggaca gggccctggc   1560

cttatttctg tgctacacat ttccggaacc caggagtccg actttaccac cggcttcaac   1620

tgcagtgccc gcaaccggct aggagaggga cgagtccaga tccacttggg ccgtagagat   1680

ttgctgccta ctgtccggat tgtggctggt gcagcatctg cagccacctc tctccttatg   1740

gtcatcactg gagtggtcct ctgctgctgg cgccatggct ctctctctaa gcaaaagaac   1800

ttggtccgga tcccaggaag cagcgagggt tccagttcac gtggccctga ggaggagaca   1860

ggcagcagtg aggaccgggg tcccattgtg cacaccgacc acagtgattt ggttcttgag   1920

gaaaaagagg ctctggagac aaaggatcca accaacggtt actacaaggt tcgaggggtc   1980

agtgtgagcc ttagccttgg ggaagctcct ggaggaggcc tcttcttgcc accgccctct   2040

ccgatcggtc tcccagggac tcctacttac tatgacttca agccacatct ggacttagtc   2100

cctccctgca gactgtacag agcgagggca ggttatctta ccacccccca tccccgtgcc   2160

ttcaccagct acatgaaacc cacatccttt ggacccccag atttgagctc tggaactccc   2220

cccttcccgt atgctacctt gtctccaccc agccaccagc gtctccagac tcatgtgtga   2280

atccatctct ccaagtgaag ggtcttggaa tcttctgttt gccatatagt gtgttgtcca   2340

gatttctggg gagtcagaac aagttgatga ccaacccctc caaaactgaa cattgaagga   2400

gggaaagatc attacaagca tcaggactgt tggtgtacac tcagttcagc caaagtggat   2460

tctccaagtg ggagcaatat ggccgctttc ccatgagaaa gacattcaag atggtgacta   2520

aatgactaaa tactttgcag agggacaaag atgggaacta gggatacgga tggaagtagt   2580

agagaagata tatgaccatc tgcatcaaga ggaaggataa catatgacaa atcaagatga   2640

aagaaataat ccaccccacc cccaccgcgt cctggccaat aagtatagcc tacatggctg   2700

ttcattatct gggaaccaaa atggccacta tcttgactcc ttccttaaag atacagaaag   2760

aattgaatcc aaggaatggg gtagggtgga aatagaagaa atgaagggga ctcttgggct   2820

aagaatactt atgtttaata ataaaagggg gaggcaaaga tgcaaaaaaa aaaaaa       2876
```

<210> SEQ ID NO 2
<211> LENGTH: 700
<212> TYPE: PRT
<213> ORGANISM: Mus musculus

<400> SEQUENCE: 2

```
Met Leu Ala Ser Ala Leu Leu Val Phe Leu Cys Cys Phe Lys Gly His
1               5                   10                  15

Ala Gly Ser Ser Pro His Phe Leu Gln Gln Pro Glu Asp Met Val Val
            20                  25                  30

Leu Leu Gly Glu Glu Ala Arg Leu Pro Cys Ala Leu Gly Ala Tyr Arg
        35                  40                  45

Gly Leu Val Gln Trp Thr Lys Asp Gly Leu Ala Leu Gly Gly Glu Arg
    50                  55                  60

Asp Leu Pro Gly Trp Ser Arg Tyr Trp Ile Ser Gly Asn Ser Ala Ser
65                  70                  75                  80
```

-continued

```
Gly Gln His Asp Leu His Ile Lys Pro Val Glu Leu Glu Asp Glu Ala
                85                  90                  95

Ser Tyr Glu Cys Gln Ala Ser Gln Ala Gly Leu Arg Ser Arg Pro Ala
            100                 105                 110

Gln Leu His Val Met Val Pro Pro Glu Ala Pro Gln Val Leu Gly Gly
        115                 120                 125

Pro Ser Val Ser Leu Val Ala Gly Val Pro Gly Asn Leu Thr Cys Arg
    130                 135                 140

Ser Arg Gly Asp Ser Arg Pro Ala Pro Glu Leu Leu Trp Phe Arg Asp
145                 150                 155                 160

Gly Ile Arg Leu Asp Ala Ser Ser Phe His Gln Thr Thr Leu Lys Asp
                165                 170                 175

Lys Ala Thr Gly Thr Val Glu Asn Thr Leu Phe Leu Thr Pro Ser Ser
            180                 185                 190

His Asp Asp Gly Ala Thr Leu Ile Cys Arg Ala Arg Ser Gln Ala Leu
        195                 200                 205

Pro Thr Gly Arg Asp Thr Ala Val Thr Leu Ser Leu Gln Tyr Pro Pro
    210                 215                 220

Met Val Thr Leu Ser Ala Glu Pro Gln Thr Val Gln Glu Gly Glu Lys
225                 230                 235                 240

Val Thr Phe Leu Cys Gln Ala Thr Ala Gln Pro Pro Val Thr Gly Tyr
                245                 250                 255

Arg Trp Ala Lys Gly Gly Ser Pro Val Leu Gly Ala Arg Gly Pro Arg
            260                 265                 270

Leu Glu Val Val Ala Asp Ala Thr Phe Leu Thr Glu Pro Val Ser Cys
        275                 280                 285

Glu Val Ser Asn Ala Val Gly Ser Ala Asn Arg Ser Thr Ala Leu Glu
    290                 295                 300

Val Leu Tyr Gly Pro Ile Leu Gln Ala Lys Pro Lys Ser Val Ser Val
305                 310                 315                 320

Asp Val Gly Lys Asp Ala Ser Phe Ser Cys Val Trp Arg Gly Asn Pro
                325                 330                 335

Leu Pro Arg Ile Thr Trp Thr Arg Met Gly Gly Ser Gln Val Leu Ser
            340                 345                 350

Ser Gly Pro Thr Leu Arg Leu Pro Ser Val Ala Leu Glu Asp Ala Gly
        355                 360                 365

Asp Tyr Val Cys Arg Ala Glu Pro Arg Arg Thr Gly Leu Gly Gly Gly
    370                 375                 380

Lys Ala Gln Ala Arg Leu Thr Val Asn Ala Pro Pro Val Val Thr Ala
385                 390                 395                 400

Leu Gln Pro Ala Pro Ala Phe Leu Arg Gly Pro Ala Arg Leu Gln Cys
                405                 410                 415

Val Val Phe Ala Ser Pro Ala Pro Asp Ser Val Val Trp Ser Trp Asp
            420                 425                 430

Glu Gly Phe Leu Glu Ala Gly Ser Leu Gly Arg Phe Leu Val Glu Ala
        435                 440                 445

Phe Pro Ala Pro Glu Val Glu Gly Gly Gln Gly Pro Gly Leu Ile Ser
    450                 455                 460

Val Leu His Ile Ser Gly Thr Gln Glu Ser Asp Phe Thr Thr Gly Phe
465                 470                 475                 480

Asn Cys Ser Ala Arg Asn Arg Leu Gly Glu Gly Arg Val Gln Ile His
                485                 490                 495

Leu Gly Arg Arg Asp Leu Leu Pro Thr Val Arg Ile Val Ala Gly Ala
            500                 505                 510
```

-continued

```
Ala Ser Ala Ala Thr Ser Leu Leu Met Val Ile Thr Gly Val Val Leu
        515                 520                 525

Cys Cys Trp Arg His Gly Ser Leu Ser Lys Gln Lys Asn Leu Val Arg
    530                 535                 540

Ile Pro Gly Ser Ser Glu Gly Ser Ser Ser Arg Gly Pro Glu Glu Glu
545                 550                 555                 560

Thr Gly Ser Ser Glu Asp Arg Gly Pro Ile Val His Thr Asp His Ser
                565                 570                 575

Asp Leu Val Leu Glu Glu Lys Glu Ala Leu Glu Thr Lys Asp Pro Thr
            580                 585                 590

Asn Gly Tyr Tyr Lys Val Arg Gly Val Ser Val Ser Leu Ser Leu Gly
        595                 600                 605

Glu Ala Pro Gly Gly Gly Leu Phe Leu Pro Pro Pro Ser Pro Ile Gly
    610                 615                 620

Leu Pro Gly Thr Pro Thr Tyr Tyr Asp Phe Lys Pro His Leu Asp Leu
625                 630                 635                 640

Val Pro Pro Cys Arg Leu Tyr Arg Ala Arg Ala Gly Tyr Leu Thr Thr
                645                 650                 655

Pro His Pro Arg Ala Phe Thr Ser Tyr Met Lys Pro Thr Ser Phe Gly
            660                 665                 670

Pro Pro Asp Leu Ser Ser Gly Thr Pro Pro Phe Pro Tyr Ala Thr Leu
        675                 680                 685

Ser Pro Pro Ser His Gln Arg Leu Gln Thr His Val
    690                 695                 700


<210> SEQ ID NO 3
<211> LENGTH: 2243
<212> TYPE: DNA
<213> ORGANISM: Mus musculus

<400> SEQUENCE: 3

gagagaattg tgtgcagaga gaggctccag tccagcgtgg tgtgagaggc gtgctatcaa      60

gaaagaagtt ggaggggaac cagtgcaacc ctaactctac gagatcttgg ggtacacaca     120

ctcgggatgc tggcctccgc cctcctcgtt ttcctttgct gtttcaaagg acatgcaggg     180

tggtcccggt actggatatc ggggaattca gccagtggcc agcatgacct ccacattaag     240

cctgtggaat tggaagatga ggcatcgtat gagtgccagg cttcgcaagc aggtctccga     300

tcacgaccag cccaactgca cgtgatggtc cccccagaag ctccccaggt actaggcggc     360

ccctctgtgt ctctggttgc tggagttcct ggaaatctga cctgtcggag tcgtggggat     420

tcccgacctg cccctgaact actgtggttc cgagatggga tccggctgga tgcgagcagc     480

ttccaccaga ccacgctgaa ggacaaggcc actggaacag tggaaaacac cttattcctg     540

accccttcca gtcatgatga tggcgccacc ttgatctgca gagcgcgaag ccaggccctg     600

cccacaggga gggacacagc tgttacactg agccttcagt atcccccaat ggtgactctg     660

tctgctgagc cccagactgt gcaggaggga gagaaggtga ctttcctgtg tcaagccact     720

gcccagcctc ctgtcactgg ctacaggtgg gcgaaggggg gatccccggt gctcggggca     780

cgtgggccaa ggttggaggt cgttgcagat gccactttcc tgactgagcc ggtgtcctgc     840

gaggtcagca acgcggtcgg aagcgccaac cgcagcacgg cgctggaagt gttgtatgga     900

cccattctgc aggcaaaacc taagtccgtg tccgtggacg tggggaaaga tgcctccttc     960

agctgtgtct ggcgcgggaa cccacttcca cggataacct ggacccgcat gggtggctct    1020

caggtgctga gctccgggcc cacgctgcgg cttccgtccg tggcactgga ggatgcgggc    1080
```

```
gactatgtat gcagggctga gccgaggaga acgggtctgg gaggcggcaa agcgcaggcg   1140

aggctgactg tgaacgcacc ccctgtagtg acagccctgc aacctgcacc agcctttctg   1200

aggggtcctg ctcgcctcca gtgtgtggtg tttgcctccc ctgccccaga ctcggtggtt   1260

tggtcttggg acgagggctt cttggaggca ggctcactgg gcaggttcct agtggaagcc   1320

ttcccagccc cggaagtgga ggggggacag ggccctggcc ttatttctgt gctacacatt   1380

tccggaaccc aggagtccga ctttaccacc ggcttcaact gcagtgcccg caaccggcta   1440

ggagagggac gagtccagat ccacttgggc cgtagagatt tgctgcctac tgtccggatt   1500

gtggctggtg cagcatctgc agccacctct ctccttatgg tcatcactgg agtggtcctc   1560

tgctgctggc gccatggctc tctctctaag caaaagaact tggtccggat cccaggaagc   1620

agcgagggtt ccagttcacg tggccctgag gaggagacag gcagcagtga ggaccggggt   1680

cccattgtgc acaccgacca cagtgatttg gttcttgagg aaaaagaggc tctggagaca   1740

aaggatccaa ccaacggtta ctacaaggtt cgaggggtca gtgtgagcct tagccttggg   1800

gaagctcctg gaggaggcct cttcttgcca ccgccctctc cgatcggtct cccagggact   1860

cctacttact atgacttcaa gccacatcag gacttagtcc ctccctgcag actgtacaga   1920

gcgagggcag gttatcttac cacccccat ccccgtgcct tcaccagcta catgaaaccc   1980

acatcctttg gacccccaga tttgagctct ggaactcccc ccttcccgta tgctaccttg   2040

tctccaccca gccaccagcg tctccagact catgtgtgaa tccatctctc caagtgaagg   2100

gtcttggaat cttctgtttg ccatatagtg tgttgtccag atttctgggg agtcagaaca   2160

agttgatgac caacccctcc aaaactgaac attgaaggag ggaaagatca ttacaagcat   2220

caggactgtt ggtgtacact cag                                           2243
```

<210> SEQ ID NO 4
<211> LENGTH: 650
<212> TYPE: PRT
<213> ORGANISM: Mus musculus

<400> SEQUENCE: 4

```
Met Leu Ala Ser Ala Leu Leu Val Phe Leu Cys Cys Phe Lys Gly His
1               5                   10                  15

Ala Gly Trp Ser Arg Tyr Trp Ile Ser Gly Asn Ser Ala Ser Gly Gln
            20                  25                  30

His Asp Leu His Ile Lys Pro Val Glu Leu Glu Asp Glu Ala Ser Tyr
        35                  40                  45

Glu Cys Gln Ala Ser Gln Ala Gly Leu Arg Ser Arg Pro Ala Gln Leu
    50                  55                  60

His Val Met Val Pro Pro Glu Ala Pro Gln Val Leu Gly Gly Pro Ser
65                  70                  75                  80

Val Ser Leu Val Ala Gly Val Pro Gly Asn Leu Thr Cys Arg Ser Arg
                85                  90                  95

Gly Asp Ser Arg Pro Ala Pro Glu Leu Leu Trp Phe Arg Asp Gly Ile
            100                 105                 110

Arg Leu Asp Ala Ser Ser Phe His Gln Thr Thr Leu Lys Asp Lys Ala
        115                 120                 125

Thr Gly Thr Val Glu Asn Thr Leu Phe Leu Thr Pro Ser Ser His Asp
    130                 135                 140

Asp Gly Ala Thr Leu Ile Cys Arg Ala Arg Ser Gln Ala Leu Pro Thr
145                 150                 155                 160

Gly Arg Asp Thr Ala Val Thr Leu Ser Leu Gln Tyr Pro Pro Met Val
```

-continued

```
                165                 170                 175

Thr Leu Ser Ala Glu Pro Gln Thr Val Gln Glu Gly Glu Lys Val Thr
            180                 185                 190

Phe Leu Cys Gln Ala Thr Ala Gln Pro Pro Val Thr Gly Tyr Arg Trp
        195                 200                 205

Ala Lys Gly Gly Ser Pro Val Leu Gly Ala Arg Gly Pro Arg Leu Glu
    210                 215                 220

Val Val Ala Asp Ala Thr Phe Leu Thr Glu Pro Val Ser Cys Glu Val
225                 230                 235                 240

Ser Asn Ala Val Gly Ser Ala Asn Arg Ser Thr Ala Leu Glu Val Leu
                245                 250                 255

Tyr Gly Pro Ile Leu Gln Ala Lys Pro Lys Ser Val Ser Val Asp Val
            260                 265                 270

Gly Lys Asp Ala Ser Phe Ser Cys Val Trp Arg Gly Asn Pro Leu Pro
        275                 280                 285

Arg Ile Thr Trp Thr Arg Met Gly Gly Ser Gln Val Leu Ser Ser Gly
    290                 295                 300

Pro Thr Leu Arg Leu Pro Ser Val Ala Leu Glu Asp Ala Gly Asp Tyr
305                 310                 315                 320

Val Cys Arg Ala Glu Pro Arg Arg Thr Gly Leu Gly Gly Gly Lys Ala
                325                 330                 335

Gln Ala Arg Leu Thr Val Asn Ala Pro Pro Val Val Thr Ala Leu Gln
            340                 345                 350

Pro Ala Pro Ala Phe Leu Arg Gly Pro Ala Arg Leu Gln Cys Val Val
        355                 360                 365

Phe Ala Ser Pro Ala Pro Asp Ser Val Val Trp Ser Trp Asp Glu Gly
    370                 375                 380

Phe Leu Glu Ala Gly Ser Leu Gly Arg Phe Leu Val Glu Ala Phe Pro
385                 390                 395                 400

Ala Pro Glu Val Glu Gly Gly Gln Gly Pro Gly Leu Ile Ser Val Leu
                405                 410                 415

His Ile Ser Gly Thr Gln Glu Ser Asp Phe Thr Thr Gly Phe Asn Cys
            420                 425                 430

Ser Ala Arg Asn Arg Leu Gly Glu Gly Arg Val Gln Ile His Leu Gly
        435                 440                 445

Arg Arg Asp Leu Leu Pro Thr Val Arg Ile Val Ala Gly Ala Ala Ser
    450                 455                 460

Ala Ala Thr Ser Leu Leu Met Val Ile Thr Gly Val Val Leu Cys Cys
465                 470                 475                 480

Trp Arg His Gly Ser Leu Ser Lys Gln Lys Asn Leu Val Arg Ile Pro
                485                 490                 495

Gly Ser Ser Glu Gly Ser Ser Ser Arg Gly Pro Glu Glu Glu Thr Gly
            500                 505                 510

Ser Ser Glu Asp Arg Gly Pro Ile Val His Thr Asp His Ser Asp Leu
        515                 520                 525

Val Leu Glu Glu Lys Glu Ala Leu Glu Thr Lys Asp Pro Thr Asn Gly
    530                 535                 540

Tyr Tyr Lys Val Arg Gly Val Ser Val Ser Leu Ser Leu Gly Glu Ala
545                 550                 555                 560

Pro Gly Gly Gly Leu Phe Leu Pro Pro Pro Ser Pro Ile Gly Leu Pro
                565                 570                 575

Gly Thr Pro Thr Tyr Tyr Asp Phe Lys Pro His Gln Asp Leu Val Pro
            580                 585                 590
```

-continued

```
Pro Cys Arg Leu Tyr Arg Ala Arg Ala Gly Tyr Leu Thr Thr Pro His
        595                 600                 605

Pro Arg Ala Phe Thr Ser Tyr Met Lys Pro Thr Ser Phe Gly Pro Pro
    610                 615                 620

Asp Leu Ser Ser Gly Thr Pro Pro Phe Pro Tyr Ala Thr Leu Ser Pro
625                 630                 635                 640

Pro Ser His Gln Arg Leu Gln Thr His Val
                645                 650


<210> SEQ ID NO 5
<211> LENGTH: 864
<212> TYPE: DNA
<213> ORGANISM: Mus musculus

<400> SEQUENCE: 5

gaggccgaga tgacttccaa ggaggacggc aaggcggcgc caggggagga gcggcgacgc      60

agccctctgg accacctgcc gccgcccgcc aactccaaca agccgctgac gccgttcagc     120

atcgaggaca tcctcaacaa gccgtccgtg cggagaagtt actcgctgtg tggggcggcg     180

cacctgctgg cggccgcgga caagcacgcg ccgggcggct tgcccctggc gggccgcgct     240

ctgctctcgc agacctcgcc tctctgcgcc ttggaggagc tcgccagcaa gacctttaag     300

gggctggagg tcagcgtcct gcaggcagcc gaaggccgcg atgggatgac catctttggg     360

cagaggcaga cgcccaagaa acggcgaaaa tcacgcacgg ccttcaccaa ccaccagatc     420

tacgagttgg agaaacgctt tctataccag aagtacctgt ccccggcaga tcgcgaccaa     480

attgcgcagc agctgggcct caccaatgca caggtcatca cctggttcca gaaccggcgc     540

gccaagctca agcgggacct agaggagatg aaggccgacg tggagtctgc caagaaactg     600

ggccccagcg ggcagatgga catcgtggcg ctggccgaac tcgagcagaa ctcggaggct     660

tcgggcggtg gcggcggcgg tggctgcggc agggctaagt ctaggccggg ttctcctgcg     720

ctgcccccag gcgccccgca ggccccgggc ggaggaccct tgcagctctc gcccgcctct     780

ccactcacgg accagcgggc cagcagccag gactgctcag aggatgagga agatgaagag     840

atcgacgtgg acgattgagc tgtg                                            864


<210> SEQ ID NO 6
<211> LENGTH: 282
<212> TYPE: PRT
<213> ORGANISM: Mus musculus

<400> SEQUENCE: 6

Met Thr Ser Lys Glu Asp Gly Lys Ala Ala Pro Gly Glu Glu Arg Arg
1               5                   10                  15

Arg Ser Pro Leu Asp His Leu Pro Pro Pro Ala Asn Ser Asn Lys Pro
            20                  25                  30

Leu Thr Pro Phe Ser Ile Glu Asp Ile Leu Asn Lys Pro Ser Val Arg
        35                  40                  45

Arg Ser Tyr Ser Leu Cys Gly Ala Ala His Leu Leu Ala Ala Ala Asp
    50                  55                  60

Lys His Ala Pro Gly Gly Leu Pro Leu Ala Gly Arg Ala Leu Leu Ser
65                  70                  75                  80

Gln Thr Ser Pro Leu Cys Ala Leu Glu Glu Leu Ala Ser Lys Thr Phe
                85                  90                  95

Lys Gly Leu Glu Val Ser Val Leu Gln Ala Ala Glu Gly Arg Asp Gly
            100                 105                 110

Met Thr Ile Phe Gly Gln Arg Gln Thr Pro Lys Lys Arg Arg Lys Ser
```

-continued

```
        115                 120                 125

Arg Thr Ala Phe Thr Asn His Gln Ile Tyr Glu Leu Glu Lys Arg Phe
    130                 135                 140

Leu Tyr Gln Lys Tyr Leu Ser Pro Ala Asp Arg Asp Gln Ile Ala Gln
145                 150                 155                 160

Gln Leu Gly Leu Thr Asn Ala Gln Val Ile Thr Trp Phe Gln Asn Arg
                165                 170                 175

Arg Ala Lys Leu Lys Arg Asp Leu Glu Glu Met Lys Ala Asp Val Glu
            180                 185                 190

Ser Ala Lys Lys Leu Gly Pro Ser Gly Gln Met Asp Ile Val Ala Leu
        195                 200                 205

Ala Glu Leu Glu Gln Asn Ser Glu Ala Ser Gly Gly Gly Gly Gly Gly
    210                 215                 220

Gly Cys Gly Arg Ala Lys Ser Arg Pro Gly Ser Pro Ala Leu Pro Pro
225                 230                 235                 240

Gly Ala Pro Gln Ala Pro Gly Gly Gly Pro Leu Gln Leu Ser Pro Ala
                245                 250                 255

Ser Pro Leu Thr Asp Gln Arg Ala Ser Ser Gln Asp Cys Ser Glu Asp
            260                 265                 270

Glu Glu Asp Glu Glu Ile Asp Val Asp Asp
        275                 280
```

<210> SEQ ID NO 7
<211> LENGTH: 1305
<212> TYPE: DNA
<213> ORGANISM: Homo sapiens

<400> SEQUENCE: 7

```
ggggccccgc gccggcccgc gccctgccca gtgcggcctc cttccacccg ccgctgcctg     60

gcccgcgccg tccggccgag ctgcccggcg ggctggtccc cgcgcccgag ccgcccggcc    120

gggaccccga acaaggccga gatgacttcc aaggaggacg gcaaggcggc gccgggggag    180

gagcggcgcc gcagcccgct ggaccacctg cctccgcctg ccaactccaa caagccagac    240

gccgttcagc atcgaggaca tcctcaacaa gccgtctgtg cggagaagtt actcgctgcg    300

tggggcggcg cacctgctgg ccgccgcgga caagcacgcg cagggcggct tgccctggcg    360

ggccgcgcgc tgctctcgaa gacctcgccg ctgtgcgcgc tggaggagct cgccagcaag    420

acgtttaagg ggctggaggt cagcgttctg caggcagccg aaggccgcga cggtatgacc    480

atctttgggc agcggcagac ccctaagaag cggcgaaagt cgcgcacggc cttcaccaac    540

caccagatct atgaattgga aaagcgcttt ctataccaga agtacctgtc cccgccgat    600

cgcgaccaaa tcgcgcagca gctgggcctc accaacgcgc aagtcatcac ctggttccag    660

aatcggcgcg ctaagctcaa gcgggaactg gaggagatga aggccgacgt ggagtccccc    720

aagaaactgg gccccagcgg gcagatggac atcgtggcgc tggccgaact cgagcagaac    780

tcggaggcca cagccggcgg tggcggcggc tgcggcaggg ccaagtcgag gcccggctct    840

ccggtcctcc ccccaggcgc cccgaaggcc cccgggcgct gcgccctgca gctctcgcct    900

gcctctccgc tcacggacca gccggccagc agccaggact gctcggagga cgaggaagac    960

gaagagatcg acgtggacga ttgagcggcg ccccgggtct tccgccgccc tgggctccta   1020

gcgctcgaaa gcccaacgcc tcccggaccg gaccgccgag gggagctggg acctcctctg   1080

ccactcccgc ctcctcccct gtccccggac tcggctcctg gcagccgcct cttccctctc   1140

gaagcaataa acccaggctg gccggccggg ccggccgcca ccagcggcct ccgccgcccc   1200
```

-continued

```
ggaagccctc gccgagcaat tctgtatggc ttctatataa atatttaaac ctatatagcg   1260

ggttctcccc aaaaaaaaaa aaaaaaaaaa aaaaaaaaaa aaaaa                   1305


<210> SEQ ID NO 8
<211> LENGTH: 280
<212> TYPE: PRT
<213> ORGANISM: Homo sapiens

<400> SEQUENCE: 8

Met Thr Ser Lys Glu Asp Gly Lys Ala Ala Pro Gly Glu Glu Arg Arg
1               5                   10                  15

Arg Ser Pro Leu Asp His Leu Pro Pro Pro Ala Asn Ser Asn Lys Pro
            20                  25                  30

Asp Ala Val Gln His Arg Gly His Pro Gln Gln Ala Val Cys Ala Glu
        35                  40                  45

Lys Leu Leu Ala Ala Trp Gly Gly Ala Pro Ala Gly Arg Arg Gly Gln
    50                  55                  60

Ala Arg Ala Gly Arg Leu Ala Leu Ala Gly Arg Ala Leu Leu Ser Lys
65                  70                  75                  80

Thr Ser Pro Leu Cys Ala Leu Glu Glu Leu Ala Ser Lys Thr Phe Lys
                85                  90                  95

Gly Leu Glu Val Ser Val Leu Gln Ala Ala Glu Gly Arg Asp Gly Met
            100                 105                 110

Thr Ile Phe Gly Gln Arg Gln Thr Pro Lys Lys Arg Arg Lys Ser Arg
        115                 120                 125

Thr Ala Phe Thr Asn His Gln Ile Tyr Glu Leu Glu Lys Arg Phe Leu
    130                 135                 140

Tyr Gln Lys Tyr Leu Ser Pro Ala Asp Arg Asp Gln Ile Ala Gln Gln
145                 150                 155                 160

Leu Gly Leu Thr Asn Ala Gln Val Ile Thr Trp Phe Gln Asn Arg Arg
                165                 170                 175

Ala Lys Leu Lys Arg Glu Leu Glu Glu Met Lys Ala Asp Val Glu Ser
            180                 185                 190

Pro Lys Lys Leu Gly Pro Ser Gly Gln Met Asp Ile Val Ala Leu Ala
        195                 200                 205

Glu Leu Glu Gln Asn Ser Glu Ala Thr Ala Gly Gly Gly Gly Gly Cys
    210                 215                 220

Gly Arg Ala Lys Ser Arg Pro Gly Ser Pro Val Leu Pro Pro Gly Ala
225                 230                 235                 240

Pro Lys Ala Pro Gly Arg Cys Ala Leu Gln Leu Ser Pro Ala Ser Pro
                245                 250                 255

Leu Thr Asp Gln Pro Ala Ser Ser Gln Asp Cys Ser Glu Asp Glu Glu
            260                 265                 270

Asp Glu Glu Ile Asp Val Asp Asp
        275                 280


<210> SEQ ID NO 9
<211> LENGTH: 1248
<212> TYPE: DNA
<213> ORGANISM: Mus musculus

<400> SEQUENCE: 9

atggatatgc actgcaaagc agaccccttc tccgcgatgc accggcacgg gggtgtgaac     60

cagctcgggg gggtgtttgt gaacggccgg cccctacccg acgtggtgag gcagcgcatc    120

gtggagctgg cccaccaggg tgtgcggccc tgtgacatct cccggcagct gcgggtcagc    180
```

```
catggctgtg tcagcaaaat cctgggcagg tactacgaga ctggcagcat caagcccgga    240

gtgattggtg gctccaagcc caaggtggca acgcccaaag tggtggacaa gattgccgaa    300

tacaagcgac agaacccgac tatgttcgcc tgggagatcc gtgcacagct gctacgcgag    360

ggcatctgcg ataatgacac agttcccagt gtctcatcca tcaacaggat catccggacc    420

aaagttcagc agcctttcca cccaacgccg gatggggcag ggacaggagt gactgccccc    480

ggccacacca tcgttcccag cacggcctcc cctcctgttt ccagcgcctc taacgaccca    540

gtgggatcct actccatcaa cggatcctg gggattcctc gctccaacgg tgagaagagg    600

aaacgcgagg aagtcgaggt atacactgat cctgcccaca ttagaggagg tggaggttta    660

catctggtct ggactttaag agatgtgtct gagggctctg tccctaatgg agactcccag    720

agtggtgtgg acagtttgcg gaagcacctg cgagccgaca ccttcaccca gcagcagctg    780

gaagctctgg atcgagtctt tgagcgtcct tcctatcccg atgtcttcca ggcatcagag    840

cacatcaaat cagaacaggg gaatgaatac tctctcccag ccctgacccc tgggcttgat    900

gaagtcaagt ccagtctatc tgcatcggcc aaccctgagc tgggcagcaa tgtgtcaggc    960

acacagacgt accccgttgt gaccggtcgt gatatgacga gcaccactct acctggttac   1020

cccccgcatt tgccccccac tggccaggga agctaccta cctccaccct ggcaggaatg   1080

gtgcctggga gcgagttctc aggcaaccca tacagccatc cccagtacac cgcctacaat   1140

gaggcttgga gattcagcaa ccccgcctta ctaagttccc cttattatta tagtgccgcc   1200

ccccggtccg cccctgccgc tcgtgccgct gcctatgacc gccactag               1248
```

<210> SEQ ID NO 10
<211> LENGTH: 415
<212> TYPE: PRT
<213> ORGANISM: Mus musculus

<400> SEQUENCE: 10

```
Met Asp Met His Cys Lys Ala Asp Pro Phe Ser Ala Met His Arg His
1               5                   10                  15

Gly Gly Val Asn Gln Leu Gly Gly Val Phe Val Asn Gly Arg Pro Leu
            20                  25                  30

Pro Asp Val Val Arg Gln Arg Ile Val Glu Leu Ala His Gln Gly Val
        35                  40                  45

Arg Pro Cys Asp Ile Ser Arg Gln Leu Arg Val Ser His Gly Cys Val
    50                  55                  60

Ser Lys Ile Leu Gly Arg Tyr Tyr Glu Thr Gly Ser Ile Lys Pro Gly
65                  70                  75                  80

Val Ile Gly Gly Ser Lys Pro Lys Val Ala Thr Pro Lys Val Val Asp
                85                  90                  95

Lys Ile Ala Glu Tyr Lys Arg Gln Asn Pro Thr Met Phe Ala Trp Glu
            100                 105                 110

Ile Arg Ala Gln Leu Leu Arg Glu Gly Ile Cys Asp Asn Asp Thr Val
        115                 120                 125

Pro Ser Val Ser Ser Ile Asn Arg Ile Ile Arg Thr Lys Val Gln Gln
    130                 135                 140

Pro Phe His Pro Thr Pro Asp Gly Ala Gly Thr Gly Val Thr Ala Pro
145                 150                 155                 160

Gly His Thr Ile Val Pro Ser Thr Ala Ser Pro Pro Val Ser Ser Ala
                165                 170                 175

Ser Asn Asp Pro Val Gly Ser Tyr Ser Ile Asn Gly Ile Leu Gly Ile
            180                 185                 190
```

```
Pro Arg Ser Asn Gly Glu Lys Arg Lys Arg Glu Glu Val Glu Val Tyr
        195                 200                 205

Thr Asp Pro Ala His Ile Arg Gly Gly Gly Gly Leu His Leu Val Trp
    210                 215                 220

Thr Leu Arg Asp Val Ser Glu Gly Ser Val Pro Asn Gly Asp Ser Gln
225                 230                 235                 240

Ser Gly Val Asp Ser Leu Arg Lys His Leu Arg Ala Asp Thr Phe Thr
                245                 250                 255

Gln Gln Gln Leu Glu Ala Leu Asp Arg Val Phe Glu Arg Pro Ser Tyr
            260                 265                 270

Pro Asp Val Phe Gln Ala Ser Glu His Ile Lys Ser Glu Gln Gly Asn
        275                 280                 285

Glu Tyr Ser Leu Pro Ala Leu Thr Pro Gly Leu Asp Glu Val Lys Ser
    290                 295                 300

Ser Leu Ser Ala Ser Ala Asn Pro Glu Leu Gly Ser Asn Val Ser Gly
305                 310                 315                 320

Thr Gln Thr Tyr Pro Val Val Thr Gly Arg Asp Met Thr Ser Thr Thr
                325                 330                 335

Leu Pro Gly Tyr Pro Pro His Leu Pro Pro Thr Gly Gln Gly Ser Tyr
            340                 345                 350

Pro Thr Ser Thr Leu Ala Gly Met Val Pro Gly Ser Glu Phe Ser Gly
        355                 360                 365

Asn Pro Tyr Ser His Pro Gln Tyr Thr Ala Tyr Asn Glu Ala Trp Arg
    370                 375                 380

Phe Ser Asn Pro Ala Leu Leu Ser Ser Pro Tyr Tyr Tyr Ser Ala Ala
385                 390                 395                 400

Pro Arg Ser Ala Pro Ala Ala Arg Ala Ala Ala Tyr Asp Arg His
                405                 410                 415


<210> SEQ ID NO 11
<211> LENGTH: 3421
<212> TYPE: DNA
<213> ORGANISM: Homo sapiens

<400> SEQUENCE: 11

cgggggcctg gccgcgcgct cccctcccgc aggcgccacc tcggacatcc ccgggattgc      60

tacttctctg ccaacttcgc caactcgcca gcacttggag aggcccggct cccctcccgg     120

cgccctctga ccgcccccgc cccgcggcgc tctccgacca ccgcctctcg gatgaccagg     180

ttccagggga gctgagcgag tcgcctcccc cgcccagctt cagccctggc tgcagctgca     240

gcgcgagcca tgcgccccca gtgcaccccg gcccaccgcc ccggggccat tctgctgacc     300

gcccagcccc gagccccgac agtggcaagt tgcggctact gcagttgcaa gctccggcca     360

acccggagga gccccacggg gaaggcagtc gtgcgccccc cgcccccggg cgccccgcag     420

cagccgggcg ttcactcatc ctccctcccc caccgtccct cccttttctc ctcaagtcct     480

gaagttgagt ttgagaggcg acacggcggc ggcgccgcgc tgctcccgct cctctgcctc     540

cccatggata tgcactgcaa agcagacccc ttctccgcga tgcacccagg gcacgggggt     600

gtgaaccagc tcgggggggt gtttgtgaac ggccggcccc tacccgacgt ggtgaggcag     660

cgcatcgtgg agctggccca ccagggtgtg cggccctgtg acatctcccg gcagctgcgg     720

gtcagccacg gctgtgtcag caaaatcctg ggcaggtact acgagaccgg cagcatcaag     780

ccgggtgtga tcggtggctc caagcccaaa gtggcgacgc ccaaagtggt ggacaagatt     840

gctgaataca aacgacagaa cccgactatg ttcgcctggg agattcgaga ccggctcctg     900
```

-continued

```
gccgagggca tctgtgacaa tgacacagtg cccagcgtct cttccatcaa cagaatcatc    960
cggaccaaag ttcagcagcc tttccaccca acgccggatg ggctgggac aggagtgacc   1020
gcccctggcc acaccattgt tcccagcacg gcctcccctc ctgtttccag cgcctccaat   1080
gacccagtgg gatcctactc catcaatggg atcctgggga ttcctcgctc caatggtgag   1140
aagaggaaac gtgatgaaga tgtgtctgag ggctcagtcc ccaatggaga ttcccagagt   1200
ggtgtggaca gtttgcggaa gcacttgcga gctgacacct tcacccagca gcagctggaa   1260
gctttggatc gggtctttga gcgtccttcc taccctgacg tcttccaggc atcagagcac   1320
atcaaatcag aacaggggaa cgagtactcc ctcccagccc tgacccctgg gcttgatgaa   1380
gtcaagtcga gtctatctgc atccaccaac cctgagctgg gcagcaacgt gtcaggcaca   1440
cagacatacc ccgttgtgac tggtcgtgac atggcgagca ccactctgcc tggttacccc   1500
cctcacgtgc cccccactgg ccagggaagc taccccacct ccaccctggc aggaatggtg   1560
cctgggagcg agttctccgg caacccgtac agccaccccc agtacacggc ctacaacgag   1620
gcttggagat tcagcaaccc cgccttacta agttcccctt attattatag tgccgccccc   1680
cggtccgccc ctgccgctcg tgccgctgcc tatgaccgcc actagttacc gcggggacca   1740
catcaagctt caggccgaca gcttcggcct ccacatcgtc cccgtctgac cccaccccgg   1800
aggagggagg accgacgcga cgcatgcctc ccggccaccg ccccagcctc accccatccc   1860
acgacccccg caacccttca catcaccccc ctcgaaggtc ggacaggacg ggtggagccg   1920
cggggcggga ccctcaggcc cgggcccacc gcccccagcc ccgcctgccg cccctccccg   1980
cctgcctgga ctgcgcggcg ccgtgagggg gattcggccc agctcgtccc ggcctccacc   2040
aagccagccc cgaagcccgc cagccaccct gccgtactcg ggcgcgacct gctggtgcgc   2100
gccggatgtt tctgtgacac acaatcagcg cggaccgcag cgcggcccag ccccgggcac   2160
ccgcctcgga cgctcgggcg ccaggagctt cgctggaggg gctgggccaa ggagattaag   2220
aagaaaacga ctttctgcag gaggaagagc ccgctgccga atccctggga aaaattcttt   2280
tcccccagtg ccagccggac tgccctcgcc ttccgggtgt gccctgtccc agaagatgga   2340
atgggggtgt gggggtccgg ctctaggaac gggctttggg ggcgtcaggt ctttccaagg   2400
ttgggaccca aggatcgggg ggcccagcag cccgcaccga tcgagccgga ctctcggctc   2460
ttcactgctc ctcctggcct gcctagttcc ccagggcccg gcacctcctg ctgcgagacc   2520
cggctctcag ccctgccttg cccctacctc agcgtctctt ccacctgctg gcctcccagt   2580
ttcccctcct gccagtcctt cgcctgtccc ttgacgccct gcatcctcct ccctgactcg   2640
cagccccatc ggacgctctc ccgggaccgc cgcaggacca gtttccatag actgcggact   2700
ggggtcttcc tccagcagtt acttgatgcc ccctcccccg acacagactc tcaatctgcc   2760
ggtggtaaga accggttctg agctggcgtc tgagctgctg cggggtggaa gtggggggct   2820
gcccactcca ctcctcccat cccctcccag cctcctcctc cggcaggaac tgaacagaac   2880
cacaaaaagt ctacatttat ttaatatgat ggtctttgca aaaaggaaca aaacaacaca   2940
aaagcccacc aggctgctgc tttgtggaaa gacggtgtgt gtcgtgtgaa ggcgaaaccc   3000
ggtgtacata accccctccc ctccgccccg ccccgcccgg ccccgtagag tccctgtcgc   3060
ccgccggccc tgcctgtaga tacgccccgc tgtctgtgct gtgagagtcg ccgctcgctg   3120
ggggggaagg gggggacaca gctacacgcc cattaaagca cagcacgtcc tgggggaggg   3180
gggcattttt tatgttacaa aaaaaaatta cgaagaaaga atctcatttg caaaatagcg   3240
aacatggtct gtgactcctc tggcctgttt gttggctctt tctctgtaat tccgtgtttt   3300
```

-continued

```
cgctttttcc tccctgcccc tctctccctc tgcccctctc tcctctccgc ttctctcccc   3360

ctctgtctct gtctctctcc gtctctgtcg ctcttgtctg tctgtctctg ctctttctcg   3420

c                                                                   3421
```

<210> SEQ ID NO 12
<211> LENGTH: 393
<212> TYPE: PRT
<213> ORGANISM: Homo sapiens

<400> SEQUENCE: 12

```
Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
    50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Asp Lys Ile Ala Glu Tyr Lys Arg Gln Asn Pro Thr Met Phe Ala Trp
            100                 105                 110

Glu Ile Arg Asp Arg Leu Leu Ala Glu Gly Ile Cys Asp Asn Asp Thr
        115                 120                 125

Val Pro Ser Val Ser Ser Ile Asn Arg Ile Ile Arg Thr Lys Val Gln
    130                 135                 140

Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Pro Val Ser Ser
                165                 170                 175

Ala Ser Asn Asp Pro Val Gly Ser Tyr Ser Ile Asn Gly Ile Leu Gly
            180                 185                 190

Ile Pro Arg Ser Asn Gly Glu Lys Arg Lys Arg Asp Glu Asp Val Ser
        195                 200                 205

Glu Gly Ser Val Pro Asn Gly Asp Ser Gln Ser Gly Val Asp Ser Leu
    210                 215                 220

Arg Lys His Leu Arg Ala Asp Thr Phe Thr Gln Gln Gln Leu Glu Ala
225                 230                 235                 240

Leu Asp Arg Val Phe Glu Arg Pro Ser Tyr Pro Asp Val Phe Gln Ala
                245                 250                 255

Ser Glu His Ile Lys Ser Glu Gln Gly Asn Glu Tyr Ser Leu Pro Ala
            260                 265                 270

Leu Thr Pro Gly Leu Asp Glu Val Lys Ser Ser Leu Ser Ala Ser Thr
        275                 280                 285

Asn Pro Glu Leu Gly Ser Asn Val Ser Gly Thr Gln Thr Tyr Pro Val
    290                 295                 300

Val Thr Gly Arg Asp Met Ala Ser Thr Thr Leu Pro Gly Tyr Pro Pro
305                 310                 315                 320

His Val Pro Pro Thr Gly Gln Gly Ser Tyr Pro Thr Ser Thr Leu Ala
                325                 330                 335

Gly Met Val Pro Gly Ser Glu Phe Ser Gly Asn Pro Tyr Ser His Pro
            340                 345                 350
```

```
Gln Tyr Thr Ala Tyr Asn Glu Ala Trp Arg Phe Ser Asn Pro Ala Leu
        355                 360                 365

Leu Ser Ser Pro Tyr Tyr Tyr Ser Ala Ala Pro Arg Ser Ala Pro Ala
    370                 375                 380

Ala Arg Ala Ala Ala Tyr Asp Arg His
385                 390


<210> SEQ ID NO 13
<211> LENGTH: 2750
<212> TYPE: DNA
<213> ORGANISM: Mus musculus

<400> SEQUENCE: 13

aacagccagg agcagtgacc gagccgctgg agctggggag agacgcgcgg aagactgggc     60

caggagacta gggaccgagg gacgcgcgcc tggggagagc caacaaggaa cccgcgggcc    120

ggacagcgac accggcaatc cgcgccaaac tgttccagcc gctggccttc tatagccgca    180

gccccaggac attctaaagc tctccaagac gccccctccc ctggcttctc gcgttgacca    240

aggaaaagaa aaagggatgg aaaaagaaag gaaggagact agaaagaaaa cccagatttg    300

ccaccgcaca aaaagagagg tggggggggac aaggaaaaaa aaaaaagtcg agcgactgtg    360

gggccggaac acaggcagcg ggatcgtggg ccgagcgatg caaggctgcg cgcccaagcg    420

gccgcgagtt gtgactgaag ccaggatgct cgtccaggcg cagtgaagag ccagaccgtg    480

ttgcctcccc aggagtccaa gcgcagggag ggccgctcgg aggacgcggc agactgcctg    540

gcaggccacc ggccgaggtg acagggctgg ggcggtgggg agcgagcgag tgcgcccggc    600

tgcgtccgcc cgaagcggac ggtccctttc catttttgac tggcacaaaa aagaaaactc    660

tccaaagggg tgggggctac ctaagcaaca actacaatca acaaaatatc ctacccaacc    720

cgccatctcc cccacacctc ggtctgcccc cgccccctcc ccaggcccag cgcgggcgcc    780

cagagcgtcc caactcactg caagaaaccg gcaatgtagg atccaaagct ttctactccc    840

gtgttctttt ctttccgtgt tttttttaaa ggggaaaacc cggtggtggg cagtctgaca    900

cgcacacaac ctgccttcat actctgacaa aagcagatgc actttgactt ctgacagctc    960

tacctcaagc tggagagaac ccagctttcc cgaatcctga gctcttggcg tcttcctttt   1020

cgtctgtttc cattttattt atttacgtcc cgccgcctct cacggtgacc ttcactcctt   1080

cgcgggcttt gagcagaaga gccgctttct agcccgcttg agactgattt tcctcgcccg   1140

gtgagctgag gtggcgctgc tccatcccgt tgccccggga ctccggggct gccctctacc   1200

agcctggtct ctccccccttt tgatttgcta gtacgggttt tttgcttgcc caactagaga   1260

gggtttcttc tttttggagg agctggttgt cttcagaagt catcccctcg actctaattg   1320

ccctgtcgct ccgggcctca ccggaccaaa ccaaagacca tggtgcactg tgcgggctgc   1380

aaaaggccca tcctggaccg tttcctcttg aacgtgttgg acagggcctg gcacgtcaag   1440

tgcgtccagt gctgtgaatg taaatgcaac ctgaccgaga agtgcttctc ccgggaaggc   1500

aagctctact gtaaaaacga cttcttccga tgtttcggta ccaaatgcgc cggttgtgcg   1560

cagggcatct ctccaagcga tctggttcgc agagcgcgaa gcaaagtgtt tcacctcaac   1620

tgcttcacct gcatgatgtg taacaagcag ctctccaccg gcgaggagct ctacatcata   1680

gacgagaaca agttcgtttg taaagaggat tacctgagta acagcagtgt cgccaaagag   1740

aacagcctcc actcggccac cacaggcagt gaccctagtt tatctccgga ttcccaagat   1800

ccatcgcagg atgatgccaa ggactctgaa agtgccaacg tctcagataa ggaaggtggt   1860

agtaatgaga atgatgatca gaacctaggt gccaaacgta ggggaccccg gaccacgatc   1920
```

```
aaagccaagc aactggagac gttgaaggca gcctttgcag ctacacccaa gcccacacgc   1980

catatccgtg agcaactggc ccaggagact ggcctcaaca tgcgtgttat ccaggtctgg   2040

ttccagaatc gacgctccaa ggagcgaagg atgaaacagc taagcgcgct aggcgcgcgg   2100

cgccacgcct ttttccgcag tcctcgtcgg atgcggccgc tggtggaccg cctggagccg   2160

ggcgaactca tccccaacgg ccccttctcc ttttacggag attaccagag tgagtactac   2220

ggtcccggag gcaactacga cttcttcccg caaggaccgc catcctctca ggctcagacg   2280

ccagtggacc taccctttgt gccatcatct ggcccttcgg ggacgcccct tggaggtctg   2340

gaccacccgc tgcctggtca ccacccttcc agtgaggcgc agcgatttac tgacatcctg   2400

gcacatcccc caggggactc ccctagtcct gagcccagct tgcccgggcc tctccactcc   2460

atgtcagcgg aggtcttcgg gcccagtcca cctttctcat ctctgtcggt caatggtgga   2520

gccagctacg ggaaccattt gtctcaccct cctgaaatga acgaggcagc cgtgtggtag   2580

cggggtctcg catgggccac gggagctcgt ggttgtacag agacgagctt ttatttcaga   2640

aaaatagatt aaaaagacaa aaaaaaaaaa acccccaaaa caaaaaagca agcctcctgc   2700

tccacttcct tcagcctcgg ggaccagtct gtttggggag actggatagc              2750
```

<210> SEQ ID NO 14
<211> LENGTH: 406
<212> TYPE: PRT
<213> ORGANISM: Mus musculus

<400> SEQUENCE: 14

```
Met Val His Cys Ala Gly Cys Lys Arg Pro Ile Leu Asp Arg Phe Leu
1               5                   10                  15

Leu Asn Val Leu Asp Arg Ala Trp His Val Lys Cys Val Gln Cys Cys
            20                  25                  30

Glu Cys Lys Cys Asn Leu Thr Glu Lys Cys Phe Ser Arg Glu Gly Lys
        35                  40                  45

Leu Tyr Cys Lys Asn Asp Phe Phe Arg Cys Phe Gly Thr Lys Cys Ala
    50                  55                  60

Gly Cys Ala Gln Gly Ile Ser Pro Ser Asp Leu Val Arg Arg Ala Arg
65                  70                  75                  80

Ser Lys Val Phe His Leu Asn Cys Phe Thr Cys Met Met Cys Asn Lys
                85                  90                  95

Gln Leu Ser Thr Gly Glu Glu Leu Tyr Ile Ile Asp Glu Asn Lys Phe
            100                 105                 110

Val Cys Lys Glu Asp Tyr Leu Ser Asn Ser Ser Val Ala Lys Glu Asn
        115                 120                 125

Ser Leu His Ser Ala Thr Thr Gly Ser Asp Pro Ser Leu Ser Pro Asp
    130                 135                 140

Ser Gln Asp Pro Ser Gln Asp Asp Ala Lys Asp Ser Glu Ser Ala Asn
145                 150                 155                 160

Val Ser Asp Lys Glu Gly Gly Ser Asn Glu Asn Asp Asp Gln Asn Leu
                165                 170                 175

Gly Ala Lys Arg Arg Gly Pro Arg Thr Thr Ile Lys Ala Lys Gln Leu
            180                 185                 190

Glu Thr Leu Lys Ala Ala Phe Ala Ala Thr Pro Lys Pro Thr Arg His
        195                 200                 205

Ile Arg Glu Gln Leu Ala Gln Glu Thr Gly Leu Asn Met Arg Val Ile
    210                 215                 220

Gln Val Trp Phe Gln Asn Arg Arg Ser Lys Glu Arg Arg Met Lys Gln
```

```
225                 230                 235                 240

Leu Ser Ala Leu Gly Ala Arg Arg His Ala Phe Phe Arg Ser Pro Arg
                245                 250                 255

Arg Met Arg Pro Leu Val Asp Arg Leu Glu Pro Gly Glu Leu Ile Pro
            260                 265                 270

Asn Gly Pro Phe Ser Phe Tyr Gly Asp Tyr Gln Ser Glu Tyr Tyr Gly
        275                 280                 285

Pro Gly Gly Asn Tyr Asp Phe Phe Pro Gln Gly Pro Pro Ser Ser Gln
    290                 295                 300

Ala Gln Thr Pro Val Asp Leu Pro Phe Val Pro Ser Ser Gly Pro Ser
305                 310                 315                 320

Gly Thr Pro Leu Gly Gly Leu Asp His Pro Leu Pro Gly His His Pro
                325                 330                 335

Ser Ser Glu Ala Gln Arg Phe Thr Asp Ile Leu Ala His Pro Pro Gly
            340                 345                 350

Asp Ser Pro Ser Pro Glu Pro Ser Leu Pro Gly Pro Leu His Ser Met
        355                 360                 365

Ser Ala Glu Val Phe Gly Pro Ser Pro Pro Phe Ser Ser Leu Ser Val
    370                 375                 380

Asn Gly Gly Ala Ser Tyr Gly Asn His Leu Ser His Pro Pro Glu Met
385                 390                 395                 400

Asn Glu Ala Ala Val Trp
                405
```

<210> SEQ ID NO 15
<211> LENGTH: 2283
<212> TYPE: DNA
<213> ORGANISM: Homo sapiens

<400> SEQUENCE: 15

```
cggccgcgag ttgtgactgg agccacgatg cacggccagg cgcggtgaga agccagcccg     60

tagtgcctcc cgaaggagcc cgggcgcagg gagggtcgcc ctgaggacac ggaggccgcc    120

aggcaggcca agggccgagg tgactgggct ggggcggtag ggaaggagcg agtgcgcctg    180

gctgcctccg cacggagttg tccctctctg ttttcgattg acacaaacac ttctccaaaa    240

gcggggaaac ctaagcaaca acagcaatca acaccaagat cttcctccta ccctcccctc    300

tttcccttct cccgcggtcg gccctcgccc cctcccccag gcccagcgcg ggcgctcggc    360

gcgtccagac ccgcggcgcg atgccggcag tttaggatcc aaagcttctc tgctcctttt    420

gttctttcct tcccttttt aaaaaaagag gggggaaatc ccagtggtgg gcagcctggc    480

acgcacacag tcgccctcat accccgacaa aagcagatgc actttgactt ctgacagctc    540

tacctcaagc cccggagaac tcagcggcgc tttcctcgca acccgagctc ggcgagtcgt    600

cgtcttcttc ttctccgttt ttatttattt atttccgttc ccgccgccgt tctcgctgac    660

cttcactcct ccgcgggctc tgagcagaag ggtcgcattc tctcccgcct gagacttctt    720

ttcctcgccc cgggagctca ggcggcgccg ctccagcccg gggccccggg actccccggc    780

tgcacacttc actgagacgc ccccccaggc cccgatcagc ctcgtttcct ccaccctact    840

ttgatttcct ggtgcgagtt ttggcttgca cggccgagtg tgtgtcctct ttttggagag    900

actggggagc tcgtgccgat tgtcttcagg agtcatcccc tgggctctac tttgcccctc    960

tctctctctg ggcctcatca gaccaaacca aagaccatgg ttcactgtgc cggctgcaaa   1020

aggcccatcc tggaccgctt tctcttgaac gtgctggaca gggcctggca cgtcaagtgc   1080

gtccagtgct gtgaatgtaa atgcaacctg accgagaagt gcttctccag ggaaggcaaa   1140
```

ctctactgca agaacgactt cttccggtgt ttcggtacca aatgcgcagg ctgcgctcag 1200
ggcatctccc ctagcgacct ggtgcggaga gcgcggagca aagtgtttca cctgaactgc 1260
ttcacctgca tgatgtgtaa caagcagctc tccactggcg aggaactcta catcatcgac 1320
gagaataagt tcgtctgcaa agaggattac ctaagtaaca gcagtgttgc caaagagaac 1380
agccttcact cggccaccac gggcagtgac cccagtttgt ctccggattc ccaagacccg 1440
tcgcaggacg acgccaagga ctcggagagc gccaacgtgt cggacaagga agcgggtagc 1500
aacgagaatg acgaccagaa cctgggcgcc aagcggcggg gaccgcgcac caccatcaaa 1560
gccaagcagc tggagacgct gaaggccgcc ttcgctgcta cacccaagcc cacccgccac 1620
atccgcgagc agctggcgca ggagaccggc ctcaacatgc gcgtcattca ggtctggttc 1680
cagaaccggc gctccaagga gcggaggatg aagcagctga gcgccctggg cgcccggcgc 1740
cacgccttct tccgcagtcc gcgccggatg cggccgctgg tggaccgcct ggagccgggc 1800
gagctcatcc ccaatggtcc cttctccttc tacggagatt accagagcga gtactacggg 1860
cccgggggca actacgactt cttcccgcaa ggcccccccgt cctcgcaggc ccagacacca 1920
gtggacctac ccttcgtgcc gtcatctggg ccgtccggga cgcccctggg tggcctggag 1980
cacccgctgc cgggccacca cccgtcgagc gaggcgcagc ggtttaccga catcctggcg 2040
cacccacccg gggactcgcc cagccccgag cccagcctgc ccgggcctct gcactccatg 2100
tcggccgagg tcttcggacc cagcccgccc ttctcgtcgc tgtcggtcaa cggtggggcg 2160
agctacggaa accacctgtc ccaccccccc gaaatgaacg aggcggccgt gtggtagcgg 2220
ggtctcgcac ggtctgcgga gttcgtggtt gtacagaaat gaacctttat ttaagaaaaa 2280
tag 2283

<210> SEQ ID NO 16
<211> LENGTH: 406
<212> TYPE: PRT
<213> ORGANISM: Homo sapiens

<400> SEQUENCE: 16

Met Val His Cys Ala Gly Cys Lys Arg Pro Ile Leu Asp Arg Phe Leu
1 5 10 15

Leu Asn Val Leu Asp Arg Ala Trp His Val Lys Cys Val Gln Cys Cys
20 25 30

Glu Cys Lys Cys Asn Leu Thr Glu Lys Cys Phe Ser Arg Glu Gly Lys
35 40 45

Leu Tyr Cys Lys Asn Asp Phe Phe Arg Cys Phe Gly Thr Lys Cys Ala
50 55 60

Gly Cys Ala Gln Gly Ile Ser Pro Ser Asp Leu Val Arg Arg Ala Arg
65 70 75 80

Ser Lys Val Phe His Leu Asn Cys Phe Thr Cys Met Met Cys Asn Lys
85 90 95

Gln Leu Ser Thr Gly Glu Glu Leu Tyr Ile Ile Asp Glu Asn Lys Phe
100 105 110

Val Cys Lys Glu Asp Tyr Leu Ser Asn Ser Ser Val Ala Lys Glu Asn
115 120 125

Ser Leu His Ser Ala Thr Thr Gly Ser Asp Pro Ser Leu Ser Pro Asp
130 135 140

Ser Gln Asp Pro Ser Gln Asp Asp Ala Lys Asp Ser Glu Ser Ala Asn
145 150 155 160

Val Ser Asp Lys Glu Ala Gly Ser Asn Glu Asn Asp Asp Gln Asn Leu

-continued

```
                165                 170                 175

Gly Ala Lys Arg Arg Gly Pro Arg Thr Thr Ile Lys Ala Lys Gln Leu
            180                 185                 190

Glu Thr Leu Lys Ala Ala Phe Ala Ala Thr Pro Lys Pro Thr Arg His
        195                 200                 205

Ile Arg Glu Gln Leu Ala Gln Glu Thr Gly Leu Asn Met Arg Val Ile
    210                 215                 220

Gln Val Trp Phe Gln Asn Arg Arg Ser Lys Glu Arg Arg Met Lys Gln
225                 230                 235                 240

Leu Ser Ala Leu Gly Ala Arg Arg His Ala Phe Phe Arg Ser Pro Arg
                245                 250                 255

Arg Met Arg Pro Leu Val Asp Arg Leu Glu Pro Gly Glu Leu Ile Pro
            260                 265                 270

Asn Gly Pro Phe Ser Phe Tyr Gly Asp Tyr Gln Ser Glu Tyr Tyr Gly
        275                 280                 285

Pro Gly Gly Asn Tyr Asp Phe Phe Pro Gln Gly Pro Pro Ser Ser Gln
    290                 295                 300

Ala Gln Thr Pro Val Asp Leu Pro Phe Val Pro Ser Ser Gly Pro Ser
305                 310                 315                 320

Gly Thr Pro Leu Gly Gly Leu Glu His Pro Leu Pro Gly His His Pro
                325                 330                 335

Ser Ser Glu Ala Gln Arg Phe Thr Asp Ile Leu Ala His Pro Pro Gly
            340                 345                 350

Asp Ser Pro Ser Pro Glu Pro Ser Leu Pro Gly Pro Leu His Ser Met
        355                 360                 365

Ser Ala Glu Val Phe Gly Pro Ser Pro Pro Phe Ser Ser Leu Ser Val
    370                 375                 380

Asn Gly Gly Ala Ser Tyr Gly Asn His Leu Ser His Pro Pro Glu Met
385                 390                 395                 400

Asn Glu Ala Ala Val Trp
                405


<210> SEQ ID NO 17
<211> LENGTH: 2405
<212> TYPE: DNA
<213> ORGANISM: Mus musculus

<400> SEQUENCE: 17

aggacacctg ctcgaagctg gagcgagcgc ccggtcgcga cccgtgacat gaggctgtga      60

ccgctgccgc cctccacgcc actctgggca gtgcagcgcc aggccggaga gcgtcggagg     120

acttgacccc gagaagtctt ggttgatccg taacggactc gcccctacag actcgcctac     180

agactaggaa ggctgagagc cacagcagcg gggaccgaga gggcctaagg gcccaggggc     240

cccaaggagg acgaggcggc ccgagccgcc ggggcgcgcg gctatgatgg tgcactgtgc     300

tggctgtgag cggcccatcc tcgaccgctt tctgctgaac gtactagacc gcgcgtggca     360

tatcaaatgt gttcaatgct gcgagtgcaa aaccaacctc tcggagaagt gcttctcacg     420

ggaaggcaag ctatactgta aaaacgactt tttcaggcgc tttggcacaa agtgcgccgg     480

ctgcgcgcaa ggtatctctc cgagcgacct ggtacggaag gcccggagca aagtcttcca     540

cctcaactgc ttcacctgta tggtgtgcaa taagcagcta tccaccggag aggagctcta     600

cgtgatcgac gagaacaagt ttgtgtgcaa ggacgactac ttaagctcct ctagcctcaa     660

ggaaggaagt ctcaactcgg tgtcgtcctg tacggaccgc agtttgtccc cggacctcca     720

ggatccgtta caggacgacc ccaaagagac cgacaattcg acctcatcgg acaaggaaac     780
```

cgctaacaac gagaatgagg aacagaactc cggcaccaaa cggcgcggcc cgcgcaccac 840
catcaaggcc aagcagctgg agacgctcaa ggcagccttc gcagccacgc ccaagcccac 900
gcgccacatt cgcgaacagc tggcacagga gacgggcctc aacatgaggg tcattcaggt 960
gtggtttcag aaccgaaggt ccaaagaacg ccgcatgaaa cagctgagcg ctctgggcgc 1020
gcggagacac gccttcttcc ggagtccgcg gcgcatgcgt cccctgggcg gccgcttgga 1080
cgagtctgag atgttggggt ctaccccata cacttattac ggagactacc aaagtgacta 1140
ctacgctccg ggaggcaatt acgatttctt cgcgcacggt ccgccgtcac aggcgcagtc 1200
ccctgccgac tccagcttcc tggcagcatc gggacctggc tcgacgccgc tgggcgcgct 1260
ggaaccgccg ctggccgggc ctcacggcgc ggacaacccc agattcaccg acatgatctc 1320
gcatccggac acgccgagcc ccgagccggg cctgcccggt gcgctgcacc ccatgccggg 1380
agaggtgttc agcggcgggc ccagcccgcc cttccccatg agcggcacca gcggctacag 1440
tggacccctg tcgcacccca accctgagct caacgaagcg gccgtatggt aaggccgagg 1500
ggctgagttg tccccctgcc accaagcccg ggacgggacg ccgcctgggt aagcctcaag 1560
agtcctctcg tgggttcgca cccaaccagg ccactcgcat caccacccct cagagctttg 1620
gcacgcgcct gcgcaatttc tcgggaccaa agtcaatatt ctgaagggtc gagattccaa 1680
gcacatctta gaagccctcc ggatccccca cccatcatca cctccttgaa ctaagagagg 1740
gggatgaggc caaggagcgg agaccatggc actacccctc cctgcgagcc gaggcattgt 1800
gaaatcctat ttctcacttt ctcttttaaa aaaagaaaga aagaaggaag gaaggaagga 1860
aggaaagaaa gaaagagagg ttgaaagggg gagagaaaga gagagagaga gagagagaga 1920
gagagagaga gagagagaga gagagagaga gagagagaga gagagagaga gagagagaga 1980
gcgcgagcga gctgaggaaa gctcagccag agaagaaaaa tgaggaggac cgccggtgaa 2040
tggtggcttt gcaggaagac aaatccacct gcgagttggc gccccctggt ggctcaatgt 2100
cagcttgtct aggaaggtgc gcggtctggg cctggccttc ctgagcccaa ctccctgctc 2160
ctccatactt tgagtctgag gggcctggca ggattcgaac cctcccaccc tgctctgacc 2220
ctgagccggg cgccaagtca ttgagcattt gcccacggat cactctccct gcccgggacc 2280
tggaggctgg gccatcagga cgaacagtat tatacttttt tggaagtcgg acgcttctag 2340
tttccttatt ttgtataaag aagaaacaaa taaagtatgt ttttgtgaaa aaaaaaaaaa 2400
aaaaa 2405

<210> SEQ ID NO 18
<211> LENGTH: 402
<212> TYPE: PRT
<213> ORGANISM: Mus musculus

<400> SEQUENCE: 18

Met Met Val His Cys Ala Gly Cys Glu Arg Pro Ile Leu Asp Arg Phe
1               5                   10                  15

Leu Leu Asn Val Leu Asp Arg Ala Trp His Ile Lys Cys Val Gln Cys
            20                  25                  30

Cys Glu Cys Lys Thr Asn Leu Ser Glu Lys Cys Phe Ser Arg Glu Gly
        35                  40                  45

Lys Leu Tyr Cys Lys Asn Asp Phe Phe Arg Arg Phe Gly Thr Lys Cys
    50                  55                  60

Ala Gly Cys Ala Gln Gly Ile Ser Pro Ser Asp Leu Val Arg Lys Ala
65                  70                  75                  80

-continued

```
Arg Ser Lys Val Phe His Leu Asn Cys Phe Thr Cys Met Val Cys Asn
                85                  90                  95

Lys Gln Leu Ser Thr Gly Glu Glu Leu Tyr Val Ile Asp Glu Asn Lys
            100                 105                 110

Phe Val Cys Lys Asp Asp Tyr Leu Ser Ser Ser Leu Lys Glu Gly
        115                 120                 125

Ser Leu Asn Ser Val Ser Ser Cys Thr Asp Arg Ser Leu Ser Pro Asp
    130                 135                 140

Leu Gln Asp Pro Leu Gln Asp Asp Pro Lys Glu Thr Asp Asn Ser Thr
145                 150                 155                 160

Ser Ser Asp Lys Glu Thr Ala Asn Asn Glu Asn Glu Glu Gln Asn Ser
                165                 170                 175

Gly Thr Lys Arg Arg Gly Pro Arg Thr Thr Ile Lys Ala Lys Gln Leu
            180                 185                 190

Glu Thr Leu Lys Ala Ala Phe Ala Ala Thr Pro Lys Pro Thr Arg His
        195                 200                 205

Ile Arg Glu Gln Leu Ala Gln Glu Thr Gly Leu Asn Met Arg Val Ile
    210                 215                 220

Gln Val Trp Phe Gln Asn Arg Arg Ser Lys Glu Arg Arg Met Lys Gln
225                 230                 235                 240

Leu Ser Ala Leu Gly Ala Arg Arg His Ala Phe Phe Arg Ser Pro Arg
                245                 250                 255

Arg Met Arg Pro Leu Gly Gly Arg Leu Asp Glu Ser Glu Met Leu Gly
            260                 265                 270

Ser Thr Pro Tyr Thr Tyr Tyr Gly Asp Tyr Gln Ser Asp Tyr Tyr Ala
        275                 280                 285

Pro Gly Gly Asn Tyr Asp Phe Phe Ala His Gly Pro Pro Ser Gln Ala
    290                 295                 300

Gln Ser Pro Ala Asp Ser Ser Phe Leu Ala Ala Ser Gly Pro Gly Ser
305                 310                 315                 320

Thr Pro Leu Gly Ala Leu Glu Pro Pro Leu Ala Gly Pro His Gly Ala
                325                 330                 335

Asp Asn Pro Arg Phe Thr Asp Met Ile Ser His Pro Asp Thr Pro Ser
            340                 345                 350

Pro Glu Pro Gly Leu Pro Gly Ala Leu His Pro Met Pro Gly Glu Val
        355                 360                 365

Phe Ser Gly Gly Pro Ser Pro Pro Phe Pro Met Ser Gly Thr Ser Gly
    370                 375                 380

Tyr Ser Gly Pro Leu Ser His Pro Asn Pro Glu Leu Asn Glu Ala Ala
385                 390                 395                 400

Val Trp
```

<210> SEQ ID NO 19
<211> LENGTH: 2084
<212> TYPE: DNA
<213> ORGANISM: Homo sapiens

<400> SEQUENCE: 19

```
aaccaggtac aagctaatac tcaacaatac tgatgccttg tttttttgc tctgtccgga      60

cagcaacgct gtagccaatt tagatatgct ataaatttaa gaggttgcca tggccacggt    120

gcgcccattg gccgctgggc cccctacgtg cagcgccacg tcaccaaatc tgaataagga    180

tgcgcgaatt acgcggcgac cagacaaaga tgaggatccg gaccgcttga aagtggggga    240

aagtgccggc gcctccgcca ccggggaaag ccgctccgca gcgccgaggc cagcagccac    300
```

```
ccgagatacc tggggaagcc cggaacaggc gccggggcgt gcggcccgtg gcatgaggtt    360

gtgaacgcca cccgcccccc accaccccac tccgggcagc ccagcgccag gccagagatt    420

gcccaaggac tggaccggct gagtcttggt ccggaccaga ctcgccctgc agctgctgag    480

acaagaggcg aagggcagcg gagggcccgg caggcccgag ggccaggggc ccaaagggag    540

ggcaaggcgg ccgaagccgc cggggcgcgg ggctatgatg gtgcactgcg ccggttgcga    600

gcggcccatc ctcgaccgct ttctgctgaa cgtgctggac cgcgcgtggc acatcaaatg    660

tgttcagtgc tgcgagtgca aaaccaacct ctcggagaag tgcttctcgc gcgagggcaa    720

gctctactgc aaaaatgact ttttcaggcg ctttggcacg aaatgcgccg gctgcgcgca    780

aggcatctcg cccagcgacc tggtgcgcaa ggcccggagc aaagtctttc acctcaactg    840

tttcacctgc atggtgtgta acaagcagct gtccaccggc gaggagctct acgtcatcga    900

cgagaacaag ttcgtgtgca aagacgacta cctgagctca tccagcctca aggagggcag    960

cctcaactca gtgtcatcct gtacggaccg cagtttgtcc ccggacctcc aggacgcact   1020

gcaggacgac cccaaagaga cggacaactc gacctcgtcg gacaaggaga cggccaacaa   1080

cgagaacgag gagcagaact cgggcaccaa gcggcgcggc ccccgcacca ccatcaaggc   1140

caagcagctg gagacgctca aggctgcctt cgccgccacg cccaagccca cgcgccacat   1200

ccgcgagcag ctggcgcagg agaccggcct caacatgcgc gtcatccagg tgtggtttca   1260

gaaccgacgg tccaaagaac gccggatgaa acagctgagc gccctaggcg cccggaggca   1320

cgccttcttc cggagtccgc ggcgcatgcg tccgctgggc ggccgcttgg acgagtctga   1380

gatgttgggg tccacccgt acacctacta cggagactac caaggcgact actacgcgcc    1440

gggaagcaac tacgacttct tcgcgcacgg cccgccttcg caggcgcagt ccccggccga   1500

ctccagcttc ctggcggcct ctggccccgg ctcgacgccg ctgggagcgc tggaaccgcc   1560

gctcgccggc ccgcacgccg cggacaaccc caggttcacc gacatgatct cgcacccgga   1620

cacaccgagc cccgagccag gcctgccggg cacgctgcac cccatgcccg gcgaggtatt   1680

cagcggcggg cccagcccgc ccttcccaat gagcggcacc agcggctaca gcggacccct   1740

gtcgcatccc aaccccgagc tcaacgaagc cgccgtgtgg taaggccgcc gggccgcccc   1800

ccgcgctcgg cccccggggg ccccgccccg aagcagcctc ctgaaaccaa aacgcccgac   1860

gcagacgcgg tgggagacgt gggtgtccct cgggggttct ctctcgggtc cgcactcaac   1920

tggcagctgc tcctcggctg ggcgccgagg gggggccgac ccccatctcc accccgcggg   1980

ctctccagga gcctcagccc accgccagta ctctcccagc aaccgcgagc aatttcttgg   2040

gaccaaagtc aatactccgg agggtcaaga gatttcgagc acgc                   2084
```

<210> SEQ ID NO 20
<211> LENGTH: 402
<212> TYPE: PRT
<213> ORGANISM: Homo sapiens

<400> SEQUENCE: 20

```
Met Met Val His Cys Ala Gly Cys Glu Arg Pro Ile Leu Asp Arg Phe
1               5                   10                  15

Leu Leu Asn Val Leu Asp Arg Ala Trp His Ile Lys Cys Val Gln Cys
            20                  25                  30

Cys Glu Cys Lys Thr Asn Leu Ser Glu Lys Cys Phe Ser Arg Glu Gly
        35                  40                  45

Lys Leu Tyr Cys Lys Asn Asp Phe Phe Arg Arg Phe Gly Thr Lys Cys
    50                  55                  60
```

-continued

```
Ala Gly Cys Ala Gln Gly Ile Ser Pro Ser Asp Leu Val Arg Lys Ala
65                  70                  75                  80

Arg Ser Lys Val Phe His Leu Asn Cys Phe Thr Cys Met Val Cys Asn
                85                  90                  95

Lys Gln Leu Ser Thr Gly Glu Glu Leu Tyr Val Ile Asp Glu Asn Lys
            100                 105                 110

Phe Val Cys Lys Asp Asp Tyr Leu Ser Ser Ser Ser Leu Lys Glu Gly
        115                 120                 125

Ser Leu Asn Ser Val Ser Ser Cys Thr Asp Arg Ser Leu Ser Pro Asp
    130                 135                 140

Leu Gln Asp Ala Leu Gln Asp Asp Pro Lys Glu Thr Asp Asn Ser Thr
145                 150                 155                 160

Ser Ser Asp Lys Glu Thr Ala Asn Asn Glu Asn Glu Glu Gln Asn Ser
                165                 170                 175

Gly Thr Lys Arg Arg Gly Pro Arg Thr Thr Ile Lys Ala Lys Gln Leu
            180                 185                 190

Glu Thr Leu Lys Ala Ala Phe Ala Ala Thr Pro Lys Pro Thr Arg His
        195                 200                 205

Ile Arg Glu Gln Leu Ala Gln Glu Thr Gly Leu Asn Met Arg Val Ile
    210                 215                 220

Gln Val Trp Phe Gln Asn Arg Arg Ser Lys Glu Arg Arg Met Lys Gln
225                 230                 235                 240

Leu Ser Ala Leu Gly Ala Arg Arg His Ala Phe Phe Arg Ser Pro Arg
                245                 250                 255

Arg Met Arg Pro Leu Gly Gly Arg Leu Asp Glu Ser Glu Met Leu Gly
            260                 265                 270

Ser Thr Pro Tyr Thr Tyr Tyr Gly Asp Tyr Gln Gly Asp Tyr Tyr Ala
        275                 280                 285

Pro Gly Ser Asn Tyr Asp Phe Phe Ala His Gly Pro Pro Ser Gln Ala
    290                 295                 300

Gln Ser Pro Ala Asp Ser Ser Phe Leu Ala Ala Ser Gly Pro Gly Ser
305                 310                 315                 320

Thr Pro Leu Gly Ala Leu Glu Pro Pro Leu Ala Gly Pro His Ala Ala
                325                 330                 335

Asp Asn Pro Arg Phe Thr Asp Met Ile Ser His Pro Asp Thr Pro Ser
            340                 345                 350

Pro Glu Pro Gly Leu Pro Gly Thr Leu His Pro Met Pro Gly Glu Val
        355                 360                 365

Phe Ser Gly Gly Pro Ser Pro Pro Phe Pro Met Ser Gly Thr Ser Gly
    370                 375                 380

Tyr Ser Gly Pro Leu Ser His Pro Asn Pro Glu Leu Asn Glu Ala Ala
385                 390                 395                 400

Val Trp
```

<210> SEQ ID NO 21
<211> LENGTH: 1914
<212> TYPE: DNA
<213> ORGANISM: Rattus norvegicus

<400> SEQUENCE: 21

```
cggcgcctcc gccaaccggg aaagccgctc gccagtgccg aagccagcag cctccgagga      60

cacctgctcg aagctggagc gagcgcccag acgcgacccg tgacatgagg ctgtgaccgc     120

cgccgccctc cacgccactc tgggcagtgc agtgccaggc cggagagcgt cggaggactt     180

gaccccgaga agtcttggtt gatctgtatc ggactcgacc ctaccgaaga ccacagacca     240
```

```
gggggggctga gagccacaga ccaggggggc tgagagccac agcagcgggg accgagaggc    300
cctaagggcc caggggcccc aaggaggacg aggcggcccg agccgccggg gcgcgcggct    360
atgatggtgc actgtgccgg ctgtgagcgg cccatcctcg accgctttct gctgaacgtg    420
ctggaccgcg cgtggcatat caaatgtgtt caatgctgcg agtgcaaaac caacctctcg    480
gagaagtgtt tctcccggga gggcaagctg tactgtaaaa acgacttctt caggcgcttt    540
ggcacaaagt gcgccggctg tgcgcaaggt atctctccca gcgacctggt gcgcaaggcc    600
cggagcaaag tcttccacct caactgcttc acctgcatgg tgtgcaacaa gcagctgtcc    660
accggagaag aactctacgt gatcgacgag aacaagtttg tgtgcaagga cgactactta    720
agctcctcta gtctcaaaga gggaagcctc aactcagtgt catcctgtac ggaccgcagt    780
ttgtctccgg acctccaaga tccgttacag gacgacccca aagagaccga caactcgacc    840
tcatcggaca aggagaccgc taacaacgag aatgaggaac agaactccgg caccaaacgg    900
cgcggcccgc gcactaccat caaggccaag cagctggaga cgctcaaggc agccttcgca    960
gccacgccca agcccacgcg ccacatccgc gaacagctgg cacaagagac cggcctcaac   1020
atgagggtca ttcaggtgtg gtttcagaac cgaaggtcca aagaacgccg catgaaacag   1080
ctgagcgctc tgggcgcccg gagacacgcc ttcttccgga gtccgcggcg catgcgtccc   1140
ctgggcggcc gcttggacga gtctgagatg ttggggtcta ccccatatac ttattatgga   1200
gactaccaaa gcgactacta cgctccggga ggcaactacg atttcttcgc gcacggcccg   1260
ccgtcgcagg cacagtctcc ggccgactca agcttcttgg cagcatcggg acctggctcg   1320
acgccgcttg gcgcgctgga accaccgctg gctgggcctc acggcgcgga caaccctagg   1380
ttcaccgaca tgatctcgca cccggacacg cccagtccgg agccaggctt gcccggagcg   1440
ctgcacccca tgccgggaga ggtgttcagc ggcgggccca gcccgccctt ccccatgagc   1500
ggcaccagcg gctacagcgg acccctgtcg caccccaatc ctgagctcaa cgaagcggcc   1560
gtatggtaag gccgaggggc cgagttgacc cctgccacca agccccggac gccgcctggg   1620
taagccacaa gagtcttctc ttgagtttgc acccaccagg caactcgcat caccacccct   1680
cagagcttcg gcacgcgcct gcacagtttc tcgggaccaa agtcaatatt ctggagggtc   1740
gagattccaa gcacacccta gaagccctcc ggaccccccac ccaaccatca cctctttgaa   1800
ttaagagggg gaggggatga gacaaggaac ggagatcgtg gtactacccc tccctgcgag   1860
ccgaggcatt gtggaatcct atttctcgct ttctcttttt aaaaagggga attc         1914
```

```
<210> SEQ ID NO 22
<211> LENGTH: 402
<212> TYPE: PRT
<213> ORGANISM: Rattus norvegicus

<400> SEQUENCE: 22

Met Met Val His Cys Ala Gly Cys Glu Arg Pro Ile Leu Asp Arg Phe
1               5                   10                  15

Leu Leu Asn Val Leu Asp Arg Ala Trp His Ile Lys Cys Val Gln Cys
            20                  25                  30

Cys Glu Cys Lys Thr Asn Leu Ser Glu Lys Cys Phe Ser Arg Glu Gly
        35                  40                  45

Lys Leu Tyr Cys Lys Asn Asp Phe Phe Arg Arg Phe Gly Thr Lys Cys
    50                  55                  60

Ala Gly Cys Ala Gln Gly Ile Ser Pro Ser Asp Leu Val Arg Lys Ala
65                  70                  75                  80
```

-continued

```
Arg Ser Lys Val Phe His Leu Asn Cys Phe Thr Cys Met Val Cys Asn
                85                  90                  95

Lys Gln Leu Ser Thr Gly Glu Glu Leu Tyr Val Ile Asp Glu Asn Lys
            100                 105                 110

Phe Val Cys Lys Asp Asp Tyr Leu Ser Ser Ser Leu Lys Glu Gly
        115                 120                 125

Ser Leu Asn Ser Val Ser Ser Cys Thr Asp Arg Ser Leu Ser Pro Asp
    130                 135                 140

Leu Gln Asp Pro Leu Gln Asp Asp Pro Lys Glu Thr Asp Asn Ser Thr
145                 150                 155                 160

Ser Ser Asp Lys Glu Thr Ala Asn Asn Glu Asn Glu Glu Gln Asn Ser
                165                 170                 175

Gly Thr Lys Arg Arg Gly Pro Arg Thr Thr Ile Lys Ala Lys Gln Leu
            180                 185                 190

Glu Thr Leu Lys Ala Ala Phe Ala Ala Thr Pro Lys Pro Thr Arg His
        195                 200                 205

Ile Arg Glu Gln Leu Ala Gln Glu Thr Gly Leu Asn Met Arg Val Ile
    210                 215                 220

Gln Val Trp Phe Gln Asn Arg Arg Ser Lys Glu Arg Arg Met Lys Gln
225                 230                 235                 240

Leu Ser Ala Leu Gly Ala Arg Arg His Ala Phe Phe Arg Ser Pro Arg
                245                 250                 255

Arg Met Arg Pro Leu Gly Gly Arg Leu Asp Glu Ser Glu Met Leu Gly
            260                 265                 270

Ser Thr Pro Tyr Thr Tyr Tyr Gly Asp Tyr Gln Ser Asp Tyr Tyr Ala
        275                 280                 285

Pro Gly Gly Asn Tyr Asp Phe Phe Ala His Gly Pro Pro Ser Gln Ala
    290                 295                 300

Gln Ser Pro Ala Asp Ser Ser Phe Leu Ala Ala Ser Gly Pro Gly Ser
305                 310                 315                 320

Thr Pro Leu Gly Ala Leu Glu Pro Pro Leu Ala Gly Pro His Gly Ala
                325                 330                 335

Asp Asn Pro Arg Phe Thr Asp Met Ile Ser His Pro Asp Thr Pro Ser
            340                 345                 350

Pro Glu Pro Gly Leu Pro Gly Ala Leu His Pro Met Pro Gly Glu Val
        355                 360                 365

Phe Ser Gly Gly Pro Ser Pro Pro Phe Pro Met Ser Gly Thr Ser Gly
    370                 375                 380

Tyr Ser Gly Pro Leu Ser His Pro Asn Pro Glu Leu Asn Glu Ala Ala
385                 390                 395                 400

Val Trp


<210> SEQ ID NO 23
<211> LENGTH: 3660
<212> TYPE: DNA
<213> ORGANISM: Mus musculus

<400> SEQUENCE: 23

gagggcgagc tgtgaggtag ctgaaggcac gcaaacctga gtgccggctg gaaagcctgg      60

atttggctat ggcattgctg tgtggccttg ggcaagtcac tctccgtctc tgggtcccac     120

ttcctttcca atctgaaaac aggattggtt tcctggcagc cggggctttc ctgaggagcg     180

gcggcatgga ggctctcacc actcagctgg ggccgggacg cgagggcagc tcctctccca     240

actccaagca agagctgcag ccctactcgg gatccagcgc ccttaaaccc aaccaggtgg     300
```

```
gcgagacgtc gctgtacggg gtacccatcg tgtcgctggt cattgatggg caggagcgcc    360
tgtgcctagc ccagatctcc aacaccctgc tcaaaaacta cagctacaat gagatccaca    420
accgccgcgt ggccctgggc atcacatgcg tgcaatgcac gccggtgcag ctggagatac    480
tgcgtcgggc cggggccatg cccatctcct ctcgccgctg tggtatgatc acaaaacgag    540
aggccgaacg cctgtgcaag tcgttcctgg gcgagcacaa gccccccaaa ctgcctgaga    600
acttcgcctt tgacgtggtg cacgagtgcg catggggctc tcggggcagc ttcatccctg    660
cccgttacaa cagctctcgt gctaagtgca tcaagtgcgg ctactgcagt atgtatttct    720
ctcccaacaa gttcatcttc cattcgcacc gcacacccga cgccaagtac actcagcccg    780
acgccgccaa ctttaactcg tggcgtcggc acctcaaact cagtgacaag tcggccaccg    840
acgaactgag ccacgcttgg gaggacgtca aggctatgtt taatggcggt acgcgcaagc    900
ggaccttctc cctgcaaggg ggcggcggag gcggcgctaa tagcgggtct ggtggtgcag    960
ggaagggcgg cgctggtggc ggtggcggtc cagggtgcgg ctcagagatg gccccaggcc   1020
caccgcccca caaaagtctg cgctgcggtg aagacgaggc ggctgggcct cccgggccac   1080
ctccaccgca tccgcagcgc gcacttggcc tggcggcggc agctagtggc cctgcaggac   1140
ctggaggacc tgggggcagc gcaggggttc gcagctaccc ggtgattcca gtgcccagca   1200
aaggttttgg cctcttgcaa aagctgcccc cgcctctttt cccgcatcct tacggtttcc   1260
ccacagcatt cggcctatgt cccaaaaagg acgacccagt gttggtcgcc ggagaaccca   1320
agggaggccc tggcaccggg agcagtgggg gcgctggcac cgccgcgggt gcgggtggcc   1380
cgggagctgg ccacttgccc ccaggagcag ggcccggccc tggtggcggc acaatgttct   1440
ggggacatca accttccggc gcagccaagg acgcagcggc ggtagctgcc gcagctgccg   1500
ccgccactgt atacccgacg tttcccatgt tctggccagc agccgggagc ctcccggtgc   1560
ctccttaccc ggccgctcag agccaagcta aggccgtagc ggccgcggtg gctgcggctg   1620
ctgctgcagc ggcggcggcg gctggcgggg gcggtcctga gtctttggac ggtgccgagc   1680
cagctaaaga gggcagcctc ggtacggagg agcgctgccc gagcgctcta tcccgcgggc   1740
ccctggacga ggacggtgcg gacgaggcgc tgccaccgtc tctgggtccc ctgccccctc   1800
cgccaccgcc acctgctcgc aaaagctcct acgtgtcagc cttccgaccc gtagttaagg   1860
atgcagagag catcgctaag ctctacggca gcgcgcgcga ggcctatggc tccggacctg   1920
ctcgcgggcc agtgcccggc accgggaccg gagggggcta cgtgagcccg gactttctga   1980
gcgagggcag ctccagctat cattctgcct cgcccgacgt ggacaccgcg gacgaaccgg   2040
aggtggacgt agagtccaac cgcttccccg acgaggaggg agcccaggac gacaccgagc   2100
ccagggcacc cagcacggga ggtggcccag acggcgacca gcctgctggg cccccatctg   2160
ttacatcctc aggcgccgac ggccccacag actctgcgga tggcgatagt cctcgccctc   2220
gccgccgcct tgggccaccg cccgctatca gatccgcatt cggggacctg gtggccgatg   2280
atgtggtgcg gagaactgag cggagtccac caagcggcgg ctatgagctg cgagagcctt   2340
gcgggcccct gggaggcccc ggggcggcca aggtgtatgc gcctgaaagg gacgaacacg   2400
tgaagagtac ggcggtggcg gcggcgctgg ggcccgcggc ctcttacctc tgcaccccag   2460
agacccacga gccggataag gaagacaatc actcgacgac agccgacgac ttggaaacca   2520
gaaaatcctt ttcagaccaa aggagtgtct cccagccaag ccctgcaaat acagatcgag   2580
gtgaggatgg gctcactttg gatgtcacag gaactcaact ggtggagaaa gatatcgaga   2640
acctggccag agaagaattg cagaaattgc ttctggagca aatggagctt cggaagaagc   2700
```

```
tggagcggga attccagagt ctcaaagata attttcagga tcaaatgaag agggaattgg   2760

cttatcggga agaaatggtg caacagctgc aaattgtcag agataccttg tgtaacgaac   2820

tggaccagga gaggaaggcc cgctatgcca tccagcagaa attaaaagaa gctcacgacg   2880

ccctgcacca cttctcctgc aagatgctga caccccggca ctgcaccggc aactgctcct   2940

tcaagcctca gctgctgccc tagcgccggc ttggccgcgc ccacgcgccc tcaagccatg   3000

ctgctccttt ctgtaaatac ccgctgcagt ggcggcccag agcgaggaac aagccattag   3060

gacctgaccg ttgtaaatac agccgcccgc ccgccggtcc ccagccgggc tccgttgggt   3120

ttcccattgt aaatactgcc tcgcccctcc tttgaactcc agggcatcag acctcaaggg   3180

gtaaactgga cccaccgggg aaagaaaggg aagaggggag acctcttcta cgacccctcc   3240

cactcgggcc cgagtagggc ctgggacccc gaatgtgaat ataacgtagc atcttcgctg   3300

gctatggccg tgcactcccc gtcctgtcca cttctgaaac tcttgttcct aacgacaacg   3360

tggctatgtg caatggagac aaactggact gtgagtctct tggttcagta ttaggttcac   3420

tttatttata ctgtaagtta ttttacttcc cctgggaccc tttccagtcc tcgttttaca   3480

ttcattcctc tttggatttg ctttgtgatt ttgttgttgt tgatgttgtt gttgttgtgt   3540

aatgtaacag cactttaaaa gggcgacaac tgactcacga gatggcgacc atcttgagcc   3600

tatttgggga gacctgtatc cgtgactttt gtttttaata aaaagaaaaa aaaatctgct   3660
```

<210> SEQ ID NO 24
<211> LENGTH: 964
<212> TYPE: PRT
<213> ORGANISM: Mus musculus

<400> SEQUENCE: 24

```
Met Ala Leu Leu Cys Gly Leu Gly Gln Val Thr Leu Arg Leu Trp Val
1               5                   10                  15

Pro Leu Pro Phe Gln Ser Glu Asn Arg Ile Gly Phe Leu Ala Ala Gly
            20                  25                  30

Ala Phe Leu Arg Ser Gly Gly Met Glu Ala Leu Thr Thr Gln Leu Gly
        35                  40                  45

Pro Gly Arg Glu Gly Ser Ser Ser Pro Asn Ser Lys Gln Glu Leu Gln
    50                  55                  60

Pro Tyr Ser Gly Ser Ser Ala Leu Lys Pro Asn Gln Val Gly Glu Thr
65                  70                  75                  80

Ser Leu Tyr Gly Val Pro Ile Val Ser Leu Val Ile Asp Gly Gln Glu
                85                  90                  95

Arg Leu Cys Leu Ala Gln Ile Ser Asn Thr Leu Leu Lys Asn Tyr Ser
            100                 105                 110

Tyr Asn Glu Ile His Asn Arg Arg Val Ala Leu Gly Ile Thr Cys Val
        115                 120                 125

Gln Cys Thr Pro Val Gln Leu Glu Ile Leu Arg Arg Ala Gly Ala Met
    130                 135                 140

Pro Ile Ser Ser Arg Arg Cys Gly Met Ile Thr Lys Arg Glu Ala Glu
145                 150                 155                 160

Arg Leu Cys Lys Ser Phe Leu Gly Glu His Lys Pro Pro Lys Leu Pro
                165                 170                 175

Glu Asn Phe Ala Phe Asp Val Val His Glu Cys Ala Trp Gly Ser Arg
            180                 185                 190

Gly Ser Phe Ile Pro Ala Arg Tyr Asn Ser Ser Arg Ala Lys Cys Ile
        195                 200                 205

Lys Cys Gly Tyr Cys Ser Met Tyr Phe Ser Pro Asn Lys Phe Ile Phe
```

```
    210                 215                 220

His Ser His Arg Thr Pro Asp Ala Lys Tyr Thr Gln Pro Asp Ala Ala
225                 230                 235                 240

Asn Phe Asn Ser Trp Arg Arg His Leu Lys Leu Ser Asp Lys Ser Ala
                245                 250                 255

Thr Asp Glu Leu Ser His Ala Trp Glu Asp Val Lys Ala Met Phe Asn
            260                 265                 270

Gly Gly Thr Arg Lys Arg Thr Phe Ser Leu Gln Gly Gly Gly Gly Gly
        275                 280                 285

Gly Ala Asn Ser Gly Ser Gly Gly Ala Gly Lys Gly Gly Ala Gly Gly
    290                 295                 300

Gly Gly Gly Pro Gly Cys Gly Ser Glu Met Ala Pro Gly Pro Pro Pro
305                 310                 315                 320

His Lys Ser Leu Arg Cys Gly Glu Asp Glu Ala Ala Gly Pro Pro Gly
                325                 330                 335

Pro Pro Pro Pro His Pro Gln Arg Ala Leu Gly Leu Ala Ala Ala Ala
            340                 345                 350

Ser Gly Pro Ala Gly Pro Gly Gly Pro Gly Gly Ser Ala Gly Val Arg
        355                 360                 365

Ser Tyr Pro Val Ile Pro Val Pro Ser Lys Gly Phe Gly Leu Leu Gln
    370                 375                 380

Lys Leu Pro Pro Pro Leu Phe Pro His Pro Tyr Gly Phe Pro Thr Ala
385                 390                 395                 400

Phe Gly Leu Cys Pro Lys Lys Asp Asp Pro Val Leu Val Ala Gly Glu
                405                 410                 415

Pro Lys Gly Gly Pro Gly Thr Gly Ser Ser Gly Gly Ala Gly Thr Ala
            420                 425                 430

Ala Gly Ala Gly Gly Pro Gly Ala Gly His Leu Pro Pro Gly Ala Gly
        435                 440                 445

Pro Gly Pro Gly Gly Gly Thr Met Phe Trp Gly His Gln Pro Ser Gly
    450                 455                 460

Ala Ala Lys Asp Ala Ala Ala Val Ala Ala Ala Ala Ala Ala Ala Thr
465                 470                 475                 480

Val Tyr Pro Thr Phe Pro Met Phe Trp Pro Ala Ala Gly Ser Leu Pro
                485                 490                 495

Val Pro Pro Tyr Pro Ala Ala Gln Ser Gln Ala Lys Ala Val Ala Ala
            500                 505                 510

Ala Val Ala Ala Ala Ala Ala Ala Ala Ala Ala Ala Ala Gly Gly Gly
        515                 520                 525

Gly Pro Glu Ser Leu Asp Gly Ala Glu Pro Ala Lys Glu Gly Ser Leu
    530                 535                 540

Gly Thr Glu Glu Arg Cys Pro Ser Ala Leu Ser Arg Gly Pro Leu Asp
545                 550                 555                 560

Glu Asp Gly Ala Asp Glu Ala Leu Pro Pro Ser Leu Gly Pro Leu Pro
                565                 570                 575

Pro Pro Pro Pro Pro Pro Ala Arg Lys Ser Ser Tyr Val Ser Ala Phe
            580                 585                 590

Arg Pro Val Val Lys Asp Ala Glu Ser Ile Ala Lys Leu Tyr Gly Ser
        595                 600                 605

Ala Arg Glu Ala Tyr Gly Ser Gly Pro Ala Arg Gly Pro Val Pro Gly
    610                 615                 620

Thr Gly Thr Gly Gly Gly Tyr Val Ser Pro Asp Phe Leu Ser Glu Gly
625                 630                 635                 640
```

```
Ser Ser Ser Tyr His Ser Ala Ser Pro Asp Val Asp Thr Ala Asp Glu
                645                 650                 655

Pro Glu Val Asp Val Glu Ser Asn Arg Phe Pro Asp Glu Glu Gly Ala
            660                 665                 670

Gln Asp Asp Thr Glu Pro Arg Ala Pro Ser Thr Gly Gly Gly Pro Asp
        675                 680                 685

Gly Asp Gln Pro Ala Gly Pro Pro Ser Val Thr Ser Ser Gly Ala Asp
    690                 695                 700

Gly Pro Thr Asp Ser Ala Asp Gly Asp Ser Pro Arg Pro Arg Arg Arg
705                 710                 715                 720

Leu Gly Pro Pro Pro Ala Ile Arg Ser Ala Phe Gly Asp Leu Val Ala
                725                 730                 735

Asp Asp Val Val Arg Arg Thr Glu Arg Ser Pro Pro Ser Gly Gly Tyr
            740                 745                 750

Glu Leu Arg Glu Pro Cys Gly Pro Leu Gly Gly Pro Gly Ala Ala Lys
        755                 760                 765

Val Tyr Ala Pro Glu Arg Asp Glu His Val Lys Ser Thr Ala Val Ala
    770                 775                 780

Ala Ala Leu Gly Pro Ala Ala Ser Tyr Leu Cys Thr Pro Glu Thr His
785                 790                 795                 800

Glu Pro Asp Lys Glu Asp Asn His Ser Thr Thr Ala Asp Asp Leu Glu
                805                 810                 815

Thr Arg Lys Ser Phe Ser Asp Gln Arg Ser Val Ser Gln Pro Ser Pro
            820                 825                 830

Ala Asn Thr Asp Arg Gly Glu Asp Gly Leu Thr Leu Asp Val Thr Gly
        835                 840                 845

Thr Gln Leu Val Glu Lys Asp Ile Glu Asn Leu Ala Arg Glu Glu Leu
    850                 855                 860

Gln Lys Leu Leu Leu Glu Gln Met Glu Leu Arg Lys Lys Leu Glu Arg
865                 870                 875                 880

Glu Phe Gln Ser Leu Lys Asp Asn Phe Gln Asp Gln Met Lys Arg Glu
                885                 890                 895

Leu Ala Tyr Arg Glu Glu Met Val Gln Gln Leu Gln Ile Val Arg Asp
            900                 905                 910

Thr Leu Cys Asn Glu Leu Asp Gln Glu Arg Lys Ala Arg Tyr Ala Ile
        915                 920                 925

Gln Gln Lys Leu Lys Glu Ala His Asp Ala Leu His His Phe Ser Cys
    930                 935                 940

Lys Met Leu Thr Pro Arg His Cys Thr Gly Asn Cys Ser Phe Lys Pro
945                 950                 955                 960

Gln Leu Leu Pro
```

<210> SEQ ID NO 25
<211> LENGTH: 2634
<212> TYPE: DNA
<213> ORGANISM: Homo sapiens

<400> SEQUENCE: 25

```
atggctttgc tgtgtggcct tgggcaagtc actctgcgta tctgggtttc acttccttcc      60

caatccgaaa acgggattgg gagcggcggc atggaggctc tcaccactca gctggggccg     120

gggcgcgagg gcagttcctc gcccaactcc aagcaggagc tgcagccgta ctcgggctcc     180

agcgctctca aacccaacca ggtgggcgag acgtcgctgt acggggtgcc cattgtgtcg     240

ctggtcatcg acggccagga gcgcctatgc ctggcgcaga tctccaacac cctcctcaag     300
```

```
aactacagct ataatgagat ccacaaccgc cgcgtggccc tgggcatcac gtgcgtgcag    360
tgcacgccgg tacagctgga gattctgcgt cgggccgggg ccatgcccat ctcgtcgcgc    420
cgctgcggca tgatcactaa gcgagaggcc gaacgcctgt gcaagtcgtt cctgggcgag    480
cacaaaccac ccaagctgcc cgagaacttc gccttcgatg tggtgcacga gtgcgcgtgg    540
ggctcgcgtg gtagcttcat ccctgcgcgt tacaacagct ctcgtgccaa gtgcatcaag    600
tgcggctact gcagcatgta cttctcgccc aacaagttca tcttccactc gcaccgaaca    660
cccgacgcca agtacacgca gcccgatgcc gccaacttca actcctggcg tcgtcacctc    720
aaactcagtg acaagtcggc cacagacgaa ctgagccatg cttgggagga ccgcggactt    780
ggcctggcga ctggagctag tggcccggcg ggcccaggag ggcccggtgg cggcgccggc    840
gtacgaagct acccggtgat cccggtgccc agcaaaggct ttgggctcct gcaaaagctg    900
cccccaccac ttttccccca tccttacggc ttccctacgg ccttcggcct atgccccaaa    960
aaggacgacc cggttttagg cgcgggcgag ccaaagggcg gtcctggcac tgggagcggc   1020
ggcggcggcg cggggacagg cgggggtgcg gggggcccgg gagccagcca cttgcccccg   1080
ggggcagggg cgggcccggg cggcggcgcc atgttctggg ggcatcaacc ctccggggca   1140
gccaaggacg cagcggcagt ggctgcagcg gccgccgccg ccactgtgta cccgacgttt   1200
cccatgttct ggccagcagc aggcagcctc ccggtaccgt cctaccccgc tgctcagagc   1260
caagccaagg ccgtggcggc agccgtggcg gcggcagcgg cggcggcagc ggcagctgct   1320
ggcagcggtg ccccagagcc cctggacggt gccgagccag ccaaagagag tggcctcggc   1380
gcggaggagc gctgcccgag cgctctgtcc cgcgggcccc tggacgaaga cggcacggac   1440
gaggcgctgc caccgcccct ggccccgttg cccccgccgc ccccgccgcc cgcacgcaaa   1500
ggctcctacg tgtcggcctt ccggccggtg gtcaaggaca ccgagagcat cgctaagctc   1560
tacgggagcg cccgggaggc gtacggcgcg gggcctgctc gggggccggg acccggcgct   1620
gggagcggcg gctacgtgag cccggacttt ctgagcgagg gcagctccag ctacaattcc   1680
gcctcgcccg acgtggacac cgcggacgag cccgaggtgg acgtggaatc caaccgcttc   1740
cccgacgacg aggacgccca agaggagacc gagcccagcg cacccagcgc agggggcggc   1800
ccagacggtg aacagcccac tggacccccct tccgccacct cctctggcgc ggacggtccc   1860
gcaaactctc ccgacggcgg cagcccccgc ccccggcgcc gcctcgggcc acccccagct   1920
ggccggcccg catttgggga cttggcagcc gaagacttgg tgcggagacc tgagaggagc   1980
ccgccaagcg gcggcggcgg ctacgagctg cgagagcctt gcgggcccct aggaggcccc   2040
gcgccggcca aggtgttcgc gcccgagagg gatgagcacg tgaagagcgc ggcggtggcg   2100
ctggggcccg cggcctccta cgtctgcacc cccgaggccc acgagccaga taaggaagac   2160
aatcactcgc ccgccgatga tttggaaacg aggaaatcct atccagacca aaggagtatc   2220
tcccagccaa gtcctgcaaa tacagacaga ggcgaagatg ggcttacctt ggatgtcaca   2280
ggaactcatt tggtggagaa agatatcgag aacctggcca gagaggaatt gcaaaaactg   2340
ctcctggaac aaatggagct ccgcaagaag ctggaacggg aatttcagag tctcaaagat   2400
aattttcagg atcaaatgaa gagggaattg gcttatcgag aagaaatggt gcaacagctg   2460
caaattgtca gagataccct gtgtaacgaa ctcgaccagg agcggaaggc gcgctatgcc   2520
atccagcaga aattgaaaga agcccacgac gccctgcacc atttctcctg caagatgctg   2580
acgccccgcc actgcactgg caactgctcc ttcaagccac cgctgttgcc ctag         2634
```

<210> SEQ ID NO 26

<211> LENGTH: 877
<212> TYPE: PRT
<213> ORGANISM: Homo sapiens

<400> SEQUENCE: 26

```
Met Ala Leu Leu Cys Gly Leu Gly Gln Val Thr Leu Arg Ile Trp Val
1               5                   10                  15

Ser Leu Pro Ser Gln Ser Glu Asn Gly Ile Gly Ser Gly Gly Met Glu
            20                  25                  30

Ala Leu Thr Thr Gln Leu Gly Pro Gly Arg Glu Gly Ser Ser Ser Pro
        35                  40                  45

Asn Ser Lys Gln Glu Leu Gln Pro Tyr Ser Gly Ser Ser Ala Leu Lys
    50                  55                  60

Pro Asn Gln Val Gly Glu Thr Ser Leu Tyr Gly Val Pro Ile Val Ser
65                  70                  75                  80

Leu Val Ile Asp Gly Gln Glu Arg Leu Cys Leu Ala Gln Ile Ser Asn
                85                  90                  95

Thr Leu Leu Lys Asn Tyr Ser Tyr Asn Glu Ile His Asn Arg Arg Val
            100                 105                 110

Ala Leu Gly Ile Thr Cys Val Gln Cys Thr Pro Val Gln Leu Glu Ile
        115                 120                 125

Leu Arg Arg Ala Gly Ala Met Pro Ile Ser Ser Arg Arg Cys Gly Met
    130                 135                 140

Ile Thr Lys Arg Glu Ala Glu Arg Leu Cys Lys Ser Phe Leu Gly Glu
145                 150                 155                 160

His Lys Pro Pro Lys Leu Pro Glu Asn Phe Ala Phe Asp Val Val His
                165                 170                 175

Glu Cys Ala Trp Gly Ser Arg Gly Ser Phe Ile Pro Ala Arg Tyr Asn
            180                 185                 190

Ser Ser Arg Ala Lys Cys Ile Lys Cys Gly Tyr Cys Ser Met Tyr Phe
        195                 200                 205

Ser Pro Asn Lys Phe Ile Phe His Ser His Arg Thr Pro Asp Ala Lys
    210                 215                 220

Tyr Thr Gln Pro Asp Ala Ala Asn Phe Asn Ser Trp Arg Arg His Leu
225                 230                 235                 240

Lys Leu Ser Asp Lys Ser Ala Thr Asp Glu Leu Ser His Ala Trp Glu
                245                 250                 255

Asp Arg Gly Leu Gly Leu Ala Thr Gly Ala Ser Gly Pro Ala Gly Pro
            260                 265                 270

Gly Gly Pro Gly Gly Gly Ala Gly Val Arg Ser Tyr Pro Val Ile Pro
        275                 280                 285

Val Pro Ser Lys Gly Phe Gly Leu Leu Gln Lys Leu Pro Pro Pro Leu
    290                 295                 300

Phe Pro His Pro Tyr Gly Phe Pro Thr Ala Phe Gly Leu Cys Pro Lys
305                 310                 315                 320

Lys Asp Asp Pro Val Leu Gly Ala Gly Glu Pro Lys Gly Gly Pro Gly
                325                 330                 335

Thr Gly Ser Gly Gly Gly Gly Ala Gly Thr Gly Gly Gly Ala Gly Gly
            340                 345                 350

Pro Gly Ala Ser His Leu Pro Pro Gly Ala Gly Ala Gly Pro Gly Gly
        355                 360                 365

Gly Ala Met Phe Trp Gly His Gln Pro Ser Gly Ala Ala Lys Asp Ala
    370                 375                 380

Ala Ala Val Ala Ala Ala Ala Ala Ala Ala Thr Val Tyr Pro Thr Phe
385                 390                 395                 400
```

```
Pro Met Phe Trp Pro Ala Ala Gly Ser Leu Pro Val Pro Ser Tyr Pro
                405                 410                 415

Ala Ala Gln Ser Gln Ala Lys Ala Val Ala Ala Ala Val Ala Ala Ala
            420                 425                 430

Ala Ala Ala Ala Ala Ala Ala Ala Gly Ser Gly Ala Pro Glu Pro Leu
        435                 440                 445

Asp Gly Ala Glu Pro Ala Lys Glu Ser Gly Leu Gly Ala Glu Glu Arg
    450                 455                 460

Cys Pro Ser Ala Leu Ser Arg Gly Pro Leu Asp Glu Asp Gly Thr Asp
465                 470                 475                 480

Glu Ala Leu Pro Pro Pro Leu Ala Pro Leu Pro Pro Pro Pro Pro Pro
                485                 490                 495

Pro Ala Arg Lys Gly Ser Tyr Val Ser Ala Phe Arg Pro Val Val Lys
            500                 505                 510

Asp Thr Glu Ser Ile Ala Lys Leu Tyr Gly Ser Ala Arg Glu Ala Tyr
        515                 520                 525

Gly Ala Gly Pro Ala Arg Gly Pro Gly Pro Gly Ala Gly Ser Gly Gly
    530                 535                 540

Tyr Val Ser Pro Asp Phe Leu Ser Glu Gly Ser Ser Ser Tyr Asn Ser
545                 550                 555                 560

Ala Ser Pro Asp Val Asp Thr Ala Asp Glu Pro Glu Val Asp Val Glu
                565                 570                 575

Ser Asn Arg Phe Pro Asp Asp Glu Asp Ala Gln Glu Glu Thr Glu Pro
            580                 585                 590

Ser Ala Pro Ser Ala Gly Gly Gly Pro Asp Gly Glu Gln Pro Thr Gly
        595                 600                 605

Pro Pro Ser Ala Thr Ser Ser Gly Ala Asp Gly Pro Ala Asn Ser Pro
    610                 615                 620

Asp Gly Gly Ser Pro Arg Pro Arg Arg Arg Leu Gly Pro Pro Pro Ala
625                 630                 635                 640

Gly Arg Pro Ala Phe Gly Asp Leu Ala Ala Glu Asp Leu Val Arg Arg
                645                 650                 655

Pro Glu Arg Ser Pro Pro Ser Gly Gly Gly Gly Tyr Glu Leu Arg Glu
            660                 665                 670

Pro Cys Gly Pro Leu Gly Gly Pro Ala Pro Ala Lys Val Phe Ala Pro
        675                 680                 685

Glu Arg Asp Glu His Val Lys Ser Ala Ala Val Ala Leu Gly Pro Ala
    690                 695                 700

Ala Ser Tyr Val Cys Thr Pro Glu Ala His Glu Pro Asp Lys Glu Asp
705                 710                 715                 720

Asn His Ser Pro Ala Asp Asp Leu Glu Thr Arg Lys Ser Tyr Pro Asp
                725                 730                 735

Gln Arg Ser Ile Ser Gln Pro Ser Pro Ala Asn Thr Asp Arg Gly Glu
            740                 745                 750

Asp Gly Leu Thr Leu Asp Val Thr Gly Thr His Leu Val Glu Lys Asp
        755                 760                 765

Ile Glu Asn Leu Ala Arg Glu Glu Leu Gln Lys Leu Leu Leu Glu Gln
    770                 775                 780

Met Glu Leu Arg Lys Lys Leu Glu Arg Glu Phe Gln Ser Leu Lys Asp
785                 790                 795                 800

Asn Phe Gln Asp Gln Met Lys Arg Glu Leu Ala Tyr Arg Glu Glu Met
                805                 810                 815

Val Gln Gln Leu Gln Ile Val Arg Asp Thr Leu Cys Asn Glu Leu Asp
```

-continued

```
            820                 825                 830

Gln Glu Arg Lys Ala Arg Tyr Ala Ile Gln Gln Lys Leu Lys Glu Ala
        835                 840                 845

His Asp Ala Leu His His Phe Ser Cys Lys Met Leu Thr Pro Arg His
    850                 855                 860

Cys Thr Gly Asn Cys Ser Phe Lys Pro Pro Leu Leu Pro
865                 870                 875


<210> SEQ ID NO 27
<211> LENGTH: 2895
<212> TYPE: DNA
<213> ORGANISM: Rattus norvegicus

<400> SEQUENCE: 27

atggcattgc tgtgtggcct tgggcaagtc actctccgtc tctgggtttc acttcctttc      60

caaactgaaa acaggattgg cttcctggca gctggggctt tcctgaggag cggcggcatg     120

gaggctctca ccactcagct ggggccggga cgcgagggca gttcctctcc caactccaag     180

caagagttgc agccctactc gggatccagc gcccttaaac ccaaccaggt gggcgagacg     240

tcgctgtacg gggtgcccat cgtgtcactg gtcattgatg ggcaggagcg cctgtgccta     300

gcccagatct ccaacactct gctcaaaaac tacagctaca atgagatcca caaccgccgc     360

gtggccctgg gcatcacgtg cgtgcagtgc acaccggtgc agctggagat cctgcgtcgg     420

gccggggcca tgcccatctc ctctcgccgt tgcggtatga tcacaaaacg agaggccgaa     480

cgcctgtgca agtccttcct gggcgagcac aagccaccca aactgcccga gaacttcgcc     540

tttgacgtgg tgcacgagtg cgcgtggggt tctcggggca gcttcattcc tgcccgttac     600

aacagctctc gtgccaagtg catcaagtgc ggttactgca gcatgtattt ctcgcccaac     660

aagttcatct tccactcgca ccgcacaccc gacgccaagt acacccagcc cgacgccgcc     720

aactttaact cgtggcgtcg gcacctcaaa ctcagtgaca agtcggccac cgacgaactg     780

agccacgctt gggaggacgt caaggctatg tttaatggcg gtacgcgcaa gcggaccttc     840

tccctgcaag gggcggcgg aggcggtgct aatagcgggt ctggtggtgc agggaagggc     900

ggcgctggtg gcggtggcgg tccggggtgc ggctcagaga tggccccagg cccaccgcct     960

cacaaaagtc tgcgctgcgg tgaagacgaa gcgtctgggc ctcccgggcc acctccaccg    1020

catccgcagc gcgcactcgg cctagcggcg gcagctaatg gccctgcagg acctggagga    1080

cctgggggca gcgcgggggt tcgcagctac cccgtgattc cagtgcccag caaaggtttt    1140

ggcctcttgc aaaagctgcc cccgcctctt ttcccgcatc cttacggttt ccccacagcc    1200

ttcggcctat gtcccaaaaa ggacgaccca gtgttggtcg ctggagagcc caagggggggc   1260

cctggcaccg ggagcggtgg gggcgctggc accgccgcgg gtgccggtgg cccgggagct    1320

ggccacttgc ccccgggagc aggacccggc cctggtggcg gaacaatgtt ctggggacat    1380

caaccttccg gcgcagccaa ggacgcagcg gcggtagctg cggcagctgc cgccgccact    1440

gtgtacccga cgtttcccat gttctggcca gctgccggga gcctcccggt gcctccttac    1500

cccgccgcgc agagccaagc taaggccgta gcggctgcag tggctgcggc tgctgctgct    1560

gcggcggcgg cggctggcgg gggcggtcct gagtctttgg acggtgcgga gccagctaag    1620

gagggcagcc tcggtacaga ggagcgctgc ccgagcgctc tatcccgcgg cccccctggac   1680

gaggacggtg cggacgaggc gctgccaccg tccctggctc ccctggcccc tccgccaccg    1740

ccacctgccc gcaaaagctc ctacgtgtca gccttccgac ccgtagtgaa ggacgcggag    1800

agcatcgcta agctctacgg cagtgcgcgc gaggcctacg gctccgggcc tgctcgtggg    1860
```

ccagtgcccg gcaccgggac cggagggggc tacgtgagcc cggactttct gagcgagggc 1920
agctcgagct atcattctgc ctcgcccgac gtggacaccg cggacgaacc ggaggtggac 1980
gtggagtcca accgcttccc cgacgaggag ggagcccagg aggacacaga gcccagcgta 2040
cccagcacgg gaggtggccc agacggtgac cagcctgctg ggcccccatc tgtcacatcc 2100
tcaggcgcag acggccccac agactctgcg gatggcgata gccctcgccc tcgccgccgc 2160
cttgggccac cgcctgcgat cagatccgca ttcggggacc tggtggctga tgatgtagtg 2220
cggagaactg agcggagccc accgaacggc ggctatgagc tacgagagcc ttgcgggccc 2280
ctgggaggcc ccgcggcggc caaggtgtat gtgcctgaga gggacgaaca cgtgaagagt 2340
gcggcggcgg cggcggcact ggggcccgca gcctcgtatc tctgcacccc agagacccac 2400
gagccagata aggaagacaa tcactcgacg acagccgacg acttggaaac cagaaaatcc 2460
ttttcagacc aaaggagtgt ctcccagcca agccctgcaa atacagatcg aggtgaagat 2520
gggcttactt tggatgtcac aggaactcaa ttggtggaga aagatatcga aaacctggcc 2580
agagaagaac tgcagaaatt gcttctggag caaatggagc ttcgaaagaa gctggagcgg 2640
gaattccaga gtctcaaaga taattttcag gatcaaatga agagggaatt ggcttatcgg 2700
gaagaaatgg tgcaacagct gcaaattgtc agagatacct tgtgtaacga actggaccag 2760
gagaggaagg cccgctatgc catccagcag aaattaaaag aagctcacga cgccctgcac 2820
cacttctcct gcaagatgct gacaccccgg cactgcacag gcaactgctc cttcaagcct 2880
ccgctgttgc cctag 2895

<210> SEQ ID NO 28
<211> LENGTH: 964
<212> TYPE: PRT
<213> ORGANISM: Rattus norvegicus

<400> SEQUENCE: 28

Met Ala Leu Leu Cys Gly Leu Gly Gln Val Thr Leu Arg Leu Trp Val
1 5 10 15

Ser Leu Pro Phe Gln Thr Glu Asn Arg Ile Gly Phe Leu Ala Ala Gly
20 25 30

Ala Phe Leu Arg Ser Gly Gly Met Glu Ala Leu Thr Thr Gln Leu Gly
35 40 45

Pro Gly Arg Glu Gly Ser Ser Ser Pro Asn Ser Lys Gln Glu Leu Gln
50 55 60

Pro Tyr Ser Gly Ser Ser Ala Leu Lys Pro Asn Gln Val Gly Glu Thr
65 70 75 80

Ser Leu Tyr Gly Val Pro Ile Val Ser Leu Val Ile Asp Gly Gln Glu
85 90 95

Arg Leu Cys Leu Ala Gln Ile Ser Asn Thr Leu Leu Lys Asn Tyr Ser
100 105 110

Tyr Asn Glu Ile His Asn Arg Arg Val Ala Leu Gly Ile Thr Cys Val
115 120 125

Gln Cys Thr Pro Val Gln Leu Glu Ile Leu Arg Arg Ala Gly Ala Met
130 135 140

Pro Ile Ser Ser Arg Arg Cys Gly Met Ile Thr Lys Arg Glu Ala Glu
145 150 155 160

Arg Leu Cys Lys Ser Phe Leu Gly Glu His Lys Pro Pro Lys Leu Pro
165 170 175

Glu Asn Phe Ala Phe Asp Val Val His Glu Cys Ala Trp Gly Ser Arg
180 185 190

```
Gly Ser Phe Ile Pro Ala Arg Tyr Asn Ser Ser Arg Ala Lys Cys Ile
        195                 200                 205

Lys Cys Gly Tyr Cys Ser Met Tyr Phe Ser Pro Asn Lys Phe Ile Phe
    210                 215                 220

His Ser His Arg Thr Pro Asp Ala Lys Tyr Thr Gln Pro Asp Ala Ala
225                 230                 235                 240

Asn Phe Asn Ser Trp Arg Arg His Leu Lys Leu Ser Asp Lys Ser Ala
                245                 250                 255

Thr Asp Glu Leu Ser His Ala Trp Glu Asp Val Lys Ala Met Phe Asn
            260                 265                 270

Gly Gly Thr Arg Lys Arg Thr Phe Ser Leu Gln Gly Gly Gly Gly Gly
        275                 280                 285

Gly Ala Asn Ser Gly Ser Gly Gly Ala Gly Lys Gly Gly Ala Gly Gly
    290                 295                 300

Gly Gly Gly Pro Gly Cys Gly Ser Glu Met Ala Pro Gly Pro Pro Pro
305                 310                 315                 320

His Lys Ser Leu Arg Cys Gly Glu Asp Glu Ala Ser Gly Pro Pro Gly
                325                 330                 335

Pro Pro Pro Pro His Pro Gln Arg Ala Leu Gly Leu Ala Ala Ala Ala
            340                 345                 350

Asn Gly Pro Ala Gly Pro Gly Gly Pro Gly Gly Ser Ala Gly Val Arg
        355                 360                 365

Ser Tyr Pro Val Ile Pro Val Pro Ser Lys Gly Phe Gly Leu Leu Gln
    370                 375                 380

Lys Leu Pro Pro Pro Leu Phe Pro His Pro Tyr Gly Phe Pro Thr Ala
385                 390                 395                 400

Phe Gly Leu Cys Pro Lys Lys Asp Asp Pro Val Leu Val Ala Gly Glu
                405                 410                 415

Pro Lys Gly Gly Pro Gly Thr Gly Ser Gly Gly Gly Ala Gly Thr Ala
            420                 425                 430

Ala Gly Ala Gly Gly Pro Gly Ala Gly His Leu Pro Pro Gly Ala Gly
        435                 440                 445

Pro Gly Pro Gly Gly Gly Thr Met Phe Trp Gly His Gln Pro Ser Gly
    450                 455                 460

Ala Ala Lys Asp Ala Ala Ala Val Ala Ala Ala Ala Ala Ala Ala Thr
465                 470                 475                 480

Val Tyr Pro Thr Phe Pro Met Phe Trp Pro Ala Ala Gly Ser Leu Pro
                485                 490                 495

Val Pro Pro Tyr Pro Ala Ala Gln Ser Gln Ala Lys Ala Val Ala Ala
            500                 505                 510

Ala Val Ala Ala Ala Ala Ala Ala Ala Ala Ala Ala Ala Gly Gly Gly
        515                 520                 525

Gly Pro Glu Ser Leu Asp Gly Ala Glu Pro Ala Lys Glu Gly Ser Leu
    530                 535                 540

Gly Thr Glu Glu Arg Cys Pro Ser Ala Leu Ser Arg Gly Pro Leu Asp
545                 550                 555                 560

Glu Asp Gly Ala Asp Glu Ala Leu Pro Pro Ser Leu Ala Pro Leu Ala
                565                 570                 575

Pro Pro Pro Pro Pro Pro Ala Arg Lys Ser Ser Tyr Val Ser Ala Phe
            580                 585                 590

Arg Pro Val Val Lys Asp Ala Glu Ser Ile Ala Lys Leu Tyr Gly Ser
        595                 600                 605

Ala Arg Glu Ala Tyr Gly Ser Gly Pro Ala Arg Gly Pro Val Pro Gly
```

```
    610                 615                 620

Thr Gly Thr Gly Gly Gly Tyr Val Ser Pro Asp Phe Leu Ser Glu Gly
625                 630                 635                 640

Ser Ser Ser Tyr His Ser Ala Ser Pro Asp Val Asp Thr Ala Asp Glu
                645                 650                 655

Pro Glu Val Asp Val Glu Ser Asn Arg Phe Pro Asp Glu Glu Gly Ala
            660                 665                 670

Gln Glu Asp Thr Glu Pro Ser Val Pro Ser Thr Gly Gly Gly Pro Asp
        675                 680                 685

Gly Asp Gln Pro Ala Gly Pro Pro Ser Val Thr Ser Ser Gly Ala Asp
    690                 695                 700

Gly Pro Thr Asp Ser Ala Asp Gly Asp Ser Pro Arg Pro Arg Arg Arg
705                 710                 715                 720

Leu Gly Pro Pro Pro Ala Ile Arg Ser Ala Phe Gly Asp Leu Val Ala
                725                 730                 735

Asp Asp Val Val Arg Arg Thr Glu Arg Ser Pro Pro Asn Gly Gly Tyr
            740                 745                 750

Glu Leu Arg Glu Pro Cys Gly Pro Leu Gly Gly Pro Ala Ala Ala Lys
        755                 760                 765

Val Tyr Val Pro Glu Arg Asp Glu His Val Lys Ser Ala Ala Ala Ala
    770                 775                 780

Ala Ala Leu Gly Pro Ala Ala Ser Tyr Leu Cys Thr Pro Glu Thr His
785                 790                 795                 800

Glu Pro Asp Lys Glu Asp Asn His Ser Thr Thr Ala Asp Asp Leu Glu
                805                 810                 815

Thr Arg Lys Ser Phe Ser Asp Gln Arg Ser Val Ser Gln Pro Ser Pro
            820                 825                 830

Ala Asn Thr Asp Arg Gly Glu Asp Gly Leu Thr Leu Asp Val Thr Gly
        835                 840                 845

Thr Gln Leu Val Glu Lys Asp Ile Glu Asn Leu Ala Arg Glu Glu Leu
    850                 855                 860

Gln Lys Leu Leu Leu Glu Gln Met Glu Leu Arg Lys Lys Leu Glu Arg
865                 870                 875                 880

Glu Phe Gln Ser Leu Lys Asp Asn Phe Gln Asp Gln Met Lys Arg Glu
                885                 890                 895

Leu Ala Tyr Arg Glu Glu Met Val Gln Gln Leu Gln Ile Val Arg Asp
            900                 905                 910

Thr Leu Cys Asn Glu Leu Asp Gln Glu Arg Lys Ala Arg Tyr Ala Ile
        915                 920                 925

Gln Gln Lys Leu Lys Glu Ala His Asp Ala Leu His His Phe Ser Cys
    930                 935                 940

Lys Met Leu Thr Pro Arg His Cys Thr Gly Asn Cys Ser Phe Lys Pro
945                 950                 955                 960

Pro Leu Leu Pro
```

<210> SEQ ID NO 29
<211> LENGTH: 4156
<212> TYPE: DNA
<213> ORGANISM: Mus musculus

<400> SEQUENCE: 29

```
gagttcagag acagagaaag gcgctgtcag actacgctcc acttggggct cgcttgccgc      60

gggtttccgc gcacccacac tttctgtggt ggtggggaca ccctgcccca atccaggccc     120

ccattctgcc caccaccccc ccgccgggat ttgagcgcca ttagctcgcg ccagtaccgg     180
```

```
gatcttcgct cagctcgcct gagtcccgcc cgctggattc gaggacccgc ttggatgctt    240

cgcctccgag cgccctcgga agatgggccg gcagctacaa gcctaaagac gtcaagggct    300

taccagtctc caaggcaaac ccggagctct aagcccgctg ttcttccgtg gaggagatgg    360

cttccagccc actgccaggg cccaatgata tcctacttgc atcgccatcg agcgccttcc    420

agcccgacgc attgagccaa ccgcggccgg gtcacgccaa ccttaaaccc aaccaggtgg    480

gccaggtgat cctctatggc attcccatcg tgtccttggt gatcgacggg caggagcgcc    540

tgtgcctggc gcagatctcc aacactcttc tcaagaactt cagctataac gagatccaca    600

accgccgagt ggctctgggc atcacgtgcg tgcagtgcac acctgtccaa ctggagatcc    660

tgcggcgggc cggggccatg cccatctctt cgcggcgttg tggcatgatc accaagcgtg    720

aggccgagcg cctttgtaag tcattcctgg gcgaaaatcg gccacccaag ctgccggaca    780

acttcgcctt cgacgtgtcg cacgagtgtg cctggggctg ccgcggcagc ttcatcccgg    840

cgcgctacaa cagctctcgc gccaagtgca tcaagtgtag ctactgcaac atgtacttct    900

cccccaacaa gttcattttc cactcccacc gcaccccaga cgccaagtac acacagccag    960

acgcggctaa cttcaattcc tggcgccgcc atctcaagct cacagacaag agccctcagg   1020

acgagctagt cttcgcctgg gaggacgtca aggccatgtt caacggtggc agccgcaagc   1080

gcgcgctacc tcaacccagc gcgcacccgg cctgtcaccc actcagttcc gtcaaggctg   1140

ctgcggtggc ggccgcagcc gcagtggccg ggggcggagg cctgctgggc ccgcacctgc   1200

tgggggctcc acccccgcca ccgccgccac caccettggc tgagctggcg ggcgcacctc   1260

acgcccatca caagcggccg cgcttcgacg acgatgacga ttccctccag gaagctgccg   1320

tggtggctgc agccagcctc tcggcagccg cagccagcct ctcggtggcc gcagccacag   1380

gcggcgccgg gccaggcgca ggtggccccg ggggtggctg cgtggccggc gtgggcgtgg   1440

gtgccagtgc gggggctggt gcagcagctg gcaccaaagg tccacgcagc tacccagtca   1500

tcccagtgcc cagcaagggt tcgttcgggg gcgtgctaca gaagttcccg ggctgcgggg   1560

gcctcttccc gcatccttac accttcccgg cagcggccgc agccttcggc ttgtgccaca   1620

agaaggagga cgcggggaca gcggccgagg ccctgggggg agcgggcgcg gggagcgcag   1680

gtgcggcgcc caaggcaggg ctgtcgggtc tcttctggcc cgcgggtcgc aaggacgcct   1740

tctaccctcc cttctgcatg ttctggccac cgcggacccc cggcgggctg cccgtgccca   1800

cctacctaca gcccccgccg cagcccccgt ctgcgctcgg ctgcgcgctg ggtgatagcc   1860

cggccctgct gcgtcaggcc ttcctggacc tggccgagcc gggcggtgca ggtggcagcg   1920

ccgaggcagc gccccctccg ggccaacctc cccccgtggt ggccaatggc cctggctccg   1980

gtcctccagc tactgggggc actggagcac gcgacacgct cttcgagtcg cccccgggcg   2040

gcagcggcgg ggactgcagc gccgggtcca cgccacccgc agagcaagga gtgacgtccg   2100

ggaccgggtc tgcgtcctcc ggagcaggct ctgtgggcac ccgagtgccg gctccccatc   2160

acccgcacct cctggaaggg cgcaaggcgg gcggcggcag ctaccaccat tccagcgcct   2220

tccgtccggt gggcggcaag gacgacgcag aaagcctggc caagctgcac ggggcgtcgg   2280

cgggcacacc ccactcagcc ccagcgcatc accatcacca ccaccatcac ccgcaccatc   2340

accaccatca ccctccgcag ccgccgtcgc cactgctgct gttgcagccc cagcccgatg   2400

agccggggtc ggagcgccac cacccagccc cgccaccccc gccaccgccg ccccctctgg   2460

ccccgcagcc gcaccaccga ggccttctgt cccccgaggg caccagctgc agctacccca   2520

gtgaggacag ctctgaagac gaggaggacg aggaggaaga gcaggaggtg gacgtggagg   2580
```

gccacaagcc actcgaaggc gaggaagagg aggacggtcg cgatcctgaa gatgaggagg 2640
aagaagatga ggagacccgg gtccttctag gagactccct ggttggcggt ggccggttcc 2700
tccagggccg agggctatcg gagaagggga gcggtcggga ccgcacgacg cccgccgtgg 2760
gtgctttccc tctagcgctg aactcctcca ggctgctaca agaggatggg aaactggggg 2820
actctggagg ctcggacctg ccggcgcccc cgccccccacc cctggccccc cagaaagcaa 2880
gcagcagtgg gggcagcagg ccaggcagcc ctgtccacca tccatcactg gaggaggagc 2940
cctcgtacaa agataatcag aaacctaagg aaaacaacca agttattata tctacaaagg 3000
atgacaactt ctcagataag aacaagggac atggcttctt catcacagat tctgattctt 3060
ctggagactt ttggagagaa agatcaggtg aacatacaca agaaaccaat tcacctcatt 3120
cgctcaaaaa ggatgtagaa aacatgggaa aagaggaact tcagaaggtt ttgtttgagc 3180
aaatagattt gcggaggcgg ctggagcaag aattccaagt gttaaaagga aatacgtcct 3240
tcccagtctt caataacttt caggatcaga tgaaaaggga actggcttac cgagaagaga 3300
tggtgcaaca gttacaaatc atcccctatg cagcaagctt gatcaggaaa gagaagcttg 3360
gcgcccatct cagcaaaagc taaaaggcga cagacccact cactcttgtt ctgtaagata 3420
cagcctacca ctgagcactt cggacctgca gaaagaagaa ctgcaaactg aaagggcttg 3480
ggcaccaaaa ccaggttcga gagaagccaa ggacaagtga cctcgcgcca gcatgggcaa 3540
ccatgtaaaa tagactgtgg cggccattca ttaggagggg ggggaggggg gagccaacca 3600
gagcggtcaa tgcttgtcac atcttttggt ggaaccaaag tttgaatatt tgtgttttga 3660
aagcatagct gatcccagag ggtaggaagt gctgagtggg gaaatgtttg tgtggtctct 3720
ttggcgccat acgattatcc tttgctcttc cggaagtaat tcatagtgga aagaggacag 3780
aatggggact taggtttaga caaacctgct ttccatacca agctggacag acacacatgg 3840
ccccttcctc tctggtactt tgcctgctgt atgaagattg tattcctctg gaaatatttt 3900
acagtttaat attgagtgta attaagaata taatcatgtt atcaaaaatg gtatttaact 3960
ctgttgtagt ttctttaaca ttcatgtgga taaaaagttt ataataaaaa aactatgacg 4020
taatagatgt gttcatgtag ttaagtgcat atatgcttgg gggcaactca gaaacgtaat 4080
gctttttaga gttattttgg cataaagtat ttgaatataa ttatttttga aaacaaaaaa 4140
aaaaaaaaaa aaaaaa 4156

<210> SEQ ID NO 30
<211> LENGTH: 1008
<212> TYPE: PRT
<213> ORGANISM: Mus musculus

<400> SEQUENCE: 30

Met Ala Ser Ser Pro Leu Pro Gly Pro Asn Asp Ile Leu Leu Ala Ser
1 5 10 15

Pro Ser Ser Ala Phe Gln Pro Asp Ala Leu Ser Gln Pro Arg Pro Gly
20 25 30

His Ala Asn Leu Lys Pro Asn Gln Val Gly Gln Val Ile Leu Tyr Gly
35 40 45

Ile Pro Ile Val Ser Leu Val Ile Asp Gly Gln Glu Arg Leu Cys Leu
50 55 60

Ala Gln Ile Ser Asn Thr Leu Leu Lys Asn Phe Ser Tyr Asn Glu Ile
65 70 75 80

His Asn Arg Arg Val Ala Leu Gly Ile Thr Cys Val Gln Cys Thr Pro
85 90 95

-continued

```
Val Gln Leu Glu Ile Leu Arg Arg Ala Gly Ala Met Pro Ile Ser Ser
            100                 105                 110

Arg Arg Cys Gly Met Ile Thr Lys Arg Glu Ala Glu Arg Leu Cys Lys
        115                 120                 125

Ser Phe Leu Gly Glu Asn Arg Pro Pro Lys Leu Pro Asp Asn Phe Ala
    130                 135                 140

Phe Asp Val Ser His Glu Cys Ala Trp Gly Cys Arg Gly Ser Phe Ile
145                 150                 155                 160

Pro Ala Arg Tyr Asn Ser Ser Arg Ala Lys Cys Ile Lys Cys Ser Tyr
                165                 170                 175

Cys Asn Met Tyr Phe Ser Pro Asn Lys Phe Ile Phe His Ser His Arg
            180                 185                 190

Thr Pro Asp Ala Lys Tyr Thr Gln Pro Asp Ala Ala Asn Phe Asn Ser
        195                 200                 205

Trp Arg Arg His Leu Lys Leu Thr Asp Lys Ser Pro Gln Asp Glu Leu
    210                 215                 220

Val Phe Ala Trp Glu Asp Val Lys Ala Met Phe Asn Gly Gly Ser Arg
225                 230                 235                 240

Lys Arg Ala Leu Pro Gln Pro Ser Ala His Pro Ala Cys His Pro Leu
                245                 250                 255

Ser Ser Val Lys Ala Ala Ala Val Ala Ala Ala Ala Ala Val Ala Gly
            260                 265                 270

Gly Gly Gly Leu Leu Gly Pro His Leu Leu Gly Ala Pro Pro Pro Pro
        275                 280                 285

Pro Pro Pro Pro Pro Leu Ala Glu Leu Ala Gly Ala Pro His Ala His
    290                 295                 300

His Lys Arg Pro Arg Phe Asp Asp Asp Asp Asp Ser Leu Gln Glu Ala
305                 310                 315                 320

Ala Val Val Ala Ala Ala Ser Leu Ser Ala Ala Ala Ala Ser Leu Ser
                325                 330                 335

Val Ala Ala Ala Thr Gly Gly Ala Gly Pro Gly Ala Gly Gly Pro Gly
            340                 345                 350

Gly Gly Cys Val Ala Gly Val Gly Val Gly Ala Ser Ala Gly Ala Gly
        355                 360                 365

Ala Ala Ala Gly Thr Lys Gly Pro Arg Ser Tyr Pro Val Ile Pro Val
    370                 375                 380

Pro Ser Lys Gly Ser Phe Gly Gly Val Leu Gln Lys Phe Pro Gly Cys
385                 390                 395                 400

Gly Gly Leu Phe Pro His Pro Tyr Thr Phe Pro Ala Ala Ala Ala Ala
                405                 410                 415

Phe Gly Leu Cys His Lys Lys Glu Asp Ala Gly Thr Ala Ala Glu Ala
            420                 425                 430

Leu Gly Gly Ala Gly Ala Gly Ser Ala Gly Ala Ala Pro Lys Ala Gly
        435                 440                 445

Leu Ser Gly Leu Phe Trp Pro Ala Gly Arg Lys Asp Ala Phe Tyr Pro
    450                 455                 460

Pro Phe Cys Met Phe Trp Pro Pro Arg Thr Pro Gly Gly Leu Pro Val
465                 470                 475                 480

Pro Thr Tyr Leu Gln Pro Pro Pro Gln Pro Pro Ser Ala Leu Gly Cys
                485                 490                 495

Ala Leu Gly Asp Ser Pro Ala Leu Leu Arg Gln Ala Phe Leu Asp Leu
            500                 505                 510

Ala Glu Pro Gly Gly Ala Gly Gly Ser Ala Glu Ala Ala Pro Pro Pro
```

```
        515                 520                 525

Gly Gln Pro Pro Pro Val Val Ala Asn Gly Pro Gly Ser Gly Pro Pro
    530                 535                 540

Ala Thr Gly Gly Thr Gly Ala Arg Asp Thr Leu Phe Glu Ser Pro Pro
545                 550                 555                 560

Gly Gly Ser Gly Gly Asp Cys Ser Ala Gly Ser Thr Pro Pro Ala Glu
                565                 570                 575

Gln Gly Val Thr Ser Gly Thr Gly Ser Ala Ser Ser Gly Ala Gly Ser
            580                 585                 590

Val Gly Thr Arg Val Pro Ala Pro His His Pro His Leu Leu Glu Gly
        595                 600                 605

Arg Lys Ala Gly Gly Gly Ser Tyr His His Ser Ser Ala Phe Arg Pro
    610                 615                 620

Val Gly Gly Lys Asp Asp Ala Glu Ser Leu Ala Lys Leu His Gly Ala
625                 630                 635                 640

Ser Ala Gly Thr Pro His Ser Ala Pro Ala His His His His His His
                645                 650                 655

His His Pro His His His His His His Pro Pro Gln Pro Pro Ser Pro
            660                 665                 670

Leu Leu Leu Leu Gln Pro Gln Pro Asp Glu Pro Gly Ser Glu Arg His
        675                 680                 685

His Pro Ala Pro Pro Pro Pro Pro Pro Pro Pro Pro Leu Ala Pro Gln
    690                 695                 700

Pro His His Arg Gly Leu Leu Ser Pro Glu Gly Thr Ser Cys Ser Tyr
705                 710                 715                 720

Pro Ser Glu Asp Ser Ser Glu Asp Glu Glu Asp Glu Glu Glu Glu Gln
                725                 730                 735

Glu Val Asp Val Glu Gly His Lys Pro Leu Glu Gly Glu Glu Glu Glu
            740                 745                 750

Asp Gly Arg Asp Pro Glu Asp Glu Glu Glu Glu Asp Glu Glu Thr Arg
        755                 760                 765

Val Leu Leu Gly Asp Ser Leu Val Gly Gly Gly Arg Phe Leu Gln Gly
    770                 775                 780

Arg Gly Leu Ser Glu Lys Gly Ser Gly Arg Asp Arg Thr Thr Pro Ala
785                 790                 795                 800

Val Gly Ala Phe Pro Leu Ala Leu Asn Ser Ser Arg Leu Leu Gln Glu
                805                 810                 815

Asp Gly Lys Leu Gly Asp Ser Gly Gly Ser Asp Leu Pro Ala Pro Pro
            820                 825                 830

Pro Pro Pro Leu Ala Pro Gln Lys Ala Ser Ser Ser Gly Gly Ser Arg
        835                 840                 845

Pro Gly Ser Pro Val His His Pro Ser Leu Glu Glu Glu Pro Ser Tyr
    850                 855                 860

Lys Asp Asn Gln Lys Pro Lys Glu Asn Asn Gln Val Ile Ile Ser Thr
865                 870                 875                 880

Lys Asp Asp Asn Phe Ser Asp Lys Asn Lys Gly His Gly Phe Phe Ile
                885                 890                 895

Thr Asp Ser Asp Ser Ser Gly Asp Phe Trp Arg Glu Arg Ser Gly Glu
            900                 905                 910

His Thr Gln Glu Thr Asn Ser Pro His Ser Leu Lys Lys Asp Val Glu
        915                 920                 925

Asn Met Gly Lys Glu Glu Leu Gln Lys Val Leu Phe Glu Gln Ile Asp
    930                 935                 940
```

```
Leu Arg Arg Arg Leu Glu Gln Glu Phe Gln Val Leu Lys Gly Asn Thr
945                 950                 955                 960

Ser Phe Pro Val Phe Asn Asn Phe Gln Asp Gln Met Lys Arg Glu Leu
                965                 970                 975

Ala Tyr Arg Glu Glu Met Val Gln Gln Leu Gln Ile Ile Pro Tyr Ala
            980                 985                 990

Ala Ser Leu Ile Arg Lys Glu Lys  Leu Gly Ala His Leu  Ser Lys Ser
        995                 1000                 1005


<210> SEQ ID NO 31
<211> LENGTH: 3045
<212> TYPE: DNA
<213> ORGANISM: Homo sapiens

<400> SEQUENCE: 31

atggcttcca gtccgctgcc agggcccaac gacatcctgc tggcgtcgcc gtcgagcgcc     60

ttccagcccg acacgctgag ccagccgcgg ccagggcacg ccaacctcaa acccaaccag    120

gtgggccagg tgatcctcta cggcattccc atcgtgtcgt tggtgatcga cgggcaagag    180

cgcctgtgcc tggcgcagat ctccaacact ctgctcaaga acttcagcta caacgagatc    240

cacaaccgtc gcgtggcact gggcatcacg tgtgtgcagt gcacgccggt gcaactggag    300

atcctgcggc gtgccggggc catgcccatc tcatcgcgcc gctgcggcat gatcaccaaa    360

cgcgaggccg agcgtctgtg caagtcgttc ctgggcgaaa acaggccgcc caagctgcca    420

gacaatttcg ccttcgacgt gtcacacgag tgcgcctggg gctgccgcgg cagcttcatt    480

cccgcgcgct acaacagctc gcgcgccaag tgcatcaaat gcagctactg caacatgtac    540

ttctcgccca acaagttcat tttccactcc caccgcacgc ccgacgccaa gtacactcag    600

ccagacgcag ccaacttcaa ctcgtggcgc cgtcatctca agctcaccga caagagtccc    660

caggacgagc tggtcttcgc ctgggaggac gtcaaggcca tgttcaacgg cggcagccgc    720

aagcgcgcac tgccccagcc gggcgcgcac cccgcctgcc acccgctcag ctctgtgaag    780

gcggccgccg tggccgccgc ggccgcggtg gccggaggcg ggggtctgct gggcccccac    840

ctgctgggtg cgcccccgcc gccgccgccg ccaccgccgc ccttggcaga gctggctggt    900

gccccgcacg cccatcacaa gcggccgcgc ttcgacgacg acgacgactc cttgcaggag    960

gccgccgtag tggccgccgc cagcctctcg gccgcagccg ccagcctctc tgtggctgct   1020

gcttcgggcg gcgcggggac tggtgggggc ggcgctgggg gtggctgtgt ggccggcgtg   1080

ggcgtgggcg cgggcgcggg ggcgggtgcc ggggcagggg ccaaaggccc gcgcagctac   1140

ccagtcatcc cggtgcccag caagggctcg ttcgggggcg tcctgcagaa gttcccgggc   1200

tgcggcgggc tcttcccgca cccctacacc ttccctgccg cggccgccgc cttcagcttg   1260

tgccataaga aagaggatgc gggtgccgcc gctgaggccc tgggggcgc gggcgcaggc   1320

ggcgcgggcg cggcgcccaa ggccggcttg tccggcctct tctggcccgc gggccgcaag   1380

gacgccttct atccgccctt ctgcatgttc tggccgccgc ggacccctgg cgggctcccg   1440

gtgcccacct acctgcagcc cccgcctcag ccgccctcgg cgctaggctg cgcgctaggc   1500

gaaagcccgg ccctgctgcg ccaggccttc ctggacctgg ctgagccagg cggtgctgct   1560

gggagcgccg aggccgcgcc cccgccgggg cagcccccgc aggtagtggc caacggcccg   1620

ggctccggcc cacctcctcc tgccgggggc gccggctctc gcgacgcgct cttcgagtcg   1680

cccccgggcg gcagcggcgg ggactgcagc gcgggctcca cgccgcccgc ggactctgtg   1740

gcagctgccg gggcaggggc cgcggccgcc gggtctggcc ccgcgggctc ccgggttccg   1800
```

-continued

```
gcgccccacc atccgcacct tctggagggg cgcaaagcgg gcggtggcag ctaccaccat   1860

tccagcgcct tccggccagt gggcggcaag gacgacgcgg agagcctggc caagctgcac   1920

ggggcgtcgg cgggcgcgcc ccactcggcc cagacgcatc cccaccacca tcaccaccct   1980

caccaccacc accaccacca ccaccccccg cagccgccgt cgccgcttct gctgctgccc   2040

ccgcagcccg acgagccggg ttccgagcgc caccacccgg ccccgccgcc gccgccgccg   2100

ccgcccccgc cgccccctct ggcccagcac ccgcaccacc gaggccttct gtctcccggg   2160

ggaaccagct gctgctaccc cagcgaggac agctccgagg acgaggacga cgaggaagaa   2220

gagcaggagg tggacgtgga gggccacaag ccccccgagg gcgaggaaga ggaggaaggt   2280

cgagaccctg acgacgacga ggaagaggac gaggagacgg aggtcctact cggcgacccc   2340

ttagtcgggg gcggccggtt cctccagggc cgagggccgt cggagaaggg gagcagccgg   2400

gaccgcgcgc cggccgtcgc gggcgcgttc ccgctcggcc tgaactcctc caggctgctg   2460

caggaagacg ggaaactcgg ggaccccggc tcggacctgc ccccgccccc gccgccgccc   2520

ctggcccccc agaaggcgag tggcggcggc agcagcagcc cgggcagccc agttcaccat   2580

ccatcactgg aggagcagcc ctcctacaaa gatagtcaga aaactaagga aaataaccaa   2640

gtaattgtat ctacaaagga tgacaacgtt ctagataaga acaaggagca tagctttttc   2700

atcacagact ctgatgcttc tggaggagat tttggagag aaagatcagg tgaacataca   2760

caagaaacca actcacctca ttcactgaaa aaggatgtag aaaatatggg gaaagaagaa   2820

cttcagaagg ttttatttga acaaatagat ttacggagac gactggaaca agaattccag   2880

gtgttaaaag gaaacacatc tttcccagta ttcaataatt ttcaggatca gatgaaaagg   2940

gagctagcct accgagaaga aatggtgcaa cagttacaaa ttatccccta tgcagcaagt   3000

ttgatcagga aagaaaagct tggcgcccat ctcagcaaaa gctaa                   3045
```

<210> SEQ ID NO 32
<211> LENGTH: 1014
<212> TYPE: PRT
<213> ORGANISM: Homo sapiens

<400> SEQUENCE: 32

```
Met Ala Ser Ser Pro Leu Pro Gly Pro Asn Asp Ile Leu Leu Ala Ser
1               5                   10                  15

Pro Ser Ser Ala Phe Gln Pro Asp Thr Leu Ser Gln Pro Arg Pro Gly
            20                  25                  30

His Ala Asn Leu Lys Pro Asn Gln Val Gly Gln Val Ile Leu Tyr Gly
        35                  40                  45

Ile Pro Ile Val Ser Leu Val Ile Asp Gly Gln Glu Arg Leu Cys Leu
    50                  55                  60

Ala Gln Ile Ser Asn Thr Leu Leu Lys Asn Phe Ser Tyr Asn Glu Ile
65                  70                  75                  80

His Asn Arg Arg Val Ala Leu Gly Ile Thr Cys Val Gln Cys Thr Pro
                85                  90                  95

Val Gln Leu Glu Ile Leu Arg Arg Ala Gly Ala Met Pro Ile Ser Ser
            100                 105                 110

Arg Arg Cys Gly Met Ile Thr Lys Arg Glu Ala Glu Arg Leu Cys Lys
        115                 120                 125

Ser Phe Leu Gly Glu Asn Arg Pro Pro Lys Leu Pro Asp Asn Phe Ala
    130                 135                 140

Phe Asp Val Ser His Glu Cys Ala Trp Gly Cys Arg Gly Ser Phe Ile
145                 150                 155                 160
```

-continued

```
Pro Ala Arg Tyr Asn Ser Ser Arg Ala Lys Cys Ile Lys Cys Ser Tyr
                165                 170                 175

Cys Asn Met Tyr Phe Ser Pro Asn Lys Phe Ile Phe His Ser His Arg
            180                 185                 190

Thr Pro Asp Ala Lys Tyr Thr Gln Pro Asp Ala Ala Asn Phe Asn Ser
        195                 200                 205

Trp Arg Arg His Leu Lys Leu Thr Asp Lys Ser Pro Gln Asp Glu Leu
    210                 215                 220

Val Phe Ala Trp Glu Asp Val Lys Ala Met Phe Asn Gly Gly Ser Arg
225                 230                 235                 240

Lys Arg Ala Leu Pro Gln Pro Gly Ala His Pro Ala Cys His Pro Leu
                245                 250                 255

Ser Ser Val Lys Ala Ala Ala Val Ala Ala Ala Ala Ala Val Ala Gly
            260                 265                 270

Gly Gly Gly Leu Leu Gly Pro His Leu Leu Gly Ala Pro Pro Pro Pro
        275                 280                 285

Pro Pro Pro Pro Pro Pro Leu Ala Glu Leu Ala Gly Ala Pro His Ala
    290                 295                 300

His His Lys Arg Pro Arg Phe Asp Asp Asp Asp Asp Ser Leu Gln Glu
305                 310                 315                 320

Ala Ala Val Val Ala Ala Ala Ser Leu Ser Ala Ala Ala Ala Ser Leu
                325                 330                 335

Ser Val Ala Ala Ala Ser Gly Gly Ala Gly Thr Gly Gly Gly Gly Ala
            340                 345                 350

Gly Gly Gly Cys Val Ala Gly Val Gly Val Gly Ala Gly Ala Gly Ala
        355                 360                 365

Gly Ala Gly Ala Gly Ala Lys Gly Pro Arg Ser Tyr Pro Val Ile Pro
    370                 375                 380

Val Pro Ser Lys Gly Ser Phe Gly Gly Val Leu Gln Lys Phe Pro Gly
385                 390                 395                 400

Cys Gly Gly Leu Phe Pro His Pro Tyr Thr Phe Pro Ala Ala Ala Ala
                405                 410                 415

Ala Phe Ser Leu Cys His Lys Lys Glu Asp Ala Gly Ala Ala Ala Glu
            420                 425                 430

Ala Leu Gly Gly Ala Gly Ala Gly Gly Ala Gly Ala Ala Pro Lys Ala
        435                 440                 445

Gly Leu Ser Gly Leu Phe Trp Pro Ala Gly Arg Lys Asp Ala Phe Tyr
    450                 455                 460

Pro Pro Phe Cys Met Phe Trp Pro Pro Arg Thr Pro Gly Gly Leu Pro
465                 470                 475                 480

Val Pro Thr Tyr Leu Gln Pro Pro Pro Gln Pro Pro Ser Ala Leu Gly
                485                 490                 495

Cys Ala Leu Gly Glu Ser Pro Ala Leu Leu Arg Gln Ala Phe Leu Asp
            500                 505                 510

Leu Ala Glu Pro Gly Gly Ala Ala Gly Ser Ala Glu Ala Ala Pro Pro
        515                 520                 525

Pro Gly Gln Pro Pro Gln Val Val Ala Asn Gly Pro Gly Ser Gly Pro
    530                 535                 540

Pro Pro Pro Ala Gly Gly Ala Gly Ser Arg Asp Ala Leu Phe Glu Ser
545                 550                 555                 560

Pro Pro Gly Gly Ser Gly Gly Asp Cys Ser Ala Gly Ser Thr Pro Pro
                565                 570                 575

Ala Asp Ser Val Ala Ala Ala Gly Ala Gly Ala Ala Ala Ala Gly Ser
            580                 585                 590
```

```
Gly Pro Ala Gly Ser Arg Val Pro Ala Pro His His Pro His Leu Leu
        595                 600                 605

Glu Gly Arg Lys Ala Gly Gly Gly Ser Tyr His His Ser Ser Ala Phe
    610                 615                 620

Arg Pro Val Gly Gly Lys Asp Asp Ala Glu Ser Leu Ala Lys Leu His
625                 630                 635                 640

Gly Ala Ser Ala Gly Ala Pro His Ser Ala Gln Thr His Pro His His
                645                 650                 655

His His His Pro His His His His His His His His Pro Pro Gln Pro
            660                 665                 670

Pro Ser Pro Leu Leu Leu Leu Pro Pro Gln Pro Asp Glu Pro Gly Ser
        675                 680                 685

Glu Arg His His Pro Ala Pro Pro Pro Pro Pro Pro Pro Pro Pro Pro
    690                 695                 700

Pro Pro Leu Ala Gln His Pro His His Arg Gly Leu Leu Ser Pro Gly
705                 710                 715                 720

Gly Thr Ser Cys Cys Tyr Pro Ser Glu Asp Ser Ser Glu Asp Glu Asp
                725                 730                 735

Asp Glu Glu Glu Glu Gln Glu Val Asp Val Glu Gly His Lys Pro Pro
            740                 745                 750

Glu Gly Glu Glu Glu Glu Glu Gly Arg Asp Pro Asp Asp Asp Glu Glu
        755                 760                 765

Glu Asp Glu Glu Thr Glu Val Leu Leu Gly Asp Pro Leu Val Gly Gly
    770                 775                 780

Gly Arg Phe Leu Gln Gly Arg Gly Pro Ser Glu Lys Gly Ser Ser Arg
785                 790                 795                 800

Asp Arg Ala Pro Ala Val Ala Gly Ala Phe Pro Leu Gly Leu Asn Ser
                805                 810                 815

Ser Arg Leu Leu Gln Glu Asp Gly Lys Leu Gly Asp Pro Gly Ser Asp
            820                 825                 830

Leu Pro Pro Pro Pro Pro Pro Pro Leu Ala Pro Gln Lys Ala Ser Gly
        835                 840                 845

Gly Gly Ser Ser Ser Pro Gly Ser Pro Val His His Pro Ser Leu Glu
    850                 855                 860

Glu Gln Pro Ser Tyr Lys Asp Ser Gln Lys Thr Lys Glu Asn Asn Gln
865                 870                 875                 880

Val Ile Val Ser Thr Lys Asp Asp Asn Val Leu Asp Lys Asn Lys Glu
                885                 890                 895

His Ser Phe Phe Ile Thr Asp Ser Asp Ala Ser Gly Gly Asp Phe Trp
            900                 905                 910

Arg Glu Arg Ser Gly Glu His Thr Gln Glu Thr Asn Ser Pro His Ser
        915                 920                 925

Leu Lys Lys Asp Val Glu Asn Met Gly Lys Glu Glu Leu Gln Lys Val
    930                 935                 940

Leu Phe Glu Gln Ile Asp Leu Arg Arg Arg Leu Glu Gln Glu Phe Gln
945                 950                 955                 960

Val Leu Lys Gly Asn Thr Ser Phe Pro Val Phe Asn Asn Phe Gln Asp
        965                 970                 975

Gln Met Lys Arg Glu Leu Ala Tyr Arg Glu Glu Met Val Gln Gln Leu
    980                 985                 990

Gln Ile Ile Pro Tyr Ala Ala Ser  Leu Ile Arg Lys Glu  Lys Leu Gly
995                 1000                1005

Ala His  Leu Ser Lys Ser
```

1010

<210> SEQ ID NO 33
<211> LENGTH: 3123
<212> TYPE: DNA
<213> ORGANISM: Mus musculus

<400> SEQUENCE: 33
gctctctccg acccgcaggc ccacgggagc ctgagctccg cctccccagg gcgcggaagc 60
tggcgaagcc ccagggattc ccatttatag cttggtttcc actcagctca gtccctccag 120
gactcgggct gagcaagttt cttccattcc cttctctcct ccctccaccc ccttctcctc 180
ctccttctcc ttcttttctt cctcctcatt cccgcctccc cttcaacctc agcagggtgc 240
aggtgtccaa ctcgaacaag ggccccaact tggactcaga tgttcccact ctcagacccc 300
ctgataatgc aggggcgccc gcctgctgcg cggacagcta ccctgagcat ccgtagccgt 360
ccgcacacaa ggcgcgggag tttctcaatg ggaagaggcc gggactctag gaggcggggc 420
gaataggatt cctcccgcct agtgggtccc tcgcagtcct agggttgcaa cccttgagcg 480
gtagagaaca ccggagactg cggatgagcc agatttcggg gacataaaat cttccagccc 540
ggagagaatt gtgtgcagag aggggctcca gtccagcgtg gtgtgagagg cgtgctatca 600
agaaagaagt tggaggggaa ccagtgcaac cctaactctg cgagatcttg ggtacacac 660 actcgggatg ctggcctccg ccctcctcgt tttcctttgc tgtttcaaag gacatgcagg 720
ctcatcgccc catttcctac aacagccaga ggacatggtg gtgctgttgg gggaggaagc 780
ccggctgccc tgcgctctgg gcgcgtacag gggctcgtg cagtggacta aggatgggct 840
ggctctaggg ggcgaaagag accttccagg gtggtcccgg tactggatat cggggaattc 900
agccagtggc cagcatgacc tccacattaa gcctgtggaa ttggaagatg aggcatcgta 960
tgagtgccag gcttcgcaag caggtctccg atcacgacca gcccaactgc acgtgatggt 1020
ccccccagaa gctccccagg tactaggcgg cccctctgtg tctctggttg ctggagttcc 1080
tggaaatctg acctgtcgga gtcgtgggga ttcacgacct gcccctgaac tactgtggtt 1140
ccgagatggg atccggctgg atgggagcag cttccaccag accacgctga aggacaaggc 1200
cactggaaca gtggaaaaca ccttattcct gacccccttcc agtcatgatg atggtgccac 1260
cttgatctgc agagcgcgaa gccaggccct gcccacaggg agggacacag ctgttacact 1320
gagccttcag tatcccccaa tggtgactct gtctgctgag ccccagactg tgcaggaggg 1380
agagaaggtg actttcctgt gtcaagccac tgcccagcct cctgtcactg gctacaggtg 1440
ggcgaagggg ggatccccgg tgcttggggc acgtgggcca aggttggagg tcgttgcaga 1500
tgccactttc ctgactgagc cggtgtcctg cgaggtcagc aacgcggtcg gaagcgccaa 1560
ccgcagcacc gcgctggaag tgttgtatgg acccattctg caggcaaaac ctaagtccgt 1620
gtccgtggac gtggggaaag atgcctcctt cagctgtgtc tggcgcggga acccacttcc 1680
acggataacc tggacccgca tgggtggctc tcaggtgctg agctccgggc ccacgctgcg 1740
gcttccgtcc gtggcactgg aggatgcggg cgactatgta tgcagggctg agccgaggag 1800
aacgggtctg ggaggcggca aagcgcaggc gaggctgact gtgaacgcac cccctgtagt 1860
gacagccctg caacctgcac cagcctttct gaggggtcct gctcgcctcc agtgtgtggt 1920
gtttgcctcc cctgccccag actcggtggt ttggtcttgg gacgagggct tcttggaggc 1980
aggctcactg ggcaggttcc tagtggaagc cttcccagcc ccggaagtgg aggggggaca 2040
gggccctggc cttatttctg tgctacacat ttccggaacc caggagtccg actttaccac 2100

-continued

```
cggcttcaac tgcagtgccc gcaaccggct aggagaggga cgagtccaga tccacttggg   2160

ccgtagagac ttgctgccta ctgtccggat tgtggctggt gcagcatctg cagccacctc   2220

tctccttatg gtcatcactg gagtggtcct ctgctgctgg cgccatggct ctctctctaa   2280

gcaaaagaac ttggtccgga tcccgggaag cagcgagggt tccagttcac gtggccctga   2340

ggaggagaca ggcagcagtg aggaccgggg tcccattgtg cacaccgacc acagtgattt   2400

ggttcttgag gaaaaagagg ctctggagac aaaggatcca accaacggtt actacagggt   2460

tcgaggggtc agtgtgagcc ttagccttgg ggaagctcct ggaggaggcc tcttcttgcc   2520

accgccctct ccgatcggtc tcccagggac tcctacttac tatgacttca agccacatct   2580

ggacttagtc cctccctgca gactgtacag agcgagggca ggttatctta ccacccccca   2640

tccccgtgcc ttcaccagct acatgaaacc cacatccttt ggacccccag aattgagctc   2700

tggaactccc cccttcccgt atgctacctt gtctccaccc agccaccagc gtctccagac   2760

tcatgtgtga atccatctct ccaagtgaag ggtcttggaa tcttctgttt gccatatagt   2820

gtgttgtcca gatttctggg gagtcagaac aagttgatga ccaacccctc caaaactgaa   2880

cattgaagga gggaaagatc attacaagca tcaggactgt tggtgtacac tcagttcagc   2940

caaagtggat tctccaagtg ggagcaatat ggccgctttc ccatgagaaa gacattcaag   3000

atggtgacta aatgactaaa tactttgcag agggacaaag atgggaacta gggatatgga   3060

tggaagtagt agagaagata tatgaccatc tgcatcaaga gaaaggataa cataagacaa   3120

atc                                                                 3123
```

<210> SEQ ID NO 34
<211> LENGTH: 700
<212> TYPE: PRT
<213> ORGANISM: Mus musculus

<400> SEQUENCE: 34

```
Met Leu Ala Ser Ala Leu Leu Val Phe Leu Cys Cys Phe Lys Gly His
1               5                   10                  15

Ala Gly Ser Ser Pro His Phe Leu Gln Gln Pro Glu Asp Met Val Val
            20                  25                  30

Leu Leu Gly Glu Glu Ala Arg Leu Pro Cys Ala Leu Gly Ala Tyr Arg
        35                  40                  45

Gly Leu Val Gln Trp Thr Lys Asp Gly Leu Ala Leu Gly Gly Glu Arg
    50                  55                  60

Asp Leu Pro Gly Trp Ser Arg Tyr Trp Ile Ser Gly Asn Ser Ala Ser
65                  70                  75                  80

Gly Gln His Asp Leu His Ile Lys Pro Val Glu Leu Glu Asp Glu Ala
                85                  90                  95

Ser Tyr Glu Cys Gln Ala Ser Gln Ala Gly Leu Arg Ser Arg Pro Ala
            100                 105                 110

Gln Leu His Val Met Val Pro Pro Glu Ala Pro Gln Val Leu Gly Gly
        115                 120                 125

Pro Ser Val Ser Leu Val Ala Gly Val Pro Gly Asn Leu Thr Cys Arg
    130                 135                 140

Ser Arg Gly Asp Ser Arg Pro Ala Pro Glu Leu Leu Trp Phe Arg Asp
145                 150                 155                 160

Gly Ile Arg Leu Asp Gly Ser Ser Phe His Gln Thr Thr Leu Lys Asp
                165                 170                 175

Lys Ala Thr Gly Thr Val Glu Asn Thr Leu Phe Leu Thr Pro Ser Ser
            180                 185                 190
```

```
His Asp Asp Gly Ala Thr Leu Ile Cys Arg Ala Arg Ser Gln Ala Leu
        195                 200                 205

Pro Thr Gly Arg Asp Thr Ala Val Thr Leu Ser Leu Gln Tyr Pro Pro
    210                 215                 220

Met Val Thr Leu Ser Ala Glu Pro Gln Thr Val Gln Glu Gly Glu Lys
225                 230                 235                 240

Val Thr Phe Leu Cys Gln Ala Thr Ala Gln Pro Pro Val Thr Gly Tyr
                245                 250                 255

Arg Trp Ala Lys Gly Gly Ser Pro Val Leu Gly Ala Arg Gly Pro Arg
            260                 265                 270

Leu Glu Val Val Ala Asp Ala Thr Phe Leu Thr Glu Pro Val Ser Cys
        275                 280                 285

Glu Val Ser Asn Ala Val Gly Ser Ala Asn Arg Ser Thr Ala Leu Glu
    290                 295                 300

Val Leu Tyr Gly Pro Ile Leu Gln Ala Lys Pro Lys Ser Val Ser Val
305                 310                 315                 320

Asp Val Gly Lys Asp Ala Ser Phe Ser Cys Val Trp Arg Gly Asn Pro
                325                 330                 335

Leu Pro Arg Ile Thr Trp Thr Arg Met Gly Gly Ser Gln Val Leu Ser
            340                 345                 350

Ser Gly Pro Thr Leu Arg Leu Pro Ser Val Ala Leu Glu Asp Ala Gly
        355                 360                 365

Asp Tyr Val Cys Arg Ala Glu Pro Arg Arg Thr Gly Leu Gly Gly Gly
    370                 375                 380

Lys Ala Gln Ala Arg Leu Thr Val Asn Ala Pro Pro Val Val Thr Ala
385                 390                 395                 400

Leu Gln Pro Ala Pro Ala Phe Leu Arg Gly Pro Ala Arg Leu Gln Cys
                405                 410                 415

Val Val Phe Ala Ser Pro Ala Pro Asp Ser Val Val Trp Ser Trp Asp
            420                 425                 430

Glu Gly Phe Leu Glu Ala Gly Ser Leu Gly Arg Phe Leu Val Glu Ala
        435                 440                 445

Phe Pro Ala Pro Glu Val Glu Gly Gly Gln Gly Pro Gly Leu Ile Ser
    450                 455                 460

Val Leu His Ile Ser Gly Thr Gln Glu Ser Asp Phe Thr Thr Gly Phe
465                 470                 475                 480

Asn Cys Ser Ala Arg Asn Arg Leu Gly Glu Gly Arg Val Gln Ile His
                485                 490                 495

Leu Gly Arg Arg Asp Leu Leu Pro Thr Val Arg Ile Val Ala Gly Ala
            500                 505                 510

Ala Ser Ala Ala Thr Ser Leu Leu Met Val Ile Thr Gly Val Val Leu
        515                 520                 525

Cys Cys Trp Arg His Gly Ser Leu Ser Lys Gln Lys Asn Leu Val Arg
    530                 535                 540

Ile Pro Gly Ser Ser Glu Gly Ser Ser Ser Arg Gly Pro Glu Glu Glu
545                 550                 555                 560

Thr Gly Ser Ser Glu Asp Arg Gly Pro Ile Val His Thr Asp His Ser
                565                 570                 575

Asp Leu Val Leu Glu Glu Lys Glu Ala Leu Glu Thr Lys Asp Pro Thr
            580                 585                 590

Asn Gly Tyr Tyr Arg Val Arg Gly Val Ser Val Ser Leu Ser Leu Gly
        595                 600                 605

Glu Ala Pro Gly Gly Gly Leu Phe Leu Pro Pro Pro Ser Pro Ile Gly
    610                 615                 620
```

-continued

```
Leu Pro Gly Thr Pro Thr Tyr Tyr Asp Phe Lys Pro His Leu Asp Leu
625                 630                 635                 640

Val Pro Pro Cys Arg Leu Tyr Arg Ala Arg Ala Gly Tyr Leu Thr Thr
                645                 650                 655

Pro His Pro Arg Ala Phe Thr Ser Tyr Met Lys Pro Thr Ser Phe Gly
            660                 665                 670

Pro Pro Glu Leu Ser Ser Gly Thr Pro Pro Phe Pro Tyr Ala Thr Leu
        675                 680                 685

Ser Pro Pro Ser His Gln Arg Leu Gln Thr His Val
    690                 695                 700
```

```
<210> SEQ ID NO 35
<211> LENGTH: 2847
<212> TYPE: DNA
<213> ORGANISM: Mus musculus

<400> SEQUENCE: 35

ggtccggaat tcccgggatg agaggggctc cagtccagcg tggtgtgaga ggcgtgctat     60

caagaaagaa gttggagggg aaccagtgca accctaactc tgcgagatct tggggtacac    120

acactcggga tgctggcctc cgccctcctc gttttccttt gctgtttcaa aggacatgca    180

ggctcatcgc cccatttcct acaacagcca gaggacatgg tggtgctgtt gggggaggaa    240

gcccggctgc cctgcgctct gggcgcgtac agggggctcg tgcagtggac taaggatggg    300

ctggctctag gggcgaaag agaccttcca gggtggtccc ggtactggat atcggggaat    360

tcagccagtg gccagcatga cctccacatt aagcctgtgg aattggaaga tgaggcatcg    420

tatgagtgcc aggcttcgca agcaggtctc cgatcacgac cagcccaact gcacgtgatg    480

gtcccccag aagctcccca ggtactaggc ggcccctctg tgtctctggt tgctggagtt    540

cctggaaatc tgacctgtcg gagtcgtggg gattcacgac ctgcccctga actactgtgg    600

ttccgagatg ggatccggct ggatgggagc agcttccacc agaccacgct gaaggacaag    660

gccactggaa cagtggaaaa caccttattc ctgacccctt ccagtcatga tgatggtgcc    720

accttgatct gcagagcgcg aagccaggcc ctgcccacag ggagggacac agctgttaca    780

ctgagccttc agtatccccc aatggtgact ctgtctgctg agccccagac tgtgcaggag    840

ggagagaagg tgactttcct gtgtcaagcc actgcccagc ctcctgtcac tggctacagg    900

tgggcgaagg ggggatcccc ggtgcttggg gcacgtgggc caaggttgga ggtcgttgca    960

gatgccactt tcctgactga gccggtgtcc tgcgaggtca gcaacgcggt cggaagcgcc   1020

aaccgcagca ccgcgctgga agtgttgtat ggacccattc tgcaggcaaa acctaagtcc   1080

gtgtccgtgg acgtggggaa agatgcctcc ttcagctgtg tctggcgcgg gaacccactt   1140

ccacggataa cctggacccg catgggtggc tctcaggtgc tgagctccgg gcccacgctg   1200

cggcttccgt ccgtggcact ggaggatgcg ggcgactatg tatgcagggc tgagccgagg   1260

agaacgggtc tgggaggcgg caaagcgcag gcgaggctga ctgtgaacgc accccctgta   1320

gtgacagccc tgcaacctgc accagccttt ctgaggggtc ctgctcgcct ccagtgtgtg   1380

gtgtttgcct cccctgcccc agactcggtg gtttggtctt gggacgaggg cttcttggag   1440

gcaggctcac tgggcaggtt cctagtggaa gccttcccag ccccggaagt ggagggggga   1500

cagggccctg gccttatttc tgtgctacac atttccggaa cccaggagtc cgactttacc   1560

accggcttca actgcagtgc ccgcaaccgg ctaggagagg gacgagtcca gatccacttg   1620

ggccgtagag acttgctgcc tactgtccgg attgtggctg gtgcagcatc tgcagccacc   1680
```

```
tctctcctta tggtcatcac tggagtggtc ctctgctgct ggcgccatgg ctctctctct   1740

aagcaaaaga acttggtccg gatcccagga agcagcgagg gttccagttc acgtggccct   1800

gaggaggaga caggcagcag tgaggaccgg ggtcccattg tgcacaccga ccacagtgat   1860

ttggttcttg aggaaaaaga ggctctggag acaaaggatc caaccaacgg ttactacagg   1920

gttcgagggg tcagtgtgag ccttagcctt ggggaagctc ctggaggagg cctcttcttg   1980

ccaccgccct ctccgatcgg tctcccaggg actcctactt actatgactt caagccacat   2040

ctggacttag tccctccctg cagactgtac agagcgaggg caggttatct taccaccccc   2100

catccccgtg ccttcaccag ctacatgaaa cccacatcct ttggaccccc agaattgagc   2160

tctggaactc ccccttccc gtatgctacc ttgtctccac ccagccacca gcgtctccag   2220

actcatgtgt gaatccatct ctccaagtga agggtcttgg aatcttctgt ttgccatata   2280

gtgtgttgtc cagatttctg ggagtcaga acaagttgat gaccaacccc tccaaaactg   2340

aacattgaag gagggaaaga tcattacaag catcaggact gttggtgtac actcagttca   2400

gccaaagtgg attctccaag tgggagcaat atggccgctt tcccatgaga aagacattca   2460

agatggtgac taaatgacta aatactttgc agagggacaa agatgggaac tagggatatg   2520

gatggaagta gtagagaaga tatatgacca tctgcatcaa gagaaaggat aacataagac   2580

aaatcaagat gaaagaaata atccacaccc cccccccac cgcgtcctgg ccaataagta   2640

tagcctacat ggctgttcat tatctgggaa ccaaaatggc cactatcttg actccttcct   2700

taaagataca gaaagaattg aatccaagga atggggtagg gtggaaatag aagaaatgaa   2760

ggggactctt gggctaagaa tacttatgtt taataataaa agggggaggc aaagaaaaaa   2820

aaaaaaaaaa aaaaaaaaaa aaaaaaa                                       2847
```

<210> SEQ ID NO 36
<211> LENGTH: 700
<212> TYPE: PRT
<213> ORGANISM: Mus musculus

<400> SEQUENCE: 36

```
Met Leu Ala Ser Ala Leu Leu Val Phe Leu Cys Cys Phe Lys Gly His
1               5                   10                  15

Ala Gly Ser Ser Pro His Phe Leu Gln Gln Pro Glu Asp Met Val Val
            20                  25                  30

Leu Leu Gly Glu Glu Ala Arg Leu Pro Cys Ala Leu Gly Ala Tyr Arg
        35                  40                  45

Gly Leu Val Gln Trp Thr Lys Asp Gly Leu Ala Leu Gly Gly Glu Arg
    50                  55                  60

Asp Leu Pro Gly Trp Ser Arg Tyr Trp Ile Ser Gly Asn Ser Ala Ser
65                  70                  75                  80

Gly Gln His Asp Leu His Ile Lys Pro Val Glu Leu Glu Asp Glu Ala
                85                  90                  95

Ser Tyr Glu Cys Gln Ala Ser Gln Ala Gly Leu Arg Ser Arg Pro Ala
            100                 105                 110

Gln Leu His Val Met Val Pro Pro Glu Ala Pro Gln Val Leu Gly Gly
        115                 120                 125

Pro Ser Val Ser Leu Val Ala Gly Val Pro Gly Asn Leu Thr Cys Arg
    130                 135                 140

Ser Arg Gly Asp Ser Arg Pro Ala Pro Glu Leu Leu Trp Phe Arg Asp
145                 150                 155                 160

Gly Ile Arg Leu Asp Gly Ser Ser Phe His Gln Thr Thr Leu Lys Asp
                165                 170                 175
```

```
Lys Ala Thr Gly Thr Val Glu Asn Thr Leu Phe Leu Thr Pro Ser Ser
            180                 185                 190

His Asp Asp Gly Ala Thr Leu Ile Cys Arg Ala Arg Ser Gln Ala Leu
        195                 200                 205

Pro Thr Gly Arg Asp Thr Ala Val Thr Leu Ser Leu Gln Tyr Pro Pro
    210                 215                 220

Met Val Thr Leu Ser Ala Glu Pro Gln Thr Val Gln Glu Gly Glu Lys
225                 230                 235                 240

Val Thr Phe Leu Cys Gln Ala Thr Ala Gln Pro Pro Val Thr Gly Tyr
                245                 250                 255

Arg Trp Ala Lys Gly Gly Ser Pro Val Leu Gly Ala Arg Gly Pro Arg
            260                 265                 270

Leu Glu Val Val Ala Asp Ala Thr Phe Leu Thr Glu Pro Val Ser Cys
        275                 280                 285

Glu Val Ser Asn Ala Val Gly Ser Ala Asn Arg Ser Thr Ala Leu Glu
    290                 295                 300

Val Leu Tyr Gly Pro Ile Leu Gln Ala Lys Pro Lys Ser Val Ser Val
305                 310                 315                 320

Asp Val Gly Lys Asp Ala Ser Phe Ser Cys Val Trp Arg Gly Asn Pro
                325                 330                 335

Leu Pro Arg Ile Thr Trp Thr Arg Met Gly Gly Ser Gln Val Leu Ser
            340                 345                 350

Ser Gly Pro Thr Leu Arg Leu Pro Ser Val Ala Leu Glu Asp Ala Gly
        355                 360                 365

Asp Tyr Val Cys Arg Ala Glu Pro Arg Arg Thr Gly Leu Gly Gly Gly
    370                 375                 380

Lys Ala Gln Ala Arg Leu Thr Val Asn Ala Pro Pro Val Val Thr Ala
385                 390                 395                 400

Leu Gln Pro Ala Pro Ala Phe Leu Arg Gly Pro Ala Arg Leu Gln Cys
                405                 410                 415

Val Val Phe Ala Ser Pro Ala Pro Asp Ser Val Val Trp Ser Trp Asp
            420                 425                 430

Glu Gly Phe Leu Glu Ala Gly Ser Leu Gly Arg Phe Leu Val Glu Ala
        435                 440                 445

Phe Pro Ala Pro Glu Val Glu Gly Gly Gln Gly Pro Gly Leu Ile Ser
    450                 455                 460

Val Leu His Ile Ser Gly Thr Gln Glu Ser Asp Phe Thr Thr Gly Phe
465                 470                 475                 480

Asn Cys Ser Ala Arg Asn Arg Leu Gly Glu Gly Arg Val Gln Ile His
                485                 490                 495

Leu Gly Arg Arg Asp Leu Leu Pro Thr Val Arg Ile Val Ala Gly Ala
            500                 505                 510

Ala Ser Ala Ala Thr Ser Leu Leu Met Val Ile Thr Gly Val Val Leu
        515                 520                 525

Cys Cys Trp Arg His Gly Ser Leu Ser Lys Gln Lys Asn Leu Val Arg
    530                 535                 540

Ile Pro Gly Ser Ser Glu Gly Ser Ser Ser Arg Gly Pro Glu Glu Glu
545                 550                 555                 560

Thr Gly Ser Ser Glu Asp Arg Gly Pro Ile Val His Thr Asp His Ser
                565                 570                 575

Asp Leu Val Leu Glu Glu Lys Glu Ala Leu Glu Thr Lys Asp Pro Thr
            580                 585                 590

Asn Gly Tyr Tyr Arg Val Arg Gly Val Ser Val Ser Leu Ser Leu Gly
```

```
        595                 600                 605

Glu Ala Pro Gly Gly Gly Leu Phe Leu Pro Pro Pro Ser Pro Ile Gly
    610                 615                 620

Leu Pro Gly Thr Pro Thr Tyr Tyr Asp Phe Lys Pro His Leu Asp Leu
625                 630                 635                 640

Val Pro Pro Cys Arg Leu Tyr Arg Ala Arg Ala Gly Tyr Leu Thr Thr
                645                 650                 655

Pro His Pro Arg Ala Phe Thr Ser Tyr Met Lys Pro Thr Ser Phe Gly
            660                 665                 670

Pro Pro Glu Leu Ser Ser Gly Thr Pro Pro Phe Pro Tyr Ala Thr Leu
        675                 680                 685

Ser Pro Pro Ser His Gln Arg Leu Gln Thr His Val
    690                 695                 700


<210> SEQ ID NO 37
<211> LENGTH: 2153
<212> TYPE: DNA
<213> ORGANISM: Homo sapiens

<400> SEQUENCE: 37

ccgcggaact ggcaggcgtt tcagagcgtc agaggctgcg gatgagcaga cttggaggac     60

tccaggccag agactaggct gggcgaagag tcgagcgtga agggggctcc gggccagggt    120

gacaggaggc gtgcttgaga ggaagaagtt gacgggaagg ccagtgcgac ggcaaatctc    180

gtgaaccttg ggggacgaat gctcaggatg cgggtccccg ccctcctcgt cctcctcttc    240

tgcttcagag ggagagcagg cccgtcgccc catttcctgc aacagccaga ggacctggtg    300

gtgctgctgg gggaggaagc ccggctgccg tgtgctctgg gcgcctactg gggggctagtt    360

cagtggacta agagtgggct ggccctaggg ggccaaaggg acctaccagg gtggtcccgg    420

tactggatat cagggaatgc agccaatggc cagcatgacc tccacattag gcccgtggag    480

ctagaggatg aagcatcata tgaatgtcag gctacacaag caggcctccg ctccagacca    540

gcccaactgc acgtgctggt ccccccagaa gccccccagg tgctgggcgg cccctctgtg    600

tctctggttg ctggagttcc tgcgaacctg acatgtcgga gccgtgggga tgcccgccct    660

acccctgaat tgctgtggtt ccgagatggg gtcctgttgg atggagccac cttccatcag    720

accctgctga aggaagggac ccctgggtca gtggagagca ccttaaccct gacccctttc    780

agccatgatg atggagccac ctttgtctgc cgggcccgga gccaggccct gcccacagga    840

agagacacag ctatcacact gagcctgcag taccccccag aggtgactct gtctgcttcg    900

ccacacactg tgcaggaggg agagaaggtc attttcctgt gccaggccac agcccagcct    960

cctgtcacag gctacaggtg ggcaaaaggg ggctctccgg tgctcggggc ccgcgggcca   1020

aggttagagg tcgtggcaga cgcctcgttc ctgactgagc ccgtgtcctg cgaggtcagc   1080

aacgccgtgg gtagcgccaa ccgcagtact gcgctggatg tgctgtttgg gccgattctg   1140

caggcaaagc cggagcccgt gtccgtggac gtgggggaag acgcttcctt cagctgcgcc   1200

tggcgcggga acccgcttcc acgggtaacc tggacccgcc gcggtggcgc gcaggtgctg   1260

ggctctggag ccacactgcg tcttccgtcg gtggggcccg aggacgcagg cgactatgtg   1320

tgcagagctg aggctgggct atcgggcctg cggggcggcg ccgcggaggc tcggctgact   1380

gtgaacgctc cccagtagt gaccgccctg cactctgcgc ctgccttcct gaggggccct   1440

gctcgcctcc agtgtctggt tttcgcctct cccgccccag atgccgtggt ctggtcttgg   1500

gatgagggct tcctggaggc ggggtcgcag ggccggttcc tggtggagac attccctgcc   1560
```

```
ccagagagcc gcgggggact gggtccgggc ctgatctctg tgctacacat ttcggggacc   1620

caggagtctg actttagcag gagctttaac tgcagtgccc ggaaccggct gggcgaggga   1680

ggtgcccagg ccagcctggg ccgtagagac ttgctgccca ctgtgcggat agtggccgga   1740

gtggccgctg ccaccacaac tctccttatg gtcatcactg ggtggccct ctgctgctgg    1800

cgccacagca aggcctcagc ctctttctcc gagcaaaaga acctgatgcg aatccctggc   1860

agcagcgacg gctccagttc acgaggtcct gaagaagagg agacaggcag ccgcgaggac   1920

cggggcccca ttgtgcacac tgaccacagt gatctggttc tggaggagga agggactctg   1980

gagaccaagg acccaaccaa cggttactac aaggtccgag gagtcagtcc acccgcgtct   2040

ccagactcac gtgtgacatc tttccaatgg aagagtcctg ggatctccaa cttgccataa   2100

tggattgttc tgatttctga ggagccagga caagttggcg accttactcc tcc          2153
```

<210> SEQ ID NO 38
<211> LENGTH: 633
<212> TYPE: PRT
<213> ORGANISM: Homo sapiens

<400> SEQUENCE: 38

```
Met Leu Arg Met Arg Val Pro Ala Leu Leu Val Leu Leu Phe Cys Phe
1               5                   10                  15

Arg Gly Arg Ala Gly Pro Ser Pro His Phe Leu Gln Gln Pro Glu Asp
            20                  25                  30

Leu Val Val Leu Leu Gly Glu Glu Ala Arg Leu Pro Cys Ala Leu Gly
        35                  40                  45

Ala Tyr Trp Gly Leu Val Gln Trp Thr Lys Ser Gly Leu Ala Leu Gly
    50                  55                  60

Gly Gln Arg Asp Leu Pro Gly Trp Ser Arg Tyr Trp Ile Ser Gly Asn
65                  70                  75                  80

Ala Ala Asn Gly Gln His Asp Leu His Ile Arg Pro Val Glu Leu Glu
                85                  90                  95

Asp Glu Ala Ser Tyr Glu Cys Gln Ala Thr Gln Ala Gly Leu Arg Ser
            100                 105                 110

Arg Pro Ala Gln Leu His Val Leu Val Pro Pro Glu Ala Pro Gln Val
        115                 120                 125

Leu Gly Gly Pro Ser Val Ser Leu Val Ala Gly Val Pro Ala Asn Leu
    130                 135                 140

Thr Cys Arg Ser Arg Gly Asp Ala Arg Pro Thr Pro Glu Leu Leu Trp
145                 150                 155                 160

Phe Arg Asp Gly Val Leu Leu Asp Gly Ala Thr Phe His Gln Thr Leu
                165                 170                 175

Leu Lys Glu Gly Thr Pro Gly Ser Val Glu Ser Thr Leu Thr Leu Thr
            180                 185                 190

Pro Phe Ser His Asp Asp Gly Ala Thr Phe Val Cys Arg Ala Arg Ser
        195                 200                 205

Gln Ala Leu Pro Thr Gly Arg Asp Thr Ala Ile Thr Leu Ser Leu Gln
    210                 215                 220

Tyr Pro Pro Glu Val Thr Leu Ser Ala Ser Pro His Thr Val Gln Glu
225                 230                 235                 240

Gly Glu Lys Val Ile Phe Leu Cys Gln Ala Thr Ala Gln Pro Pro Val
                245                 250                 255

Thr Gly Tyr Arg Trp Ala Lys Gly Gly Ser Pro Val Leu Gly Ala Arg
            260                 265                 270

Gly Pro Arg Leu Glu Val Val Ala Asp Ala Ser Phe Leu Thr Glu Pro
```

```
        275                 280                 285

Val Ser Cys Glu Val Ser Asn Ala Val Gly Ser Ala Asn Arg Ser Thr
    290                 295                 300

Ala Leu Asp Val Leu Phe Gly Pro Ile Leu Gln Ala Lys Pro Glu Pro
305                 310                 315                 320

Val Ser Val Asp Val Gly Glu Asp Ala Ser Phe Ser Cys Ala Trp Arg
                325                 330                 335

Gly Asn Pro Leu Pro Arg Val Thr Trp Thr Arg Arg Gly Gly Ala Gln
            340                 345                 350

Val Leu Gly Ser Gly Ala Thr Leu Arg Leu Pro Ser Val Gly Pro Glu
        355                 360                 365

Asp Ala Gly Asp Tyr Val Cys Arg Ala Glu Ala Gly Leu Ser Gly Leu
    370                 375                 380

Arg Gly Gly Ala Ala Glu Ala Arg Leu Thr Val Asn Ala Pro Pro Val
385                 390                 395                 400

Val Thr Ala Leu His Ser Ala Pro Ala Phe Leu Arg Gly Pro Ala Arg
                405                 410                 415

Leu Gln Cys Leu Val Phe Ala Ser Pro Ala Pro Asp Ala Val Val Trp
            420                 425                 430

Ser Trp Asp Glu Gly Phe Leu Glu Ala Gly Ser Gln Gly Arg Phe Leu
        435                 440                 445

Val Glu Thr Phe Pro Ala Pro Glu Ser Arg Gly Gly Leu Gly Pro Gly
    450                 455                 460

Leu Ile Ser Val Leu His Ile Ser Gly Thr Gln Glu Ser Asp Phe Ser
465                 470                 475                 480

Arg Ser Phe Asn Cys Ser Ala Arg Asn Arg Leu Gly Glu Gly Gly Ala
                485                 490                 495

Gln Ala Ser Leu Gly Arg Arg Asp Leu Leu Pro Thr Val Arg Ile Val
            500                 505                 510

Ala Gly Val Ala Ala Ala Thr Thr Thr Leu Leu Met Val Ile Thr Gly
        515                 520                 525

Val Ala Leu Cys Cys Trp Arg His Ser Lys Ala Ser Ala Ser Phe Ser
    530                 535                 540

Glu Gln Lys Asn Leu Met Arg Ile Pro Gly Ser Ser Asp Gly Ser Ser
545                 550                 555                 560

Ser Arg Gly Pro Glu Glu Glu Glu Thr Gly Ser Arg Glu Asp Arg Gly
                565                 570                 575

Pro Ile Val His Thr Asp His Ser Asp Leu Val Leu Glu Glu Glu Gly
            580                 585                 590

Thr Leu Glu Thr Lys Asp Pro Thr Asn Gly Tyr Tyr Lys Val Arg Gly
        595                 600                 605

Val Ser Pro Pro Ala Ser Pro Asp Ser Arg Val Thr Ser Phe Gln Trp
    610                 615                 620

Lys Ser Pro Gly Ile Ser Asn Leu Pro
625                 630
```

<210> SEQ ID NO 39
<211> LENGTH: 2979
<212> TYPE: DNA
<213> ORGANISM: Homo sapiens

<400> SEQUENCE: 39

```
ccgcggaact ggcaggcgtt tcagagcgtc agaggctgcg gatgagcaga cttggaggac      60

tccaggccag agactaggct gggcgaagag tcgagcgtga agggggctcc gggccagggt     120
```

-continued

```
gacaggaggc gtgcttgaga ggaagaagtt gacgggaagg ccagtgcgac ggcaaatctc    180
gtgaaccttg ggggacgaat gctcaggatg cgggtccccg ccctcctcgt cctcctcttc    240
tgcttcagag ggagagcagg cccgtcgccc catttcctgc aacagccaga ggacctggtg    300
gtgctgctgg gggaggaagc ccggctgccg tgtgctctgg gcgcctactg ggggctagtt    360
cagtggacta agagtgggct ggccctaggg ggccaaaggg acctaccagg gtggtcccgg    420
tactggatat cagggaatgc agccaatggc cagcatgacc tccacattag gcccgtggag    480
ctagaggatg aagcatcata tgaatgtcag gctacacaag caggcctccg ctccagacca    540
gcccaactgc acgtgctggt ccccccagaa gccccccagg tgctgggcgg cccctctgtg    600
tctctggttg ctggagttcc tgcgaacctg acatgtcgga gccgtgggga tgcccgccct    660
acccctgaat tgctgtggtt ccgagatggg gtcctgttgg atggagccac cttccatcag    720
accctgctga aggaagggac ccctgggtca gtggagagca ccttaaccct gaccccttc     780
agccatgatg atggagccac ctttgtctgc cgggcccgga gccaggccct gcccacagga    840
agagacacag ctatcacact gagcctgcag tacccccag aggtgactct gtctgcttcg     900
ccacacactg tgcaggaggg agagaaggtc attttcctgt gccaggccac agcccagcct    960
cctgtcacag gctacaggtg ggcaaaaggg ggctctccgg tgctcggggc ccgcgggcca   1020
aggttagagg tcgtggcaga cgcctcgttc ctgactgagc ccgtgtcctg cgaggtcagc   1080
aacgccgtgg gtagcgccaa ccgcagtact gcgctggatg tgctgtttgg gccgattctg   1140
caggcaaagc cggagcccgt gtccgtggac gtgggggaag acgcttcctt cagctgcgcc   1200
tggcgcggga acccgcttcc acgggtaacc tggacccgcc gcggtggcgc gcaggtgctg   1260
ggctctggag ccacactgcg tcttccgtcg gtggggcccg aggacgcagg cgactatgtg   1320
tgcagagctg aggctgggct atcgggcctg cggggcggcg ccgcggaggc tcggctgact   1380
gtgaacgctc ccccagtagt gaccgccctg cactctgcgc ctgccttcct gaggggccct   1440
gctcgcctcc agtgtctggt tttcgcctct cccgccccag atgccgtggt ctggtcttgg   1500
gatgagggct tcctggaggc ggggtcgcag ggccggttcc tggtggagac attccctgcc   1560
ccagagagcc gcgggggact gggtccgggc ctgatctctg tgctacacat ttcggggacc   1620
caggagtctg actttagcag gagctttaac tgcagtgccc ggaaccggct gggcgaggga   1680
ggtgcccagg ccagcctggg ccgtagagac ttgctgccca ctgtgcggat agtggccgga   1740
gtggccgctg ccaccacaac tctccttatg gtcatcactg ggtggccct ctgctgctgg     1800
cgccacagca aggcctcagc ctctttctcc gagcaaaaga acctgatgcg aatccctggc   1860
agcagcgacg gctccagttc acgaggtcct gaagaagagg agacaggcag ccgcgaggac   1920
cggggcccca ttgtgcacac tgaccacagt gatctggttc tggaggagga agggactctg   1980
gagaccaagg acccaaccaa cggttactac aaggtccgag gagtcagtgt gagcctgagc   2040
cttggcgaag cccctggagg aggtctcttc ctgccaccac cctccccct tgggccccca    2100
gggaccccta ccttctatga cttcaaccca cacctgggca tggtcccccc ctgcagactt   2160
tacagagcca gggcaggcta tctcaccaca ccccaccctc gagctttcac cagctacatc   2220
aaacccacat cctttgggcc cccagatctg gcccccggga ctccccccctt cccatatgct  2280
gccttcccca cacctagcca cccgcgtctc cagactcacg tgtgacatct ttccaatgga   2340
agagtcctgg gatctccaac ttgccataat ggattgttct gatttctgag gagccaggac   2400
aagttggcga ccttactcct ccaaaactga acacaagggg agggaaagat cattacattt   2460
gtcaggagca tttgtataca gtcagctcag ccaaaggaga tgccccaagt gggagcaaca   2520
```

-continued

```
tggccaccca atatgcccac ctattccccg gtgtaaaaga gattcaagat ggcaggtagg   2580

ccctttgagg agagatgggg acagggcagt gggtgttggg agtttggggc cgggatggaa   2640

gttgtttcta gccactgaaa gaagatattt caagatgacc atctgcattg agaggaaagg   2700

tagcatagga tagatgaaga tgaagagcat accaggcccc accctggctc tccctgaggg   2760

gaactttgct cggccaatgg aaatgcagcc aagatggcca tatactccct aggaacccaa   2820

gatggccacc atcttgattt tactttcctt aaagactcag aaagacttgg acccaaggag   2880

tggggataca gtgagaatta ccactgttgg ggcaaaatat tgggataaaa atatttatgt   2940

ttaataataa aaaaaagtca aagaggcaaa aaaaaaaaa                         2979
```

```
<210> SEQ ID NO 40
<211> LENGTH: 708
<212> TYPE: PRT
<213> ORGANISM: Homo sapiens

<400> SEQUENCE: 40

Met Leu Arg Met Arg Val Pro Ala Leu Leu Val Leu Leu Phe Cys Phe
1               5                   10                  15

Arg Gly Arg Ala Gly Pro Ser Pro His Phe Leu Gln Gln Pro Glu Asp
            20                  25                  30

Leu Val Val Leu Leu Gly Glu Glu Ala Arg Leu Pro Cys Ala Leu Gly
        35                  40                  45

Ala Tyr Trp Gly Leu Val Gln Trp Thr Lys Ser Gly Leu Ala Leu Gly
    50                  55                  60

Gly Gln Arg Asp Leu Pro Gly Trp Ser Arg Tyr Trp Ile Ser Gly Asn
65                  70                  75                  80

Ala Ala Asn Gly Gln His Asp Leu His Ile Arg Pro Val Glu Leu Glu
                85                  90                  95

Asp Glu Ala Ser Tyr Glu Cys Gln Ala Thr Gln Ala Gly Leu Arg Ser
            100                 105                 110

Arg Pro Ala Gln Leu His Val Leu Val Pro Pro Glu Ala Pro Gln Val
        115                 120                 125

Leu Gly Gly Pro Ser Val Ser Leu Val Ala Gly Val Pro Ala Asn Leu
    130                 135                 140

Thr Cys Arg Ser Arg Gly Asp Ala Arg Pro Thr Pro Glu Leu Leu Trp
145                 150                 155                 160

Phe Arg Asp Gly Val Leu Leu Asp Gly Ala Thr Phe His Gln Thr Leu
                165                 170                 175

Leu Lys Glu Gly Thr Pro Gly Ser Val Glu Ser Thr Leu Thr Leu Thr
            180                 185                 190

Pro Phe Ser His Asp Asp Gly Ala Thr Phe Val Cys Arg Ala Arg Ser
        195                 200                 205

Gln Ala Leu Pro Thr Gly Arg Asp Thr Ala Ile Thr Leu Ser Leu Gln
    210                 215                 220

Tyr Pro Pro Glu Val Thr Leu Ser Ala Ser Pro His Thr Val Gln Glu
225                 230                 235                 240

Gly Glu Lys Val Ile Phe Leu Cys Gln Ala Thr Ala Gln Pro Pro Val
                245                 250                 255

Thr Gly Tyr Arg Trp Ala Lys Gly Gly Ser Pro Val Leu Gly Ala Arg
            260                 265                 270

Gly Pro Arg Leu Glu Val Val Ala Asp Ala Ser Phe Leu Thr Glu Pro
        275                 280                 285

Val Ser Cys Glu Val Ser Asn Ala Val Gly Ser Ala Asn Arg Ser Thr
    290                 295                 300
```

-continued

```
Ala Leu Asp Val Leu Phe Gly Pro Ile Leu Gln Ala Lys Pro Glu Pro
305                 310                 315                 320

Val Ser Val Asp Val Gly Glu Asp Ala Ser Phe Ser Cys Ala Trp Arg
                325                 330                 335

Gly Asn Pro Leu Pro Arg Val Thr Trp Thr Arg Arg Gly Gly Ala Gln
            340                 345                 350

Val Leu Gly Ser Gly Ala Thr Leu Arg Leu Pro Ser Val Gly Pro Glu
        355                 360                 365

Asp Ala Gly Asp Tyr Val Cys Arg Ala Glu Ala Gly Leu Ser Gly Leu
    370                 375                 380

Arg Gly Gly Ala Ala Glu Ala Arg Leu Thr Val Asn Ala Pro Pro Val
385                 390                 395                 400

Val Thr Ala Leu His Ser Ala Pro Ala Phe Leu Arg Gly Pro Ala Arg
                405                 410                 415

Leu Gln Cys Leu Val Phe Ala Ser Pro Ala Pro Asp Ala Val Val Trp
            420                 425                 430

Ser Trp Asp Glu Gly Phe Leu Glu Ala Gly Ser Gln Gly Arg Phe Leu
        435                 440                 445

Val Glu Thr Phe Pro Ala Pro Glu Ser Arg Gly Gly Leu Gly Pro Gly
    450                 455                 460

Leu Ile Ser Val Leu His Ile Ser Gly Thr Gln Glu Ser Asp Phe Ser
465                 470                 475                 480

Arg Ser Phe Asn Cys Ser Ala Arg Asn Arg Leu Gly Glu Gly Gly Ala
                485                 490                 495

Gln Ala Ser Leu Gly Arg Arg Asp Leu Leu Pro Thr Val Arg Ile Val
            500                 505                 510

Ala Gly Val Ala Ala Ala Thr Thr Thr Leu Leu Met Val Ile Thr Gly
        515                 520                 525

Val Ala Leu Cys Cys Trp Arg His Ser Lys Ala Ser Ala Ser Phe Ser
    530                 535                 540

Glu Gln Lys Asn Leu Met Arg Ile Pro Gly Ser Ser Asp Gly Ser Ser
545                 550                 555                 560

Ser Arg Gly Pro Glu Glu Glu Glu Thr Gly Ser Arg Glu Asp Arg Gly
                565                 570                 575

Pro Ile Val His Thr Asp His Ser Asp Leu Val Leu Glu Glu Glu Gly
            580                 585                 590

Thr Leu Glu Thr Lys Asp Pro Thr Asn Gly Tyr Tyr Lys Val Arg Gly
        595                 600                 605

Val Ser Val Ser Leu Ser Leu Gly Glu Ala Pro Gly Gly Gly Leu Phe
    610                 615                 620

Leu Pro Pro Pro Ser Pro Leu Gly Pro Pro Gly Thr Pro Thr Phe Tyr
625                 630                 635                 640

Asp Phe Asn Pro His Leu Gly Met Val Pro Pro Cys Arg Leu Tyr Arg
                645                 650                 655

Ala Arg Ala Gly Tyr Leu Thr Thr Pro His Pro Arg Ala Phe Thr Ser
            660                 665                 670

Tyr Ile Lys Pro Thr Ser Phe Gly Pro Pro Asp Leu Ala Pro Gly Thr
        675                 680                 685

Pro Pro Phe Pro Tyr Ala Ala Phe Pro Thr Pro Ser His Pro Arg Leu
    690                 695                 700

Gln Thr His Val
705
```

<210> SEQ ID NO 41
<211> LENGTH: 2973
<212> TYPE: DNA
<213> ORGANISM: Homo sapiens

<400> SEQUENCE: 41

```
ccgcggaact ggcaggcgtt tcagagcgtc agaggctgcg gatgagcaga cttggaggac     60
tccaggccag agactaggct gggcgaagag tcgagcgtga agggggctcc gggccagggt    120
gacaggaggc gtgcttgaga ggaagaagtt gacgggaagg ccagtgcgac ggcaaatctc    180
gtgaaccttg ggggacgaat gctcaggatg cgggtccccg ccctcctcgt cctcctcttc    240
tgcttcagag ggagagcagg cccgtcgccc catttcctgc aacagccaga ggacctggtg    300
gtgctgctgg gggaggaagc ccggctgccg tgtgctctgg gcgcctactg gggctagtt     360
cagtggacta agagtgggct ggccctaggg ggccaaaggg acctaccagg gtggtcccgg    420
tactggatat cagggaatgc agccaatggc cagcatgacc tccacattag gcccgtggag    480
ctagaggatg aagcatcata tgaatgtcag gctacacaag caggcctccg ctccagacca    540
gcccaactgc acgtgctggt cccccagaa gcccccagg tgctgggcgg cccctctgtg     600
tctctggttg ctggagttcc tgcgaacctg acatgtcgga gccgtgggga tgcccgccct    660
acccctgaat tgctgtggtt ccgagatggg gtcctgttgg atggagccac ctttcatcag    720
accctgctga aggaagggac ccctgggtca gtggagagca ccttaaccct gacccctttc    780
agccatgatg atggagccac ctttgtctgc cgggcccgga gccaggccct gcccacagga    840
agagacacag ctatcacact gagcctgcag taccccccag aggtgactct gtctgcttcg    900
ccacacactg tgcaggaggg agagaaggtc attttcctgt gccaggccac agcccagcct    960
cctgtcacag gctacaggtg ggcaaaaggg ggctctccgg tgctcggggc ccgcgggcca   1020
aggttagagg tcgtggcaga cgcctcgttc ctgactgagc ccgtgtcctg cgaggtcagc   1080
aacgccgtgg gtagcgccaa ccgcagtact gcgctggatg tgctgtttgg gccgattctg   1140
caggcaaagc cggagcccgt gtccgtggac gtgggggaag acgcttcctt cagctgcgcc   1200
tggcgcggga acccgcttcc acgggtaacc tggacccgcc gcggtggcgc gcaggtgctg   1260
ggctctggag ccacactgcg tcttccgtcg gtggggcccg aggacgcagg cgactatgtg   1320
tgcagagctg aggctgggct atcgggcctg cggggcggcg ccgcggaggc tcggctgact   1380
gtgaacgctc ccccagtagt gaccgccctg cactctgcgc ctgccttcct gaggggccct   1440
gctcgcctcc agtgtctggt tttcgcctct cccgccccag atgccgtggt ctggtcttgg   1500
gatgagggct tcctggaggc ggggtcgcag ggccggttcc tggtggagac attccctgcc   1560
ccagagagcc gcgggggact gggtccgggc ctgatctctg tgctacacat ttcggggacc   1620
caggagtctg actttagcag gagctttaac tgcagtgccc ggaaccggct gggcgaggga   1680
ggtgcccagg ccagcctggg ccgtagagac ttgctgccca ctgtgcggat agtggccgga   1740
gtggccgctg ccaccacaac tctccttatg gtcatcactg ggtggccct ctgctgctgg    1800
cgccacagca aggcctcagc ctctttctcc gagcaaaaga acctgatgcg aatccctggc   1860
agcagcgacg gctccagttc acgaggtcct gaagaagagg agacaggcag ccgcgaggac   1920
cggggcccca ttgtgcacac tgaccacagt gatctggttc tggaggagga agggactctg   1980
gagaccaagg acccaaccaa cggttactac aaggtccgag gagtcagtgt gagcctgagc   2040
cttggcgaag cccctggagg aggtctcttc ctgccaccac cctcccccct tgggccccca   2100
gggaccccta ccttctatga cttcaaccca cacctgggca tggtcccccc ctgcagactt   2160
tacagagcca gggcaggcta tctcaccaca ccccaccctc gagctttcac cagctacatc   2220
```

```
aaacccacat cctttgggcc cccagatctg gcccccggga ctcccccctt cccatatgct   2280

gccttcccca cacctagcca cccgcgtctc cagactcacg tgtgacatct ttccaatgga   2340

agagtcctgg gatctccaac ttgccataat ggattgttct gatttctgag gagccaggac   2400

aagttggcga ccttactcct ccaaaactga acacaagggg agggaaagat cattacattt   2460

gtcaggagca tttgtataca gtcagctcag ccaaaggaga tgccccaagt gggagcaaca   2520

tggccaccca atatgcccac ctattccccg gtgtaaaaga gattcaagat ggcaggtagg   2580

ccctttgagg agagatgggg acagggcagt gggtgttggg agtttggggc cgggatggaa   2640

gttgtttcta gccactgaaa gaagatattt caagatgacc atctgcattg agaggaaagg   2700

tagcatagga tagatgaaga tgaagagcat accaggcccc accctggctc tccctgaggg   2760

gaactttgct cggccaatgg aaatgcagcc aagatggcca tatactccct aggaacccaa   2820

aatggccacc atcttgattt tactttcctt aaagactcag aaagacttgg acccaaggag   2880

tggggataca gtgagaatta ccactgttgg ggcaaaatat tgggataaaa atatttatgt   2940

ttaataataa aaaaaagtca aagagaaaaa aaa                                 2973
```

<210> SEQ ID NO 42
<211> LENGTH: 708
<212> TYPE: PRT
<213> ORGANISM: Homo sapiens

<400> SEQUENCE: 42

```
Met Leu Arg Met Arg Val Pro Ala Leu Leu Val Leu Leu Phe Cys Phe
1               5                   10                  15

Arg Gly Arg Ala Gly Pro Ser Pro His Phe Leu Gln Gln Pro Glu Asp
            20                  25                  30

Leu Val Val Leu Leu Gly Glu Glu Ala Arg Leu Pro Cys Ala Leu Gly
        35                  40                  45

Ala Tyr Trp Gly Leu Val Gln Trp Thr Lys Ser Gly Leu Ala Leu Gly
    50                  55                  60

Gly Gln Arg Asp Leu Pro Gly Trp Ser Arg Tyr Trp Ile Ser Gly Asn
65                  70                  75                  80

Ala Ala Asn Gly Gln His Asp Leu His Ile Arg Pro Val Glu Leu Glu
                85                  90                  95

Asp Glu Ala Ser Tyr Glu Cys Gln Ala Thr Gln Ala Gly Leu Arg Ser
            100                 105                 110

Arg Pro Ala Gln Leu His Val Leu Val Pro Pro Glu Ala Pro Gln Val
        115                 120                 125

Leu Gly Gly Pro Ser Val Ser Leu Val Ala Gly Val Pro Ala Asn Leu
    130                 135                 140

Thr Cys Arg Ser Arg Gly Asp Ala Arg Pro Thr Pro Glu Leu Leu Trp
145                 150                 155                 160

Phe Arg Asp Gly Val Leu Leu Asp Gly Ala Thr Phe His Gln Thr Leu
                165                 170                 175

Leu Lys Glu Gly Thr Pro Gly Ser Val Glu Ser Thr Leu Thr Leu Thr
            180                 185                 190

Pro Phe Ser His Asp Asp Gly Ala Thr Phe Val Cys Arg Ala Arg Ser
        195                 200                 205

Gln Ala Leu Pro Thr Gly Arg Asp Thr Ala Ile Thr Leu Ser Leu Gln
    210                 215                 220

Tyr Pro Pro Glu Val Thr Leu Ser Ala Ser Pro His Thr Val Gln Glu
225                 230                 235                 240
```

-continued

```
Gly Glu Lys Val Ile Phe Leu Cys Gln Ala Thr Ala Gln Pro Pro Val
                245                 250                 255

Thr Gly Tyr Arg Trp Ala Lys Gly Gly Ser Pro Val Leu Gly Ala Arg
            260                 265                 270

Gly Pro Arg Leu Glu Val Val Ala Asp Ala Ser Phe Leu Thr Glu Pro
        275                 280                 285

Val Ser Cys Glu Val Ser Asn Ala Val Gly Ser Ala Asn Arg Ser Thr
    290                 295                 300

Ala Leu Asp Val Leu Phe Gly Pro Ile Leu Gln Ala Lys Pro Glu Pro
305                 310                 315                 320

Val Ser Val Asp Val Gly Glu Asp Ala Ser Phe Ser Cys Ala Trp Arg
                325                 330                 335

Gly Asn Pro Leu Pro Arg Val Thr Trp Thr Arg Arg Gly Gly Ala Gln
            340                 345                 350

Val Leu Gly Ser Gly Ala Thr Leu Arg Leu Pro Ser Val Gly Pro Glu
        355                 360                 365

Asp Ala Gly Asp Tyr Val Cys Arg Ala Glu Ala Gly Leu Ser Gly Leu
    370                 375                 380

Arg Gly Gly Ala Ala Glu Ala Arg Leu Thr Val Asn Ala Pro Pro Val
385                 390                 395                 400

Val Thr Ala Leu His Ser Ala Pro Ala Phe Leu Arg Gly Pro Ala Arg
                405                 410                 415

Leu Gln Cys Leu Val Phe Ala Ser Pro Ala Pro Asp Ala Val Val Trp
            420                 425                 430

Ser Trp Asp Glu Gly Phe Leu Glu Ala Gly Ser Gln Gly Arg Phe Leu
        435                 440                 445

Val Glu Thr Phe Pro Ala Pro Glu Ser Arg Gly Gly Leu Gly Pro Gly
    450                 455                 460

Leu Ile Ser Val Leu His Ile Ser Gly Thr Gln Glu Ser Asp Phe Ser
465                 470                 475                 480

Arg Ser Phe Asn Cys Ser Ala Arg Asn Arg Leu Gly Glu Gly Gly Ala
                485                 490                 495

Gln Ala Ser Leu Gly Arg Arg Asp Leu Leu Pro Thr Val Arg Ile Val
            500                 505                 510

Ala Gly Val Ala Ala Ala Thr Thr Thr Leu Leu Met Val Ile Thr Gly
        515                 520                 525

Val Ala Leu Cys Cys Trp Arg His Ser Lys Ala Ser Ala Ser Phe Ser
    530                 535                 540

Glu Gln Lys Asn Leu Met Arg Ile Pro Gly Ser Ser Asp Gly Ser Ser
545                 550                 555                 560

Ser Arg Gly Pro Glu Glu Glu Glu Thr Gly Ser Arg Glu Asp Arg Gly
                565                 570                 575

Pro Ile Val His Thr Asp His Ser Asp Leu Val Leu Glu Glu Glu Gly
            580                 585                 590

Thr Leu Glu Thr Lys Asp Pro Thr Asn Gly Tyr Tyr Lys Val Arg Gly
        595                 600                 605

Val Ser Val Ser Leu Ser Leu Gly Glu Ala Pro Gly Gly Gly Leu Phe
    610                 615                 620

Leu Pro Pro Pro Ser Pro Leu Gly Pro Pro Gly Thr Pro Thr Phe Tyr
625                 630                 635                 640

Asp Phe Asn Pro His Leu Gly Met Val Pro Pro Cys Arg Leu Tyr Arg
                645                 650                 655

Ala Arg Ala Gly Tyr Leu Thr Thr Pro His Pro Arg Ala Phe Thr Ser
            660                 665                 670
```

```
Tyr Ile Lys Pro Thr Ser Phe Gly Pro Pro Asp Leu Ala Pro Gly Thr
        675                 680                 685

Pro Pro Phe Pro Tyr Ala Ala Phe Pro Thr Pro Ser His Pro Arg Leu
    690                 695                 700

Gln Thr His Val
705


<210> SEQ ID NO 43
<211> LENGTH: 1969
<212> TYPE: DNA
<213> ORGANISM: Homo sapiens

<400> SEQUENCE: 43

accttggggg acgaatgctc aggatgcggg tccccgccct cctcgtcctc ctcttctgct      60

tcagagggag agcaggcccg tcgccccatt tcctgcaaca gccagaggac ctggtggtgc     120

tgctggggga ggaagcccgg ctgccgtgtg ctctgggcgc ctactggggg ctagttcagt     180

ggactaagag tgggctggcc ctagggggcc aaagggacct accagggtgg tcccggtact     240

ggatatcagg gaatgcagcc aatggccagc atgacctcca cattaggccc gtggagctag     300

aggatgaagc atcatatgaa tgtcaggcta cacaagcagg cctccgctcc agaccagccc     360

aactgcacgt gctggtcccc ccagaagccc cccaggtgct gggcggcccc tctgtgtctc     420

tggttgctgg agttcctgcg aacctgacat gtcggagccg tggggatgcc cgccctaccc     480

ctgaattgct gtggttccga gatggggtcc tgttggatgg agccaccttc catcagaccc     540

tgctgaagga agggacccct gggtcagtgg agagcacctt aaccctgacc cctttcagcc     600

atgatgatgg agccaccctt gtctgccggg cccggagcca ggccctgccc acaggaagag     660

acacagctat cacactgagc ctgcagtacc ccccagaggt gactctgtct gcttcgccac     720

acactgtgca ggagggagag aaggtcattt tcctgtgcca ggccacagcc cagcctcctg     780

tcacaggcta caggtgggca aaagggggct ctccggtgct cggggcccgc gggccaaggt     840

tagaggtcgt ggcagacgcc tcgttcctga ctgagcccgt gtcctgcgag gtcagcaacg     900

ccgtgggtag cgccaaccgc agtactgcgc tggatgtgct gtttgggccg attctgcagg     960

caaagccgga gcccgtgtcc gtggacgtgg gggaagacgc ttccttcagc tgcgcctggc    1020

gcgggaatcc gcttccacgg gtaacctgga cccgccgcgg tggcgcgcag gtgctgggct    1080

ctggagccac actgcgtctt ccgtcggtgg ggcccgagga cgcagacgac tatgtgtgca    1140

gagctgaggc tgggctatcg ggcctgcggg gcggcgccgc ggaggctcgg ctgactgtga    1200

acgctccccc agtagtgacc gccctgcact ctgcgcctgc cttcctgagg ggccctgctc    1260

gcctccagtg tctggttttc gcctctcccg ccccagatgc cgtggtctgg tcttgggatg    1320

agggcttcct ggaggcgggg tcgcagggtc ggttcctggt ggagacattc cctgccccag    1380

agagccgcgg gggactgggt ccgggcctga tctctgtgct acacatttcg gggacccagg    1440

agtctgactt tagcaggagc tttaactgca gtgcccggaa ccggctgggc gagggaggtg    1500

cccaggccag cctgggccgt agagacttgc tgcccactgt gcggatagtg gccggagtgg    1560

tcgctgccac cacaactctc cttatggtca tcactggggt ggccctctgc tgctggcgcc    1620

acagcaaggc ctcagcctct ttctccgagc aaaagaacct gatgcgaatc cctggcagca    1680

gcgacggctc cagttcacga ggtcctgaag aagaggagac aggcagccgc gaggaccggg    1740

gccccattgt gcacactgac cacagtgatc tggttctgga ggaggaaggg actctggaga    1800

ccaaggaccc aaccaacggt tactacaagg tccgaggagt cagtccaccc gcgtctccag    1860
```

actcacgtgt gacatctttc caatggaaga gtcctgggat ctccaacttg ccataatgga 1920
ttgttctgat ttctgaggag ccaggacaag ttggcgacct tactcctcc 1969

<210> SEQ ID NO 44
<211> LENGTH: 633
<212> TYPE: PRT
<213> ORGANISM: Homo sapiens

<400> SEQUENCE: 44

Met Leu Arg Met Arg Val Pro Ala Leu Leu Val Leu Leu Phe Cys Phe
1 5 10 15

Arg Gly Arg Ala Gly Pro Ser Pro His Phe Leu Gln Gln Pro Glu Asp
20 25 30

Leu Val Val Leu Leu Gly Glu Glu Ala Arg Leu Pro Cys Ala Leu Gly
35 40 45

Ala Tyr Trp Gly Leu Val Gln Trp Thr Lys Ser Gly Leu Ala Leu Gly
50 55 60

Gly Gln Arg Asp Leu Pro Gly Trp Ser Arg Tyr Trp Ile Ser Gly Asn
65 70 75 80

Ala Ala Asn Gly Gln His Asp Leu His Ile Arg Pro Val Glu Leu Glu
85 90 95

Asp Glu Ala Ser Tyr Glu Cys Gln Ala Thr Gln Ala Gly Leu Arg Ser
100 105 110

Arg Pro Ala Gln Leu His Val Leu Val Pro Pro Glu Ala Pro Gln Val
115 120 125

Leu Gly Gly Pro Ser Val Ser Leu Val Ala Gly Val Pro Ala Asn Leu
130 135 140

Thr Cys Arg Ser Arg Gly Asp Ala Arg Pro Thr Pro Glu Leu Leu Trp
145 150 155 160

Phe Arg Asp Gly Val Leu Leu Asp Gly Ala Thr Phe His Gln Thr Leu
165 170 175

Leu Lys Glu Gly Thr Pro Gly Ser Val Glu Ser Thr Leu Thr Leu Thr
180 185 190

Pro Phe Ser His Asp Asp Gly Ala Thr Leu Val Cys Arg Ala Arg Ser
195 200 205

Gln Ala Leu Pro Thr Gly Arg Asp Thr Ala Ile Thr Leu Ser Leu Gln
210 215 220

Tyr Pro Pro Glu Val Thr Leu Ser Ala Ser Pro His Thr Val Gln Glu
225 230 235 240

Gly Glu Lys Val Ile Phe Leu Cys Gln Ala Thr Ala Gln Pro Pro Val
245 250 255

Thr Gly Tyr Arg Trp Ala Lys Gly Gly Ser Pro Val Leu Gly Ala Arg
260 265 270

Gly Pro Arg Leu Glu Val Val Ala Asp Ala Ser Phe Leu Thr Glu Pro
275 280 285

Val Ser Cys Glu Val Ser Asn Ala Val Gly Ser Ala Asn Arg Ser Thr
290 295 300

Ala Leu Asp Val Leu Phe Gly Pro Ile Leu Gln Ala Lys Pro Glu Pro
305 310 315 320

Val Ser Val Asp Val Gly Glu Asp Ala Ser Phe Ser Cys Ala Trp Arg
325 330 335

Gly Asn Pro Leu Pro Arg Val Thr Trp Thr Arg Arg Gly Gly Ala Gln
340 345 350

Val Leu Gly Ser Gly Ala Thr Leu Arg Leu Pro Ser Val Gly Pro Glu
355 360 365

```
Asp Ala Asp Asp Tyr Val Cys Arg Ala Glu Ala Gly Leu Ser Gly Leu
    370                 375                 380

Arg Gly Gly Ala Ala Glu Ala Arg Leu Thr Val Asn Ala Pro Pro Val
385                 390                 395                 400

Val Thr Ala Leu His Ser Ala Pro Ala Phe Leu Arg Gly Pro Ala Arg
                405                 410                 415

Leu Gln Cys Leu Val Phe Ala Ser Pro Ala Pro Asp Ala Val Val Trp
            420                 425                 430

Ser Trp Asp Glu Gly Phe Leu Glu Ala Gly Ser Gln Gly Arg Phe Leu
        435                 440                 445

Val Glu Thr Phe Pro Ala Pro Glu Ser Arg Gly Gly Leu Gly Pro Gly
    450                 455                 460

Leu Ile Ser Val Leu His Ile Ser Gly Thr Gln Glu Ser Asp Phe Ser
465                 470                 475                 480

Arg Ser Phe Asn Cys Ser Ala Arg Asn Arg Leu Gly Glu Gly Gly Ala
                485                 490                 495

Gln Ala Ser Leu Gly Arg Arg Asp Leu Leu Pro Thr Val Arg Ile Val
            500                 505                 510

Ala Gly Val Val Ala Ala Thr Thr Thr Leu Leu Met Val Ile Thr Gly
        515                 520                 525

Val Ala Leu Cys Cys Trp Arg His Ser Lys Ala Ser Ala Ser Phe Ser
    530                 535                 540

Glu Gln Lys Asn Leu Met Arg Ile Pro Gly Ser Ser Asp Gly Ser Ser
545                 550                 555                 560

Ser Arg Gly Pro Glu Glu Glu Glu Thr Gly Ser Arg Glu Asp Arg Gly
                565                 570                 575

Pro Ile Val His Thr Asp His Ser Asp Leu Val Leu Glu Glu Glu Gly
            580                 585                 590

Thr Leu Glu Thr Lys Asp Pro Thr Asn Gly Tyr Tyr Lys Val Arg Gly
        595                 600                 605

Val Ser Pro Pro Ala Ser Pro Asp Ser Arg Val Thr Ser Phe Gln Trp
    610                 615                 620

Lys Ser Pro Gly Ile Ser Asn Leu Pro
625                 630
```

<210> SEQ ID NO 45
<211> LENGTH: 2003
<212> TYPE: DNA
<213> ORGANISM: Homo sapiens

<400> SEQUENCE: 45

```
ccgcggaact ggcaggcgtt tcagagcgtc agaggctgcg gatgagcaga cttggaggac     60

tccaggccag agactaggct gggcgaagag tcgagcgtga agggggctcc gggccagggt    120

gacaggaggc gtgcttgaga ggaagaagtt gacgggaagg ccagtgcgac ggcaaatctc    180

gtgaaccttg ggggacgaat gctcaggatg cgggtccccg ccctcctcgt cctcctcttc    240

tgcttcagag ggagagcagg gtggtcccgg tactggatat cagggaatgc agccaatggc    300

cagcatgacc tccacattag gcccgtggag ctagaggatg aagcatcata tgaatgtcag    360

gctacacaag caggcctccg ctccagacca gcccaactgc acgtgctggt cccccccagaa   420

gccccccagg tgctgggcgg cccctctgtg tctctggttg ctggagttcc tgcgaacctg    480

acatgtcgga gccgtgggga tgcccgccct accccctgaat tgctgtggtt ccgagatggg   540

gtcctgttgg atggagccac cttccatcag accctgctga aggaagggac ccctgggtca    600
```

gtggagagca ccttaaccct gacccctttc agccatgatg atggagccac ctttgtctgc 660
cgggcccgga gccaggccct gcccacagga agagacacag ctatcacact gagcctgcag 720
taccccccag aggtgactct gtctgcttcg ccacacactg tgcaggaggg agagaaggtc 780
attttcctgt gccaggccac agcccagcct cctgtcacag gctacaggtg ggcaaaaggg 840
ggctctccgg tgctcggggc ccgcgggcca aggttagagg tcgtggcaga cgcctcgttc 900
ctgactgagc ccgtgtcctg cgaggtcagc aacgccgtgg gtagcgccaa ccgcagtact 960
gcgctggatg tgctgtttgg gccgattctg caggcaaagc cggagcccgt gtccgtggac 1020
gtgggggaag acgcttcctt cagctgcgcc tggcgcggga acccgcttcc acgggtaacc 1080
tggacccgcc gcggtggcgc gcaggtgctg ggctctggag ccacactgcg tcttccgtcg 1140
gtggggcccg aggacgcagg cgactatgtg tgcagagctg aggctgggct atcgggcctg 1200
cggggcggcg ccgcggaggc tcggctgact gtgaacgctc ccccagtagt gaccgccctg 1260
cactctgcgc ctgccttcct gaggggccct gctcgcctcc agtgtctggt tttcgcctct 1320
cccgccccag atgccgtggt ctggtcttgg gatgagggct tcctggaggc ggggtcgcag 1380
ggccggttcc tggtggagac attccctgcc ccagagagcc gcgggggact gggtccgggc 1440
ctgatctctg tgctacacat ttcggggacc caggagtctg actttagcag gagctttaac 1500
tgcagtgccc ggaaccggct gggcgaggga ggtgcccagg ccagcctggg ccgtagagac 1560
ttgctgccca ctgtgcggat agtggccgga gtggccgctg ccaccacaac tctccttatg 1620
gtcatcactg ggtggccct ctgctgctgg cgccacagca aggcctcagc ctctttctcc 1680
gagcaaaaga acctgatgcg aatccctggc agcagcgacg gctccagttc acgaggtcct 1740
gaagaagagg agacaggcag ccgcgaggac cggggcccca ttgtgcacac tgaccacagt 1800
gatctggttc tggaggagga agggactctg gagaccaagg acccaaccaa cggttactac 1860
aaggtccgag gagtcagtcc acccgcgtct ccagactcac gtgtgacatc tttccaatgg 1920
aagagtcctg ggatctccaa cttgccataa tggattgttc tgatttctga ggagccagga 1980
caagttggcg accttactcc tcc 2003

<210> SEQ ID NO 46
<211> LENGTH: 583
<212> TYPE: PRT
<213> ORGANISM: Homo sapiens

<400> SEQUENCE: 46

Met Leu Arg Met Arg Val Pro Ala Leu Leu Val Leu Leu Phe Cys Phe
1 5 10 15

Arg Gly Arg Ala Gly Trp Ser Arg Tyr Trp Ile Ser Gly Asn Ala Ala
20 25 30

Asn Gly Gln His Asp Leu His Ile Arg Pro Val Glu Leu Glu Asp Glu
35 40 45

Ala Ser Tyr Glu Cys Gln Ala Thr Gln Ala Gly Leu Arg Ser Arg Pro
50 55 60

Ala Gln Leu His Val Leu Val Pro Pro Glu Ala Pro Gln Val Leu Gly
65 70 75 80

Gly Pro Ser Val Ser Leu Val Ala Gly Val Pro Ala Asn Leu Thr Cys
85 90 95

Arg Ser Arg Gly Asp Ala Arg Pro Thr Pro Glu Leu Leu Trp Phe Arg
100 105 110

Asp Gly Val Leu Leu Asp Gly Ala Thr Phe His Gln Thr Leu Leu Lys
115 120 125

```
Glu Gly Thr Pro Gly Ser Val Glu Ser Thr Leu Thr Leu Thr Pro Phe
    130                 135                 140

Ser His Asp Asp Gly Ala Thr Phe Val Cys Arg Ala Arg Ser Gln Ala
145                 150                 155                 160

Leu Pro Thr Gly Arg Asp Thr Ala Ile Thr Leu Ser Leu Gln Tyr Pro
                165                 170                 175

Pro Glu Val Thr Leu Ser Ala Ser Pro His Thr Val Gln Glu Gly Glu
            180                 185                 190

Lys Val Ile Phe Leu Cys Gln Ala Thr Ala Gln Pro Pro Val Thr Gly
        195                 200                 205

Tyr Arg Trp Ala Lys Gly Gly Ser Pro Val Leu Gly Ala Arg Gly Pro
    210                 215                 220

Arg Leu Glu Val Val Ala Asp Ala Ser Phe Leu Thr Glu Pro Val Ser
225                 230                 235                 240

Cys Glu Val Ser Asn Ala Val Gly Ser Ala Asn Arg Ser Thr Ala Leu
                245                 250                 255

Asp Val Leu Phe Gly Pro Ile Leu Gln Ala Lys Pro Glu Pro Val Ser
            260                 265                 270

Val Asp Val Gly Glu Asp Ala Ser Phe Ser Cys Ala Trp Arg Gly Asn
        275                 280                 285

Pro Leu Pro Arg Val Thr Trp Thr Arg Arg Gly Gly Ala Gln Val Leu
    290                 295                 300

Gly Ser Gly Ala Thr Leu Arg Leu Pro Ser Val Gly Pro Glu Asp Ala
305                 310                 315                 320

Gly Asp Tyr Val Cys Arg Ala Glu Ala Gly Leu Ser Gly Leu Arg Gly
                325                 330                 335

Gly Ala Ala Glu Ala Arg Leu Thr Val Asn Ala Pro Pro Val Val Thr
            340                 345                 350

Ala Leu His Ser Ala Pro Ala Phe Leu Arg Gly Pro Ala Arg Leu Gln
        355                 360                 365

Cys Leu Val Phe Ala Ser Pro Ala Pro Asp Ala Val Val Trp Ser Trp
    370                 375                 380

Asp Glu Gly Phe Leu Glu Ala Gly Ser Gln Gly Arg Phe Leu Val Glu
385                 390                 395                 400

Thr Phe Pro Ala Pro Glu Ser Arg Gly Gly Leu Gly Pro Gly Leu Ile
                405                 410                 415

Ser Val Leu His Ile Ser Gly Thr Gln Glu Ser Asp Phe Ser Arg Ser
            420                 425                 430

Phe Asn Cys Ser Ala Arg Asn Arg Leu Gly Glu Gly Gly Ala Gln Ala
        435                 440                 445

Ser Leu Gly Arg Arg Asp Leu Leu Pro Thr Val Arg Ile Val Ala Gly
    450                 455                 460

Val Ala Ala Ala Thr Thr Thr Leu Leu Met Val Ile Thr Gly Val Ala
465                 470                 475                 480

Leu Cys Cys Trp Arg His Ser Lys Ala Ser Ala Ser Phe Ser Glu Gln
                485                 490                 495

Lys Asn Leu Met Arg Ile Pro Gly Ser Ser Asp Gly Ser Ser Ser Arg
            500                 505                 510

Gly Pro Glu Glu Glu Glu Thr Gly Ser Arg Glu Asp Arg Gly Pro Ile
        515                 520                 525

Val His Thr Asp His Ser Asp Leu Val Leu Glu Glu Glu Gly Thr Leu
    530                 535                 540

Glu Thr Lys Asp Pro Thr Asn Gly Tyr Tyr Lys Val Arg Gly Val Ser
545                 550                 555                 560
```

```
Pro Pro Ala Ser Pro Asp Ser Arg Val Thr Ser Phe Gln Trp Lys Ser
            565                 570                 575

Pro Gly Ile Ser Asn Leu Pro
        580


<210> SEQ ID NO 47
<211> LENGTH: 1819
<212> TYPE: DNA
<213> ORGANISM: Homo sapiens

<400> SEQUENCE: 47

accttggggg acgaatgctc tggatgcggg tccccgccct cctcgtcctc ctcttctgct      60

tcagagggag agcagggtgg tcccggtact ggatatcagg gaatgcagcc aatggccagc     120

atgacctcca cattaggccc gtggagctag aggatgaagc atcatatgaa tgtcaggcta     180

cacaagcagg cctccgctcc agaccagccc aactgcacgt gctggtcccc ccagaagccc     240

cccaggtgct gggcggcccc tctgtgtctc tggttgctgg agttcctgcg aacctgacat     300

gtcggagccg tggggatgcc cgccctaccc ctgaattgct gtggttccga gatggggtcc     360

tgttggatgg agccaccttc catcagaccc tgctgaagga agggacccct gggtcagtgg     420

agagcacctt aaccctgacc cctttcagcc atgatgatgg agccaccttt gtctgccggg     480

cccggagcca ggccctgccc acaggaagag acacagctat cacactgagc ctgcagtacc     540

ccccagaggt gactctgtct gcttcgccac acactgtgca ggagggagag aaggtcattt     600

tcctgtgcca ggccacagcc cagcctcctg tcacaggcta caggtgggca aaagggggct     660

ctccggtgct cggggcccgc gggccaaggt tagaggtcgt ggcagacgcc tcgttcctga     720

ctgagcccgt gtcctgcgag gtcagcaacg ccgtgggtag cgccaaccgc agtactgcgc     780

tggatgtgct gtttgggccg attctgcagg caaagccgga gcccgtgtcc gtggacgtgg     840

gggaagacgc ttccttcagc tgcgcctggc gcgggaatcc gcttccacgg gtaacctgga     900

cccgccgcgg tggcgcgcag gtgctgggct ctggagccac actgcgtctt ccgtcggtgg     960

ggcccgagga cgcagacgac tatgtgtgca gagctgaggc tgggctatcg ggtctgcggg    1020

gcggcgccgt ggaggctcgg ctgactgtgg acgctccccc agtagtgacc gccctgcact    1080

ctgcgcctgc cttcctgagg ggccctgctc gcctccagtg tctggttttc gcctctcccg    1140

ccccagatgc cgtggtctgg tcttgggatg agggcttcct ggaggcgggg tcgcagggtc    1200

ggttcctggt ggagacattc cctgccccag agagccgcgg gggactgggt ccgggcctga    1260

tctctgtgct acacatttcg gggacccagg agtctgactt tagcaggagc tttaactgca    1320

gtgcccggaa ccggctgggc gagggaggtg cccaggccag cctgggccgt agagacttgc    1380

tgcccactgt gcggatagtg gccggagtgg tcgctgccac cacaactctc cttatggtca    1440

tcactggggt ggccctctgc tgctggcgcc acagcaaggc ctcagcctct ttctccgagc    1500

aaaagaacct gatgcgaatc cctggcagca gcgacggctc cagttcacga ggtcctgaag    1560

aagaggagac aggcagccgc gaggaccggg gccccattgt gcacactgac cacagtgatc    1620

tggttctgga ggaggaaggg actctggaga ccaaggaccc aaccaacggt tactacaagg    1680

tccgaggagt cagtccaccc gcgtctccag actcacgtgt gacatctttc caatggaaga    1740

gtcctgggat ctccaacttg ccataatgga ttgttctgat ttctgaggag ccaggacaag    1800

ttggcgacct tactcctcc                                                 1819


<210> SEQ ID NO 48
<211> LENGTH: 583
```

<212> TYPE: PRT
<213> ORGANISM: Homo sapiens

<400> SEQUENCE: 48

```
Met Leu Trp Met Arg Val Pro Ala Leu Leu Val Leu Leu Phe Cys Phe
1               5                   10                  15

Arg Gly Arg Ala Gly Trp Ser Arg Tyr Trp Ile Ser Gly Asn Ala Ala
            20                  25                  30

Asn Gly Gln His Asp Leu His Ile Arg Pro Val Glu Leu Glu Asp Glu
        35                  40                  45

Ala Ser Tyr Glu Cys Gln Ala Thr Gln Ala Gly Leu Arg Ser Arg Pro
    50                  55                  60

Ala Gln Leu His Val Leu Val Pro Pro Glu Ala Pro Gln Val Leu Gly
65                  70                  75                  80

Gly Pro Ser Val Ser Leu Val Ala Gly Val Pro Ala Asn Leu Thr Cys
                85                  90                  95

Arg Ser Arg Gly Asp Ala Arg Pro Thr Pro Glu Leu Leu Trp Phe Arg
            100                 105                 110

Asp Gly Val Leu Leu Asp Gly Ala Thr Phe His Gln Thr Leu Leu Lys
        115                 120                 125

Glu Gly Thr Pro Gly Ser Val Glu Ser Thr Leu Thr Leu Thr Pro Phe
    130                 135                 140

Ser His Asp Asp Gly Ala Thr Phe Val Cys Arg Ala Arg Ser Gln Ala
145                 150                 155                 160

Leu Pro Thr Gly Arg Asp Thr Ala Ile Thr Leu Ser Leu Gln Tyr Pro
                165                 170                 175

Pro Glu Val Thr Leu Ser Ala Ser Pro His Thr Val Gln Glu Gly Glu
            180                 185                 190

Lys Val Ile Phe Leu Cys Gln Ala Thr Ala Gln Pro Pro Val Thr Gly
        195                 200                 205

Tyr Arg Trp Ala Lys Gly Gly Ser Pro Val Leu Gly Ala Arg Gly Pro
    210                 215                 220

Arg Leu Glu Val Val Ala Asp Ala Ser Phe Leu Thr Glu Pro Val Ser
225                 230                 235                 240

Cys Glu Val Ser Asn Ala Val Gly Ser Ala Asn Arg Ser Thr Ala Leu
                245                 250                 255

Asp Val Leu Phe Gly Pro Ile Leu Gln Ala Lys Pro Glu Pro Val Ser
            260                 265                 270

Val Asp Val Gly Glu Asp Ala Ser Phe Ser Cys Ala Trp Arg Gly Asn
        275                 280                 285

Pro Leu Pro Arg Val Thr Trp Thr Arg Arg Gly Gly Ala Gln Val Leu
    290                 295                 300

Gly Ser Gly Ala Thr Leu Arg Leu Pro Ser Val Gly Pro Glu Asp Ala
305                 310                 315                 320

Asp Asp Tyr Val Cys Arg Ala Glu Ala Gly Leu Ser Gly Leu Arg Gly
                325                 330                 335

Gly Ala Val Glu Ala Arg Leu Thr Val Asp Ala Pro Pro Val Val Thr
            340                 345                 350

Ala Leu His Ser Ala Pro Ala Phe Leu Arg Gly Pro Ala Arg Leu Gln
        355                 360                 365

Cys Leu Val Phe Ala Ser Pro Ala Pro Asp Ala Val Val Trp Ser Trp
    370                 375                 380

Asp Glu Gly Phe Leu Glu Ala Gly Ser Gln Gly Arg Phe Leu Val Glu
385                 390                 395                 400
```

```
Thr Phe Pro Ala Pro Glu Ser Arg Gly Gly Leu Gly Pro Gly Leu Ile
                405                 410                 415

Ser Val Leu His Ile Ser Gly Thr Gln Glu Ser Asp Phe Ser Arg Ser
            420                 425                 430

Phe Asn Cys Ser Ala Arg Asn Arg Leu Gly Glu Gly Gly Ala Gln Ala
        435                 440                 445

Ser Leu Gly Arg Arg Asp Leu Leu Pro Thr Val Arg Ile Val Ala Gly
    450                 455                 460

Val Val Ala Ala Thr Thr Thr Leu Leu Met Val Ile Thr Gly Val Ala
465                 470                 475                 480

Leu Cys Cys Trp Arg His Ser Lys Ala Ser Ala Ser Phe Ser Glu Gln
                485                 490                 495

Lys Asn Leu Met Arg Ile Pro Gly Ser Ser Asp Gly Ser Ser Ser Arg
            500                 505                 510

Gly Pro Glu Glu Glu Glu Thr Gly Ser Arg Glu Asp Arg Gly Pro Ile
        515                 520                 525

Val His Thr Asp His Ser Asp Leu Val Leu Glu Glu Glu Gly Thr Leu
    530                 535                 540

Glu Thr Lys Asp Pro Thr Asn Gly Tyr Tyr Lys Val Arg Gly Val Ser
545                 550                 555                 560

Pro Pro Ala Ser Pro Asp Ser Arg Val Thr Ser Phe Gln Trp Lys Ser
                565                 570                 575

Pro Gly Ile Ser Asn Leu Pro
            580


<210> SEQ ID NO 49
<211> LENGTH: 2959
<212> TYPE: DNA
<213> ORGANISM: Homo sapiens

<400> SEQUENCE: 49

atgcacttga gtgcaccttg agtctccagc ctctcaagga accgggagat caggccatca      60

gcgtctcagc cagcaaaggc ctgaaccacc agtcccttat aaccctgcgt ttcagagcgt     120

cagaggcgtg cttgagagga agaagttgac gggaaggcca gtgcgacggc aaatctcgtg     180

aaccttgggg gacgaatgct caggatgcgg gtccccgccc tcctcgtcct cctcttctgc     240

ttcagaggga gagcaggccc gtcgccccat ttcctgcaac agccagagga cctggtggtg     300

ctgctggggg aggaagcccg gctgccgtgt gctctgggcg cctactgggg gctagttcag     360

tggactaaga gtgggctggc cctagggggc caaagggacc taccagggtg gtcccggtac     420

tggatatcag ggaatgcagc caatggccag catgacctcc acattaggcc cgtggagcta     480

gaggatgaag catcatatga atgtcaggct acacaagcag gcctccgctc cagaccagcc     540

caactgcacg tgctggtccc cccagaagcc ccccaggtgc tgggcggccc ctctgtgtct     600

ctggttgctg gagttcctgc gaacctgaca tgtcggagcc gtggggatgc ccgccctacc     660

cctgaattgc tgtggttccg agatggggtc ctgttggatg gagccacctt ccatcagacc     720

ctgctgaagg aagggacccc tgggtcagtg gagagcacct taaccctgcc cacaggaaga     780

gacacagcta tcacactgag cctgcagtac cccccagagg tgactctgtc tgcttcgcca     840

cacactgtgc aggagggaga gaaggtcatt ttcctgtgcc aggccacagc ccagcctcct     900

gtcacaggct acaggtgggc aaaagggggc tctccggtgc tcggggcccg cgggccaagg     960

ttagaggtcg tggcagacgc ctcgttcctg actgagcccg tgtcctgcga ggtcagcaac    1020

gccgtgggta gcgccaaccg cagtactgcg ctggatgtgc tgtttgggcc gattctgcag    1080
```

```
gcaaagccgg agcccgtgtc cgtggacgtg ggggaagacg cttccttcag ctgcgcctgg   1140
cgcgggaacc cgcttccacg ggtaacctgg acccgccgcg gtggcgcgca ggtgctgggc   1200
tctggagcca cactgcgtct tccgtcggtg gggcccgagg acgcaggcga ctatgtgtgc   1260
agagctgagg ctgggctatc gggcctgcgg ggcggcgccg cggaggctcg gctgactgtg   1320
aacgctcccc cagtagtgac cgccctgcac tctgcgcctg ccttcctgag ggccctgct    1380
cgcctccagt gtctggtttt cgcctctccc gccccagatg ccgtggtctg gtcttgggat   1440
gagggcttcc tggaggcggg gtcgcagggc cggttcctgg tggagacatt ccctgcccca   1500
gagagccgcg gggactgggg tccgggcctg atctctgtgc tacacatttc ggggacccag   1560
gagtctgact ttagcaggag ctttaactgc agtgcccgga accggctggg cgagggaggt   1620
gcccaggcca gcctgggccg tagagacttg ctgcccactg tgcggatagt ggccggagtg   1680
gccgctgcca ccacaactct ccttatggtc atcactgggg tggccctctg ctgctggcgc   1740
cacagcaagg cctcagcctc tttctccgag caaaagaacc tgatgcgaat ccctggcagc   1800
agcgacggct ccagttcacg aggtcctgaa gaagaggaga caggcagccg cgaggaccgg   1860
ggccccattg tgcacactga ccacagtgat ctggttctgg aggaggaagg gactctggag   1920
accaaggacc caaccaacgg ttactacaag gtccgaggag tcagtgtgag cctgagcctt   1980
ggcgaagccc ctggaggagg tctcttcctg ccaccaccct ccccccttgg gcccccaggg   2040
acccctacct tctatgactt caacccacac ctgggcatgg tccccccctg cagactttac   2100
agagccaggg caggctatct caccacaccc caccctcgag ctttcaccag ctacatcaaa   2160
cccacatcct ttgggccccc agatctggcc cccgggactc cccccttccc atatgctgcc   2220
ttccccacac ctagccaccc gcgtctccag actcacgtgt gacatctttc caatggaaga   2280
gtcctgggat ctccaacttg ccataatgga ttgttctgat ttctgaggag ccaggacaag   2340
ttggcgacct tactcctcca aaactgaaca caaggggagg gaaagatcat tacatttgtc   2400
aggagcattt gtatacagtc agctcagcca aaggagatgc cccaagtggg agcaacatgg   2460
ccacccaata tgcccaccta ttccccggtg taaaagagat tcaagatggc aggtaggccc   2520
tttgaggaga gatggggaca gggcagtggg tgttgggagt ttggggccgg gatggaagtt   2580
gtttctagcc actgaaagaa gatatttcaa gatgaccatc tgcattgaga ggaaaggtag   2640
cataggatag atgaagatga agagcatacc aggccccacc ctggctctcc ctgaggggaa   2700
ctttgctcgg ccaatggaaa tgcagccaag atggccatat actccctagg aacccaagat   2760
ggccaccatc ttgattttac tttccttaaa gactcagaaa gacttggacc caaggagtgg   2820
ggatacagtg agaattacca ctgttggggc aaaatattgg gataaaaata tttatgttta   2880
ataataaaaa aaagtcaaag aggaaaaaaa aaaaaaaaaa aaaaaaaaaa aaaaaaaaaa   2940
aaaaaaaaaa aaaaaaaaa                                                2959
```

<210> SEQ ID NO 50
<211> LENGTH: 688
<212> TYPE: PRT
<213> ORGANISM: Homo sapiens

<400> SEQUENCE: 50

```
Met Leu Arg Met Arg Val Pro Ala Leu Leu Val Leu Leu Phe Cys Phe
1               5                   10                  15

Arg Gly Arg Ala Gly Pro Ser Pro His Phe Leu Gln Gln Pro Glu Asp
            20                  25                  30

Leu Val Val Leu Leu Gly Glu Glu Ala Arg Leu Pro Cys Ala Leu Gly
        35                  40                  45
```

```
Ala Tyr Trp Gly Leu Val Gln Trp Thr Lys Ser Gly Leu Ala Leu Gly
    50                  55                  60

Gly Gln Arg Asp Leu Pro Gly Trp Ser Arg Tyr Trp Ile Ser Gly Asn
65                  70                  75                  80

Ala Ala Asn Gly Gln His Asp Leu His Ile Arg Pro Val Glu Leu Glu
                85                  90                  95

Asp Glu Ala Ser Tyr Glu Cys Gln Ala Thr Gln Ala Gly Leu Arg Ser
            100                 105                 110

Arg Pro Ala Gln Leu His Val Leu Val Pro Pro Glu Ala Pro Gln Val
        115                 120                 125

Leu Gly Gly Pro Ser Val Ser Leu Val Ala Gly Val Pro Ala Asn Leu
    130                 135                 140

Thr Cys Arg Ser Arg Gly Asp Ala Arg Pro Thr Pro Glu Leu Leu Trp
145                 150                 155                 160

Phe Arg Asp Gly Val Leu Leu Asp Gly Ala Thr Phe His Gln Thr Leu
                165                 170                 175

Leu Lys Glu Gly Thr Pro Gly Ser Val Glu Ser Thr Leu Thr Leu Pro
            180                 185                 190

Thr Gly Arg Asp Thr Ala Ile Thr Leu Ser Leu Gln Tyr Pro Pro Glu
        195                 200                 205

Val Thr Leu Ser Ala Ser Pro His Thr Val Gln Glu Gly Glu Lys Val
    210                 215                 220

Ile Phe Leu Cys Gln Ala Thr Ala Gln Pro Pro Val Thr Gly Tyr Arg
225                 230                 235                 240

Trp Ala Lys Gly Gly Ser Pro Val Leu Gly Ala Arg Gly Pro Arg Leu
                245                 250                 255

Glu Val Val Ala Asp Ala Ser Phe Leu Thr Glu Pro Val Ser Cys Glu
            260                 265                 270

Val Ser Asn Ala Val Gly Ser Ala Asn Arg Ser Thr Ala Leu Asp Val
        275                 280                 285

Leu Phe Gly Pro Ile Leu Gln Ala Lys Pro Glu Pro Val Ser Val Asp
    290                 295                 300

Val Gly Glu Asp Ala Ser Phe Ser Cys Ala Trp Arg Gly Asn Pro Leu
305                 310                 315                 320

Pro Arg Val Thr Trp Thr Arg Arg Gly Gly Ala Gln Val Leu Gly Ser
                325                 330                 335

Gly Ala Thr Leu Arg Leu Pro Ser Val Gly Pro Glu Asp Ala Gly Asp
            340                 345                 350

Tyr Val Cys Arg Ala Glu Ala Gly Leu Ser Gly Leu Arg Gly Gly Ala
        355                 360                 365

Ala Glu Ala Arg Leu Thr Val Asn Ala Pro Pro Val Val Thr Ala Leu
    370                 375                 380

His Ser Ala Pro Ala Phe Leu Arg Gly Pro Ala Arg Leu Gln Cys Leu
385                 390                 395                 400

Val Phe Ala Ser Pro Ala Pro Asp Ala Val Val Trp Ser Trp Asp Glu
                405                 410                 415

Gly Phe Leu Glu Ala Gly Ser Gln Gly Arg Phe Leu Val Glu Thr Phe
            420                 425                 430

Pro Ala Pro Glu Ser Arg Gly Gly Leu Gly Pro Gly Leu Ile Ser Val
        435                 440                 445

Leu His Ile Ser Gly Thr Gln Glu Ser Asp Phe Ser Arg Ser Phe Asn
    450                 455                 460

Cys Ser Ala Arg Asn Arg Leu Gly Glu Gly Gly Ala Gln Ala Ser Leu
```

```
465                 470                 475                 480

Gly Arg Arg Asp Leu Leu Pro Thr Val Arg Ile Val Ala Gly Val Ala
                485                 490                 495

Ala Ala Thr Thr Thr Leu Leu Met Val Ile Thr Gly Val Ala Leu Cys
            500                 505                 510

Cys Trp Arg His Ser Lys Ala Ser Ala Ser Phe Ser Glu Gln Lys Asn
        515                 520                 525

Leu Met Arg Ile Pro Gly Ser Ser Asp Gly Ser Ser Ser Arg Gly Pro
    530                 535                 540

Glu Glu Glu Glu Thr Gly Ser Arg Glu Asp Arg Gly Pro Ile Val His
545                 550                 555                 560

Thr Asp His Ser Asp Leu Val Leu Glu Glu Glu Gly Thr Leu Glu Thr
                565                 570                 575

Lys Asp Pro Thr Asn Gly Tyr Tyr Lys Val Arg Gly Val Ser Val Ser
            580                 585                 590

Leu Ser Leu Gly Glu Ala Pro Gly Gly Gly Leu Phe Leu Pro Pro Pro
        595                 600                 605

Ser Pro Leu Gly Pro Pro Gly Thr Pro Thr Phe Tyr Asp Phe Asn Pro
    610                 615                 620

His Leu Gly Met Val Pro Pro Cys Arg Leu Tyr Arg Ala Arg Ala Gly
625                 630                 635                 640

Tyr Leu Thr Thr Pro His Pro Arg Ala Phe Thr Ser Tyr Ile Lys Pro
                645                 650                 655

Thr Ser Phe Gly Pro Pro Asp Leu Ala Pro Gly Thr Pro Pro Phe Pro
            660                 665                 670

Tyr Ala Ala Phe Pro Thr Pro Ser His Pro Arg Leu Gln Thr His Val
        675                 680                 685


<210> SEQ ID NO 51
<211> LENGTH: 2591
<212> TYPE: DNA
<213> ORGANISM: Pan troglodytes

<400> SEQUENCE: 51

atgctcagga tgcgggtccc cgccctcctc gtcctcctct tctgcttcag agggagcgca     60

ggcccatcgc cccatttcct gcaacagcca gaggacctgg tggtgctgct gggggaggaa    120

gcccggctgc cgtgtgctct gggcgcctac tgggggctag ttcagtggac taagagtggg    180

ctggccctag gggccaaagg ggacctacca gggtggtccc ggtactggat atcagggaat    240

gcagccaatg gccagcatga cctccacatt aggcccgtgg agctagagga tgaagcatca    300

tatgaatgtc aggctacaca agcaggcctc cgctccagac cagcccaact gcacgtgctg    360

gtacccccag aagcccccca ggtgctgggc ggcccctctg tgtctctggt tgctggagtt    420

cctgcgaacc tgacatgtcg gagccgtggg gatgcccgcc ctacccctga attgctgtgg    480

ttccgagatg gggtcctgtt ggatggaacc accttccatc agaccctgct gaaggaaggg    540

acccctgggt cagtggagag caccttaacc ctgacccctt tcagccatga tgatggagcc    600

acctttgtct gccgggcccg gagccaggcc ctgccctcag gaagagacac ggctatcaca    660

ctgagcctgc agtacccccc agaggtgact ctgtctgctt cgccacacac tgtgcaggag    720

ggagagaagg tcattttcct gtgccaggcc acagaccagc ctcctgtcac aggctacagg    780

gaggacgaag acccagaatc caccacaatg ggaccaggc ttcctacaaa tccggcttct     840

gacgcccctt ccctgtcgca ggtgctgggc tctggagcca cactgcatct tccgtcggta    900

gggcccgagg acgcaggcga ctatgtgtgc agagctgagc ctgggctatc gggcctgggg    960
```

```
ggcggcgccg cggaggctcg gctgactgtg aacgctcccc cagtagtgac cgccctgcac   1020
tctgcgcctg ccttcctgag gggccctgct cgcctccagt gtctggtttt cgcctctccc   1080
gccccagatg ccgtggtctg gtcttgggat gagggcttcc tggaggcggg gtcgcagggc   1140
cggttcctgg tggagacatt ccctgcccca gagagccgcg gggactgggg tccgggcctg   1200
atctctgtgc tacacatttc ggggacccag gagtctgact ttagcaggag ctttaactgc   1260
agtgcccgga accggctggg cgagggaggt gcccaggcca gcctgggccg tagagacttg   1320
ctgcccactg tgcggatagt ggccggagtg gccgctgcca ccacgactct ccttatggtc   1380
atcactgggg tggccctctg ctgctggcgc cacagcaagg cctcagcctc tttctccgag   1440
caaaagaacc tgatgcgaat ccctggcagc agcgacggct ccagttcgcg aggtcctgaa   1500
gaagaggaga caggcagccg cgaggaccgg ggccccattg tgcacactga ccacagtgat   1560
ctggttctgg aggaggaagg gactctggag accaaggacc caaccaacgg ttactacaag   1620
gtccgaggag tcagtgtgag cctgagcctt ggcgaagccc ctggaggagg cctcttcctg   1680
ccaccaccct ccccccttgg gcccccaggg accccctacct tctatgactt caacccacac   1740
ctgggcatgg tccccccctg cagactttac agagccaggg caggctatct caccacaccc   1800
caccctcgag ctttcaccag ctacatcaaa cccacatcct ttgggccccc agatctggcc   1860
cccgggactc ccccccttccc atgtgctgcc ttccccacac ctagccaccc gcgtctccag   1920
actcatgtgt gacatctttc cagtggaaga gtcctgggat ctccaacttg ccataatgga   1980
ttgttctgat ttctgaggag ccaggacaag ttggcgacct tactcctcca aaactgaaca   2040
cagggggagg gaaagatcat tacatttgtc aggagcattt gtgtacagtc agctcagcca   2100
aaggagatgc cccaagtggg agcaacgtgg ccacccaata tgcccaccta ttccccggtg   2160
taaaagagat tcaagatggc aggtaggccc tttgaggaga gatggggaca gggcagtggg   2220
tgttgggagt ttggggccgg gatggaagtt gtttctagcc actgaaagaa gatatttcaa   2280
gatgaccatc tgcattgaga ggaaaggtag cataggatag atgaagatga agagcatacc   2340
aggccccacc ctggctctcc ctgaggggaa ttttgctcgg ccaatggaaa tgcagccaag   2400
atggccatat actccctagg aacccaagat ggccaccatc ttgattttac tttccttaaa   2460
gactcagaaa gacttggact caaggagtgg ggatacagtg agaattacca ctgttggggc   2520
aaaggggatt cttgggataa aaatatttat gtttaataat aaaaaaaagt caaagaggca   2580
agtgtgtctt a                                                         2591
```

<210> SEQ ID NO 52
<211> LENGTH: 643
<212> TYPE: PRT
<213> ORGANISM: Pan troglodytes

<400> SEQUENCE: 52

```
Met Leu Arg Met Arg Val Pro Ala Leu Leu Val Leu Leu Phe Cys Phe
1               5                   10                  15

Arg Gly Ser Ala Gly Pro Ser Pro His Phe Leu Gln Gln Pro Glu Asp
            20                  25                  30

Leu Val Val Leu Leu Gly Glu Glu Ala Arg Leu Pro Cys Ala Leu Gly
        35                  40                  45

Ala Tyr Trp Gly Leu Val Gln Trp Thr Lys Ser Gly Leu Ala Leu Gly
    50                  55                  60

Gly Gln Arg Asp Leu Pro Gly Trp Ser Arg Tyr Trp Ile Ser Gly Asn
65                  70                  75                  80
```

-continued

```
Ala Ala Asn Gly Gln His Asp Leu His Ile Arg Pro Val Glu Leu Glu
                85                  90                  95

Asp Glu Ala Ser Tyr Glu Cys Gln Ala Thr Gln Ala Gly Leu Arg Ser
            100                 105                 110

Arg Pro Ala Gln Leu His Val Leu Val Pro Pro Glu Ala Pro Gln Val
        115                 120                 125

Leu Gly Gly Pro Ser Val Ser Leu Val Ala Gly Val Pro Ala Asn Leu
    130                 135                 140

Thr Cys Arg Ser Arg Gly Asp Ala Arg Pro Thr Pro Glu Leu Leu Trp
145                 150                 155                 160

Phe Arg Asp Gly Val Leu Leu Asp Gly Thr Thr Phe His Gln Thr Leu
                165                 170                 175

Leu Lys Glu Gly Thr Pro Gly Ser Val Glu Ser Thr Leu Thr Leu Thr
            180                 185                 190

Pro Phe Ser His Asp Asp Gly Ala Thr Phe Val Cys Arg Ala Arg Ser
        195                 200                 205

Gln Ala Leu Pro Ser Gly Arg Asp Thr Ala Ile Thr Leu Ser Leu Gln
    210                 215                 220

Tyr Pro Pro Glu Val Thr Leu Ser Ala Ser Pro His Thr Val Gln Glu
225                 230                 235                 240

Gly Glu Lys Val Ile Phe Leu Cys Gln Ala Thr Asp Gln Pro Pro Val
                245                 250                 255

Thr Gly Tyr Arg Glu Asp Glu Asp Pro Glu Ser Thr Thr Met Gly Thr
            260                 265                 270

Arg Leu Pro Thr Asn Pro Ala Ser Asp Ala Pro Ser Leu Ser Gln Val
        275                 280                 285

Leu Gly Ser Gly Ala Thr Leu His Leu Pro Ser Val Gly Pro Glu Asp
    290                 295                 300

Ala Gly Asp Tyr Val Cys Arg Ala Glu Pro Gly Leu Ser Gly Leu Gly
305                 310                 315                 320

Gly Gly Ala Ala Glu Ala Arg Leu Thr Val Asn Ala Pro Pro Val Val
                325                 330                 335

Thr Ala Leu His Ser Ala Pro Ala Phe Leu Arg Gly Pro Ala Arg Leu
            340                 345                 350

Gln Cys Leu Val Phe Ala Ser Pro Ala Pro Asp Ala Val Val Trp Ser
        355                 360                 365

Trp Asp Glu Gly Phe Leu Glu Ala Gly Ser Gln Gly Arg Phe Leu Val
    370                 375                 380

Glu Thr Phe Pro Ala Pro Glu Ser Arg Gly Gly Leu Gly Pro Gly Leu
385                 390                 395                 400

Ile Ser Val Leu His Ile Ser Gly Thr Gln Glu Ser Asp Phe Ser Arg
                405                 410                 415

Ser Phe Asn Cys Ser Ala Arg Asn Arg Leu Gly Glu Gly Gly Ala Gln
            420                 425                 430

Ala Ser Leu Gly Arg Arg Asp Leu Leu Pro Thr Val Arg Ile Val Ala
        435                 440                 445

Gly Val Ala Ala Ala Thr Thr Thr Leu Leu Met Val Ile Thr Gly Val
    450                 455                 460

Ala Leu Cys Cys Trp Arg His Ser Lys Ala Ser Ala Ser Phe Ser Glu
465                 470                 475                 480

Gln Lys Asn Leu Met Arg Ile Pro Gly Ser Ser Asp Gly Ser Ser Ser
                485                 490                 495

Arg Gly Pro Glu Glu Glu Glu Thr Gly Ser Arg Glu Asp Arg Gly Pro
            500                 505                 510
```

```
Ile Val His Thr Asp His Ser Asp Leu Val Leu Glu Glu Glu Gly Thr
        515                 520                 525

Leu Glu Thr Lys Asp Pro Thr Asn Gly Tyr Tyr Lys Val Arg Gly Val
    530                 535                 540

Ser Val Ser Leu Ser Leu Gly Glu Ala Pro Gly Gly Gly Leu Phe Leu
545                 550                 555                 560

Pro Pro Pro Ser Pro Leu Gly Pro Pro Gly Thr Pro Thr Phe Tyr Asp
                565                 570                 575

Phe Asn Pro His Leu Gly Met Val Pro Pro Cys Arg Leu Tyr Arg Ala
            580                 585                 590

Arg Ala Gly Tyr Leu Thr Thr Pro His Pro Arg Ala Phe Thr Ser Tyr
        595                 600                 605

Ile Lys Pro Thr Ser Phe Gly Pro Pro Asp Leu Ala Pro Gly Thr Pro
    610                 615                 620

Pro Phe Pro Cys Ala Ala Phe Pro Thr Pro Ser His Pro Arg Leu Gln
625                 630                 635                 640

Thr His Val


<210> SEQ ID NO 53
<211> LENGTH: 3019
<212> TYPE: DNA
<213> ORGANISM: Bos taurus

<400> SEQUENCE: 53

atgggaagag ggcgggtctc ccagggggcg ggccggggcg gggcgagtgg aaaccagccc      60

tccagggtct ctccgagacc tggcgcgcct aactggcagg cgtttcagag cggcggagtc     120

tgcggcggag cagacgaggg gacctccagg tcagagagag gggagcttct agcctggggc     180

gaagagtcaa gagcggaggg gactccaggc cagagtggtg ggaagtgtgc tccgaggaag     240

gaactggcag ggaagccagt gcaacagcaa gtctgctgga tcttgggcga cacacttagg     300

atgctcgtgc ccgtactcct cgtcctctcc ttctgcctca gggggcgtgc aggcctggca     360

ccccactttc tgcaacagcc agaggaccag gtagttctgt tgggagacga ggcccgactg     420

ccctgtgccc tgggcgacta ccggggactg gttcagtgga ctaaggacgg gctggctcta     480

gggggcgaaa gggaccttcc aggctggtcc cggtactgga tatcagggaa tgcagcaagt     540

ggccagcatg acctccacat tagacccgtg gagctagagg atcaagcatc gtatgaatgt     600

caagcgacac aagccggcct ccgctctcga ccagcccaac tgcatgtgct ggtgcctcca     660

gacccccccc aggtgctggg cggcccctct gtgtctctgg ttgctggggt tcctgcgaat     720

ctgacctgtc ggagccgtgg tgatgcccac cctacccctg agctgctgtg gtttcgagat     780

gggatccgac tggacggggc catcttccgc cagactcctt tgaaggaagg aaccatcggg     840

tcagtggaga gcatcttgtc tttgacccct tccagccatg atgatggagc caccttggtt     900

tgccgggccc ggagccaggc cctgcctgca gggaaggaca cagctgtaac actaagcctg     960

cagtaccccc cagtggtgac tctgtctgca gaaccacaga cagtgcagga gggagagaag    1020

gtcactttcc tatgccaggc cacagcccag cctcctgtca ccggctatag atgggcaaag    1080

gggggctccc cggtgctcgg ggcccgaggg ccaatgctgg agatagtggc tgacgcttca    1140

ttcctgactg cgccggtgtc ctgcgaggtc agcaatgcag tgggtagcgc caaccgcagc    1200

acagcgctgg acgtgcagtt tggggcgatt ctgcaggcaa agccgaaagc cttgtcggtg    1260

gacgtaggag aagacgcctc cttcagctgt gtctggcgcg ggaatccgct cccacgggta    1320

acctggaccc gccgcgggga cgcacaggtg ctggcctccg ggcccacgct gcgtcttccc    1380
```

```
gcggtggggc ccgaggatgc aggcgactac gtgtgcaggg ccgagccggg gctctcaggc   1440

cggggcggtg gctctgcaga agctaggctg actgtgaacg ctcccccagt agtgaccgct   1500

ctgcactctg cgcccgcctt cctgaggggc cccgcccgcc tccagtgtct agtcttcgct   1560

tcccccaccc cagaagcagt ggtctggtct tgggatgagg gcttcctgac ggcggggtca   1620

cggggtcggt tcctggtgga gactttccca gccccagagg gcctcaaggg acagggtcca   1680

ggcctgatct ccgtgctaca catttcgggg acccaggagt ccgactttca ccggggcttc   1740

aactgcactg cccggaaccg attgggtgag ggaggcaccc aggtcagcct gggccgtaga   1800

gatttgctgc ccactgtgcg gattgtggcc ggagtggccg ccatggccat gactctcctt   1860

atgatcatca ctggggtggc cctctgctgc tggcgccatg gcaggggtca gtcctctttc   1920

tccaagcaaa agaacctggt gcgaatccca gggagcagtg atggctccag ttccaggggc   1980

cccgaggagg agacaggcat cagcaaagac cagggcccca tcgtgcacac ggaccacagt   2040

gacctggttc tggatgagga gggggctctg gagaccaagg acccaaccaa tggttactac   2100

aaggtccgag gagtcagtgt gagcctgagc cttggagaag cccccggagg aggtctcttc   2160

ctaccaccct cctcccctct tggacctcca ggaacccccta ccttctatga cttcaatcca   2220

catcttggca tggtccctcc ctgcagacta tatagatccc gggcaggcta tctcaccaca   2280

ccccatcctc gagcttttac cagctacatc aaacccacat cctttggacc cccagatctg   2340

gcccccagca ctccccccctt cccatatgct gccttcccca cgcccagcca cccacgtctc   2400

cagactcatg tgtgacatct ctccagctga agagtcctgg gatcttcaac ttgcacaatg   2460

gattgtcctg atttctgagt aaccagaaca aactggcaac cctatccttc caaaattgaa   2520

ccttgagggg agggaaagat cattgcagtt gcctgggtca ttgcgagaaa gccactgggc   2580

ttgcctcttc ctctgtataa aagagattca agagggcaga tgggcccttt gcagagggat   2640

ggggacaggg gttatgggag ttagggacag agaaggaaat tgcttccaaa cattgaaaga   2700

agagatttca agatggccac ccacattaag aagaaaggca acataaagca gatcaagata   2760

caggacctgt ccttgctatc cctgaggggt actttgtttc acccatggaa ttgctgccaa   2820

aatggccatt cattccctgg gaatccaaga tggccaccat cttgattctt tctaccttcc   2880

ttaaaggccc tggaagaacc ggacccaagg agtaaggaca gggtgaaagc tgttgtggtg   2940

gtgggaaggg ggaaaggagt ggtgttggaa tctgggaatg agaatattta tgttcaatta   3000

aaaaaaaaaa aagttgcaa                                                 3019
```

<210> SEQ ID NO 54
<211> LENGTH: 804
<212> TYPE: PRT
<213> ORGANISM: Bos taurus

<400> SEQUENCE: 54

```
Met Gly Arg Gly Arg Val Ser Gln Gly Ala Gly Arg Gly Gly Ala Ser
1               5                   10                  15

Gly Asn Gln Pro Ser Arg Val Ser Pro Arg Pro Gly Ala Pro Asn Trp
            20                  25                  30

Gln Ala Phe Gln Ser Gly Gly Val Cys Gly Gly Ala Asp Glu Gly Thr
        35                  40                  45

Ser Arg Ser Glu Arg Gly Glu Leu Leu Ala Trp Gly Glu Glu Ser Arg
    50                  55                  60

Ala Glu Gly Thr Pro Gly Gln Ser Gly Gly Lys Cys Ala Pro Arg Lys
65                  70                  75                  80
```

```
Glu Leu Ala Gly Lys Pro Val Gln Gln Gln Val Cys Trp Ile Leu Gly
                85                  90                  95

Asp Thr Leu Arg Met Leu Val Pro Val Leu Leu Val Leu Ser Phe Cys
            100                 105                 110

Leu Arg Gly Arg Ala Gly Leu Ala Pro His Phe Leu Gln Gln Pro Glu
        115                 120                 125

Asp Gln Val Val Leu Leu Gly Asp Glu Ala Arg Leu Pro Cys Ala Leu
    130                 135                 140

Gly Asp Tyr Arg Gly Leu Val Gln Trp Thr Lys Asp Gly Leu Ala Leu
145                 150                 155                 160

Gly Gly Glu Arg Asp Leu Pro Gly Trp Ser Arg Tyr Trp Ile Ser Gly
                165                 170                 175

Asn Ala Ala Ser Gly Gln His Asp Leu His Ile Arg Pro Val Glu Leu
            180                 185                 190

Glu Asp Gln Ala Ser Tyr Glu Cys Gln Ala Thr Gln Ala Gly Leu Arg
        195                 200                 205

Ser Arg Pro Ala Gln Leu His Val Leu Val Pro Pro Asp Pro Pro Gln
    210                 215                 220

Val Leu Gly Gly Pro Ser Val Ser Leu Val Ala Gly Val Pro Ala Asn
225                 230                 235                 240

Leu Thr Cys Arg Ser Arg Gly Asp Ala His Pro Thr Pro Glu Leu Leu
                245                 250                 255

Trp Phe Arg Asp Gly Ile Arg Leu Asp Gly Ala Ile Phe Arg Gln Thr
            260                 265                 270

Pro Leu Lys Glu Gly Thr Ile Gly Ser Val Glu Ser Ile Leu Ser Leu
        275                 280                 285

Thr Pro Ser Ser His Asp Asp Gly Ala Thr Leu Val Cys Arg Ala Arg
    290                 295                 300

Ser Gln Ala Leu Pro Ala Gly Lys Asp Thr Ala Val Thr Leu Ser Leu
305                 310                 315                 320

Gln Tyr Pro Pro Val Val Thr Leu Ser Ala Glu Pro Gln Thr Val Gln
                325                 330                 335

Glu Gly Glu Lys Val Thr Phe Leu Cys Gln Ala Thr Ala Gln Pro Pro
            340                 345                 350

Val Thr Gly Tyr Arg Trp Ala Lys Gly Gly Ser Pro Val Leu Gly Ala
        355                 360                 365

Arg Gly Pro Met Leu Glu Ile Val Ala Asp Ala Ser Phe Leu Thr Ala
    370                 375                 380

Pro Val Ser Cys Glu Val Ser Asn Ala Val Gly Ser Ala Asn Arg Ser
385                 390                 395                 400

Thr Ala Leu Asp Val Gln Phe Gly Pro Ile Leu Gln Ala Lys Pro Lys
                405                 410                 415

Ala Leu Ser Val Asp Val Gly Glu Asp Ala Ser Phe Ser Cys Val Trp
            420                 425                 430

Arg Gly Asn Pro Leu Pro Arg Val Thr Trp Thr Arg Arg Gly Asp Ala
        435                 440                 445

Gln Val Leu Ala Ser Gly Pro Thr Leu Arg Leu Pro Ala Val Gly Pro
    450                 455                 460

Glu Asp Ala Gly Asp Tyr Val Cys Arg Ala Glu Pro Gly Leu Ser Gly
465                 470                 475                 480

Arg Gly Gly Gly Ser Ala Glu Ala Arg Leu Thr Val Asn Ala Pro Pro
                485                 490                 495
```

```
Val Val Thr Ala Leu His Ser Ala Pro Ala Phe Leu Arg Gly Pro Ala
            500                 505                 510

Arg Leu Gln Cys Leu Val Phe Ala Ser Pro Thr Pro Glu Ala Val Val
        515                 520                 525

Trp Ser Trp Asp Glu Gly Phe Leu Thr Ala Gly Ser Arg Gly Arg Phe
    530                 535                 540

Leu Val Glu Thr Phe Pro Ala Pro Glu Gly Leu Lys Gly Gln Gly Pro
545                 550                 555                 560

Gly Leu Ile Ser Val Leu His Ile Ser Gly Thr Gln Glu Ser Asp Phe
                565                 570                 575

His Arg Gly Phe Asn Cys Thr Ala Arg Asn Arg Leu Gly Glu Gly Gly
            580                 585                 590

Thr Gln Val Ser Leu Gly Arg Arg Asp Leu Leu Pro Thr Val Arg Ile
        595                 600                 605

Val Ala Gly Val Ala Ala Met Ala Met Thr Leu Leu Met Ile Ile Thr
    610                 615                 620

Gly Val Ala Leu Cys Cys Trp Arg His Gly Arg Gly Gln Ser Ser Phe
625                 630                 635                 640

Ser Lys Gln Lys Asn Leu Val Arg Ile Pro Gly Ser Ser Asp Gly Ser
                645                 650                 655

Ser Ser Arg Gly Pro Glu Glu Glu Thr Gly Ile Ser Lys Asp Gln Gly
            660                 665                 670

Pro Ile Val His Thr Asp His Ser Asp Leu Val Leu Asp Glu Glu Gly
        675                 680                 685

Ala Leu Glu Thr Lys Asp Pro Thr Asn Gly Tyr Tyr Lys Val Arg Gly
    690                 695                 700

Val Ser Val Ser Leu Ser Leu Gly Glu Ala Pro Gly Gly Gly Leu Phe
705                 710                 715                 720

Leu Pro Pro Ser Ser Pro Leu Gly Pro Pro Gly Thr Pro Thr Phe Tyr
                725                 730                 735

Asp Phe Asn Pro His Leu Gly Met Val Pro Pro Cys Arg Leu Tyr Arg
            740                 745                 750

Ser Arg Ala Gly Tyr Leu Thr Thr Pro His Pro Arg Ala Phe Thr Ser
        755                 760                 765

Tyr Ile Lys Pro Thr Ser Phe Gly Pro Pro Asp Leu Ala Pro Ser Thr
    770                 775                 780

Pro Pro Phe Pro Tyr Ala Ala Phe Pro Thr Pro Ser His Pro Arg Leu
785                 790                 795                 800

Gln Thr His Val
```

<210> SEQ ID NO 55
<211> LENGTH: 291
<212> TYPE: DNA
<213> ORGANISM: Artificial
<220> FEATURE:
<223> OTHER INFORMATION: synthetic poly A addition sequence of bovine growth hormone

<400> SEQUENCE: 55

```
aagctttcta gagggcccgt ttaaacccgc tgatcagcct cgactgtgcc ttctagttgc      60

cagccatctg ttgtttgccc ctcccccgtg ccttccttga ccctggaagg tgccactccc     120

actgtccttt cctaataaaa tgaggaaatt gcatcgcatt gtctgagtag gtgtcattct     180

attctggggg gtggggtggg gcaggacagc aagggggagg attgggaaga caatagcagg     240

catgctgggg atgcggtggg ctctatggct tctgaggcgg aaagactcga g              291
```

<210> SEQ ID NO 56
<211> LENGTH: 32
<212> TYPE: DNA
<213> ORGANISM: Artificial
<220> FEATURE:
<223> OTHER INFORMATION: synthetic DNA insert into Asp718I/BamHI site of pSP73-polyA

<400> SEQUENCE: 56
gtaccactag tgctagcacg cgtgcggccg cg 32

<210> SEQ ID NO 57
<211> LENGTH: 32
<212> TYPE: DNA
<213> ORGANISM: Artificial
<220> FEATURE:
<223> OTHER INFORMATION: synthetic DNA insert into Asp718I/BamHI site of pSP73-polyA

<400> SEQUENCE: 57
gatccgcggc cgcacgcgtg ctagcactag tg 32

<210> SEQ ID NO 58
<211> LENGTH: 3261
<212> TYPE: DNA
<213> ORGANISM: Mus musculus

<400> SEQUENCE: 58
atcgattagg agcctatggt ggcacttgtg agcaccagca gcttgtttgt tgctgtcttc 60
cctgagcctc tctctgtgtg ccctgctttt ctgttctttc aatctctttc taactcgccc 120
ttctctcttc cctccctccc tccctccctt ccttctttct cttatcttcc taccattgtc 180
tgtgactgtc gcagtctttc tgtcccggca tcgccttttc tgccctttttc tccccctttc 240 tcccccgtta acagttcttt ctctgagctc taaccccaag accttaaaaa tgcccccttc 300
tctctgtttt tctttactat cacctccctc tcacccactc acaggtactc aaagagcacc 360
ggctgctcta agtccagcag gttcacgaac ccaaagcagt cagccacagc actgagcatt 420
gcttggaccc agtgtgaact cattctgctg cttcccccaa gtccttcctg agtctgccca 480
gccgggcaat gaaatcccct gtcagcacat gccaggaaca ttctttggtg cctccccagc 540
ccgggtgacc ccaaggcccc gggagagcat ttctgatcag ggccatctcc agctcaggat 600
ggaacgcaga gctaggcctg tgtgcgtggg aaggctacaa cccccccccc aggacatcct 660
tgctctttgc agcccagact gtggcatgta ccgcacccct gctggtgaat atgcaggagt 720
gtgttgttaa accaagagag tatgggacag agagaagcca cttctgtggg tatgggtttc 780
agagtgtgcg tgttccaggg gagacgagag cagattttca tctgtggacg tatttggagt 840
gtctcatatg ggtgtgcaca gagcatccag acagtcagca ggactgtgtc cgcagacctc 900
agtgtgtgga aacctggtgt gctcagacgc agataaacat agggtggggg gtccctggga 960
gctgaagcac ctgaatccct gggccatgtg agggccttct gtttcctcaa ctcctccatc 1020
ttcccttgtg tgtgtgtgtg tgtgtgtgtg tatgtcttgc taggatgatt tatcttctta 1080
ttcttctcca cgtctttaat tccatctccc ccctcctcct cctcctccat tcctaccccc 1140
ttctcatttt ctgtcactct tgctgccccc tctgtgtctg gtccttgaat tttagaagca 1200
tatgttgact ggcctgccct cccaacctgg gtgcacagat gaattcgcct gggataagcc 1260
cctgctgcct gcttatctcc tgcaggaatt gcaactgttc tcttttgccc catattccct 1320
acaaacctct cacctcccgg ctgcttcttc tccaggaggc agtccaggca tctggcctga 1380 gccccccctca cagctctcta ccaagggtga gccctctggt ctttctttcc cacccagccc 1440
cattattgat tcattaccct tggtccacat tcccatctcc aaacctatca acacctcctg 1500
ggcaatggat tgcatacaga ccaagccagg gagtctgcta tggggccttt gccagatggt 1560
atctttgggg gccaaggtgt agagctgtca gttgctggag cctttaatta gtgcaaacct 1620
tctacactca cctttggctg ttttccttct ctgaatgctc tggggatccc aggctctcca 1680
tttttccatc ccgtggcccc agagtgccag gaaagggaag ctgtgtcagg tgtctggaaa 1740
aacagcctct cacctgactt cctcccgggg acttaggagt cctgggctca agtctgtcct 1800
atttcaaaac tcagaagcca ggagttcaga tttaggtgtg aggcctccta ggactctctt 1860
ttccaggccc ccagcctgca atccctccac ttctacagga ctcagcacag ctgttcagtc 1920
tgttggtttt cccatcctcg gggcccctag ggggtgagtg agaacgagac tggatgtcaa 1980
atccagtagc tttaagactt aagaccagac attctgaaac tggctcaact ccaccacact 2040
gcagcctgca aggcttctca gccagcagag aagtctgaac tatccccctg gggcaagtcc 2100
aaccctctga tatttagaag taccagtctg agccccaaat gtcatttatt tctgagaggt 2160
ccaggaatgt cagacccggg gtctcaggcc cccaacctcc ccccctccag ccccttcagt 2220
gagctcaggg tccctcccac ctgctctgcc agctgcactg cgtgggaacg cccagctggg 2280
ctgcaccgga gctgtcagga caagctgtgc ggttcccagc ctccctccct gcctgccaga 2340
gccagggcac tgctgcctcc cagccgtcgc ccggcaacca ctcaccactc ggatgggcca 2400
gggactgctg ggtggagaga ggggacgggt gggtgggtac tgctgggtcc tgggaaagga 2460
ggaactcctg gaggggaggg ggcgggctag attcctagat cttaaggtac gtgtatggct 2520
tgcagggata acagagcagc agggagtatt ttgggaaata gggagtattt gggaaatagg 2580
gagcagaaac cctcttctct caaggctcct aaatggtcct tcagcacctg ggtgccctct 2640
ctccgacccg caggcccacg ggagcctgag ctccgcctcc ccagggcgcg gaagctggcg 2700
aagccccagg gattcccatt tatagcttgg tttccactca gctcagtccc tccaggactc 2760
gggctgagca agtttcttcc attcccttct ctcctccctc cacccccttc tcctcctcct 2820
tctccttctt ttcttcctcc tcattcccgc ctccccttca acctcagcag ggtgcaggtg 2880
tccaactcga acaagggccc caacttggac tcagatgttc ccactctcag accccctgat 2940
aatgccgtcc gcacacaagg cgcgggagtt tctcaatggg aagaggccgg gactctagga 3000
ggcggggcga ataggattcc tcccgcctag tgggtccctc gcagtcctag ggttgcaacc 3060
cttgagcggt agagaacacc ggagactgcg gatgagccag atttcgggga cataaaatct 3120
tccagcccgg agagaattgt gtgcagagag gggctccagt ccagcgtggt gtgagaggcg 3180
tgctatcaag aaagaagttg gaggggaacc agtgcaaccc taactctgcg agatcttggg 3240
gtacacacac tcgggggtac c 3261

<210> SEQ ID NO 59
<211> LENGTH: 798
<212> TYPE: DNA
<213> ORGANISM: Mus musculus

<400> SEQUENCE: 59
ggtaccatgc cgcgctcctt cctggtggat tcccttgtgc tgcgggaagc cagcgacaag 60
aaggctccgg agggcagccc gccaccgctc ttcccctacg cggtcccgcc gccgcacgcg 120
ctccacggcc tctcgccggg cgcctgccac gcgcgcaagg ccggcttgct gtgcgtgtgt 180
cccctctgtg tcaccgcttc gcagctgcac gggccccccg ggccgccggc actgccgcta 240
ctcaaggcgt ccttccctcc cttcggatcg cagtactgcc acgcacccct gggccgccag 300

-continued

```
cactccgtgt cccctggagt cgcccacggc ccggccgcgg ccgcagcagc tgctgcactc    360

taccagacct cctacccgct gccggatccc agacagtttc actgcatctc tgtggacagc    420

agctcgaacc agctgcccag cagcaagagg atgcggacgg cgttcaccag cacacagctc    480

ctggagctgg agcgagagtt cgcctccaac atgtacctct cccgcctgcg gcgcatcgag    540

atcgcgacct atctgaacct gtccgagaag caggtgaaga tctggtttca gaaccgccgg    600

gtgaagcaca agaaagaagg caaaggcagt aaccaccgcg gcggagctgg ggcgggggcc    660

ggcgggggcg caccgcaagg ctgcaagtgc tcttcgctct cctcagccaa atgctcagag    720

gacgacgacg aattgcccat gtctccatct tcctccggga aggatgacag agatctcaca    780

gtcactccgt aggtcgac                                                  798


<210> SEQ ID NO 60
<211> LENGTH: 6
<212> TYPE: PRT
<213> ORGANISM: Artificial
<220> FEATURE:
<223> OTHER INFORMATION: synthetic histidine tag, 6x His purification
      tag

<400> SEQUENCE: 60

His His His His His His
1               5


<210> SEQ ID NO 61
<211> LENGTH: 10
<212> TYPE: PRT
<213> ORGANISM: Artificial
<220> FEATURE:
<223> OTHER INFORMATION: synthetic histidine tag, 10x His purification
      tag

<400> SEQUENCE: 61

His His His His His His His His His His
1               5                   10
```

GABA NEURON PROGENITOR CELL MARKER 65B13

CROSS-REFERENCE TO RELATED APPLICATIONS

This application is a U.S. National Stage Application of PCT/JP2008/052039, filed Feb. 7, 2008, which claims the benefit of Japanese Application No. 2007-031075, filed Feb. 9, 2007, the contents of which are hereby incorporated by reference in their entirety.

REFERENCE TO A "SEQUENCE LISTING," A TABLE, OR A COMPUTER PROGRAM LISTING APPENDIX SUBMITTED AS AN ASCII TEXT FILE

The Sequence Listing written in file - 202.TXT, created on Jul. 16, 2012, 245,760 bytes, machine format IBM-PC, MS-Windows operating system, is hereby incorporated by reference in its entirety for all purposes.

TECHNICAL FIELD

The present invention provides a 65B13 gene as a marker for GABA neuron progenitor cells, and relates to the use of the gene in identifying GABA neuron progenitor cells.

BACKGROUND ART

The brain functions by forming a complex network from a great variety of neurons. Its failure may result in various neurological diseases. To treat such diseases, transplantation and regeneration therapies are currently investigated. The most important thing in these therapeutic methods is to correctly identify various types of neurons in transplantation materials. Furthermore, from the viewpoint of improvement of safety and therapeutic effect, it is desirable to isolate only the type of cells that are needed for transplantation.

The cerebellum works on smooth motor functions such as regulation of balance, posture, and voluntary movement. The failure of cerebellar function due to cerebellar tumor, cerebellar vermis degeneration caused by chronic alcoholism, spinocerebellar degeneration, or such results in dynamic ataxia and balance disorder. Functional recovery can be achieved by replenishing lost neurons and reconstituting the network. There are about five types of neurons in the cerebellum including Purkinje cell, and formation of a proper network of the respective neurons according to organogenic program enables neurotransmission.

There is an area called "dorsal horn" in the dorsal spinal cord. Dorsal root ganglion neurons that detect stimuli from the periphery transmit signals to the dorsal horn interneurons, and the signals are further transmitted to the brain. The dorsal horn contains excitatory glutamatergic neurons and inhibitory GABA neurons. The balance between the two adequately regulates the signal transmission. Inactivation of GABA neurons results in chronic pain, etc.

The development of spinal cord and cerebellar GABA neurons is being studied, and their origin is nearly elucidated. However, there are few markers to identify their progenitor cells, and no cell-surface marker has been identified. Thus, techniques for isolating viable progenitor cells have not yet been developed.

The 65B13 gene is known to be transiently expressed in dopamine-producing neuron progenitor cells after the termination of cell division (see Patent Document 1); however, there is no report published on the connection between the gene and GABA neuron. Furthermore, it has been reported that the types of spinal cord interneurons and Purkinje cells can be identified by using the expression of the Corl1 or Corl2 gene as an indicator, respectively (see Patent Documents 2 and 3). However, to date there is no known marker that can selectively identify GABA neuron progenitor cells. The transcription factor Ptf1a is known to be expressed in GABA progenitor cells; however, it is a transcription factor, and there is no known membrane protein that is useful as a selection marker (Non-Patent Documents 1 and 2).

Patent Document 1: WO2004/038018

Patent Document 2: WO2006/022243

Patent Document 3: WO2006/082826

Non-Patent Document 1: Glasgow S M, Henke R M, Macdonald R J, Wright C V, Johnson J E. Ptf1a determines GABAergic over glutamatergic neuronal cell fate in the spinal cord dorsal horn. Development. 2005 December; 132(24):5461-9.

Non-Patent Document 2: Fuse T, Matsuo N, Sone M, Watanabe M, Bito H, Terashima T, Wright C V, Kawaguchi Y, Nakao K, Nabeshima Y. Ptf1a, a bHLH transcriptional gene, defines GABAergic neuronal fates in cerebellum. Neuron. 2005 Jul. 21; 47(2):201-13.

DISCLOSURE OF THE INVENTION

Problems to be Solved by the Invention

The present invention was achieved in view of the above circumstances. An objective of the present invention is to provide markers that enable selective identification of GABA neuron progenitor cells. Another objective of the present invention is to provide methods of using the markers as an indicator to identify GABA neuron progenitor cells, and reagents for use in these methods.

Means for Solving the Problems

The present inventors identified a selective marker, 65B13, for GABA neuron progenitor cells in the spinal dorsal horn and cerebellum, and successfully isolated GABA neuron progenitor cells using antibodies that bind to the protein encoded by the gene. Specifically, 65B13 was demonstrated to be useful as a marker to isolate GABA-producing neuron progenitor cells in the spinal dorsal horn and cerebellum.

GABA neuron progenitor cells can be efficiently identified or isolated by using the marker identified by the present inventors as an indicator.

The present invention relates to markers that enable selective identification of GABA neuron progenitor cells, methods of using the markers as an indicator to identify GABA neuron progenitor cells, and reagents for use in the methods. More specifically, the present invention provides:

[1] a method for detecting a GABA-producing neuron progenitor cell, which comprises the step of detecting the expression of a polynucleotide that can hybridize to a polynucleotide selected from (i), (ii), (iii), and (iv) below, or to a complementary sequence thereof:

(i) a polynucleotide comprising the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49;

(ii) a polynucleotide that is selectively expressed in a GABA-producing neuron progenitor cell, which is an amino acid sequence encoded by a nucleotide sequence comprising an insertion, substitution, deletion of one or more nucleotides, and/or addition of one or more nucleotides to either or both ends thereof, in the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49;

(iii) a polynucleotide that is selectively expressed in a GABA-producing neuron progenitor cell and hybridizes under stringent conditions to a polynucleotide comprising the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49; and (iv) a polynucleotide that is selectively expressed in a GABA-producing neuron progenitor cell and has 70% or higher sequence identity to a polynucleotide comprising the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49;

[2] the method of [1], wherein the step of detecting the expression of a polynucleotide comprises the steps of:

(a) contacting a test cell sample with a polynucleotide that can hybridize to the polynucleotide selected in [1] or to a complementary sequence thereof, or with a probe comprising the polynucleotide; and (b) detecting reactivity;

[3] the method of [2], wherein the probe is contacted with mRNA prepared from the test cell sample or a complementary DNA (cDNA) transcribed from the mRNA in step (a);

[4] the method of [1], wherein the step of detecting the expression of a polynucleotide that can hybridize to the polynucleotide selected in [1] or to a complementary sequence thereof comprises the steps of:

(a-1) conducting gene amplification using a polynucleotide derived from the test cell sample as a template, and a primer comprising a polynucleotide that can hybridize to the polynucleotide selected in [1] or to a complementary sequence thereof, or a set of primers comprising a polynucleotide that can hybridize to the polynucleotide selected in [1] or to a complementary sequence thereof; and (b-1) detecting the resulting amplification product;

[5] the method of [4], wherein mRNA prepared from the test cell sample or a complementary DNA (cDNA) transcribed from the mRNA is used as a template in step (a-1);

[6] the method of any one of [1] to [5], wherein the detection step is followed by the step of separating a GABA-producing neuron progenitor cell from the detected sample;

[7] the method of any one of [1] to [6], which further comprises the step of detecting or selecting a GABA-producing neuron progenitor cell, using as an indicator the expression of a gene selected from the group consisting of the Corl1, Pax2, Lim1/2, Lbx1, and Corl2 genes;

[8] a method for detecting or selecting a GABA-producing neuron progenitor cell, which comprises the step of detecting a protein selected from:

(v) a protein comprising the amino acid sequence of SEQ ID NO: 2, 4, 34, 36, 38, 40, 42, 44, 46, 48, or 50;

(vi) a protein that is selectively expressed in a GABA-producing neuron progenitor cell and comprises an amino acid sequence comprising an insertion, substitution, deletion of one or more amino acids in the amino acid sequence of SEQ ID NO: 2, 4, 34, 36, 38, 40, 42, 44, 46, 48, or 50, and/or addition of one or more amino acids to either or both ends thereof;

(vii) a protein that is selectively expressed in a GABA-producing neuron progenitor cell and encoded by a polynucleotide that hybridizes under stringent conditions to a polynucleotide encoding the amino acid sequence of SEQ ID NO: 2, 4, 34, 36, 38, 40, 42, 44, 46, 48, or 50; and (viii) a protein that is selectively expressed in a GABA-producing neuron progenitor cell and comprises an amino acid sequence having 70% or higher identity to the amino acid sequence of SEQ ID NO: 2, 4, 34, 36, 38, 40, 42, 44, 46, 48, or 50;

[9] a method for detecting or selecting a GABA-producing neuron progenitor cell, which comprises the step of detecting a marker protein translated from a marker protein mRNA transcribed under the control of a promoter linked to a polynucleotide encoding the marker protein to express the mRNA, wherein the protein to be translated from the mRNA is selected from:

(v) a protein comprising the amino acid sequence of SEQ ID NO: 2, 4, 34, 36, 38, 40, 42, 44, 46, 48, or 50;

(vi) a protein that is selectively expressed in a GABA-producing neuron progenitor cell and comprises an amino acid sequence comprising an insertion, substitution, deletion of one or more amino acids in the amino acid sequence of SEQ ID NO: 2, 4, 34, 36, 38, 40, 42, 44, 46, 48, or 50, and/or addition of one or more amino acids to either or both ends thereof;

(vii) a protein that is selectively expressed in a GABA-producing neuron progenitor cell and encoded by a polynucleotide that hybridizes under stringent conditions to a polynucleotide encoding the amino acid sequence of SEQ ID NO: 2, 4, 34, 36, 38, 40, 42, 44, 46, 48, or 50; and (viii) a protein that is selectively expressed in a GABA-producing neuron progenitor cell and comprises an amino acid sequence having 70% or higher identity to the amino acid sequence of SEQ ID NO: 2, 4, 34, 36, 38, 40, 42, 44, 46, 48, or 50;

[10] the method of [8] or [9], wherein the step of detecting the protein comprises the steps of:

(d) contacting a test cell sample with an antibody that binds to the protein selected in [8] or [9]; and (e) detecting reactivity;

[11] the method of any one of [8] to [10], wherein the detection step is followed by the step of separating a GABA-producing neuron progenitor cell from the detected sample;

[12] the method of any one of [8] to [11], wherein the GABA-producing neuron progenitor cell marker protein other than the protein selected in [8] is a protein encoded by a gene selected from the group consisting of the Corl1, Pax2, Lim1/2, Lbx1, and Corl2 genes;

[13] a kit for detecting a GABA-producing neuron progenitor cell, which comprises a probe, a primer, or a set of primers that enable detection of the expression of a polynucleotide that can hybridize to a polynucleotide selected from (i), (ii), (iii), and (iv) below, or to a complementary sequence thereof:

(i) a polynucleotide comprising the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49;

(ii) a polynucleotide encoding a protein that is selectively expressed in a GABA-producing neuron progenitor cell and which comprises an amino acid sequence encoded by a nucleotide sequence comprising an insertion, substitution, deletion of one or more nucleotides, and/or addition of one or more nucleotides to either or both ends thereof, in the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49;

(iii) a polynucleotide encoding a protein that is selectively expressed in a GABA-producing neuron progenitor cell, which hybridizes under a stringent condition to a polynucleotide comprising the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49; and (iv) a polynucleotide encoding a protein that is selectively expressed in a GABA-producing neuron progenitor cell, which has 70% or higher sequence identity to a polynucleotide comprising the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49;

[14] the kit of [13] for detecting or selecting a GABA-producing neuron progenitor cell, which further comprises a polynucleotide that hybridizes to the transcript of one or more genes selected from the group consisting of the Lbx1, Pax2, Lim1/2, Corl1, and Corl2 genes;

[15] the kit of [13] or [14], which further comprises a cerebellar cell or spinal cord cell;

[16] a kit for detecting or selecting a GABA-producing neuron progenitor cell, which comprises an antibody that binds to a protein selected from:

(v) a protein comprising the amino acid sequence of SEQ ID NO: 2, 4, 34, 36, 38, 40, 42, 44, 46, 48, or 50;

(vi) a protein that is selectively expressed in a GABA-producing neuron progenitor cell and comprises an amino acid sequence comprising an insertion, substitution, deletion of one or more amino acids in the amino acid sequence of SEQ ID NO: 2, 4, 34, 36, 38, 40, 42, 44, 46, 48, or 50, and/or addition of one or more amino acids to either or both ends thereof;

(vii) a protein that is selectively expressed in a GABA-producing neuron progenitor cell and encoded by a polynucleotide that hybridizes under stringent conditions to a polynucleotide encoding the amino acid sequence of SEQ ID NO: 2, 4, 34, 36, 38, 40, 42, 44, 46, 48, or 50; and (viii) a protein that is selectively expressed in a GABA-producing neuron progenitor cell and comprises an amino acid sequence having 70% or higher identity to the amino acid sequence of SEQ ID NO: 2, 4, 34, 36, 38, 40, 42, 44, 46, 48, or 50;

[17] a kit for detecting or selecting a GABA-producing neuron progenitor cell, which comprises a polynucleotide comprising a polynucleotide encoding a marker protein linked to a promoter to express the mRNA translated into a protein selected from:

(v) a protein comprising the amino acid sequence of SEQ ID NO: 2, 4, 34, 36, 38, 40, 42, 44, 46, 48, or 50;

(vi) a protein that is selectively expressed in a GABA-producing neuron progenitor cell and comprises an amino acid sequence comprising an insertion, substitution, deletion of one or more amino acids in the amino acid sequence of SEQ ID NO: 2, 4, 34, 36, 38, 40, 42, 44, 46, 48, or 50, and/or addition of one or more amino acids to either or both ends thereof;

(vii) a protein that is selectively expressed in a GABA-producing neuron progenitor cell and encoded by a polynucleotide that hybridizes under stringent conditions to a polynucleotide encoding the amino acid sequence of SEQ ID NO: 2, 4, 34, 36, 38, 40, 42, 44, 46, 48, or 50; and (viii) a protein that is selectively expressed in a GABA-producing neuron progenitor cell and comprises an amino acid sequence having 70% or higher identity to the amino acid sequence of SEQ ID NO: 2, 4, 34, 36, 38, 40, 42, 44, 46, 48, or 50;

[18] the kit of [16] or [17] for detecting or selecting a GABA-producing neuron progenitor cell, which further comprises in combination an antibody that binds to a protein encoded by one or more genes selected from the group consisting of the Lbx1, Pax2, Lim1/2, Corl1, and Corl2 genes;

[19] the kit of any one of [16] to [18], which further comprises a cerebellar cell or spinal cord cell;

[20] the kit of [15] or [19], wherein the target cerebellar cell for detection is a Purkinje cell;

[21] the kit of [15] or [19], wherein the target spinal cord cell for detection is dI4 or dILA;

[22] a method of screening for a substance that is effective for differentiating a GABA-producing neuron progenitor cell, which comprises the steps of:

(I) contacting a test compound with a cell that can differentiate into a GABA-producing neuron progenitor cell; and (II) detecting the expression of the polynucleotide of a GABA-producing neuron progenitor cell, which can hybridize to a nucleotide sequence selected from (i), (ii), (iii), and (iv) below, or to a complementary sequence thereof:

(i) a polynucleotide comprising the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49;

(ii) a polynucleotide encoding a protein that is selectively expressed in a GABA-producing neuron progenitor cell and which comprises an amino acid sequence encoded by a nucleotide sequence comprising an insertion, substitution, deletion of one or more nucleotides, and/or addition of one or more nucleotides to either or both ends thereof, in the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49;

(iii) a polynucleotide encoding a protein that is selectively expressed in a GABA-producing neuron progenitor cell, which hybridizes under a stringent condition to a polynucleotide comprising the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49; and (iv) a polynucleotide encoding a protein that is selectively expressed in a GABA-producing neuron progenitor cell, which has 70% or higher sequence identity to a polynucleotide comprising the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49;

[23] the method of [22], which further comprises step (III) of selecting a compound which detects the expression of the polynucleotide in step (II);

[24] a method of screening for a substance that is effective for differentiating a GABA-producing neuron progenitor cell, which comprises the steps of:

(IV) contacting a test compound with a cell that can differentiate into a GABA-producing neuron progenitor cell; and (V) detecting a protein selected from:

(v) a protein comprising the amino acid sequence of SEQ ID NO: 2, 4, 34, 36, 38, 40, 42, 44, 46, 48, or 50;

(vi) a protein that is selectively expressed in a GABA-producing neuron progenitor cell and comprises an amino acid sequence comprising an insertion, substitution, deletion of one or more amino acids in the amino acid sequence of SEQ ID NO: 2, 4, 34, 36, 38, 40, 42, 44, 46, 48, or 50, and/or addition of one or more amino acids to either or both ends thereof;

(vii) a protein that is selectively expressed in a GABA-producing neuron progenitor cell and encoded by a polynucleotide that hybridizes under stringent conditions to a polynucleotide encoding the amino acid sequence of SEQ ID NO: 2, 4, 34, 36, 38, 40, 42, 44, 46, 48, or 50; and (viii) a protein that is selectively expressed in a GABA-producing neuron progenitor cell and comprises an amino acid sequence having 70% or higher identity to the amino acid sequence of SEQ ID NO: 2, 4, 34, 36, 38, 40, 42, 44, 46, 48, or 50;

[25] a method of screening for a substance that is effective for differentiating a GABA-producing neuron progenitor cell, which comprises the steps of:

(IV-1) contacting a test compound with a cell that can differentiate into a GABA-producing neuron progenitor cell; and (V-1) detecting a marker protein translated from a marker protein mRNA transcribed under the control of a promoter linked to a polynucleotide encoding the marker protein to express the mRNA, wherein the protein to be translated from the mRNA is selected from:

(v) a protein comprising the amino acid sequence of SEQ ID NO: 2, 4, 34, 36, 38, 40, 42, 44, 46, 48, or 50;

(vi) a protein that is selectively expressed in a GABA-producing neuron progenitor cell and comprises an amino acid sequence comprising an insertion, substitution, deletion of one or more amino acids in the amino acid sequence of SEQ ID NO: 2, 4, 34, 36, 38, 40, 42, 44, 46, 48, or 50, and/or addition of one or more amino acids to either or both ends thereof;

(vii) a protein that is selectively expressed in a GABA-producing neuron progenitor cell and encoded by a polynucleotide that hybridizes under stringent conditions to a polynucleotide encoding the amino acid sequence of SEQ ID NO: 2, 4, 34, 36, 38, 40, 42, 44, 46, 48, or 50; and (viii) a protein that is selectively expressed in a GABA-producing neuron progenitor cell and comprises an amino acid sequence having 70% or higher identity to the amino acid sequence of SEQ ID NO: 2, 4, 34, 36, 38, 40, 42, 44, 46, 48, or 50;

[26] the method of [24] or [25], which further comprises step (VI) of selecting a compound which detects the protein in step (V);

[27] a method for producing a GABA-producing neuron progenitor cell, which comprises the steps of:

(VII) obtaining a cell population potentially containing a GABA-producing neuron progenitor cell;

(VIII) detecting a GABA-producing neuron progenitor cell using the method of any one of [1] to [12]; and (IX) growing the cell detected or selected in step (VIII);

[28] the production method of [27], wherein the GABA-producing neuron progenitor cell is used to treat spinal cord injury or cerebellar degeneration;

[29] a GABA-producing neuron progenitor cell population obtained by the steps of:

(VII) obtaining a cell population potentially containing a GABA-producing neuron progenitor cell;

(VIII) detecting or selecting a GABA-producing neuron progenitor cell using the method of any one of [1] to [12]; and (IX) growing the cell detected in step (VIII);

[30] a reagent for detecting or selecting a GABA-producing neuron progenitor cell, which comprises a probe, a primer, or a set of primers that enable to detect the expression of a polynucleotide that can hybridize to a polynucleotide selected from (i), (ii), (iii), and (iv) below, or to a complementary sequence thereof:

(i) a polynucleotide comprising the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49;

(ii) a polynucleotide encoding a protein that is selectively expressed in a GABA-producing neuron progenitor cell and which comprises an amino acid sequence encoded by a nucleotide sequence comprising an insertion, substitution, deletion of one or more nucleotides, and/or addition of one or more nucleotides to either or both ends thereof, in the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49;

(iii) a polynucleotide encoding a protein that is selectively expressed in a GABA-producing neuron progenitor cell, which hybridizes under a stringent condition to a polynucleotide comprising the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49; and (iv) a polynucleotide encoding a protein that is selectively expressed in a GABA-producing neuron progenitor cell, which has 70% or higher sequence identity to a polynucleotide comprising the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49;

[31] the reagent of [30] for detecting or selecting a cerebellar cell or spinal cord cell, which further comprises in combination a polynucleotide that hybridizes to a transcript of one or more genes selected from the group consisting of the Lbx1, Pax2, Lim1/2, Corl1, and Corl2 genes;

[32] the reagent of [30] or [31], which further comprises a cerebellar cell or spinal cord cell;

[33] a reagent for detecting or selecting a GABA-producing neuron progenitor cell, which comprises an antibody that binds to a protein selected from:

(v) a protein comprising the amino acid sequence of SEQ ID NO: 2, 4, 34, 36, 38, 40, 42, 44, 46, 48, or 50;
(vi) a protein that is selectively expressed in a GABA-producing neuron progenitor cell and comprises an amino acid sequence comprising an insertion, substitution, deletion of one or more amino acids in the amino acid sequence of SEQ ID NO: 2, 4, 34, 36, 38, 40, 42, 44, 46, 48, or 50, and/or addition of one or more amino acids to either or both ends thereof;
(vii) a protein that is selectively expressed in a GABA-producing neuron progenitor cell and encoded by a polynucleotide that hybridizes under stringent conditions to a polynucleotide encoding the amino acid sequence of SEQ ID NO: 2, 4, 34, 36, 38, 40, 42, 44, 46, 48, or 50; and
(viii) a protein that is selectively expressed in a GABA-producing neuron progenitor cell and comprises an amino acid sequence having 70% or higher identity to the amino acid sequence of SEQ ID NO: 2, 4, 34, 36, 38, 40, 42, 44, 46, 48, or 50;
[34] a reagent for detecting or selecting a GABA-producing neuron progenitor cell, which comprises a polynucleotide comprising a polynucleotide encoding a marker protein linked to a promoter to express the mRNA translated into a protein selected from:
(v) a protein comprising the amino acid sequence of SEQ ID NO: 2, 4, 34, 36, 38, 40, 42, 44, 46, 48, or 50;
(vi) a protein that is selectively expressed in a GABA-producing neuron progenitor cell and comprises an amino acid sequence comprising an insertion, substitution, deletion of one or more amino acids in the amino acid sequence of SEQ ID NO: 2, 4, 34, 36, 38, 40, 42, 44, 46, 48, or 50, and/or addition of one or more amino acids to either or both ends thereof;
(vii) a protein that is selectively expressed in a GABA-producing neuron progenitor cell and encoded by a polynucleotide that hybridizes under stringent conditions to a polynucleotide encoding the amino acid sequence of SEQ ID NO: 2, 4, 34, 36, 38, 40, 42, 44, 46, 48, or 50; and
(viii) a protein that is selectively expressed in a GABA-producing neuron progenitor cell and comprises an amino acid sequence having 70% or higher identity to the amino acid sequence of SEQ ID NO: 2, 4, 34, 36, 38, 40, 42, 44, 46, 48, or 50;
[35] the reagent of [33] or [34] for detecting or selecting a GABA-producing neuron progenitor cell, which further comprises in combination an antibody that binds to a protein encoded by one or more genes selected from the group consisting of the Lbx1, Pax2, Lim1/2, Corl1, and Corl2 genes;
[36] the reagent of any one of [33] to [35], which further comprises a cerebellar cell or spinal cord cell;
[37] the reagent of any one of [33] to [36], wherein the target cerebellar cell for detection is a Purkinje cell;
[38] the reagent of any one of [33] to [36], wherein the target spinal cord cell for detection is dI4 or dILA;
[39] a polynucleotide for detecting or selecting a GABA-producing neuron progenitor cell for use in regeneration medicine to treat cerebellar degeneration or spinal cord injury, which can hybridize to a polynucleotide selected from (i), (ii), (iii), and (iv) below, or to a complementary sequence thereof:
(i) a polynucleotide comprising the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49;
(ii) a polynucleotide encoding a protein that is selectively expressed in a GABA-producing neuron progenitor cell and which comprises an amino acid sequence encoded by a nucleotide sequence comprising an insertion, substitution, deletion of one or more nucleotides, and/or addition of one or more nucleotides to either or both ends thereof, in the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49;
(iii) a polynucleotide encoding a protein that is selectively expressed in a GABA-producing neuron progenitor cell, which hybridizes under a stringent condition to a polynucleotide comprising the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49; and
(iv) a polynucleotide encoding a protein that is selectively expressed in a GABA-producing neuron progenitor cell, which has 70% or higher sequence identity to a polynucleotide comprising the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49;
[40] the polynucleotide of [39] for detecting or selecting a GABA-producing neuron progenitor cell, wherein the GABA-producing neuron progenitor cell is a spinal cord or cerebellar GABA-producing neuron progenitor cell;

[41] the polynucleotide of [39] or [40] for detection or selection, which comprises a polynucleotide comprising at least 10 consecutive nucleotides of the nucleotide sequence of [39] or [40] or a complementary sequence thereof;

[42] the polynucleotide of [39] or [40] for detection or selection, which comprises a polynucleotide comprising at least 15 consecutive nucleotides of the nucleotide sequence of [39] or [40] or a complementary sequence thereof;

[43] a probe comprising the detection polynucleotide of any one of [39] to [42];

[44] a primer comprising the detection polynucleotide of any one of [39] to [42];

[45] a primer set comprising two or more of the detection polynucleotides, each of which is shown in any one of [39] to [42];

[46] an antibody for detecting or selecting a GABA-producing neuron progenitor cell for use in regeneration medicine to treat cerebellar degeneration or spinal cord injury, which binds to a protein selected from:

(v) a protein comprising the amino acid sequence of SEQ ID NO: 2, 4, 34, 36, 38, 40, 42, 44, 46, 48, or 50;

(vi) a protein that is selectively expressed in a GABA-producing neuron progenitor cell and comprises an amino acid sequence comprising an insertion, substitution, deletion of one or more amino acids in the amino acid sequence of SEQ ID NO: 2, 4, 34, 36, 38, 40, 42, 44, 46, 48, or 50, and/or addition of one or more amino acids to either or both ends thereof;

(vii) a protein that is selectively expressed in a GABA-producing neuron progenitor cell and encoded by a polynucleotide that hybridizes under stringent conditions to a polynucleotide encoding the amino acid sequence of SEQ ID NO: 2, 4, 34, 36, 38, 40, 42, 44, 46, 48, or 50; and (viii) a protein that is selectively expressed in a GABA-producing neuron progenitor cell and comprises an amino acid sequence having 70% or higher identity to the amino acid sequence of SEQ ID NO: 2, 4, 34, 36, 38, 40, 42, 44, 46, 48, or 50;

[47] the antibody of [46], wherein the GABA-producing neuron progenitor cell is a cerebellar cell or spinal cord cell;

[48] the antibody of [46] or [47], which binds to a polypeptide comprising the entire or at least six consecutive amino acid residues of the amino acid sequence of positions 21 to 510 in the amino acid sequence of SEQ ID NO: 2, 4, 38, 40, 42, or 44; the amino acid sequence of positions 20 to 513 in the amino acid sequence of SEQ ID NO: 34 or 36; the amino acid sequence of positions 21 to 460 in the amino acid sequence of SEQ ID NO: 46 or 48; or the amino acid sequence of positions 21 to 490 in the amino acid sequence of SEQ ID NO: 50;

[49] the antibody of any one of [46] to [48], which binds to a polypeptide comprising at least six amino acid residues;

[50] a GABA-producing neuron progenitor cell for use in regeneration medicine to treat cerebellar degeneration or spinal cord injury, which is detected or selected by using a polynucleotide that can hybridize to a polynucleotide selected from (i), (ii), (iii), and (iv) below, or to a complementary sequence thereof:

(i) a polynucleotide comprising the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49;

(ii) a polynucleotide encoding a protein that is selectively expressed in a GABA-producing neuron progenitor cell and which comprises an amino acid sequence encoded by a nucleotide sequence comprising an insertion, substitution, deletion of one or more nucleotides, and/or addition of one or more nucleotides to either or both ends thereof, in the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49;

(iii) a polynucleotide encoding a protein that is selectively expressed in a GABA-producing neuron progenitor cell, which hybridizes under a stringent condition to a polynucleotide comprising the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49; and (iv) a polynucleotide encoding a protein that is selectively expressed in a GABA-producing neuron progenitor cell, which has 70% or higher sequence identity to a polynucleotide comprising the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49;

[51] the GABA-producing neuron progenitor cell of [50], wherein the GABA-producing neuron progenitor cell is a spinal cord or cerebellar GABA-producing neuron progenitor cell;

[52] the GABA-producing neuron progenitor cell of [50] or [51], wherein the polynucleotide comprises at least 10 consecutive nucleotides of a polynucleotide selected from (i), (ii), (iii), and (iv) below, or a complementary sequence thereof;

[53] the GABA-producing neuron progenitor cell of [50] or [51], wherein the polynucleotide comprises at least 15 consecutive nucleotides of a polynucleotide selected from (i), (ii), (iii), and (iv) below, or a complementary sequence thereof;

[54] a GABA-producing neuron progenitor cell for use in regeneration medicine to treat cerebellar degeneration or spinal cord injury, which has been detected or selected by using an antibody that binds to a protein selected from:

(v) a protein comprising the amino acid sequence of SEQ ID NO: 2, 4, 34, 36, 38, 40, 42, 44, 46, 48, or 50;

(vi) a protein that is selectively expressed in a GABA-producing neuron progenitor cell and comprises an amino acid sequence comprising an insertion, substitution, deletion of one or more amino acids in the amino acid sequence of SEQ ID NO: 2, 4, 34, 36, 38, 40, 42, 44, 46, 48, or 50, and/or addition of one or more amino acids to either or both ends thereof;

(vii) a protein that is selectively expressed in a GABA-producing neuron progenitor cell and encoded by a polynucleotide that hybridizes under stringent conditions to a polynucleotide encoding the amino acid sequence of SEQ ID NO: 2, 4, 34, 36, 38, 40, 42, 44, 46, 48, or 50; and (viii) a protein that is selectively expressed in a GABA-producing neuron progenitor cell and comprises an amino acid sequence having 70% or higher identity to the amino acid sequence of SEQ ID NO: 2, 4, 34, 36, 38, 40, 42, 44, 46, 48, or 50;

[55] the GABA-producing neuron progenitor cell of [54], wherein the GABA-producing neuron progenitor cell is a cerebellar or spinal cord GABA-producing neuron progenitor cell;

[56] the GABA-producing neuron progenitor cell of [54] or [55], wherein the antibody binds to a polypeptide comprising the entire or at least six consecutive amino acid residues of the amino acid sequence of positions 21 to 510 in the amino acid sequence of SEQ ID NO: 2, 4, 34, 36, 38, 40, 42, 44, 46, 48, or 50;

[57] the GABA-producing neuron progenitor cell of any one of [54] to [56], wherein the antibody binds to a polypeptide comprising at least six amino acid residues;

[58] a method for treating cerebellar degeneration or spinal cord injury, which comprises transplanting a GABA-producing neuron progenitor cell detected or selected by using a polynucleotide that can hybridize to a polynucleotide selected from (i), (ii), (iii), and (iv) below, or to a complementary sequence thereof:

(i) a polynucleotide comprising the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49;

(ii) a polynucleotide encoding a protein that is selectively expressed in a GABA-producing neuron progenitor cell and which comprises an amino acid sequence encoded by a nucleotide sequence comprising an insertion, substitution, deletion of one or more nucleotides, and/or addition of one or more nucleotides to either or both ends thereof, in the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49;

(iii) a polynucleotide encoding a protein that is selectively expressed in a GABA-producing neuron progenitor cell, which hybridizes under a stringent condition to a polynucleotide comprising the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49; and (iv) a polynucleotide encoding a protein that is selectively expressed in a GABA-producing neuron progenitor cell, which has 70% or higher sequence identity to a polynucleotide comprising the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49;

[59] the method of [58] for transplanting a GABA-producing neuron progenitor cell, wherein the GABA-producing neuron progenitor cell is a spinal cord or cerebellar GABA-producing neuron progenitor cell;

[60] the method of [58] or [59] for transplanting a GABA-producing neuron progenitor cell, wherein the polynucleotide comprises at least 10 consecutive nucleotides of a polynucleotide selected from (i), (ii), (iii), and (iv) mentioned above, or a complementary sequence thereof;

[61] the method of [58] or [59] for transplanting a GABA-producing neuron progenitor cell, wherein the polynucleotide comprises at least 15 consecutive nucleotides of a polynucleotide selected from (i), (ii), (iii), and (iv) mentioned above, or a complementary sequence thereof;

[62] a method for treating cerebellar degeneration or spinal cord injury, which comprises transplanting a GABA-producing neuron progenitor cell selected by using an antibody that binds to a protein selected from:

(v) a protein comprising the amino acid sequence of SEQ ID NO: 2, 4, 34, 36, 38, 40, 42, 44, 46, 48, or 50;

(vi) a protein that is selectively expressed in a GABA-producing neuron progenitor cell and comprises an amino acid sequence comprising an insertion, substitution, deletion of one or more amino acids in the amino acid sequence of SEQ ID NO: 2, 4, 34, 36, 38, 40, 42, 44, 46, 48, or 50, and/or addition of one or more amino acids to either or both ends thereof;

(vii) a protein that is selectively expressed in a GABA-producing neuron progenitor cell and encoded by a polynucleotide that hybridizes under stringent conditions to a polynucleotide encoding the amino acid sequence of SEQ ID NO: 2, 4, 34, 36, 38, 40, 42, 44, 46, 48, or 50; and (viii) a protein that is selectively expressed in a GABA-producing neuron progenitor cell and comprises an amino acid sequence having 70% or higher identity to the amino acid sequence of SEQ ID NO: 2, 4, 34, 36, 38, 40, 42, 44, 46, 48, or 50;

[63] the method of [62] for transplanting a GABA-producing neuron progenitor cell, wherein the GABA-producing neuron progenitor cell is a cerebellar or spinal cord GABA-producing neuron progenitor cell;

[64] the method of [62] or [63] for transplanting a GABA-producing neuron progenitor cell, wherein the antibody binds to a polypeptide comprising the entire or at least six consecutive amino acid residues of the amino acid sequence of positions 21 to 510 in the amino acid sequence of SEQ ID NO: 2, 4, 38, 40, 42, or 44; the amino acid sequence of positions 20 to 513 in the amino acid sequence of SEQ ID NO: 34 or 36; the amino acid sequence of positions 21 to 460 in the amino acid sequence of SEQ ID NO: 46 or 48; or the amino acid sequence of positions 21 to 490 in the amino acid sequence of SEQ ID NO: 50; and

[65] the method of any one of [62] to [64] for transplanting a GABA-producing neuron progenitor cell, wherein the antibody binds to a polypeptide comprising at least six amino acid residues.

BRIEF DESCRIPTION OF THE DRAWINGS

FIG. 5A shows a result of flow cytometry analysis using an anti-65B13 antibody; FIG. 5B shows marker staining of the isolated 65B13-positive cells after two days of culture.

FIG. 6A shows the result of expression analysis at E12.5; FIG. 6B shows the result of expression analysis at E14.5. In FIG. 6B, the left and right photographs show the expression of 65B13 or Pax2, respectively.

FIG. 7A shows results for the cerebella and 65B13-positive cells isolated from the E12.5 cerebella. FIG. 7B shows results of the cerebella and 65B13-positive cells isolated from the E14.5 cerebella.

BEST MODE FOR CARRYING OUT THE INVENTION

Figure 1:
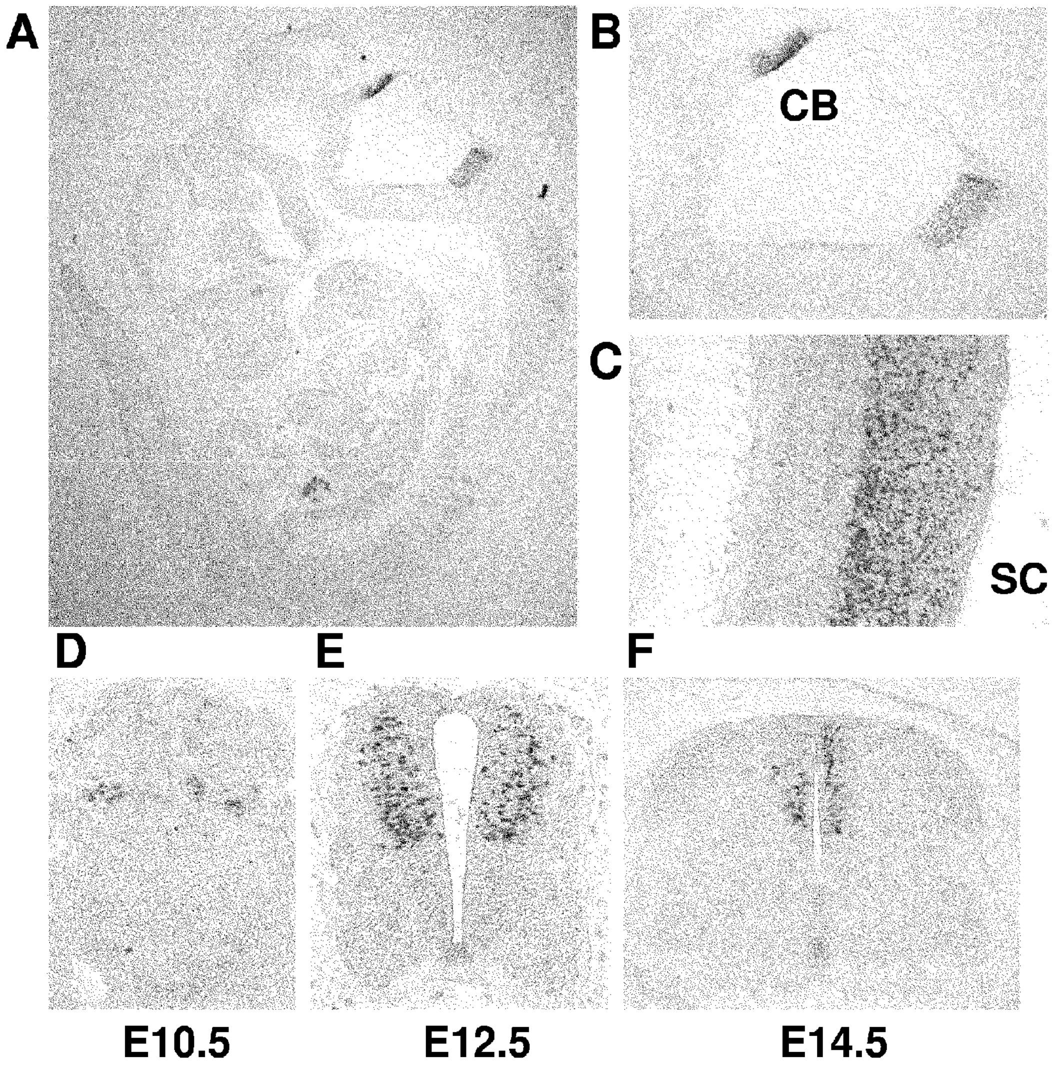
FIG. 1 shows the expression pattern of the 65B13 gene in the nervous system of fetal mouse. A, E12.5 sagittal section; B, E12.5 cerebellar primordium; C, E12.5 spinal cord; D, E10.5 spinal cord; E, E12.5 spinal cord; F, E14.5 spinal cord. CB, cerebellar primordium; SC, spinal cord.

The present inventors demonstrated that the 65B13 gene was selectively expressed in GABA neuron progenitor cells of spinal dorsal horn and cerebellum.

The present invention provides polynucleotides for detecting or selecting GABA-producing neuron progenitor cells.

The 65B13 gene of the present invention includes, for example, two types of genes named 65B13-a and 65B13-b, which are alternative isoforms of the 65B13 gene. The respective nucleotide sequences are shown in SEQ ID NOs: 1 and 3, and the amino acid sequences encoded by the genes are shown in SEQ ID NOs: 2 and 4. The coding region of 65B13-a starts with A at position 178 in SEQ ID NO: 1, and extends to the stop codon at positions 2278 to 2280, encoding a protein of 700 amino acids. The 17 amino acid residues encoded by the sequence of positions 178 to 228 constitute a signal sequence, while the 17 amino acid residues encoded by the sequence of positions 1717 to 1767 constitute a transmembrane region. On the other hand, the coding region of 65B13-b starts with A at position 127 in SEQ ID NO: 2 and extends to the stop codon at positions 2277 to 2079, encoding a protein of 650 amino acids. The 17 amino acid residues encoded by the sequence of positions 127 to 178 constitute a signal sequence, while the 17 amino acid residues encoded by the sequence of positions 1516 to 1566 constitute a transmembrane region. Furthermore, the 65B13 gene of the present invention also includes, for example, the genes of SEQ ID NOs: 33, 35, 37, 39, 41, 43, 45, 47, and 49. The amino acid sequences encoded by the genes are shown in SEQ ID NOs: 34, 36, 38, 40, 42, 44, 46, 48, and 50, respectively. The coding region of SEQ ID NO: 33 starts with A at position 668 and extends to the stop codon at positions 2768 to 2770, encoding a protein of 700 amino acids. The 19 amino acid residues encoded by the sequence of positions 668 to 724 constitute a signal sequence, while the 494 amino acid residues encoded by the sequence of positions 725 to 2206 constitute an extracellular domain. The coding region of SEQ ID NO: 35 starts with A at position 130 and extends to the stop codon at positions 2230 to 2232, encoding a protein of 700 amino acids. The 19 amino acid residues encoded by the sequence of positions 130 to 186 constitute a signal sequence, while the 494 amino acid residues encoded by the sequence of positions 187 to 1668 constitute an extracellular domain. The coding region of SEQ ID NO: 37 starts with A at position 199 and extends to the stop codon at positions 2098 to 2100, encoding a protein of 633 amino acids. The 20 amino acid residues encoded by the sequence of positions 199 to 258 constitute a signal sequence, while the 490 amino acid residues encoded by the sequence of positions 259 to 1728 constitute an extracellular domain. The coding region of SEQ ID NO: 39 starts with A at position 199 and extends to the stop codon at positions 2323 to 2325, encoding a protein of 708 amino acids. The 20 amino acid residues encoded by the sequence of positions 199 to 258 constitute a signal sequence, while the 490 amino acid residues encoded by the sequence of positions 259 to 1728 constitute an extracellular domain. The coding region of SEQ ID NO: 41 starts with A at position 199 and extends to the stop codon at positions 2323 to 2325, encoding a protein of 708 amino acids. The 20 amino acid residues encoded by the sequence of positions 199 to 258 constitute a signal sequence, while the 490 amino acid residues encoded by the sequence of positions 259 to 1728 constitute an extracellular domain. The coding region of SEQ ID NO: 43 starts with A at position 15 and extends to the stop codon at positions 1914 to 1916, encoding a protein of 633 amino acids. The 20 amino acid residues encoded by the sequence of positions 15 to 74 constitute a signal sequence, while the 490 amino acid residues encoded by the sequence of positions 75 to 1544 constitute an extracellular domain. The coding region of SEQ ID NO: 45 starts with A at position 199 and extends to the stop codon at positions 1948 to 1950, encoding a protein of 583 amino acids. The 20 amino acid residues encoded by the sequence of positions 199 to 258 constitute a signal sequence, while the 440 amino acid residues encoded by the sequence of positions 259 to 1578 constitute an extracellular domain. The coding region of SEQ ID NO: 47 starts with A at position 15 and extends to the stop codon at positions 1764 to 1766, encoding a protein of 583 amino acids. The 20 amino acid residues encoded by the sequence of positions 15 to 74 constitute a signal sequence, while the 440 amino acid residues encoded by the sequence of positions 75 to 1394 constitute an extracellular domain. The coding region of SEQ ID NO: 49 starts with A at position 196 and extends to the stop codon at positions 2260 to 2262, encoding a protein of 688 amino acids. The 20 amino acid residues encoded by the sequence of positions 196 to 255 constitute a signal sequence, while the 470 amino acid residues encoded by the sequence of positions 256 to 1665 constitute an extracellular domain. In addition, the 65B13 gene of the present invention also includes, for example, the sequences of accession numbers XM_994164, AL136654, XM_512603, XR_012248, XM_541684, and XM_583222.

In a preferred embodiment, the polynucleotides of the present invention include polynucleotides for detecting or selecting GABA-producing neuron progenitor cells, which can hybridize to a nucleotide selected from (i), (ii), (iii), and (iv) below, or to a complementary sequence thereof.

(i) a polynucleotide comprising the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49;

(ii) a polynucleotide encoding a protein that is selectively expressed in a GABA-producing neuron progenitor cell and which comprises an amino acid sequence encoded by a nucleotide sequence comprising an insertion, substitution, deletion of one or more nucleotides, and/or addition of one or more nucleotides to either or both ends thereof, in the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49;

(iii) a polynucleotide encoding a protein that is selectively expressed in a GABA-producing neuron progenitor cell, which hybridizes under a stringent condition to a polynucleotide comprising the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49; and (iv) a polynucleotide encoding a protein that is selectively expressed in a GABA-producing neuron progenitor cell, which has 70% or higher sequence identity to a polynucleotide comprising the nucleotide sequence of positions 178 to 2280 in SEQ ID NO: 1; the nucleotide sequence of positions 127 to 2079 in SEQ ID NO: 3; the nucleotide sequence of positions 668 to 2770 in SEQ ID NO: 33; the nucleotide sequence of positions 130 to 2232 in SEQ ID NO: 35; the nucleotide sequence of positions 199 to 2100 in SEQ ID NO: 37; the nucleotide sequence of positions 199 to 2325 in SEQ ID NO: 39; the nucleotide sequence of positions 15 to 2325 in SEQ ID NO: 41; the nucleotide sequence of positions 15 to 1916 in SEQ ID NO: 43; the nucleotide sequence of positions 199 to 1950 in SEQ ID NO: 45; the nucleotide sequence of positions 15 to 1766 in SEQ ID NO: 47; or the nucleotide sequence of positions 196 to 2262 in SEQ ID NO: 49.

In the present invention, a "polynucleotide" refers to a polymer comprising nucleotides or nucleotide pairs of multiple deoxyribonucleic acids (DNA) or ribonucleic acids (RNA), and includes DNA, cDNA, genomic DNA, chemically synthesized DNA, and RNA. If needed, polynucleotides can also contain non-naturally occurring nucleotides such as 4-acetylcytidine, 5-(carboxyhydroxymethyl)uridine, 2'-O-methylcytidine, 5-carboxymethylaminomethyl-2-thiouridine, 5-carboxymethylaminomethyluridine, dihydrouridine, 2'-O-methylpseudouridine, β-D-galactosylqueuosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, β-D-mannosylqueuosine, 5-methoxycarbonylmethyl-2-thiouridine, 5-methoxycarbonylmethyluridine, 5-methoxyuridine, 2-methylthio-N6-isopentenyladenosine, N-((9-β-D-ribofuranosyl-2-methylthiopurin-6-yl)carbamoyl)threonine, N-((9-β-D-ribofuranosylpurin-6-yl)N-methylcarbamoyl) threonine, uridine-5-oxyacetic acid-methyl ester, uridine-5-oxyacetic acid, wybutoxosine, pseudouridine, queuosine, 2-thiocytidine, 5-methyl-2-thiouridine, 2-thiouridine, 4-thiouridine, 5-methyluridine, N-((9-β-D-ribofuranosylpurin-6-yl)carbamoyl)threonine, 2'-O-methyl-5-methyluridine, 2'-O-methyluridine, wybutosine, and 3-(3-amino-3-carboxy propyl)uridine.

The polynucleotides of the present invention can also be produced by chemical synthesis based on the known sequence of 65B13. Alternatively, such polynucleotides can be prepared from 65B13 gene-expressing cells using hybridization, PCR, etc.

Meanwhile, the phrase "functionally equivalent" means that a target protein has the same biological property as a 65B13 protein (for example, the amino acid sequence of SEQ ID NO: 2, 4, 34, 36, 38, 40, 42, 44, 46, 48, or 50). The biological property of a 65B13 protein (for example, the amino acid sequence of SEQ ID NO: 2, 4, 34, 36, 38, 40, 42, 44, 46, 48, or 50) includes, for example, the olfactory nerve network pattern. Furthermore, the selective expression in GABA neuron progenitor cells can also be regarded as a function (biological property).

Accordingly, whether a target protein has the equivalent biological property as the amino acid sequence of SEQ ID NO: 2, 4, 34, 36, 38, 40, 42, 44, 46, 48, or 50 identified by the present inventors can be assessed by those skilled in the art, for example, by testing for the olfactory nerve network pattern or selective expression in GABA neuron progenitor cells.

The polynucleotides of the present invention also include polynucleotides that hybridize under stringent conditions to a polynucleotide comprising the nucleotide sequence of positions 178 to 2280 in SEQ ID NO: 1, the nucleotide sequence of positions 127 to 2079 in SEQ ID NO: 3, the nucleotide sequence of positions 668 to 2770 in SEQ ID NO: 33, the nucleotide sequence of positions 130 to 2232 in SEQ ID NO: 35, the nucleotide sequence of positions 199 to 2100 in SEQ ID NO: 37, the nucleotide sequence of positions 199 to 2325 in SEQ ID NO: 39, the nucleotide sequence of positions 15 to 2325 in SEQ ID NO: 41, the nucleotide sequence of positions 15 to 1916 in SEQ ID NO: 43, the nucleotide sequence of positions 199 to 1950 in SEQ ID NO: 45, the nucleotide sequence of positions 15 to 1766 in SEQ ID NO: 47, or the nucleotide sequence of positions 196 to 2262 in SEQ ID NO: 49, and each of which encodes a protein that is functionally equivalent (a preferred function is the selective expression in GABA-producing neuron progenitor cells) to a protein comprising the amino acid sequence of SEQ ID NO: 2, 4, 34, 36, 38, 40, 42, 44, 46, 48, or 50. The polypeptides also include isoforms, alternative isoforms, and allelic mutants of 65B13.

Such polynucleotides can be obtained from cDNA libraries and genomic libraries of animals such as humans, mice, rats, rabbits, hamsters, chickens, pigs, cows, goats, sheep, monkeys, and dogs by known hybridization methods such as colony hybridization, plaque hybridization, and Southern blotting using as a probe a polynucleotide comprising the nucleotide sequence of positions 1 to 2876 in SEQ ID NO: 1, the nucleotide sequence of positions 1 to 2243 in SEQ ID NO: 3, the nucleotide sequence of positions 1 to 3123 in SEQ ID NO: 33, the nucleotide sequence of positions 1 to 3247 in SEQ ID NO: 35, the nucleotide sequence of positions 1 to 2153 in SEQ ID NO: 37, the nucleotide sequence of positions 1 to 2979 in SEQ ID NO: 39, the nucleotide sequence of positions 1 to 2973 in SEQ ID NO: 41, the nucleotide sequence of positions 1 to 1969 in SEQ ID NO: 43, the nucleotide sequence of positions 1 to 2003 in SEQ ID NO: 45, the nucleotide sequence of positions 1 to 1819 in SEQ ID NO: 47, or the nucleotide sequence of positions 1 to 2959 in SEQ ID NO: 49; preferably the nucleotide sequence of positions 178 to 2280 in SEQ ID NO: 1, the nucleotide sequence of positions 127 to 2079 in SEQ ID NO: 3, the nucleotide sequence of positions 668 to 2770 in SEQ ID NO: 33, the nucleotide sequence of positions 130 to 2232 in SEQ ID NO: 35, the nucleotide sequence of positions 199 to 2100 in SEQ ID NO: 37, the nucleotide sequence of positions 199 to 2325 in SEQ ID NO: 39, the nucleotide sequence of positions 15 to 2325 in SEQ ID NO: 41, the nucleotide sequence of positions 15 to 1916 in SEQ ID NO: 43, the nucleotide sequence of positions 199 to 1950 in SEQ ID NO: 45, the nucleotide sequence of positions 15 to 1766 in SEQ ID NO: 47, or the nucleotide sequence of positions 196 to 2262 in SEQ ID NO: 49. Regarding methods for constructing cDNA libraries, one can refer to "Molecular Cloning, A Laboratory Manual $2^{nd}$ ed." (Cold Spring Harbor Press (1989)). It is also possible to use cDNA libraries and genomic libraries available on the market.

More specifically, in constructing a cDNA library, total RNA is first prepared from cells, organs, tissues, or such that express a polynucleotide of the present invention, by known techniques such as guanidine ultracentrifugation (Chirwin et al. Biochemistry 1979, 18:5294-5299) or AGPC (Chomczynski and Sacchi Anal. Biochem. 1987, 162:156-159), followed by mRNA purification using an mRNA purification kit (Pharmacia), etc. A kit for direct mRNA preparation, such as the QuickPrep mRNA Purification Kit (Pharmacia), may also be used. Next, cDNA is synthesized from the resulting mRNA using reverse transcriptase. cDNA synthesis kits such as the AMV Reverse Transcriptase First-strand cDNA Synthesis Kit (Seikagaku Corporation) are also available commercially. Other methods that use the 5'-RACE method to synthesize and amplify cDNA by PCR may also be used (Frohman et al. Proc. Natl. Acad. Sci. USA 1988, 85:8998-9002; Belyaysky et al. Nucleic Acids Res. 1989, 17:2919-32). In addition, in order to construct cDNA libraries containing a high percentage of full-length clones, known techniques such as the oligo-capping method (Maruyama and Sugano. Gene 1994, 138: 171-4; Suzuki. Gene 1997, 200:149-56) can also be employed. The cDNA obtained in this manner is then incorporated into a suitable vector.

Examples of hybridization conditions in the present invention include "2×SSC, 0.1% SDS, 50° C.", "2×SSC, 0.1% SDS, 42° C.", and "1×SSC, 0.1% SDS, 37° C.". Examples of conditions of higher stringency include "2×SSC, 0.1% SDS, 65° C.", "0.5×SSC, 0.1% SDS, 42° C.", and "0.2×SSC, 0.1% SDS, 65° C.". More specifically, a method that uses the Rapid-hyb buffer (Amersham Life Science) can be carried out by performing pre-hybridization at 68° C. for 30 minutes or more, adding a probe to allow hybrid formation at 68° C. for one hour or more, washing three times in 2×SSC, 0.1% SDS at room temperature for 20 minutes each, washing three times in 1×SSC, 0.1% SDS at 37° C. for 20 minutes each, and finally washing twice in 1×SSC, 0.1% SDS at 50° C. for 20 minutes each. This can also be carried out using, for example, the Expresshyb Hybridization Solution (CLONTECH), by performing pre-hybridization at 55° C. for 30 minutes or more, adding a labeled probe and incubating at 37° C. to 55° C. for one hour or more, washing three times in 2×SSC, 0.1%

SDS at room temperature for 20 minutes each, and washing once at 37° C. for 20 minutes with 1×SSC, 0.1% SDS. Here, conditions of higher stringency can be achieved by increasing the temperature for pre-hybridization, hybridization, or second wash. For example, the pre-hybridization and hybridization temperature can be raised to 60° C., and to 68° C. for higher stringency. In addition to conditions such as salt concentration of the buffer and temperature, a person with ordinary skill in the art can also integrate other conditions such as probe concentration, probe length, and reaction time, to obtain isoforms of 65B13 of the present invention, allelic mutants, and corresponding genes derived from other organisms.

References such as "Molecular Cloning, A Laboratory Manual $2^{nd}$ ed." (Cold Spring Harbor Press (1989), Sections 9.47-9.58), "Current Protocols in Molecular Biology" (John Wiley & Sons (1987-1997), Sections 6.3-6.4), "DNA Cloning 1: Core Techniques, A Practical Approach $2^{nd}$ ed." (Oxford University (1995), Section 2.10 for conditions in particular) can be referred to for detailed information on hybridization procedures. Examples of hybridizing polynucleotides include polynucleotides containing a nucleotide sequence that has at least 50% or more, preferably 70%, more preferably 80%, and even more preferably 90% (for example, 95% or more, or 99%) identity with a nucleotide sequence comprising the nucleotide sequence of positions 178 to 2280 in SEQ ID NO: 1, the nucleotide sequence of positions 127 to 2079 in SEQ ID NO: 3, the nucleotide sequence of positions 668 to 2770 in SEQ ID NO: 33, the nucleotide sequence of positions 130 to 2232 in SEQ ID NO: 35, the nucleotide sequence of positions 199 to 2100 in SEQ ID NO: 37, the nucleotide sequence of positions 199 to 2325 in SEQ ID NO: 39, the nucleotide sequence of positions 15 to 2325 in SEQ ID NO: 41, the nucleotide sequence of positions 15 to 1916 in SEQ ID NO: 43, the nucleotide sequence of positions 199 to 1950 in SEQ ID NO: 45, the nucleotide sequence of positions 15 to 1766 in SEQ ID NO: 47, or the nucleotide sequence of positions 196 to 2262 in SEQ ID NO: 49. Such identities can be determined by the BLAST algorithm (Altschul. Proc. Natl. Acad. Sci. USA 1990, 87:2264-8; Karlin and Altschul. Proc. Natl. Acad. Sci. USA 1993, 90:5873-7). Examples of programs that have been developed based on this algorithm include the BLASTX program for determining the identity of amino acid sequences, and the BLASTN program for nucleotide sequences (Altschul et al. J. Mol. Biol. 1990, 215:403-10). These programs can be used for the sequences of the present invention. One can refer to, for example, http://www.ncbi.nlm.nih.gov for a specific example of analysis methods.

The 65B13 isoforms or allelic mutants, and other genes with a 65B13-like structure and function can be obtained from cDNA libraries and genome libraries of animals such as humans, mice, rats, rabbits, hamsters, chickens, pigs, cows, goats, sheep, monkeys, and dogs by designing primers based on the nucleotide sequence of positions 178 to 2280 in SEQ ID NO: 1, the nucleotide sequence of positions 127 to 2079 in SEQ ID NO: 3, the nucleotide sequence of positions 668 to 2770 in SEQ ID NO: 33, the nucleotide sequence of positions 130 to 2232 in SEQ ID NO: 35, the nucleotide sequence of positions 199 to 2100 in SEQ ID NO: 37, the nucleotide sequence of positions 199 to 2325 in SEQ ID NO: 39, the nucleotide sequence of positions 15 to 2325 in SEQ ID NO: 41, the nucleotide sequence of positions 15 to 1916 in SEQ ID NO: 43, the nucleotide sequence of positions 199 to 1950 in SEQ ID NO: 45, the nucleotide sequence of positions 15 to 1766 in SEQ ID NO: 47, or the nucleotide sequence of positions 196 to 2262 in SEQ ID NO: 49, using gene amplification technology (PCR) (Current Protocols in Molecular Biology (John Wiley & Sons (1987), Sections 6.1-6.4)).

The polynucleotide sequences of the present invention can be confirmed by using conventional sequence determination methods. For example, the dideoxynucleotide chain termination method (Sanger et al. Proc. Natl. Acad. Sci. USA 1977, 74:5463) can be used. In addition, sequences can also be analyzed using a suitable DNA sequencer.

A "protein" in the present invention can also be referred to as a "polypeptide" in general. A "polypeptide" of the present invention refers to a peptide polymer encoded by a polynucleotide of the present invention. Preferred examples include proteins having the amino acid sequence described in SEQ ID NO: 2, 4, 34, 36, 38, 40, 42, 44, 46, 48, or 50. The polypeptides of the present invention may comprise naturally occurring or modified amino acid residues. Examples of amino acid residue modifications include acylation, acetylation, amidation, arginylation, GPI anchor formation, crosslinking, γ-carboxylation, cyclization, covalent crosslink formation, glycosylation, oxidation, covalent bonding of a lipid or fat derivative, cystine formation, disulfide bond formation, selenoylation, demethylation, protein fragmentation treatment, covalent bonding of a nucleotide or nucleotide derivative, hydroxylation, pyroglutamate formation, covalent bonding of a flavin, prenylation, covalent bonding with a heme portion, covalent bonding of phosphatidyl inositol, formylation, myristoylation, methylation, ubiquitination, iodination, racemization, ADP-ribosylation, sulfation, and phosphorylation. Moreover, the polypeptides of the present invention include precursors containing a signal peptide portion, mature proteins lacking a signal peptide portion, and fusion proteins modified with other peptide sequences. Peptide sequences to be added to a polypeptide of the present invention can be selected from sequences that facilitate protein purification using, for example, pcDNA3.1/Myc-His vector (Invitrogen), or those that confer stability in recombinant protein production. Examples of such sequences are influenza agglutinin (HA), glutathione S transferase (GST), substance P, multiple histidine tag (such as 6×His (SEQ ID NO:60) and 10×His (SEQ ID NO:61)), protein C fragment, maltose-binding protein (MBP), immunoglobulin constant region, α-tubulin fragment, (β-galactosidase, B-tag, c-myc fragment, E-tag (epitope on a monoclonal phage), FLAG (Hopp et al. Bio/Technol. 1988, 6:1204-10), lck tag, p18 HIV fragment, HSV-tag (human simple Herpes virus glycoprotein), SV40T antigen fragment, T7-tag (T7 gene 10 protein), and VSV-GP fragment (vesicular stomatitis virus glycoprotein).

The GABA-producing neuron progenitor cells of the present invention preferably include, but are not limited to, GABA-producing neuron progenitor cells of the spinal cord and cerebellum.

The length of a polynucleotide of the present invention is not particularly limited, as long as it allows for detection or selection of GABA-producing neuron progenitor cells. The polynucleotides of the present invention also include the so-called "oligonucleotides". In general, the polynucleotides of the present invention comprise at least ten consecutive nucleotides in the nucleotide sequence of the present invention or a complementary sequence thereof, and preferably comprise at least 15 consecutive nucleotides.

Furthermore, the present invention also provides nucleotide chains complementary to a polynucleotide for detecting or selecting GABA-producing neuron progenitor cells of the present invention, which comprise at least 15 consecutive nucleotides. Such polynucleotides comprising a nucleotide sequence that contains at least 15 consecutive nucleotides are useful as probes for detecting the generation of GABA-producing neuron progenitor cells or as primers for detecting GABA-producing neuron progenitor cells.

The nucleotide chain normally consists of 15 to 100, and preferably 15 to 35 nucleotides and the polynucleotide is appropriately labeled with a radioisotope, non-radioactive compound, or the like when used as a probe. The nucleotide chain preferably consists of at least 15 and preferably 30 nucleotides when used as a primer. A primer can be designed to have a restriction enzyme recognition sequence, a tag or such, added to the 5'-end side thereof, and at the 3' end, a sequence complementary to a target sequence. A nucleotide chain of the present invention can hybridize with a polynucleotide of the present invention. Moreover, mutations of a polynucleotide of the present invention within cells can be detected using these probes or primers. In some cases, such mutations may cause abnormalities in the activity or expression of the polypeptides of the present invention; therefore, nucleotide chains of the present invention are thought to be useful for disease diagnosis, etc.

Here, a "complementary sequence" refers to not only cases where at least 15 consecutive nucleotides of the nucleotide sequence completely pair with the template, but also includes those that have at least 70%, preferably 80%, more preferably 90%, and even more preferably 95% or more (for example, 97% or 99%) of the consecutive nucleotides paired with the template. Pair formation refers to the formation of a chain, in which T (U in the case of an RNA) corresponds to A, A corresponds to T or U, G corresponds to C, and C corresponds to G in the nucleotide sequence of the template polynucleotide. Identities can be determined by methods similar to that used in the aforementioned polynucleotide hybridization.

The present invention also provides primer sets comprising two or more polynucleotides for detecting or selecting GABA-producing neuron progenitor cells of the present invention.

The present invention also provides antibodies that bind to the translation products of the 65B13 gene, which are used in regeneration medicine to treat cerebellar degeneration or spinal cord injury. In a preferred embodiment, the present invention provides antibodies for detecting or selecting GABA-producing neuron progenitor cells, which bind to, for example, a protein selected from:

(v) a protein comprising the amino acid sequence of SEQ ID NO: 2, 4, 34, 36, 38, 40, 42, 44, 46, 48, or 50;

(vi) a protein comprising an amino acid sequence that comprises an insertion, substitution, deletion of one or more amino acids in the amino acid sequence of SEQ ID NO: 2, 4, 34, 36, 38, 40, 42, 44, 46, 48, or 50, and/or addition of one or more amino acids to either or both ends thereof, which is functionally equivalent to a protein comprising the amino acid sequence of SEQ ID NO: 2, 4, 34, 36, 38, 40, 42, 44, 46, 48, or 50;

(vii) a protein encoded by a polynucleotide that hybridizes under stringent conditions to a polynucleotide encoding the amino acid sequence of SEQ ID NO: 2, 4, 34, 36, 38, 40, 42, 44, 46, 48, or 50, which is functionally equivalent to a protein comprising the amino acid sequence of SEQ ID NO: 2, 4, 34, 36, 38, 40, 42, 44, 46, 48, or 50; and (viii) a protein comprising an amino acid sequence having 70% or higher identity to the amino acid sequence of SEQ ID NO: 2, 4, 34, 36, 38, 40, 42, 44, 46, 48, or 50, which comprises the amino acid sequence of SEQ ID NO: 2, 4, 34, 36, 38, 40, 42, 44, 46, 48, or 50.

Herein, "equivalent function to a protein comprising the amino acid sequence of SEQ ID NO: 2, 4, 34, 36, 38, 40, 42, 44, 46, 48, or 50" preferably refers to the selective expression in GABA-producing neuron progenitor cells.

Furthermore, in a preferred embodiment, the antibodies bind to a polypeptide of the present invention which is an extracellular domain of GABA-producing neuron progenitor cells. The extracellular domains of polypeptides used in the present invention can be searched using the program, PSORT (http://psort.ims.u-tokyo.ac.jp/), etc. Specifically, extracellular domains obtained using the PSORT program are: the amino acid sequences of positions 21 to 510 in the amino acid sequence of SEQ ID NO: 2, 4, 38, 40, 42, or 44; of positions 20 to 513 in the amino acid sequence of SEQ ID NO: 34 or 36; of positions 21 to 460 in the amino acid sequence of SEQ ID NO: 46 or 48; and of positions 21 to 490 in the amino acid sequence of SEQ ID NO: 50.

It is well known that a mutant polypeptide comprising an amino acid sequence, in which one or more amino acids are deleted, inserted, substituted, or added, maintains the same biological activity as the original polypeptide (Mark et al. Proc. Natl. Acad. Sci. USA 1984, 81:5662-6; Zoller and Smith. Nucleic Acids Res. 1982, 10:6487-500; Wang et al. Science 1984, 224:1431-3; Dalbadie-McFarland et al. Proc. Natl. Acad. Sci. USA 1982, 79:6409-13).

Here, an amino acid substitution refers to a mutation in which one or more amino acid residues in a sequence are changed to a different type of amino acid residue. When the amino acid sequence encoded by a polynucleotide of the present invention is altered by such a substitution, a conservative substitution is preferably carried out if the function of the protein is to be maintained. A conservative substitution means altering a sequence so that it encodes an amino acid that has properties similar to those of the amino acid before substitution. Amino acids can be classified, based on their properties, into non-polar amino acids (Ala, Ile, Leu, Met, Phe, Pro, Trp, Val), non-charged amino acids (Asn, Cys, Gln, Gly, Ser, Thr, Tyr), acidic amino acids (Asp, Glu), basic amino acids (Arg, His, Lys), neutral amino acids (Ala, Asn, Cys, Gln, Gly, Ile, Leu, Met, Phe, Pro, Ser, Thr, Trp, Tyr, Val), aliphatic amino acids (Ala, Gly), branched amino acids (Ile, Leu, Val), hydroxyamino acids (Ser, Thr), amide-type amino acids (Gln, Asn), sulfur-containing amino acids (Cys, Met), aromatic amino acids (His, Phe, Trp, Tyr), heterocyclic amino acids (His, Trp), imino acids (Pro, 4Hyp), etc. In particular, substitutions among Ala, Val, Leu, and Ile; Ser and Thr; Asp and Glu; Asn and Gln; Lys and Arg; and Phe and Tyr are preferable in order to maintain protein properties. There are no particular limitations on the number and sites of the mutated amino acids, as long as the amino acid encoded by the polynucleotide has 65B13 antigenicity.

A polynucleotide encoding an amino acid sequence, in which one or more amino acids are deleted, inserted, substituted, or added to the amino acid sequence of SEQ ID NO: 2, 4, 34, 36, 38, 40, 42, 44, 46, 48, or 50, can be prepared according to methods such as site-directed mutagenesis described in "Molecular Cloning, A Laboratory Manual 2$^{nd}$ ed." (Cold Spring Harbor Press (1989)), "Current Protocols in Molecular Biology" (John Wiley & Sons (1987-1997), Sections 8.1-8.5), Hashimoto-Goto et al. (Gene 1995, 152:271-5), Kunkel (Proc. Natl. Acad. Sci. USA 1985, 82:488-92), Kramer and Fritz (Method. Enzymol. 1987, 154:350-67), Kunkel (Method. Enzymol. 1988, 85:2763-6), etc.

The above-described proteins of the present invention also include proteins encoded by polynucleotides that hybridize under stringent conditions to a polynucleotide encoding the amino acid sequence of SEQ ID NO: 2, 4, 34, 36, 38, 40, 42, 44, 46, 48, or 50, which are functionally equivalent to a protein comprising the amino acid sequence of SEQ ID NO: 2, 4, 34, 36, 38, 40, 42, 44, 46, 48, or 50.

"Equivalent function to a protein comprising the amino acid sequence of SEQ ID NO: 2, 4, 34, 36, 38, 40, 42, 44, 46, 48, or 50" preferably refers to the selective expression in GABA-producing neuron progenitor cells.

Examples of hybridization conditions in the present invention include "2×SSC, 0.1% SDS, 50° C.", "2×SSC, 0.1% SDS, 42° C.", and "1×SSC, 0.1% SDS, 37° C.". Examples of conditions of higher stringency include "2×SSC, 0.1% SDS, 65° C.", "0.5×SSC, 0.1% SDS, 42° C.", and "0.2×SSC, 0.1% SDS, 65° C.". More specifically, a method that uses the Rapid-hyb buffer (Amersham Life Science) can be carried out by performing pre-hybridization at 68° C. for 30 minutes or more, adding a probe to allow hybrid formation at 68° C. for one hour or more, washing three times in 2×SSC, 0.1% SDS at room temperature for 20 minutes each, washing three times in 1×SSC, 0.1% SDS at 37° C. for 20 minutes each, and finally washing twice in 1×SSC, 0.1% SDS at 50° C. for 20 minutes each. This can also be carried out using, for example, the Expresshyb Hybridization Solution (CLONTECH), by performing pre-hybridization at 55° C. for 30 minutes or more, adding a labeled probe and incubating at 37° C. to 55° C. for one hour or more, washing three times in 2×SSC, 0.1% SDS at room temperature for 20 minutes each, and washing once at 37° C. for 20 minutes with 1×SSC, 0.1% SDS. Here, conditions of higher stringency can be achieved by increasing the temperature for pre-hybridization, hybridization, or second wash. For example, the pre-hybridization and hybridization temperature can be raised to 60° C., and to 68° C. for higher stringency. In addition to conditions such as salt concentration of the buffer and temperature, a person with ordinary skill in the art can also integrate other conditions such as probe concentration, probe length, and reaction time, to obtain 65B13 isoforms, allelic mutants, and corresponding genes derived from other organisms.

References such as "Molecular Cloning, A Laboratory Manual $2^{nd}$ ed." (Cold Spring Harbor Press (1989), Sections 9.47-9.58), "Current Protocols in Molecular Biology" (John Wiley & Sons (1987-1997), Sections 6.3-6.4), "DNA Cloning 1: Core Techniques, A Practical Approach $2^{nd}$ ed." (Oxford University (1995), Section 2.10 for conditions) can be referred to for detailed information on hybridization procedures. Examples of hybridizing polynucleotides include polynucleotides containing a nucleotide sequence that has at least 50% or more, preferably 70%, more preferably 80%, and even more preferably 90% (for example, 95% or more, or 99%) identity with a polynucleotide encoding the amino acid sequence of SEQ ID NO: 2, 4, 34, 36, 38, 40, 42, 44, 46, 48, or 50. Such identities can be determined by the BLAST algorithm (Altschul. Proc. Natl. Acad. Sci. USA 1990, 87:2264-8; Karlin and Altschul. Proc. Natl. Acad. Sci. USA 1993, 90:5873-7). Examples of programs that have been developed based on this algorithm include the BLASTX program for determining the identity of amino acid sequences, and the BLASTN program for nucleotide sequences (Altschul et al. J. Mol. Biol. 1990, 215:403-10). These programs can be used for the sequences of the present invention. One can refer to, for example, http://www.ncbi.nlm.nih.gov for a specific example of analysis methods.

The 65B13 isoforms or allelic mutants, and other genes with a 65B13-like structure or function can be obtained from cDNA libraries and genome libraries of animals such as humans, mice, rats, rabbits, hamsters, chickens, pigs, cows, goats, sheep, monkeys, and dogs by designing primers based on the nucleotide sequence of positions 178 to 2280 in SEQ ID NO: 1, the nucleotide sequence of positions 127 to 2079 in SEQ ID NO: 3, the nucleotide sequence of positions 668 to 2770 in SEQ ID NO: 33, the nucleotide sequence of positions 130 to 2232 in SEQ ID NO: 35, the nucleotide sequence of positions 199 to 2100 in SEQ ID NO: 37, the nucleotide sequence of positions 199 to 2325 in SEQ ID NO: 39, the nucleotide sequence of positions 15 to 2325 in SEQ ID NO: 41, the nucleotide sequence of positions 15 to 1916 in SEQ ID NO: 43, the nucleotide sequence of positions 199 to 1950 in SEQ ID NO: 45, the nucleotide sequence of positions 15 to 1766 in SEQ ID NO: 47, or the nucleotide sequence of positions 196 to 2262 in SEQ ID NO: 49, using gene amplification technology (PCR) (Current Protocols in Molecular Biology (John Wiley & Sons (1987), Sections 6.1-6.4)).

Antibodies of the present invention also include polyclonal antibodies, monoclonal antibodies, chimeric antibodies, single-chain antibodies (scFV) (Huston et al. Proc. Natl. Acad. Sci. USA 1988, 85:5879-83; The Pharmacology of Monoclonal Antibody, vol. 113, Rosenburg and Moore ed., Springer Verlag (1994) pp. 269-315), humanized antibodies, multispecific antibodies (LeDoussal et al. Int. J. Cancer Suppl. 1992, 7:58-62; Paulus. Behring Inst. Mitt. 1985, 78:118-32; Millstein and Cuello. Nature 1983, 305:537-9; Zimmermann Rev. Physiol. Biochem. Pharmacol. 1986, 105: 176-260; Van Dijk et al. Int. J. Cancer 1989, 43:944-9), and antibody fragments such as Fab, Fab', F(ab')2, Fc, and Fv. Moreover, an antibody of the present invention may also be modified by PEG and such, as necessary. An antibody of the present invention may also be produced in the form of a fusion protein with β-galactosidase, maltose-binding protein, GST, green fluorescent protein (GFP), or such, to allow detection without the use of a secondary antibody. In addition, an antibody may be modified by labeling with biotin or such to allow recovery using avidin, streptoavidin, etc.

An antibody of the present invention can be produced using a polypeptide of the present invention, a fragment thereof, or a cell in which a polypeptide or polypeptide fragment of the present invention is expressed, as a sensitized antigen. In addition, a short polypeptide of the present invention or a fragment thereof may also be used as an immunogen by coupling to a carrier such as bovine serum albumin, Keyhole Limpet Hemocyanin, and ovalbumin. In addition, a polypeptide of the present invention or a fragment thereof may be used in combination with a known adjuvant such as aluminum adjuvant, Freund's complete (or incomplete) adjuvant, or pertussis adjuvant, to enhance the immune response to an antigen.

Polyclonal antibodies can be obtained from, for example, the serum of an immunized animal after immunizing a mammal with a polypeptide of the present invention or a fragment thereof, together with an adjuvant as necessary. Although there are no particular limitations on the mammals used, typical examples include rodents, lagomorphs, and primates. Specific examples include rodents such as mice, rats, and hamsters; lagomorphs such as rabbits; and primates such as monkeys including cynomolgus monkeys, rhesus monkeys, baboons, and chimpanzees. Animal immunization is carried out by suitably diluting and suspending a sensitized antigen in phosphate-buffered saline (PBS) or physiological saline, mixing with an adjuvant as necessary until emulsified, and injecting into an animal intraperitoneally or subcutaneously. The sensitized antigen mixed with Freund's incomplete adjuvant is preferably administered several times, every 4 to 21 days. Antibody production can be confirmed by measuring the level of an antibody of interest in the serum using conventional methods. Finally, the serum itself may be used as a polyclonal antibody, or it may be further purified. See, for example, "Current Protocols in Molecular Biology" (John Wiley & Sons (1987), Sections 11.12-11.13), for specific methods.

A monoclonal antibody can be produced by removing the spleen from an animal immunized in the manner described above, separating immunocytes from the spleen, and fusing with a suitable myeloma cell using polyethylene glycol (PEG) or such to establish hybridomas. Cell fusion can be carried out according to the Milstein method (Galfre and Milstein. Methods Enzymol. 1981, 73:3-46). Here, suitable myeloma cells are exemplified particularly by cells that allow chemical selection of fused cells. When using such myeloma cells, fused hybridomas are selected by culturing in a culture medium (HAT culture medium) that contains hypoxanthine, aminopterin, and thymidine, which destroy cells other than the fused cells. Next, a clone that produces an antibody against a polypeptide of the present invention or a fragment thereof is selected from the established hybridomas. Subsequently, the selected clone is introduced into the abdominal cavity of a mouse or such, and ascite is collected to obtain a monoclonal antibody. See, in addition, "Current Protocols in Molecular Biology" (John Wiley & Sons (1987), Sections 11.4-11.11) for information on specific methods.

Hybridomas can also be obtained by first sensitizing human lymphocytes that have been infected by EB virus with an immunogen in vitro, and fusing the sensitized lymphocytes with human myeloma cells (such as U266) to obtain hybridomas that produce human antibodies (Japanese Patent Application Kokai Publication No. (JP-A) S63-17688 (unexamined, published Japanese patent application)). In addition, human antibodies can also be obtained by using antibody-producing cells generated by sensitizing a transgenic animal with a human antibody gene repertoire (WO92/03918; WO93/02227; WO94/02602; WO94/25585; WO96/33735; WO96/34096; Mendez et al. Nat. Genet. 1997, 15:146-156, etc.). Methods that do not use hybridomas can be exemplified by a method in which a cancer gene is introduced to immortalize immunocytes such as antibody-producing lymphocytes.

In addition, antibodies can also be produced by genetic recombination techniques (see Borrebaeck and Larrick (1990) Therapeutic Monoclonal Antibodies, MacMillan Publishers Ltd., UK). First, a gene that encodes an antibody is cloned from hybridomas or antibody-producing cells (such as sensitized lymphocytes). The resulting gene is then inserted into a suitable vector, the vector is introduced into a host, and the host is then cultured to produce the antibody. This type of recombinant antibody is also included in the antibodies of the present invention. Typical examples of recombinant antibodies include chimeric antibodies comprising a non-human antibody-derived variable region and a human antibody-derived constant region, and humanized antibodies comprising a non-human-derived antibody complementarity determining region (CDR), human antibody-derived framework region (FR), and human antibody constant region (Jones et al. Nature 1986, 321:522-5; Reichmann et al. Nature 1988, 332: 323-9; Presta. Curr. Op. Struct. Biol. 1992, 2:593-6; Methods Enzymol. 1991, 203:99-121).

Antibody fragments of the present invention can be produced by treating the aforementioned polyclonal or monoclonal antibodies with enzymes such as papain or pepsin. Alternatively, an antibody fragment can be produced by genetic engineering techniques using a gene that encodes an antibody fragment (see Co et al. J. Immunol. 1994, 152:2968-76; Better and Horwitz. Methods Enzymol. 1989, 178:476-96; Pluckthun and Skerra. Methods Enzymol. 1989, 178:497-515; Lamoyi. Methods Enzymol. 1986, 121:652-63; Rousseaux et al. 1986, 121:663-9; Bird and Walker. Trends Biotechnol. 1991, 9:132-7).

The multispecific antibodies of the present invention include bispecific antibodies (BsAb), diabodies (Db), etc. Multispecific antibodies can be produced by methods such as (1) chemically coupling antibodies having different specificities with different types of bifunctional linkers (Paulus Behring Inst. Mill. 1985, 78:118-32), (2) fusing hybridomas that secrete different monoclonal antibodies (Millstein and Cuello. Nature 1983, 305:537-9), or (3) transfecting eukaryotic cell expression systems, such as mouse myeloma cells, with a light chain gene and a heavy chain gene of different polyclonal antibodies (four types of DNA), followed by the isolation of a bispecific monovalent portion (Zimmermann. Rev. Physio. Biochem. Pharmacol. 1986, 105:176-260; Van Dijk et al. Int. J. Cancer 1989, 43:944-9). On the other hand, diabodies are dimer antibody fragments comprising two bivalent polypeptide chains that can be constructed by gene fusion. They can be produced using known methods (see Holliger et al. Proc. Natl. Acad. Sci. USA 1993, 90:6444-8; EP404097; WO93/11161).

Recovery and purification of antibodies and antibody fragments can be carried out using Protein A and Protein G, or according to known protein purification techniques (Antibodies: A Laboratory Manual, Ed. Harlow and David Lane, Cold Spring Harbor Laboratory (1988)). For example, when using Protein A to purify an antibody of the present invention, known Protein A columns such as Hyper D, POROS, or Sepharose F.F. (Pharmacia) can be used. The concentration of the resulting antibody can be determined by measuring the absorbance or by enzyme linked immunoadsorbent assay (ELISA).

Antigen-binding activity of an antibody can be determined by absorbance measurement, or by using fluorescent antibody methods, enzyme immunoassay (EIA) methods, radioimmunoassay (RIA) methods, or ELISA. When ELISA is used, an antibody of the present invention is first immobilized onto a support such as a plate. A polypeptide of the present invention is added, and then a sample containing the antibody of interest is added. Here, samples containing an antibody of interest include, for example, culture supernatants of antibody-producing cells, purified antibodies, etc. Next, a secondary antibody that recognizes an antibody of the present invention is added, followed by the incubation of the plate. Subsequently, the plate is washed and the label attached to the secondary antibody is detected. Namely, if a secondary antibody is labeled with alkaline phosphatase, the antigen binding activity can be determined by adding an enzyme substrate such as p-nitrophenyl phosphate, and measuring the absorbance. In addition, a commercially available system such as BIAcore (Pharmacia) can also be used to evaluate antibody activities.

The antibodies of the present invention can recognize or detect a polypeptide of the present invention or a fragment thereof. Furthermore, since the antibodies recognize a polypeptide of the present invention or a fragment thereof, they can recognize or detect cells or the like expressing the polypeptide or a fragment thereof. In addition, the antibodies can be used to purify a polypeptide of the present invention or a fragment thereof. The antibodies can also be used to purify cells or the like expressing the polypeptide of the present invention or a fragment thereof.

The antibodies of the present invention preferably bind to a polypeptide comprising the entire or at least six consecutive amino acid residues of the amino acid sequence of positions 21 to 510 in the amino acid sequence of SEQ ID NO: 2, 4, 38, 40, 42, or 44; the amino acid sequence of positions 20 to 513 in the amino acid sequence of SEQ ID NO: 34 or 36; the amino acid sequence of positions 21 to 460 in the amino acid sequence of SEQ ID NO: 46 or 48; or the amino acid sequence of positions 21 to 490 in the amino acid sequence of SEQ ID NO: 50, and more preferably bind to a polypeptide comprising at least six consecutive amino acid residues of the above amino acid sequence.

Furthermore, the present invention relates to methods for detecting or selecting GABA-producing neuron progenitor cells, which comprise detecting the expression of the above-described polynucleotides of the present invention.

In a preferred embodiment, the methods of the present invention comprise the step of detecting the expression of a polynucleotide that can hybridize to a polynucleotide of the present invention selected from (i), (ii), (iii), and (iv) described above, or to a complementary sequence thereof.

The "step of detecting the expression of a polynucleotide" in the above-described methods of the present invention preferably comprises the steps of:

(a) contacting a test cell sample with a polynucleotide that can hybridize to a polynucleotide selected by the above-described methods of the present invention or to a complementary sequence thereof, or with a probe comprising the polynucleotide; and (b) detecting reactivity.

Alternatively, in a preferred embodiment of the methods of the present invention, first, the test cell sample is contacted with a polynucleotide of the present invention or with a probe comprising the polynucleotide. For example, it is possible to contact such a probe with mRNA prepared from the test cell sample or with a complementary DNA (cDNA) transcribed from the mRNA.

The absence and presence of reactivity is then determined in these methods. Herein, the presence of reactivity generally means that the contacted polynucleotide hybridizes (reacts) with the target sequence.

The steps of the above-described methods of the present invention may include, for example, the steps of:

(a-1) conducting gene amplification using as a template a polynucleotide derived from the test cell sample, and polynucleotides of the present invention or primers comprising the polynucleotides of the present invention, or a set of primers comprising the polynucleotides of the present invention; and (b-1) detecting the resulting amplification products.

The "gene amplification method" in the above step includes known methods, for example, PCR. Furthermore, the amplification products generated by the amplification method can also be detected by known methods.

Meanwhile, for example, mRNA prepared from a test cell sample or complementary DNA (cDNA) transcribed from the mRNA may be used as a template in step (a-1) described above.

The detection step may be followed by the step of isolating GABA-producing neuron progenitor cells from the detected sample.

Since the protein encoded by the 65B13 gene of the present invention is a membrane protein, viable GABA-producing neuron progenitor cells can be isolated (separate) by using the protein as an indicator.

In addition, the methods of the present invention may comprise, in addition to the above-described step, the step of detecting or selecting GABA-producing neuron progenitor cells using the expression of a gene selected from the group consisting of Corl1, Pax2, Lim1/2, Lbx1, and Corl2 genes as an indicator.

In a preferred embodiment of the present invention, the methods include methods comprising the step of detecting a protein selected from (v), (vi), (vii), and (viii) described above.

Specifically, the protein detection step comprises the steps of:

(d) contacting a test cell sample with an antibody that binds to a protein selected through the above-described step of detecting or selecting GABA-producing neuron progenitor cells; and (e) detecting reactivity.

The proteins of the present invention can be detected by contacting an antibody of the present invention with cell samples that may contain GABA-producing neuron progenitor cells, and detecting reactivity. The antibody may be immobilized onto appropriate carriers for use before contact with the cells. Alternatively, cells bound to the antibody can be selectively collected through affinity purification using the antibody after contacting and binding the cells with the antibody. For example, when an antibody of the present invention is linked to biotin, the cells can be purified by adding the cell sample to a plate or column immobilized with avidin or streptavidin.

The detection step may be followed by the step of isolating GABA-producing neuron progenitor cells from the detected sample. In the present invention, GABA-producing neuron progenitor cells can be efficiently separated by flow cytometry using an anti-65B13 antibody.

Figure 10:
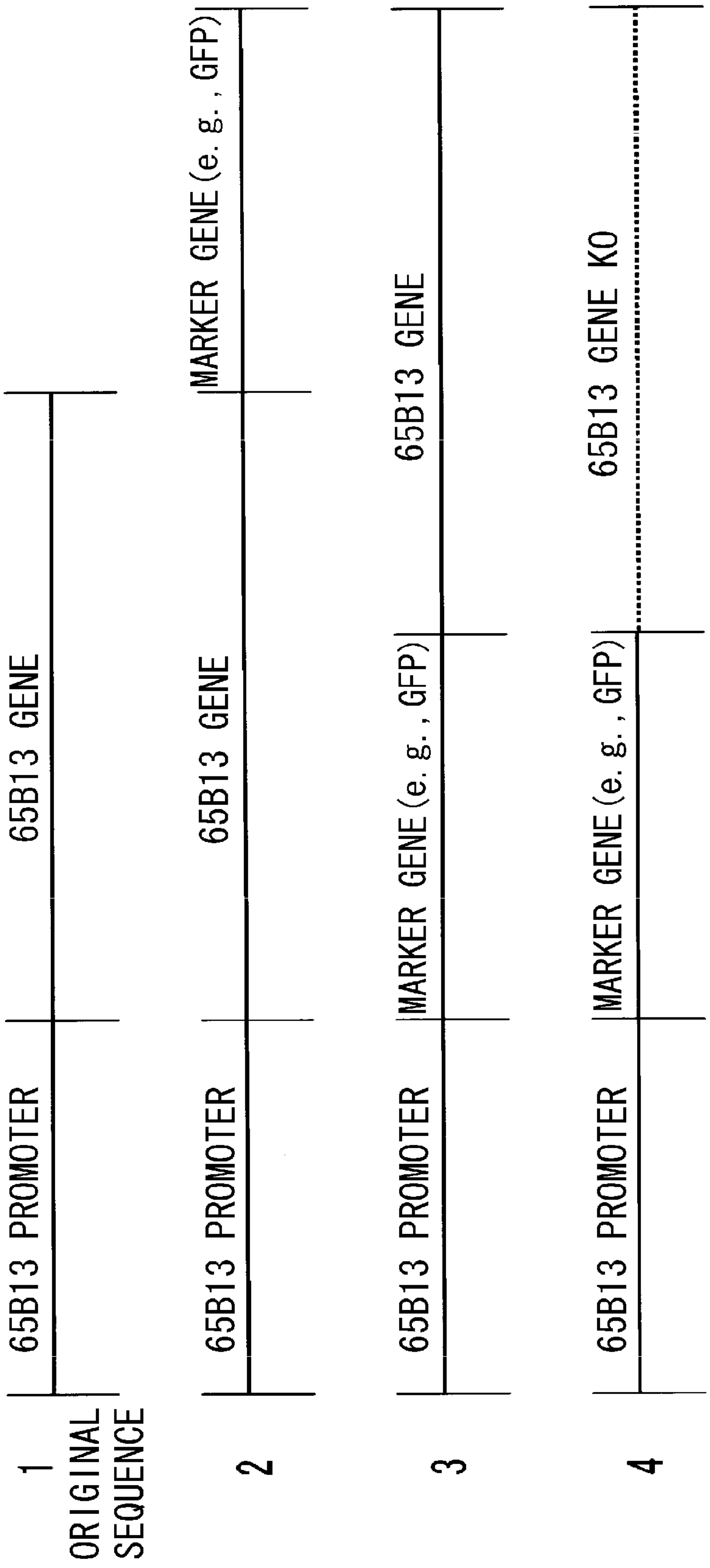
FIG. 10 shows the structures of DNA constructs that can be used to select GABA-producing neuron progenitor cells.

Alternatively, GABA-producing neuron progenitor cells can also be selected using a 65B13 promoter (including modified promoters) (see, for example, JP-A No. 2002-51775). For example, it is possible to transfect cells with a vector carrying a construct in which a gene encoding a detectable marker such as GFP is linked to a promoter portion obtained by analyzing the 65B13 expression region (analysis of the 65B13 expression region is described later). The construct may have a structure where the 65B13 gene is linked upstream or downstream of the marker gene under the control of the expression regulatory sequence (including promoters, enhancers, etc.). Alternatively, the maker gene can be knocked-in at the 65B13 locus. In a preferred embodiment, the construct includes, for example, constructs having any one of Structures 2 to 4 schematically illustrated in FIG. 10. In any case, expression of the marker gene is detected specifically in GABA-producing neuron progenitor cells, and this enables specific cell detection.

The cell samples used in the methods are culture media containing in vitro differentiated GABA-producing neurons. GABA-producing neurons can be differentiated in vitro by known methods, using known ES cells or the like as a starting material. In general, GABA-producing neurons can be differentiated by co-culturing nerve tissue-derived supporting cell layer with brain tissues obtained from an area containing GABA-producing neurons. The cell sample used for selection of GABA-producing neuron progenitor cells of the present invention may be a group of cells separated or cultured by any method.

In addition, it is necessary that a support used in immobilizing an antibody or a polypeptide of the present invention is safe to cells. Examples of such a support include synthetic or naturally occurring organic polymer compounds, inorganic materials such as glass beads, silica gel, alumina, and activated charcoal, and those that have their surfaces coated with a polysaccharide or synthetic polymer. There are no particular limitations on the form of the support, examples of which include films, fibers, granules, hollow fibers, non-woven fabric, porous supports, or honeycombed supports, and the contact surface area can be controlled by changing its thickness, surface area, width, length, shape, and size in various ways.

Marker proteins for GABA-producing neuron progenitor cells other than the proteins selected by the methods of the present invention include, for example, proteins encoded by genes selected from the group consisting of the Corl1, Pax2, Lim1/2, Lbx1, and Corl2 genes.

In the methods of the present invention, a transcript of the 65B13 gene can be detected by contacting a polynucleotide of the present invention with nucleic acid extract derived from a cell sample, and detecting for nucleic acid that hybridizes to the polynucleotide in the nucleic acid extract.

The polynucleotide probe is preferably labeled with radioisotope or non-radioactive compound to detect a transcript of the 65B13 gene. Such radioisotopes to be used as a label include, for example, $^{35}S$ and $^{3}H$. When a radiolabeled polynucleotide probe is used, RNA that binds to a marker can be detected by detecting silver particles by emulsion autoradiography. Meanwhile, as for conventional non-radioisotopic compounds that are used to label polynucleotide probes include biotin and digoxigenin are known. The detection of biotin-labeled markers can be achieved, for example, using fluorescent labeled avidin or avidin labeled with an enzyme such as alkaline phosphatase or horseradish peroxidase. On the other hand, the detection of digoxigenin-labeled markers can be achieved by using fluorescent labeled anti-digoxigenin antibody or anti-digoxigenin antibody labeled with an enzyme such as alkaline phosphatase or horseradish peroxidase. When enzyme labeling is used, the detection can be made by allowing stable dye to deposit at marker positions by incubating with an enzyme substrate.

When polynucleotide primers are used for detection of a transcript of the 65B13 gene, 65B13 gene transcripts can be detected by amplifying nucleic acid that hybridizes to the polynucleotide primers, for example, using techniques such as RT-PCR.

The detection of translation products of the 65B13 gene with the methods of the present invention can be made by contacting the antibody described above with protein extract of cell samples and then detecting proteins bound to the antibody. As described above, assay methods for antigen binding activities of antibodies include absorbance measurement, fluorescent antibody method, enzyme immunoassay (EIA), radioimmunoassay (RIA), ELISA, etc.

In the context of the present invention, highly accurate identification can be achieved by detecting, in addition to a transcript or translation product of the 65B13 gene, the transcripts or translation products of one or more genes selected from the group consisting of Lbx1, Pax2, Lim1/2, Corl1, and Corl2. Such methods are also included in the present invention.

Furthermore, the present invention provides kits for detecting or selecting GABA-producing neuron progenitor cells. The kits of the present invention may comprise, for example, probes, primers, or primer sets that enable detection of the expression of a polynucleotide that can hybridize to a polynucleotide selected from (i), (ii), (iii), and (iv) described above, or to a complementary sequence thereof. The kits may also comprise appropriate buffers, etc. Furthermore, the packages may contain instruction manuals containing a description of how to use the kits.

The kits of the present invention may further comprise polynucleotides that hybridize to transcripts of one or more genes selected from the group consisting of the Lbx1, Pax2, Lim1/2, Corl1, and Corl2 genes.

The kits of the present invention may further comprise cerebellar cells or spinal cord cells.

In an embodiment of the present invention, the kits for detecting or selecting GABA-producing neuron progenitor cells include kits containing antibodies that bind to a protein selected from (v), (vi), (vii), and (viii) described above.

The kits may further contain in combination antibodies that bind to proteins encoded by one or more genes selected from the group consisting of Lbx1, Pax2, Lim1/2, Corl1, and Corl2 genes.

The kits may further contain cerebellar cells or spinal cord cells.

Meanwhile, the preferred target cerebellar cells in the methods or kits of the present invention are Purkinje cells, and the preferred target spinal cord cells are dI4 and dILA.

Furthermore, the expression of a polynucleotide of the present invention can be used as an indicator to screen for substances that are effective in differentiating GABA-producing neuron progenitor cells.

The present invention provides methods of screening for substances that are effective for differentiating GABA-producing neuron progenitor cells. Since compounds obtained through screening by the methods of the present invention have the activity of differentiating GABA-producing neuron progenitor cells, they are expected to become candidate compounds useful for treating diseases caused by defects in GABA-producing neurons. Target diseases of treatment using a compound obtained by the screening methods include, for example, spinocerebellar ataxia.

In a preferred embodiment, the above-described screening methods of the present invention comprise the steps of:

(I) contacting a test compound with cells that can differentiate into GABA-producing neuron progenitor cells; and (II) detecting in GABA-producing neuron progenitor cells the expression of a polynucleotide that can hybridize to a nucleotide sequence selected from (i), (ii), (iii), and (vi) described above or to a complementary sequence thereof.

Here, the "test substance" may be any type of compound, examples of which include the expression products of gene libraries, synthetic low molecular weight compound libraries, synthetic peptide libraries, antibodies, substances released by bacteria, cell (microbial, plant, or animal) extracts, cell (microbial, plant, or animal) culture supernatants, purified or partially purified polypeptides, marine organisms, plant or animal extracts, soil, random phage peptide display libraries, etc.

Furthermore, since 65B13 is expressed specifically in differentiated GABA-producing neuron progenitor cells, it can be used in screening for reagents that differentiate GABA-producing neuron progenitor cells. Specifically, whether a test sample has the ability to differentiate GABA-producing neuron progenitor cells can be assessed by inducing the differentiation into GABA-producing neuron progenitor cells from cells having the ability to differentiate into GABA-producing neuron progenitor cells in the presence of the test sample, and detecting the expression of 65B13 in the differentiated cells. Thus, the present invention provides methods of screening for candidate compounds as a reagent that differentiates GABA-producing neuron progenitor cells, which use as an indicator the expression of 65B13 and comprise the steps of:

(f) inducing the differentiation into GABA-producing neuron progenitor cells from cells having the ability to differentiate into GABA-producing neuron progenitor cells in the presence of a test sample;

(g) detecting the transcript or translation product of the 65B13 gene in the differentiated cells; and (h) selecting a compound that increases the level of the transcript or translation product as compared to that detected in the absence of the test sample.

In the above methods, the preferred "cells having the ability to differentiate into GABA-producing neuron progenitor cells" are cell samples containing cells that can be differentiated into GABA-producing neuron progenitor cells, such as multipotent ES cells.

The transcript or translation product of the 65B13 gene of the present invention can be detected using polynucleotides that hybridize to a transcript of the 65B13 gene or antibodies that bind to a translation product of the 65B13 gene, as described above.

In the present invention, cell growth and differentiation can be detected by comparing the cell condition with when the test substance is not contacted. Cell growth and differentiation can be assessed through morphological observation under a microscope, or detecting or quantifying substances produced upon cell differentiation.

Cell differentiation can be assessed by comparing the expression level of the 65B13 gene with that in the absence of a test sample. Specifically, when a test sample increases the level of transcript or translation product of the 65B13 gene as compared to that in the absence of the test sample, the test sample can be judged to have the ability to differentiate nerve cells. "Increase" means that, for example, the level becomes twice, preferably five times, and more preferably ten or more times.

In a preferred embodiment of the present invention, the screening methods of the present invention further comprise the step of selecting compounds with which the expression of the polynucleotide is detected in step (II).

In another preferred embodiment of the present invention, the screening methods of the present invention also include, for example, methods comprising the steps of:

(IV) contacting a test compound with cells having the ability to differentiate into GABA-producing neuron progenitor cells; and (V) detecting a protein selected from (v), (vi), (vii), and (viii) described above.

In a preferred embodiment, the above-described methods further comprise step (VI) of selecting compounds with which the protein is detected in step (V).

The above methods may comprise use of the 65B13 promoter (including modified promoters) (as a means) to detect proteins. For example, it is possible to transfect cells with a vector carrying a construct in which a gene encoding a detectable marker such as green fluorescent protein (GFP) is linked to a promoter portion obtained by analyzing the expression region of 65B13. Alternatively, a marker gene can be knocked-in at the 65B13 locus. In both cases, the expression of the marker gene is detected in a manner specific to GABA-producing neuron progenitor cells, and thus enables detection of the protein. The protein expression can be detected by methods (means) for detecting protein expression, and therefore the methods can also be used as methods (means) for detecting the protein-encoding gene.

In this case, "the gene encoding a marker is linked to a promoter portion" means that the gene encoding the marker is linked to the promoter portion in an expressible manner. The gene may be directly linked to the promoter, or the gene may be linked distantly to but still under the control of the promoter. Furthermore, the promoter portion obtained by analyzing the 65B13 expression region may be replaced with another promoter, as long as the promoter for 65B13 enables the expression of the 65B13 region.

The present invention also provides methods for producing a cell population of GABA-producing neurons. Such methods include, for example, methods comprising the steps of:

(VII) obtaining a cell population potentially containing GABA-producing neuron progenitor cells;

(VIII) detecting GABA-producing neuron progenitor cells using a method of the present invention for detecting or selecting GABA-producing neuron progenitor cells; and (IX) growing cells detected or selected in step (VIII).

The GABA-producing neuron progenitor cells obtained by the production methods described above are used, for example, in treating spinal cord injury or cerebellar degeneration.

The GABA-producing neuron progenitor cells obtained by the production methods described above are also included in the present invention. It is preferable that cells produced by the above-described methods of the present invention are viable cells.

Since cells obtained in the present invention are GABA-producing neuron progenitor cells, they are preferable in transplant therapy for degenerative diseases and such in terms of their safety, survival rate, and network formation ability, compared to mixed cell populations or GABA-producing neurons carrying an exogenous gene. Moreover, since cells (or cell populations) of the present invention obtained according to the methods are progenitor cells, they can be differentiated into a suitable stage by selecting in vitro conditions such as media, and are preferable materials for various types of neural transplant therapy. When neuron progenitor cells obtained using the methods of the present invention are used in transplants, preferably $1\times10^3$ to $1\times10^6$ neurons, and more preferably $5\times10^4$ to $6\times10^4$ neurons are transplanted. The primary method is stereotaxic surgery in which a cell suspension is transplanted into the brain. In addition, cells may also be transplanted by microsurgery. See, Backlund et al. (J. Neurosurg. 1985, 62:169-73), Lindvall et al. (Ann. Neurol. 1987, 22:457-68), or Madrazo et al. (New Engl. J. Med. 1987, 316:831-4) for methods of transplanting neuron tissues.

Moreover, the cells of the present invention can also be used to isolate genes specific to GABA-producing neuron progenitor cells, and genes specific to each stage of the maturation from progenitor cells into GABA-producing neurons. They can also be used for searching therapeutic targets for degenerative diseases, elucidating the maturation process of GABA-producing neurons, and in screenings using maturation as an indicator.

The present invention also provides reagents for detecting or selecting GABA-producing neuron progenitor cells. When identifying cell type by the reagents of the present invention, the representative target cerebellar cell is Purkinje cells and the representative target spinal cord cells are dI4 and dILA.

Herein, the "cell type identification" means not only when target cells are identified to be of a specific cell type, but also when target cells are judged not to be of a specific cell type. For example, when the 65B13 gene is substantially expressed in target cerebellar cells, the cells can be identified to be "possibly Purkinje cells" or the cells can be judged "not to be Purkinje cells". When the 65B13 gene is not substantially expressed in target spinal cord cells, the cells can be identified to be "possibly dI4 or dILA" or the cells can be judged to be "neither dI4 nor dILA".

In an embodiment, the reagents of the present invention include, for example, reagents for detecting or selecting GABA-producing neuron progenitor cells, which comprise probes, primers, or primer sets that enable detection of the expression of a polynucleotide that can hybridize to a polynucleotide selected from (i), (ii), (iii), and (iv) described above, or to a complementary sequence thereof.

The present invention also provides reagents for detecting or selecting cerebellar cells or spinal cord cells. For the reagents, the above-described reagents for detecting or selecting GABA-producing neuron progenitor cells may be appropriately combined with other known markers. Such reagents enable thorough cell type identification. Thus, in a preferred embodiment, the present invention provides reagents for detecting or selecting cerebellar cells or spinal cord cells, which comprise a combination of the above-described reagents for detecting or selecting GABA-producing neuron progenitor cells and polynucleotides that hybridize to the transcripts of one or more genes selected from the group consisting of Lbx1, Pax2, Lim1/2, Corl1, and Corl2 genes.

The sequences of the above-described marker genes are known as listed below.

The nucleotide sequence of mouse Lbx1 is shown in SEQ ID NO: 5 and the amino acid sequence is shown in SEQ ID NO: 6; the nucleotide sequence of human Lbx1 is shown in SEQ ID NO: 7 and the amino acid sequence is shown in SEQ ID NO: 8.

The nucleotide sequence of mouse Pax2 is shown in SEQ ID NO: 9 and the amino acid sequence is shown in SEQ ID NO: 10; the nucleotide sequence of human Pax2 is shown in SEQ ID NO: 11 and the amino acid sequence is shown in SEQ ID NO: 12.

The nucleotide sequence of mouse Lim1 is shown in SEQ ID NO: 13 and the amino acid sequence is shown in SEQ ID NO: 14; the nucleotide sequence of human Lim1 is shown in SEQ ID NO: 15 and the amino acid sequence is shown in SEQ ID NO: 16.

The nucleotide sequence of mouse Lim2 is shown in SEQ ID NO: 17 and the amino acid sequence is shown in SEQ ID NO: 18; the nucleotide sequence of human Lim2 is shown in SEQ ID NO: 19 and the amino acid sequence is shown in SEQ ID NO: 20; the nucleotide sequence of rat Lim2 is shown in SEQ ID NO: 21 and the amino acid sequence is shown in SEQ ID NO: 22.

The nucleotide sequence of mouse Corl1 is shown in SEQ ID NO: 23 and the amino acid sequence is shown in SEQ ID NO: 24; the nucleotide sequence of human Corl1 is shown in SEQ ID NO: 25 and the amino acid sequence is shown in SEQ ID NO: 26; the nucleotide sequence of rat Corl1 is shown in SEQ ID NO: 27 and the amino acid sequence is shown in SEQ ID NO: 28.

The nucleotide sequence of mouse Corl2 is shown in SEQ ID NO: 29 and the amino acid sequence is shown in SEQ ID NO: 30; the nucleotide sequence of human Corl2 is shown in SEQ ID NO: 31 and the amino acid sequence is shown in SEQ ID NO: 32.

The above-described reagents may further comprise cerebellar cells or spinal cord cells.

In another embodiment, the reagents of the present invention for detecting or selecting GABA-producing neuron progenitor cells include, for example, reagents for detecting or selecting GABA-producing neuron progenitor cells, which comprise antibodies that bind to a protein selected from (v), (vi), (vii), and (viii) described above.

The above-described reagents for detecting or selecting GABA-producing neuron progenitor cells may further comprise in combination antibodies that bind to proteins encoded by one or more genes selected from the group consisting of Lbx1, Pax2, Lim1/2, Corl1, and Corl2 genes.

The above-described reagents may further comprise cerebellar cells or spinal cord cells.

Cerebellar cells that can be identified using the above-described reagents include Purkinje cells, while spinal cord cells that can be identified using the above-described reagents include dI4 and dILA.

All prior-art documents cited in the specification have been incorporated herein by reference.

EXAMPLES

Hereinbelow, the present invention is specifically described with reference to the Examples; however, it should not be construed as being limited thereto.

Example 1

65B13 Expression Analysis in Fetal Spinal Cord and Isolation of 65B13-Positive Cells 65B13 (Neph3) is selectively expressed in several areas of fetal brain (FIG. 1; WO2004/038018; Minaki Y, Mizuhara E, Morimoto K, Nakatani T, Sakamoto Y, Inoue Y, Satoh K, Imai T, Takai Y, Ono Y. Migrating postmitotic neural precursor cells in the ventricular zone extend apical processes and form adherens junctions near the ventricle in the developing spinal cord. Neurosci Res. 2005, 52(3):250-62). In the midbrain, dopaminergic neuron progenitor cells have been demonstrated to express 65B13 (WO2004/038018); however, the types of cells that express 65B13 remain unidentified in other areas. Thus, the present inventors attempted to identify 65B13-expressing cells in the spinal cord and cerebellar primordia.

First, detailed analysis was carried out to clarify the expression of 65B13 in the spinal cord. The analysis was performed by the method described in WO2004/038018. In E10.5 mouse spinal cord, expression of the 65B13 mRNA was restricted to a very narrow dorsal area (FIG. 1D). At E12.5, 65B13 was observed to be expressed in a broader dorsal area (FIG. 1E), and the pattern remained unaltered until E14.5 (FIG. 1F) (Minaki Y, Mizuhara E, Morimoto K, Nakatani T, Sakamoto Y, Inoue Y, Satoh K, Imai T, Takai Y, Ono Y. Migrating postmitotic neural precursor cells in the ventricular zone extend apical processes and form adherens junctions near the ventricle in the developing spinal cord. Neurosci Res. 2005, 52(3):250-62).

Figure 2:
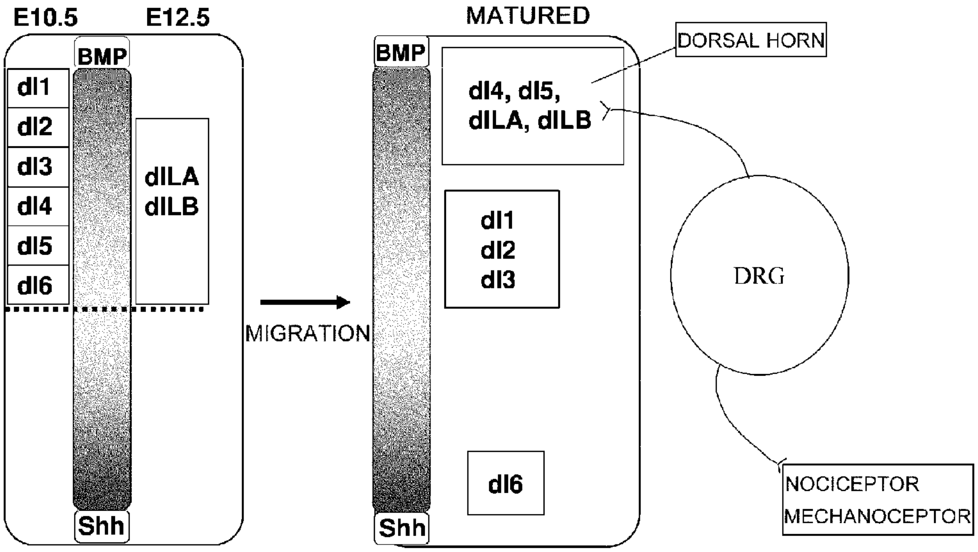
FIG. 2A shows a developmental scheme for the dorsal spinal cord.
FIG. 2B shows identification markers for various neurons.

It is known that in the spinal cord, six types of neurons are generated at an early stage (E10.5 to E11.5) of development and two types of neurons are generated at a late stage (E12 to E13.5) (FIG. 2; Caspary T, Anderson K V. Patterning cell types in the dorsal spinal cord: what the mouse mutants say. Nat Rev Neurosci. 2003, 4(4):289-97; Helms A W, Johnson J E. Specification of dorsal spinal cord interneurons. Curr Opin Neurobiol. 2003, 13(1):42-9; Matise M. A dorsal elaboration in the spinal cord. Neuron. 2002, 34(4):491-3). Of these, four types (dI4, dI5, dILA, and dILB) form the dorsal horn and transmit sensory, pain, and other signals from the periphery to center. Of these dorsal horn neurons, two types (dI4 and dILA) are GABA-producing inhibitory neurons, and the remaining two (dI5 and dILB) are glutamic acid-producing excitatory neurons (FIG. 2).

At an early stage of development, spinal dorsal neurons are generated from each of the six domains arranged in the dorsoventral direction. To determine the types of 65B13-positive cells, the expression of 65B13 (at the protein level) was compared to those of various neuron markers according to the protocol described below.

Mouse E10.5 embryos were collected and fixed in 4% PFA/PBS(−) at 4° C. for two hours. After replacing with 20% sucrose/PBS(−) at 4° C. overnight, the embryos were embedded in OCT. Sections of 12-μm thickness were prepared and placed onto slide glasses. Then, the sections were dried at room temperature for 30 minutes, and again wetted with PBS(−). Next, after 30 minutes of blocking (BlockAce) at room temperature, a primary antibody was reacted at room temperature for one hour. The reaction was followed by incubation at 4° C. overnight. The sections were washed three times with 0.1% Tween-20/PBS(−) at room temperature for 15 minutes each, and then incubated with a fluorescently labeled secondary antibody at room temperature for one hour. After washing in the same way, the sections were washed with PBS(−) at room temperature for ten minutes, and then mounted. The primary antibodies used were: 65B13 (see WO2004/038018; Minaki Y, Mizuhara E, Morimoto K, Nakatani T, Sakamoto Y, Inoue Y, Satoh K, Imai T, Takai Y, Ono Y. Migrating postmitotic neural precursor cells in the ventricular zone extend apical processes and form adherens junctions near the ventricle in the developing spinal cord. Neurosci Res. 2005, 52(3):250-62), Pax2 (purchased from Zymed), and Mash1 (purchased from BD PharMingen).

Figure 3:
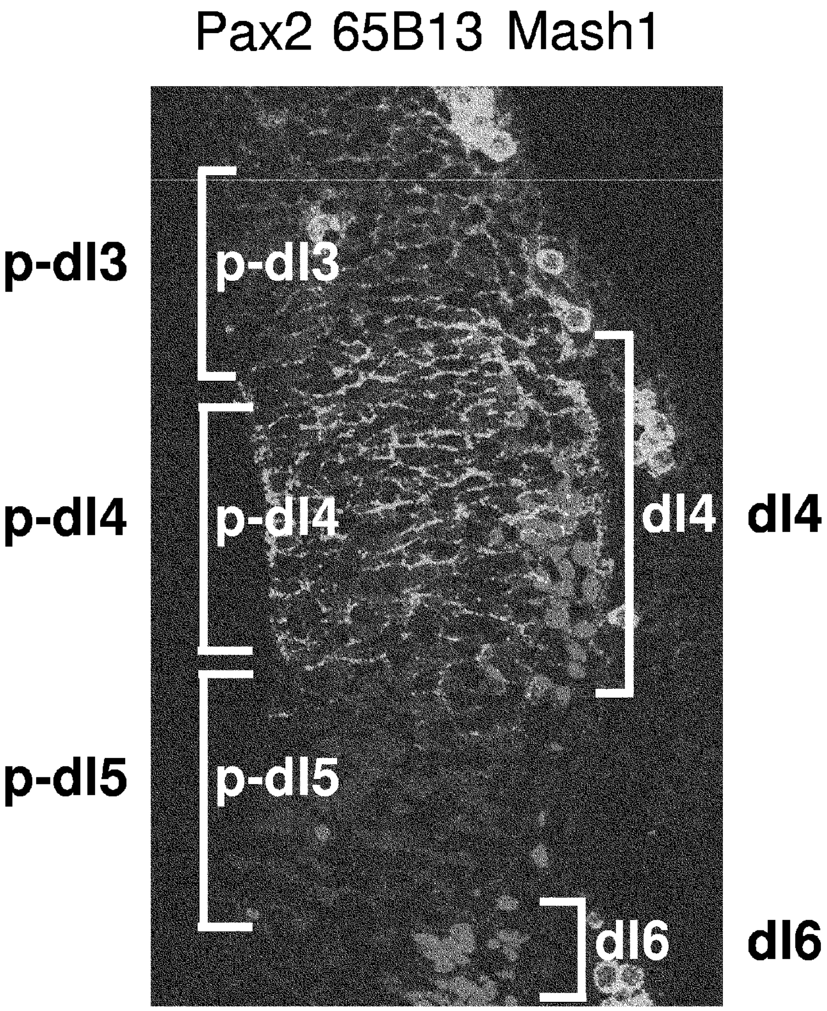
FIG. 3 shows a comparison of the 65B13, Mash1, and Pax2 expressions in the spinal cord of E10.5 mouse.

The result showed that 65B13 was selectively expressed in the dI4 region (FIG. 3). Furthermore, the finding that 65B13 is expressed only within the ventricular zone (VZ) containing undifferentiated progenitor cells (FIG. 1) demonstrates that 65B13-positive cells in E10.5 spinal cord were progenitor cells of dI4.

Next, 65B13-positive cells at a late stage (E12.5) of development were identified by the same method as described above. The Corl1 antibody used was described in WO2006/022243 and Mizuhara E, Nakatani T, Minaki Y, Sakamoto Y, Ono Y. Corl1, a novel neuronal lineage-specific transcriptional corepressor for the homeodomain transcription factor Lbx1. J Biol. Chem. 2005, 280(5):3645-55.

Figure 4:
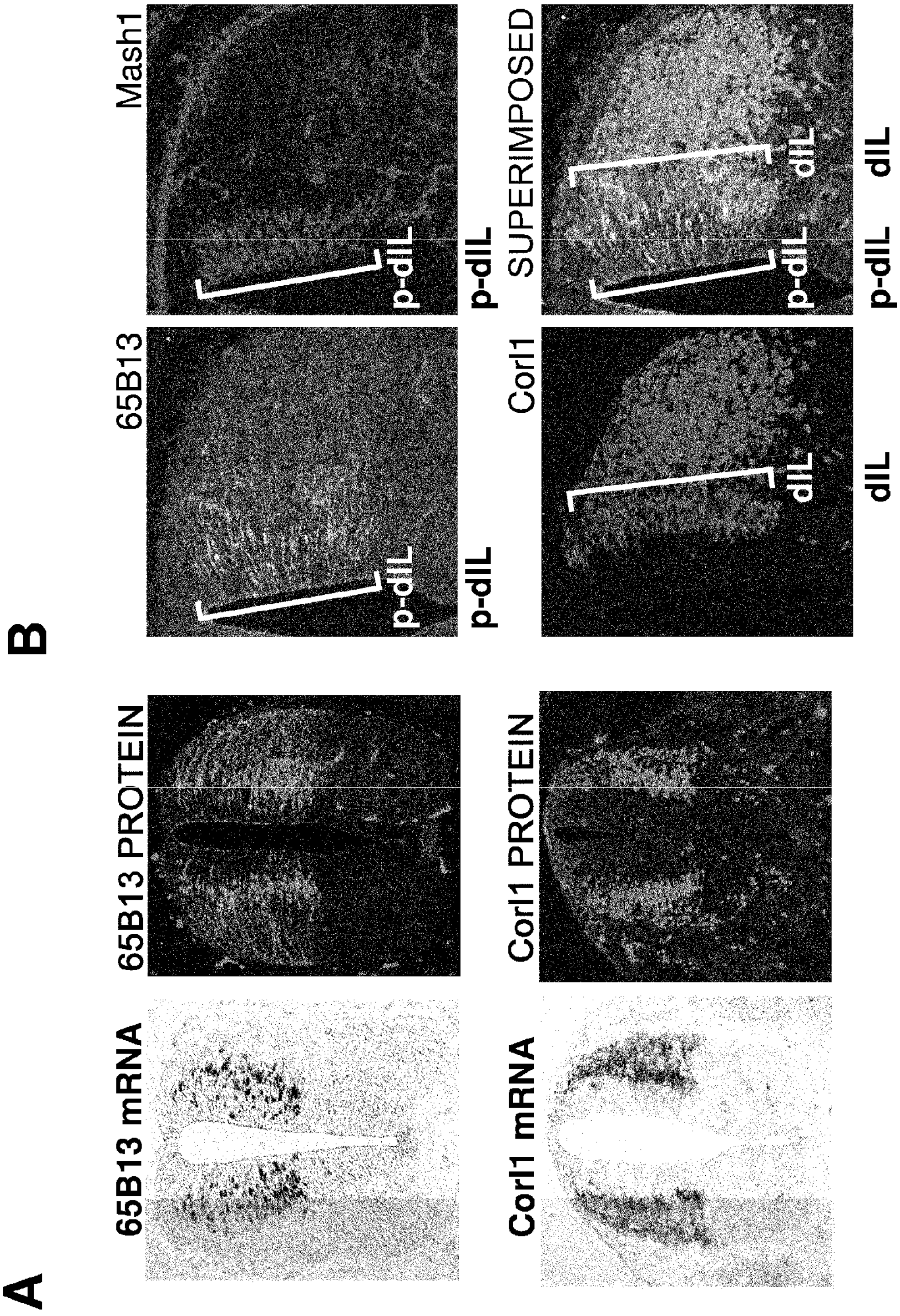
FIG. 4 shows a comparison of the 65B13, Corl1, and Mash1 expressions in the spinal cord of E12.5 mouse.

At E12.5, 65B13 was found to be expressed broadly in the VZ of dorsal spinal cord (FIG. 1). The spatial expression pattern along the dorsoventral axis (FIG. 4A) was identical to the pattern of progenitor cell-selective Mash1 expression in dILA and dILB, and the pattern of Corl1 expression in these neurons (Mizuhara E, Nakatani T, Minaki Y, Sakamoto Y, Ono Y. Corl1, a novel neuronal lineage-specific transcriptional corepressor for the homeodomain transcription factor Lbx1. J Biol. Chem. 2005, 280(5):3645-55). This finding demonstrates that 65B13 is selectively expressed in progenitor cells of either or both of dILA and dILB. Unlike at the early stage, two types of neurons develop at this stage in the same area of dorsal spinal cord; therefore, the cell types cannot be identified according to their expression sites. In this context, to identify the cell types, 65B13-positive cells were isolated and cultured using the protocol described below.

First, spinal cord mass was excised from E12.5 mice and dispersed using Cell Suspension Buffer (Invitrogen). Then, without fixation and permeability treatment, the cells were stained at 4° C. for 20 minutes using an anti-65B13 monoclonal antibody (100 times diluted purified antibody, 1% bovine fetal serum, 1 mM EDTA/SDIA differentiation medium (Kawasaki et al. Neuron 2000, 28(1):31-40)). After washing three times with 1 mM EDTA/PBS containing 1% bovine fetal serum at 4° C. for three minutes, the cells were stained with a PE-labeled anti-hamster IgG antibody (Jackson; 10 μg/ml, 1% bovine fetal serum, 1 mM EDTA/SDIA differentiation medium) at 4° C. for 30 minutes and washed in the same way as described above. After staining, 65B13-expressing cells were separated with a cell sorter. The isolated cells were placed onto slide glasses coated with poly-L-ornithine (Sigma, 0.002% in PBS), laminin (Invitrogen, 5 μg/ml in PBS), and fibronectin (Sigma, 5 μg/ml in PBS) and cultured at 37° C. for two days in SDIA differentiation medium supplemented with Knockout Serum Replacement (Gibco, 5%), N2 (Invitrogen, 1×), B27 (Invitrogen, 1×), ascorbic acid (Sigma, 200 μM), and BDNF (Invitrogen, 20 ng/ml). The cultured cells were fixed with 2% PFA/PBS at 4° C. for 20 minutes, and then washed twice with PBS at 4° C. for 10 minutes. Then, cell permeability treatment was performed using 0.3% Triton X-100/PBS at room temperature for 30 minutes, and the cells were blocked with 10% normal donkey serum/BlockAce at room temperature for 20 minutes. Next, the cells were incubated with a primary antibody (10% normal donkey serum, 2.5% BlockAce, 0.1% Triton X-100/PBS) at room temperature for one hour and then at 4° C. overnight. On the next day, after washing three times with 0.1% Triton X-100/PBS at room temperature for ten minutes, the cells were incubated with a fluorescently labeled secondary antibodies (all from Jackson, 10 μg/ml, 10% normal donkey serum, 2.5% BlockAce, 0.1% Triton X-100/PBS) at room temperature for 30 minutes. After washing in the same way as described above, the cells were washed with PBS at room temperature for five minutes, mounted, and observed. The primary antibodies used were: Lim1/2 (purchased from Developmental Studies Hybridoma Bank), HuC/D (purchased from Molecular Probe), and Gad65 (purchased from BD PharMingen). The antibody Lmx1b was prepared by the method described below. First, an expression vector was constructed for a GST fusion protein with amino acids of 271 to 306 of Lmx1b as an immunization antigen. After the resulting vector was introduced into *E. coli* (JM109 strain), the expression was induced with IPTG. The fusion protein was collected using glutathione beads. After rabbits were immunized several times with the fusion proteins, blood was collected from the rabbits. Anti-Lmx1b polyclonal antibody was obtained by affinity purification of the serum using the same GST-Lmx1b antigen used in the immunization. Nuclear staining was performed using SYTOX Green (Molecular Probe).

Figure 5:
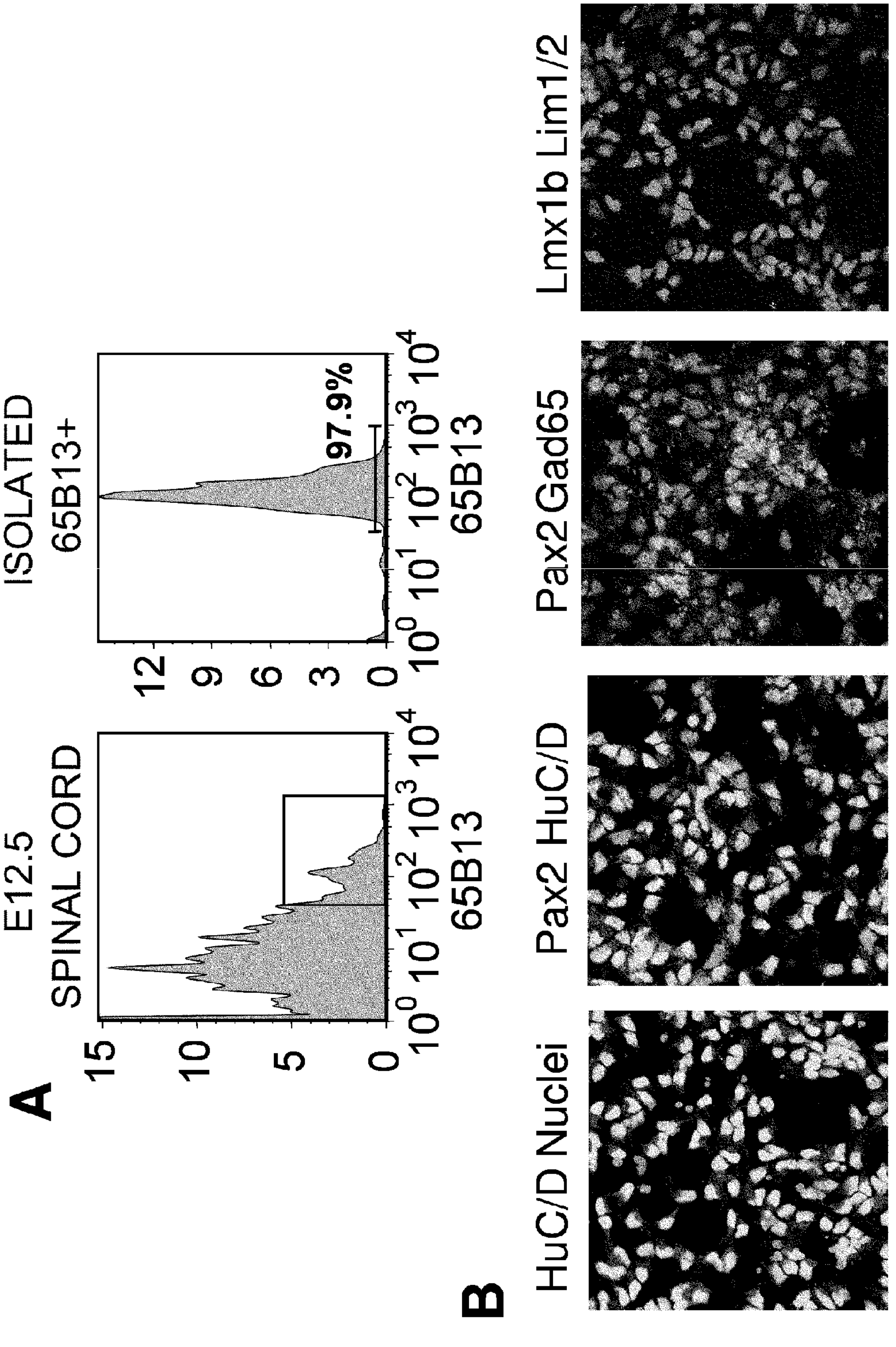
FIG. 5 shows differentiation of 65B13-positive cells isolated from the spinal cord of E12.5 mouse into GABA-producing dILA neurons.

The first finding was that 65B13-expressing cells in the dorsal spinal cord can be isolated alive by using an anti-65B13 antibody (FIG. 5A). Another finding was that almost the entire population of 65B13-expressing cells in the dorsal spinal cord differentiated into HuC/D-positive neurons after two days of culturing, and nearly all of the neurons were Lim1/2-positive and Gad1-positive GABA-producing dILA neurons (FIG. 5B). Thus, in E12.5 spinal cord, 65B13 was revealed to be selectively expressed in progenitor cells of dILA. Specifically, it was demonstrated that in the fetal spinal cord, 65B13 was specifically expressed in GABA neuron progenitor cells (dI4 and dILA) of the dorsal horn, and these progenitor cells can be separated by using an anti-65B13 antibody.

Example 2

65B13 Expression Analysis in Cerebellar Primordium and Isolation of 65B13-Positive Cells The cerebellum is constituted of glutamic acid-producing granule cells and GABA-producing neurons such as Purkinje cells, Golgi cells, stellate cells, and basket cells (Wang V Y, Zoghbi H Y. Genetic regulation of cerebellar development. Nat Rev Neurosci. 2001, 2(7):484-91). The granule cells are known to develop in the rhombic lip region at E12.5 to E14.5 (Wang V Y, Zoghbi H Y. Genetic regulation of cerebellar development. Nat Rev Neurosci. 2001, 2(7):484-91). By contrast, the development of GABA-producing neurons is still poorly understood. However, recent findings suggest that Purkinje cells are generated at E11.5 to E13.5 in the dorsal rhombomere 1 (cerebellar primordium area) (Chizhikov V V, Lindgren A G, Currie D S, Rose M F, Monuki E S, Millen K J. The roof plate regulates cerebellar cell-type specification and proliferation. Development. 2006, 133(15):2793-804). Although there is no detailed report on Golgi cells, they are thought to be generated at a late stage (E13.5 to E15.5) of development in the same region. The stellate cells and basket cells are thought to be generated from progenitor cells in the white matter after birth (Zhang L, Goldman J E. Generation of cerebellar interneurons from dividing progenitors in white matter. Neuron. 1996, 16(1):47-54).

To identify 65B13-expressing cells in the cerebellar primordium, the spatial expression pattern of 65B13 was compared to those of various markers by the same methods described in Example 1. The anti-Corl2 antibody used was the same as described in WO2006/082826.

Figure 6:
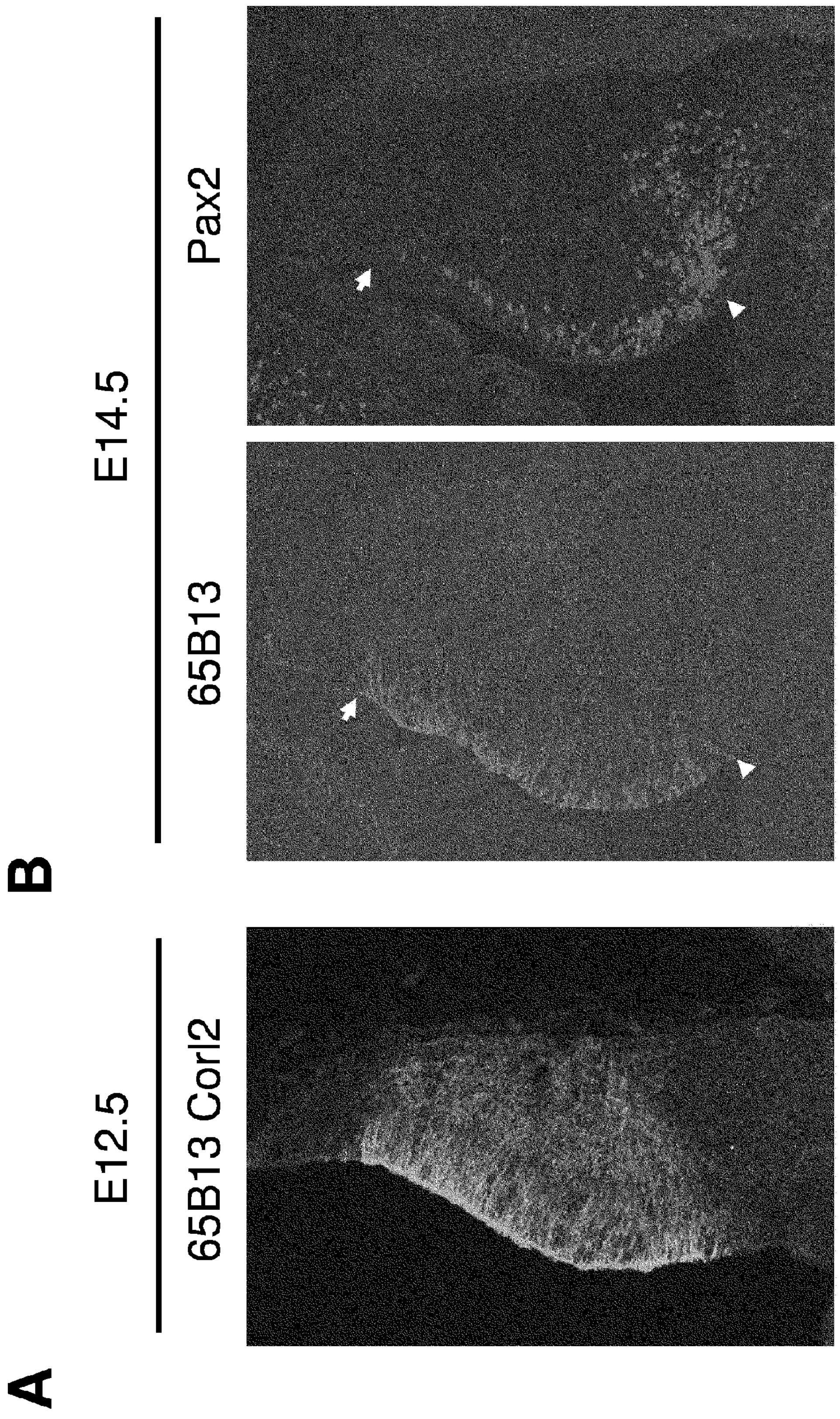
FIG. 6 shows a comparison of the 65B13, Corl2, and Pax2 expressions in the fetal cerebellar primordium.

The result showed that in the cerebellar primordium of E12.5, 65B13 was selectively expressed in VZ where Corl2-positive Purkinje cells develop (FIG. 6A). In addition, neurons that are thought to be Pax2-positive Golgi cells revealed to start to emerge at E14.5 in the same 65B13-positive area (Maricich S M, Herrup K. Pax-2 expression defines a subset of GABAergic interneurons and their precursors in the developing murine cerebellum. J Neurobiol. 1999, 41(2):281-94) (FIG. 6B).

Thus, experiments were carried out to isolate and culture 65B13-positive cells for the purpose of confirming that the 65B13-positive cells are progenitor cells of Purkinje and Golgi cells.

Figure 7:
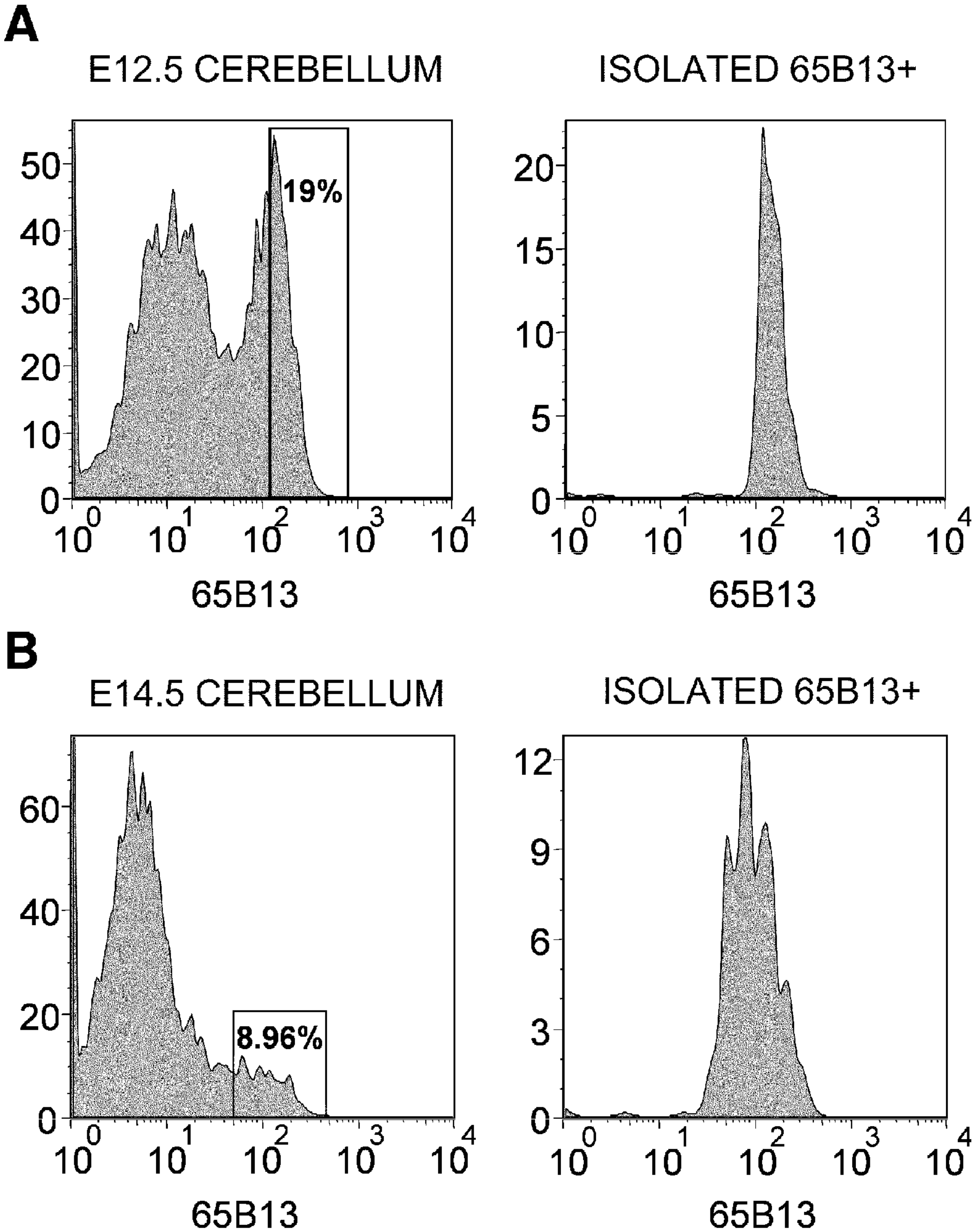
FIG. 7 shows that 65B13-positive cells could be isolated from the cerebellar primordia of fetal mouse.
Figure 8:
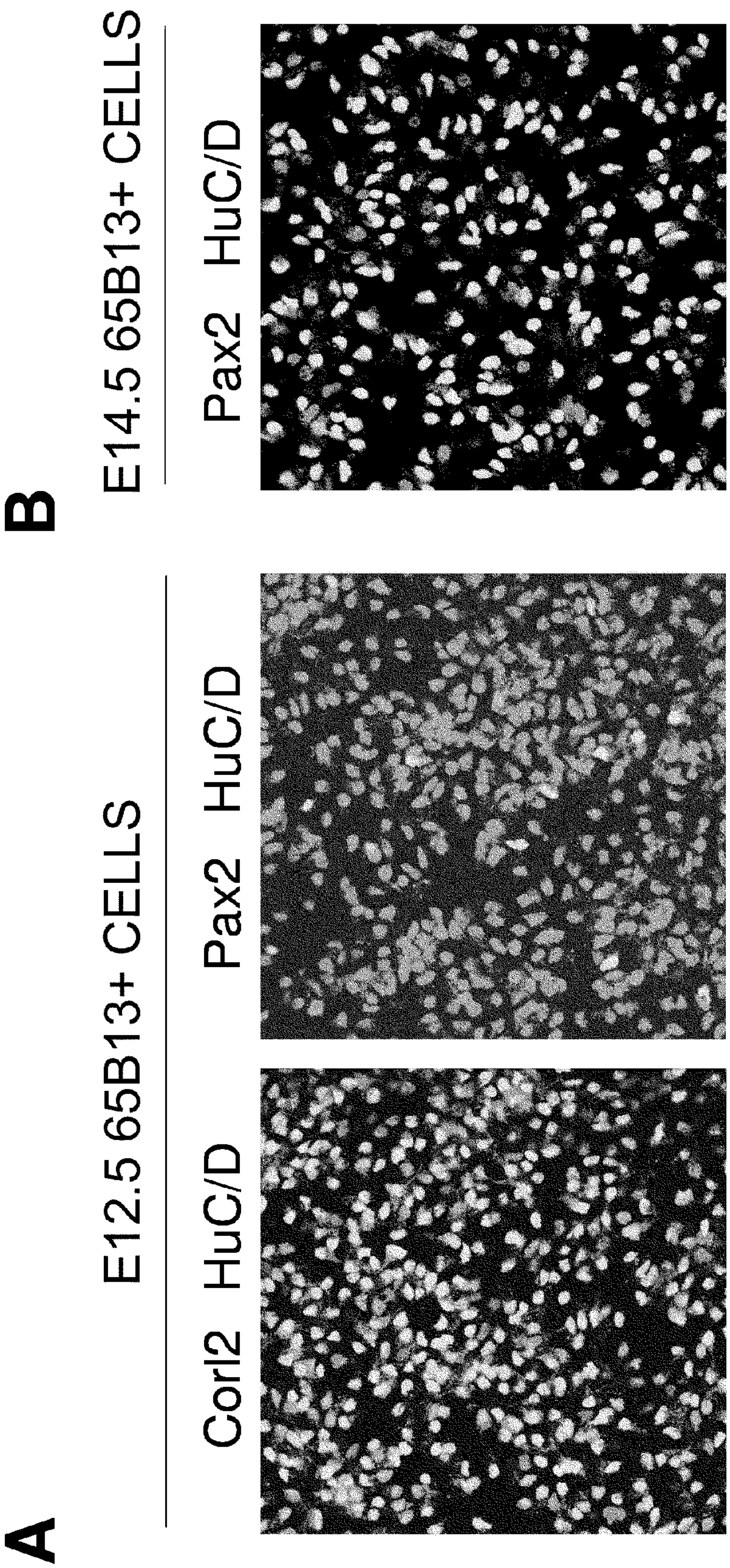
FIG. 8 shows differentiation of 65B13-positive cells isolated from the cerebellar primordia of E12.5 (A) and E14.5 (B) mice into GABA-producing Purkinje cells and GABA-producing Golgi cells, respectively.

The cerebellar primordium areas at E12.5 and E14.5 were excised, and 65B13-positive cells were detected and isolated by the same method as described in Example 1 using a cell sorter. The result showed that 65B13-positive cells could be isolated alive from the cerebellar primordium areas at both of the developmental stages (FIG. 7). Furthermore, it was demonstrated that almost the entire population of the cells differentiated into neurons after two days of culturing, and nearly all of the E12.5 65B13-positive cells differentiated into Corl2-positive Purkinje cells (FIG. 8A) while nearly all of the E14.5 65B13-positive cells differentiated into Pax2-positive Golgi cell-like neurons (FIG. 8B). Thus, it was revealed that in the fetal cerebellum, 65B13 was selectively expressed in progenitor cells of Purkinje and Golgi cells, and these progenitor cells could be separated by using an anti-65B13 antibody. Specifically, 65B13 was demonstrated to be useful as a marker for separating GABA-producing neuron progenitor cells in the spinal dorsal horn and cerebellum.

Example 3

Isolation of ES Cell-Derived Spinal Dorsal Horn GABA Neuron Progenitor Cells Next, to assess whether in vitro differentiated GABA neuron progenitor cells can be separated by using 65B13 as a marker, spinal cord nerve cells differentiated from ES cells (Wichterle H, Lieberam I, Porter J A, Jessell T M. Directed differentiation of embryonic stem cells into motor neurons. Cell 2002, 110(3):385-97) were separated according to the protocol described below.

10 ml of Glasgow Minimum Essential Medium (Invitrogen) supplemented with 5% fetal calf blood, 2 mM L-glutamine (Invitrogen), 0.1 mM non-essential amino acid (Invitrogen), 1 mM sodium pyruvate (Sigma), 0.1 mM 2-mercaptoethanol (Sigma), 100 U/ml penicillin (Invitrogen), and 100 μg/ml streptomycin (Invitrogen) was added to a 10-cm dish. $1.5\times10^6$ cells were cultured in the dish at 37° C. under 5% carbon dioxide and 95% humidity for two days. The resulting cell mass (EB) was harvested and placed in the medium described above. After adding 2 μM retinoic acid (Sigma), the cell mass was further cultured for four days. Then, the mass was dispersed into cells by the same method as described in Example 1. After staining with the anti-65B13 antibody, the cells were isolated with a cell sorter.

Figure 9:
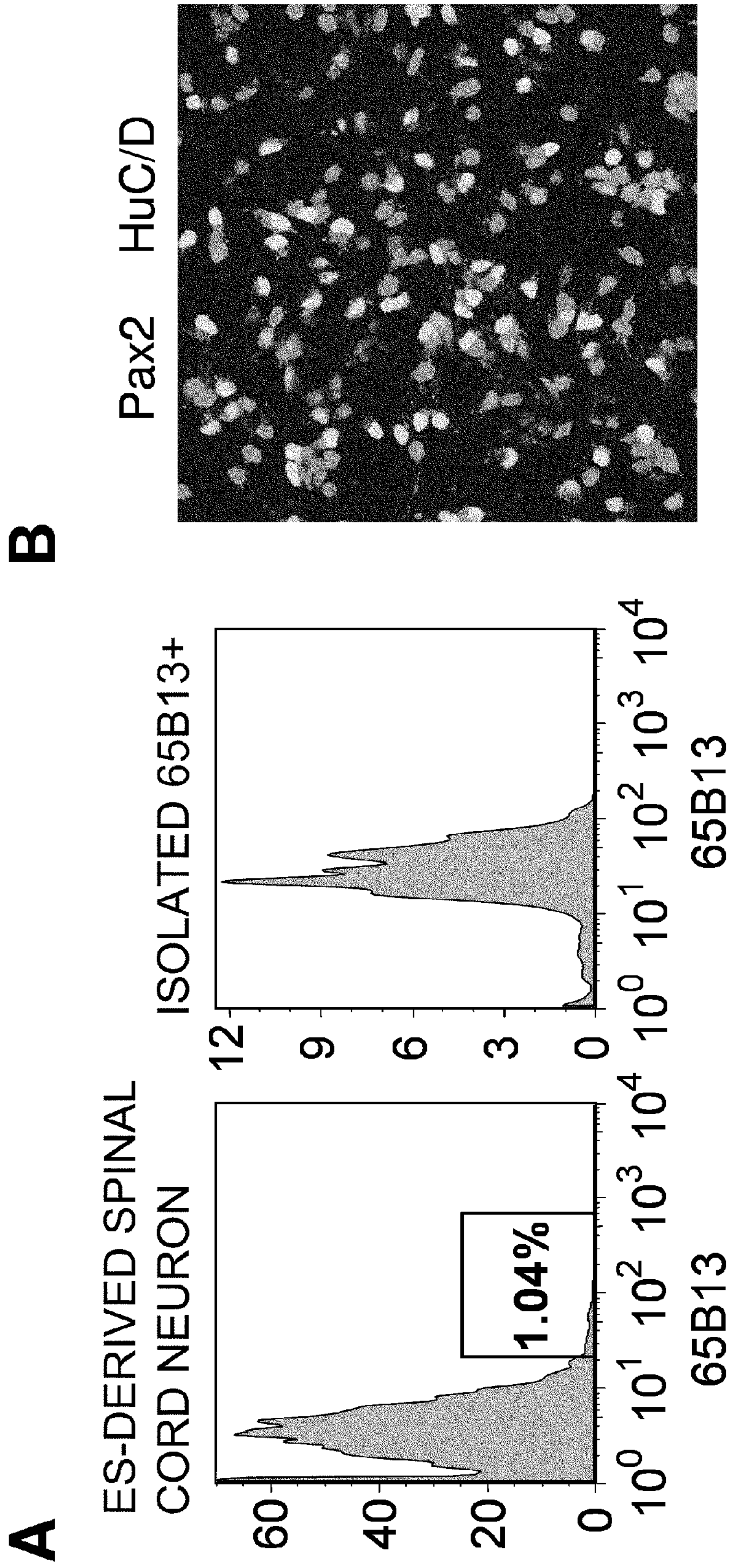
FIG. 9 shows 65B13-positive cells could be isolated from a population of in vitro differentiated spinal cord neurons derived from ES cells and their differentiation into GABA-producing neurons.

As a result, 65B13-positive cells were detected in the population of spinal cord cells differentiated from ES cells. This demonstrates that, like fetal spinal cord cells, dorsal spinal cord neuron progenitor cells derived from ES cells express 65B13 (FIG. 9A). It was also observed that about 50% of the isolated cells differentiated into HuC/D-positive neurons and about 70% of the neurons differentiated into Pax2-positive GABA neurons (FIG. 9B). Thus, 65B13 was demonstrated to be a useful marker for separating not only fetal but also ES cell-derived GABA neuron progenitor cells.

Example 4

Expression of Foreign Genes Using the 65B13 Promoter Specifically in GABA-Producing Neuron Progenitor Cells Next, whether foreign genes can be expressed in a GABA-producing neuron progenitor cell-specific manner using the 65B13 promoter was assessed by creating transgenic mice and analyzing the expression of foreign genes according to the protocol described below.

First, the poly A addition sequence of bovine growth hormone (SEQ ID NO: 55; derived from Invitrogen pcDNA3.1+ vector) was amplified and inserted into the HindIII/XhoI site of pSP73 (Promega) to construct pSP73-polyA. Then, the synthetic DNAs of SEQ ID NOs: 56 and 57 were annealed to each other and inserted into the Asp718I/BamHI site of pSP73-polyA to construct pSP73-polyA II. A mouse genomic fragment (SEQ ID NO: 58) located about 3.2 kb upstream of the translation initiation codon of 65B13 was inserted into the ClaI/Asp718I site of pSP73-polyA II to construct pN3. Finally, mouse Gsh1 cDNA (SEQ ID NO: 59) was inserted as a foreign gene into the Asp718I/SalI site of pN3 to construct pN3-Gsh1. After linearized with ClaI, pN3-Gsh1 was injected into the pronuclei of mouse fertilized eggs according to the method of Gordon et al. (Gordon J W, Scangos G A, Plotkin D J, Barbosa J A, Ruddle F H. Genetic transformation of mouse embryos by microinjection of purified DNA. Proc Natl Acad Sci USA. 1980 December; 77(12): 7380-4), and the eggs were transplanted into foster mothers. The fetuses were recovered at embryonic day 12.5, and the expression of Neph3 and Gsh1 in the cerebellar primordia was analyzed by the methods described in Example 1. An anti-Gsh1 antibody was prepared by the method described below. First, an expression vector was constructed for a GST fusion protein with amino acids of 1 to 72 of Gsh1 as an immunization antigen. After the resulting vector was introduced into *E. coli* (JM109 strain), the expression was induced with IPTG. The fusion protein was collected using glutathione beads. After the rats were immunized with the fusion protein collected, lymphocytes were collected and fused with myeloma cell P3U1. Thus, anti-Gsh1 antibody-producing hybridomas were obtained (hybridoma preparation was outsourced to Kohjin Bio Co.).

Figure 11:
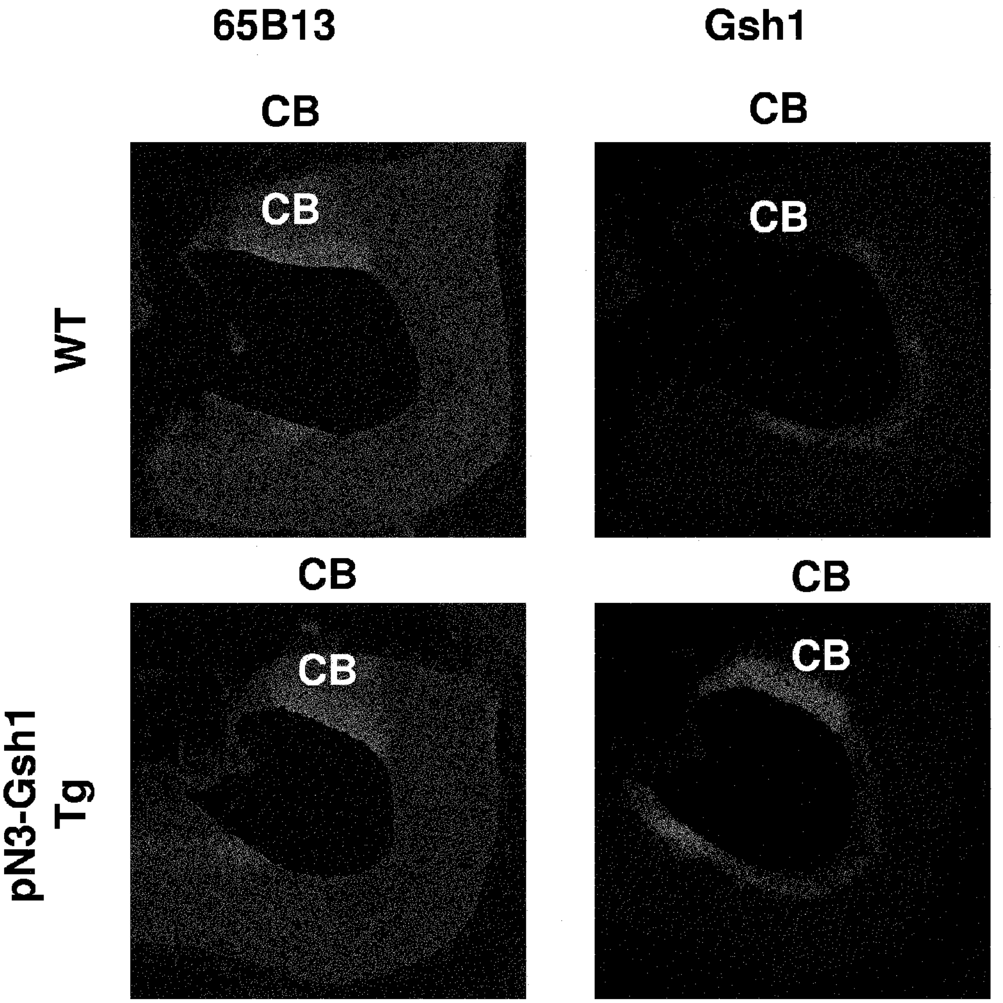
FIG. 11 shows that a foreign gene (Gsh1) could be expressed specifically in GABA-producing neuron progenitor cells by using the 65B13 promoter.

The result showed that the wild-type cerebellum expressed Gsh1 only in a very small ventral fraction of 65B13-positive GABA-producing neuron progenitor cells, while the transgenic mice expressed Gsh1 specifically in the entire 65B13-positive area (FIG. 11). This finding demonstrates that foreign genes can be expressed in a GABA-producing neuron progenitor cell-specific manner by using the 65B13 promoter.

Industrial Applicability

The present invention identified a selective marker 65B13 for spinal dorsal horn and cerebellar GABA neuron progenitor cells, and successfully isolated GABA neuron progenitor cells by using an antibody against 65B13. This technique can provide viable GABA neuron progenitor cells, and is expected to be useful in preparing materials for transplantation therapy for degenerative diseases, search of specific genes, discovery of drugs targeting GABA neurons, etc.

Since the marker gene identified by the present inventors encodes a membrane protein, the marker can be used as an indicator to detect and select GABA neuron progenitor cells and to isolate (separate) viable GABA neuron progenitor cells.

Highly pure GABA neurons can be obtained by methods for preparing GABA neuron progenitor cells using the marker of the present invention. Thus, the methods are applicable to drug discovery, for example, targeting pain associated with spinal cord GABA neurons, or cerebellar degeneration associated with cerebellar GABA neurons.

Sequence Listing Free Texts

SEQ ID NO: 33 Mouse 65B13 NM_172898 extracellular: 20-513 a.a.

SEQ ID NO: 35 Mouse 65B13 BC052773 extracellular: 20-513 a.a.

SEQ ID NO: 37 Human 65B13 NM_032123 extracellular: 21-510 a.a.

SEQ ID NO: 39 Human 65B13 NM_199180 extracellular: 21-510 a.a.

SEQ ID NO: 41 Human 65B13 AY358742 extracellular: 21-510 a.a.

SEQ ID NO: 43 Human 65B13 AY305301 extracellular: 21-510 a.a.

SEQ ID NO: 45 Human 65B13 NM_199179 extracellular: 21-460 a.a.

SEQ ID NO: 47 Human 65B13 AY305302 extracellular: 21-460 a.a.

SEQ ID NO: 49 Human 65B13 BC064925 extracellular: 21-490 a.a.

SEQ ID NO: 51 Chimpanzee 65B13 (predicted) XM_512603 extracellular: 21-445 a.a.

SEQ ID NO: 53 Cattle 65B13 (predicted) XM_583222 extracellular: 44-607 a.a.

The invention claimed is:

1. A method for isolating, separating, or selecting GABA-producing neuron progenitor cells, comprising: (a) identifying the expression of 65B13 in cells of a cell sample comprising in vitro differentiated GABA-producing neuron progenitor cells or GABA-producing neuron progenitor cells obtained from the spinal dorsal horn or the cerebellum, wherein 65B13 is selectively expressed in GABA-producing neuron progenitor cells; and (b) isolating, separating, or selecting cells expressing 65B13 from the cell sample.

2. The method of claim 1, wherein the cell sample is a human cerebellar cell sample and identifying the expression of 65B13 in cells of the cerebellar cell sample is achieved by detecting a 65B13 translated product.

3. The method of claim 1, wherein the cell sample is a murine cerebellar cell sample and identifying the expression of 65B13 in cells of the cerebellar cell sample is achieved by detecting a 65B13 translated product.

4. The method of claim 1, wherein the cell sample is a human spinal dorsal horn cell sample and identifying the expression of 65B13 in cells of the spinal dorsal horn sample is achieved by detecting a 65B13 translated product.

5. The method of claim 1, wherein the cell sample is a murine spinal dorsal horn cell sample and identifying the expression of 65B13 in cells of the spinal dorsal horn sample is achieved by detecting a 65B13 translated product.

6. The method of claim 1, wherein the cell sample comprises in vitro differentiated human GABA-producing neuron progenitor cells and identifying the expression of 65B13 in cells of the cell sample is achieved by detecting a 65B13 translated product.

7. The method of claim 1, wherein the cell sample comprises in vitro differentiated murine GABA-producing neuron progenitor cells and identifying the expression of 65B13 in cells of the cell sample is achieved by detecting a 65B13 translated product.

8. A method for isolating, separating, or selecting GABA-producing neuron progenitor cells, comprising: contacting a cell sample comprising in vitro differentiated GABA-producing neuron progenitor cells or GABA-producing neuron progenitor cells obtained from the spinal dorsal horn or the cerebellum with an anti-65B13 antibody, wherein the cells bound by the anti-65B13 antibody comprise GABA-producing neuron progenitor cells; and isolating, separating, or selecting cells bound by the anti-65B13 antibody from the cell sample.

9. The method of claim 8, wherein the cell sample is a human cerebellar cell sample and the anti-65B13 antibody binds to the human 65B13 protein of SEQ ID NO:38, SEQ ID NO:40, SEQ ID NO:42, SEQ ID NO:44, SEQ ID NO:46, SEQ ID NO:48, or SEQ ID NO:50.

10. The method of claim 9, wherein the cells bound by the anti-65B13 antibody are isolated using flow cytometry.

11. The method of claim 8, wherein the cell sample is a human spinal dorsal horn cell sample and the anti-65B13 antibody binds to the human 65B13 protein of SEQ ID NO:38, SEQ ID NO:40, SEQ ID NO:42, SEQ ID NO:44, SEQ ID NO:46, SEQ ID NO:48, or SEQ ID NO:50.

12. The method of claim 11, wherein the cells bound by the anti-65B13 antibody are isolated using flow cytometry.

13. The method of claim 8, wherein the cell sample comprises in vitro differentiated human GABA-producing neuron progenitor cells and the anti-65B13 antibody binds to the human 65B13 protein of SEQ ID NO:38, SEQ ID NO:40, SEQ ID NO:42, SEQ ID NO:44, SEQ ID NO:46, SEQ ID NO:48, or SEQ ID NO:50.

14. The method of claim 13, wherein the cells bound by the anti-65B13 antibody are isolated using flow cytometry.

15. The method of claim 8, wherein the cell sample is a murine cerebellar cell sample and the anti-65B13 antibody binds to the murine 65B13 protein of SEQ ID NO:2, SEQ ID NO:4, SEQ ID NO:34, or SEQ ID NO:36.

16. The method of claim 15, wherein the cells bound by the anti-65B13 antibody are isolated using flow cytometry.

17. The method of claim 8, wherein the cell sample is a murine spinal dorsal horn cell sample and the anti-65B13 antibody binds to the murine 65B13 protein of SEQ ID NO:2, SEQ ID NO:4, SEQ ID NO:34, or SEQ ID NO:36.

18. The method of claim 17, wherein the cells bound by the anti-65B13 antibody are isolated using flow cytometry.

19. The method of claim 8, wherein the cell sample comprises in vitro differentiated murine GABA-producing neuron progenitor cells and the anti-65B13 antibody binds to the murine 65B13 protein of SEQ ID NO:2, SEQ ID NO:4, SEQ ID NO:34, or SEQ ID NO:36.

20. The method of claim 19, wherein the cells bound by the anti-65B13 antibody are isolated using flow cytometry.

21. A method for isolating, separating, or selecting a GABA-producing neuron progenitor cells, which comprises the step of: (a) detecting expression of a protein in a cell sample comprising in vitro differentiated GABA-producing neuron progenitor cells or GABA-producing neuron progenitor cells obtained from the spinal dorsal horn or the cerebellum, wherein the protein: a protein comprising the amino acid sequence of SEQ ID NO: 2, 4, 34, 36, 38, 40, 42, 44, 46, 48, or 50; a protein that is selectively expressed in a GABA-producing neuron progenitor cell and encoded by a polynucleotide that hybridizes under conditions of hybridization at 65° C. in 0.2×SSC and 0.1% SDS to a polynucleotide encoding the amino acid sequence of SEQ ID NO: 2, 4, 34, 36, 38, 40, 42, 44, 46, 48, or 50; or a protein that is selectively expressed in a GABA-producing neuron progenitor cell and comprises an amino acid sequence having 70% or higher identity to the amino acid sequence of SEQ ID NO: 2, 4, 34, 36, 38, 40, 42, 44, 46, 48, or 50; and (b) isolating, separating, or selecting cells expressing the protein from the cell sample.

22. A method for isolating, separating, or selecting GABA-producing neuron progenitor cells, which comprises the step of: detecting expression of a marker protein in a cell sample comprising in vitro differentiated GABA-producing neuron progenitor cells or GABA-producing neuron progenitor cells obtained from the spinal dorsal horn or the cerebellum, wherein the marker protein is translated from a marker protein mRNA transcribed under the control of a promoter linked to a polynucleotide encoding the marker protein to express the mRNA, wherein the protein to be translated from the mRNA is: a protein comprising the amino acid sequence of SEQ ID NO: 2, 4, 34, 36, 38, 40, 42, 44, 46, 48, or 50; a protein that is selectively expressed in a GABA-producing neuron progenitor cell and encoded by a polynucleotide that hybridizes under conditions of hybridization at 65° C. in 0.2×SSC and 0.1% SDS to a polynucleotide encoding the amino acid sequence of SEQ ID NO: 2, 4, 34, 36, 38, 40, 42, 44, 46, 48, or 50; or a protein that is selectively expressed in a GABA-producing neuron progenitor cell and comprises an amino acid sequence having 70% or higher identity to the amino acid sequence of SEQ ID NO: 2, 4, 34, 36, 38, 40, 42, 44, 46, 48, or 50; and (b) isolating, separating, or selecting cells expressing the marker protein from the cell sample.

23. The method of claim 21 or 22, wherein the step of detecting expression comprises the steps of: contacting the cell sample with an antibody that binds to the protein selected in claim 8 or 9; and detecting reactivity.

24. The method of claim 21, further comprising detecting expression of any one or a combination of genes selected from the group consisting of Corl1, Pax2, Lim1/2, Lbx1, and Corl2.

25. The method of claim 21, wherein the cell sample comprises fetal cells.

26. The method of claim 21, wherein the cell sample comprises GABA-producing neuron progenitor cells obtained from the cerebellum.

27. The method of claim 21, wherein the cell sample comprises GABA-producing neuron progenitor cells obtained from the spinal dorsal horn.

28. The method of claim 21, wherein the cell sample comprises in vitro differentiated GABA-producing neuron progenitor cells.

29. The method of claim 28, wherein the in vitro differentiated GABA-producing neuron progenitor cells are embryonic stem cell-derived GABA-producing neuron progenitor cells.

30. The method of claim 22, wherein the cell sample comprises fetal cells.

31. The method of claim 22, wherein the cell sample comprises GABA-producing neuron progenitor cells obtained from the cerebellum.

32. The method of claim 22, wherein the cell sample comprises GABA-producing neuron progenitor cells obtained from the spinal dorsal horn.

33. The method of claim 22, wherein the cell sample comprises in vitro differentiated GABA- producing neuron progenitor cells.

34. The method of claim 33, wherein the in vitro differentiated GABA-producing neuron progenitor cells are embryonic stem cell-derived GABA-producing neuron progenitor cells.

35. The method of claim 21, wherein the method comprises isolating cells expressing the protein from the cell sample.

36. The method of claim 22, wherein the method comprises isolating cells expressing the protein from the cell sample.

37. The method of claim 1, wherein the method comprises isolating cells expressing 65B13 from the cell sample.

38. The method of claim 8, wherein the method comprises isolating cells bound by the anti-65B13 antibody from the cell sample.

* * * * *

UNITED STATES PATENT AND TRADEMARK OFFICE

CERTIFICATE OF CORRECTION

PATENT NO. : 8,609,405 B2
APPLICATION NO. : 12/524153
DATED : December 17, 2013
INVENTOR(S) : Yuichi Ono, Yasuko Nakagawa and Eri Mizuhara It is certified that error appears in the above-identified patent and that said Letters Patent is hereby corrected as shown below:

Title Page 2, References Cited, Right Column
Line 17, OTHER PUBLICATIONS, after "3672-3682" insert --, Apr. 7, 2004--.

In the Claims
Column 200
Claim 23, Line 18, replace "8 or 9" with --21 or 22--.

Column 200
Claim 47, Line 47, replace "GABA- producing" with --GABA-producing--.

Signed and Sealed this
Twenty-second Day of April, 2014

Michelle K. Lee
*Deputy Director of the United States Patent and Trademark Office*